US008765739B2

(12) United States Patent
Ikegashira et al.

(10) Patent No.: US 8,765,739 B2
(45) Date of Patent: Jul. 1, 2014

(54) AZETIDINE COMPOUND AND PHARMACEUTICAL USE THEREOF

(75) Inventors: Kazutaka Ikegashira, Takatsuki (JP); Taku Ikenogami, Takatsuki (JP); Naoki Ogawa, Takatsuki (JP); Tatsuya Matsumoto, Takatsuki (JP); Takahiro Oka, Takatsuki (JP); Takuya Matsuo, Takatsuki (JP); Takayuki Yamasaki, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 89 days.

(21) Appl. No.: 12/780,146

(22) Filed: May 14, 2010

(65) Prior Publication Data
US 2010/0331301 A1 Dec. 30, 2010

Related U.S. Application Data

(60) Provisional application No. 61/216,820, filed on May 21, 2009.

(30) Foreign Application Priority Data

May 14, 2009 (JP) .................................. 2009-117813

(51) Int. Cl.
*A61K 31/496* (2006.01)
*A61K 31/4427* (2006.01)
*A61K 31/4439* (2006.01)
*A61K 31/5377* (2006.01)
*A61K 31/551* (2006.01)
*C07D 401/06* (2006.01)
*C07D 401/14* (2006.01)
*C07D 405/14* (2006.01)
*C07D 409/14* (2006.01)
*C07D 413/14* (2006.01)

(52) U.S. Cl.
CPC ............ *C07D 401/06* (2013.01); *C07D 405/14* (2013.01); *C07D 409/14* (2013.01); *C07D 401/14* (2013.01); *C07D 413/14* (2013.01)
USPC .................. 514/218; 514/235.5; 514/253.12; 514/318; 514/340; 514/343; 540/575; 544/364; 544/131; 546/194; 546/268.1; 546/278.4; 546/278.7

(58) Field of Classification Search
None
See application file for complete search history.

(56) References Cited

U.S. PATENT DOCUMENTS 6,376,670 B1 4/2002 Cuny et al.
2009/0054411 A1 2/2009 Cook et al.
2009/0197859 A1 8/2009 Collantes et al.

FOREIGN PATENT DOCUMENTS

| WO | WO2007/071955 A1 | 6/2007 |
| WO | WO 2007/119046 | 10/2007 |
| WO | WO2008/005456 | 1/2008 |
| WO | WO 2008/029084 | 3/2008 |
| WO | WO 2009/098576 | 8/2009 |

OTHER PUBLICATIONS

Hamilton Nature Reviews/Immunology, vol. 8,p. 533-544 (2008).*
Hume et al.Blood Journal Hematology, pp. 1-36 (2011) Available online at:http://bloodjournal.hematologylibrary.org/site/misc/rights.xhtml#reprints.*
Paniagua et al. Arthritis Research and Therapy,vol. 12, pp. 1-15 (2010).*
Rheumatoid Arhtritis, from Drugs.com,10 pages, retrieved from the Internet at http://www.drugs.com/rheumatoid-arthritis.html?printable=1 on Mar. 2, 2014.*
International Search Report from PCT/JP2010/058188, Aug. 3, 2010.
Conway, et al., Effects of the cFMS Kinase Inhibitor 5-(3-Methoxy-4-((4-methoxybenzyl)oxy)benzyl)pyrimidine-2, 4-diamine (GW2580) in Normal and Arthritic Rats, Journal of Pharmacology and Experimental Therapeutics, 326(1): 41-50, (2008).
Paniagua et al., "c-Fms-mediated differentiation and priming of monocyte lineage cells play a central role in autoimmune arthritis," Arthritis Research & Therapy, 1-15, (2010).
Patel, et al., "Colony-Stimulating Factor-1 Receptor Inhibitors for the Treatment of Cancer and Inflammatory Disease," Current Topics in Medicinal Chemistry, 9:599-610, (2009).
Supplementary European Search Report and Supplementary Search Opinion for European Application No. EP 10 77 4995, dated Oct. 8, 2012.
Enders, D. et al., "(S)-(---)-1-Amino-2-Methoxymethylpyrrolidine (SAMP) and (R)-(+)-1-Amino-2-Methoxymethylpyrrolidine (RAMP), Versatile Chiral Auxiliaries," *Organic Syntheses, Coll.*, vol. 8, p. 26 (1993); vol. 65, p. 173 (1987).
Huang, H. et al., "Pyridol[2,3-*d*]pyrimidin-5-ones: A Novel Class of Antiinflammatory Macrophage Colony-Stimulating Factor-1 Receptor Inhibitors," *J. Med. Chem.*, 52:1081-1099 (2009).
Kemp, D.S. et al., *Organic Chemistry*, Worth Publishers, NY, pp. 88-89 and p. 338 (1980).

(Continued)

*Primary Examiner* — Emily Bernhardt
(74) *Attorney, Agent, or Firm* — Fish & Richardson P.C.

(57) ABSTRACT

Compounds of formula [I]:

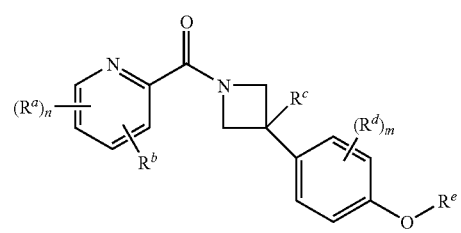

wherein each symbol is as defined in the description, or a pharmaceutically acceptable salts or solvates thereof.

10 Claims, No Drawings

(56) References Cited

OTHER PUBLICATIONS

Paniagua, R.T. et al., "Selective tyrosine kinase inhibition by imatinib mesylate for the treatment of autoimmune arthritis," *J. Clin. Invest.*, 116:2633-2642 (2006).

Smith. L.H., "Tetrahydrofurfuryl Bromide," *Organic Synthesis, Coll.*, vol. 3, p. 793 (1955); vol. 23, p. 88 (1943).
STN Tokyo Search Report, dated 2013, 85 pages.

* cited by examiner

AZETIDINE COMPOUND AND PHARMACEUTICAL USE THEREOF

CROSS REFERENCE TO RELATED APPLICATIONS

This application claims the benefit of priority of U.S. provisional application Ser. No. 61/216,820, filed May 21, 2009, and Japanese application serial number 2009117813, filed May 14, 2009. The disclosures of the prior applications are considered part of (and are incorporated by reference in) the disclosure of this application.

TECHNICAL FIELD

The present invention relates to azetidine compounds and medicinal use thereof. Specifically, the present invention relates to inhibitors of colony-stimulating factor 1 receptor (CSF-1R), compounds for preventing or treating autoimmune disease, inflammatory disease, osteoporosis, osteolysis or cancer, and medicinal use thereof.

BACKGROUND ART

CSF-1R is a kind of receptor tyrosine kinases, and ligand thereof is macrophage colony-stimulating factor (M-CSF).

CSF-1R is generally expressed at myeloid cells in mononuclear phagocyte system and at progenitor cells in bone marrow. Differentiation, proliferation, survival and migration of monocyte-macrophage lineage cells are stimulated by the activation of CSF-1R.

Moreover, macrophages produce inflammatory mediators such as interleukin and lymphokine, and lead to differentiation, proliferation and activation of a variety of immune cells. These immune cells are involved in pathological conditions of rheumatoid arthritis and multiple sclerosis. In addition, these immune cells are also involved in pathological conditions of inflammatory disease such as inflammatory bowel disease, glomerulonephritis, diabetic nephritis.

In Op/op mice which miss endogenous M-CSF, macrophages are reduced systemically and thus collagen-induced arthritis is improved. Besides, Ki20227 which is a specific inhibitor of CSF-1R improves swellings and bone destructions in mice with collagen-induced arthritis. In addition, Ki20227 improves the condition of rats suffering from experimental autoimmune encephalomyelitis that are an animal model of multiple sclerosis. Moreover, it is known that anti-M-CSF antibody improves renal dysfunction and enhances renal function in db/db mice which are an animal model of diabetic nephropathy.

The activation of CSF-1R promotes differentiation of osteoclastic precursors into mature osteoclasts. Osteoclasts promote bone destruction and bone absorption and play a key role in osteoporosis including bone loss after ovariectomy and in osteolysis associated with cancers.

In Op/op mice, osteoclasts are reduced and thus the bone density is increased. Besides, osteolysis in Op/op mice which is developed by transplanted cancer cells is improved compared with that in normal mice. Moreover, Ki20227 which is a CSF-1R specific inhibitor improves bone absorption induced by metastatic cancer in rat.

The overexpression of CSF-1R or M-CSF and activation of CSF-1R are found in prostate cancer, lung cancer, renal cancer, pancreatic cancer, breast cancer, ovarian cancer, endometrial carcinoma, bone marrow dysplasia, acute myeloid leukemia, chronic myeloid leukemia and the like.

Tumor-associated macrophages (TAMs) are involved in neoangiogenesis, invasion and cancer-progression of cancers such as breast cancer, endometrial carcinoma, renal cancer, lung cancer and cervical cancer as well as aggravated prognosis thereof. M-CSF plays a key role in regulating the TAMs. Thus, it is considered that CSF-1R inhibitors have an anticancer effect through their direct action on these cancers or their indirect action via TAMs. The proliferation of transplanted cancer cells in Op/op mice is more suppressed compared with that in normal mice.

On the basis of these findings, CSF-1R inhibitors are considered to be useful for preventing or treating rheumatoid arthritis, multiple sclerosis, osteoporosis including bone loss after ovariectomy, osteolysis, and cancer such as lung cancer and breast cancer.

In addition, CSF-1R inhibitors are considered to be useful for preventing or treating diabetic nephropathy.

SUMMARY OF THE INVENTION

Technical Problem to be Solved by the Present Invention

An object of the present invention is to provide novel CSF-1R inhibitors. Moreover, another object of the present invention is to provide medicaments of preventing or treating rheumatoid arthritis, multiple sclerosis, osteoporosis including bone loss after ovariectomy, osteolysis, and cancer such as lung cancer and breast cancer.

A further object of the present invention is to provide medicaments of preventing or treating diabetic nephropathy.

Means for Solving the Problems

The present inventors have found that azetidine compounds of the following formula (I) have CSF-1R inhibitory action and thereby have completed the present invention.

That is, the present invention provides the following aspects.

[1] A compound of formula [I]:

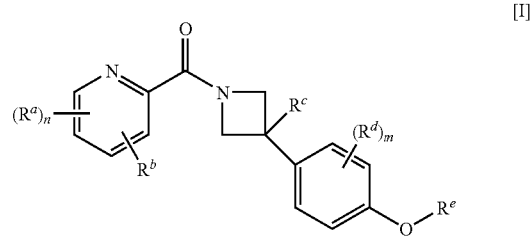

wherein
$R^a$ is
(1) $C_{1-6}$ alkyl group, or
(2) halogen atom;
n is an integer selected from 0, or 1 to 3;
$R^b$ is a group selected from the following (1) to (8)
(1) hydrogen atom,
(2) halogen atom,
(3) $C_{1-6}$ alkyl group which may be substituted with the same or different 1 to 5 substituents selected from Group A,
(4) —O—$(CH_2)_{n1}$—$(O)_{n2}$—$R^{b1}$ wherein
$R^{b1}$ is hydrogen atom, or $C_{1-6}$ alkyl group which may be substituted with the same or different 1 to 5 substituents selected from Group A, n1 is an integer selected from 0 or 1 to 4, and
n2 is 0 or 1,
provided that n1 is an integer selected from 1 to 4 when n2 is 1, (5)

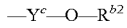

wherein
$Y^c$ is $C_{1-6}$ alkylene which may be substituted with the same or different 1 to 5 substituents selected from $C_{1-4}$ alkyl group or hydroxyl group, and
$R^{b2}$ is $C_{1-6}$ alkyl group which is substituted with the same or different 1 to 5 substituents selected from Group A,
(6) —CH=CH—C(=O)—$R^{b3}$ wherein $R^{b3}$ is $C_{1-6}$ alkyl group which may be substituted with the same or different 1 to 5 substituents selected from Group A,
(7) —$NR^{b4}R^{b5}$ wherein $R^{b4}$ and $R^{b5}$ are independently selected from hydrogen atom or $C_{1-6}$ alkyl group, or
(8)

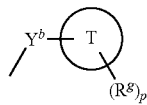

wherein
$Y^b$ is a group selected from the following (i) to (v):
(i) single bond,
(ii) $C_{1-6}$ alkylene which may be substituted with $C_{1-4}$ alkyl group,
(iii)

wherein $Y^{b1}$ and $Y^{b2}$ are independently selected from single bond, or alkylene which may be substituted with the same or different 1 to 5 substituents selected from $C_{1-4}$ alkyl group, halogen atom or hydroxyl group,
(iv) —O—$(CH_2)_{n4}$—C(=O)—, or
(v) —O—$(CH_2)_{n5}$—O—C(=O)—,
wherein n4 and n5 is an integer selected from 1 to 4;
cyclic moiety T is
(i) nonaromatic monocyclic heterocyclic group wherein the nonaromatic monocyclic heterocyclic ring consists of carbon atoms and 1 to 4 hetero atoms independently-selected from nitrogen atom, oxygen atom or sulfur atom, and is 3 to 7-membered,
(ii) monocyclic heteroaromatic group wherein the monocyclic heteroaromatic ring consists of carbon atoms and 1 to 4 hetero atoms independently-selected from nitrogen atom, oxygen atom or sulfur atom, and is 3 to 7-membered, or
(iii) $C_{6-10}$ aryl group;
$R^g$ is a group independently-selected from the following (i) to (vii):
(i) halogen atom,
(ii) $C_{1-6}$ alkyl group wherein $C_{1-6}$ alkyl may be substituted with the same or different 1 to 5 —$OR^{g1}$ or —C(=O)—$OR^{g1}$,
(iii) —C(=O)—$OR^{g2}$,
(iv) —C(=O)—$R^{g3}$,
(v) —C(=O)—$NR^{g4}R^{g5}$,
(vi) —$OR^{g6}$, or
(vii) —$SO_2$—$R^{g7}$,
wherein
$R^{g1}$, $R^{g2}$, $R^{g4}$, $R^{g5}$, $R^{g6}$, and $R^{g7}$ are independently selected from hydrogen atom or $C_{1-6}$ alkyl group, and
$R^{g3}$ is $C_{1-6}$ alkyl group which may be substituted with hydroxyl group;
p is an integer selected from 0, or 1 to 4;
$R^c$ is hydrogen atom or hydroxyl group;
$R^d$ is a group selected from the following (1) to (4):

(1) —$OR^{d1}$ wherein $R^{d1}$ is hydrogen atom or $C_{1-6}$ alkyl group which may be substituted with the same or different 1 to 5 halogen atoms,
(2) halogen atom,
(3) —C(=O)—$OR^{d2}$ wherein $R^{d2}$ is hydrogen atom or $C_{1-6}$ alkyl group, or
(4) $C_{1-6}$ alkyl group which may be substituted with the same or different 1 to 5 halogen atoms;
m is an integer selected from 0, or 1 to 4;
$R^e$ is a group selected from the following (1) or (2):
(1) $C_{1-12}$ alkyl group, or
(2)

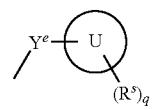

wherein
$Y^e$ is $C_{1-6}$ alkylene which may be substituted with $C_{1-4}$ alkyl group;
cyclic moiety U is a group selected from the following (i) to (v):
(i) $C_{6-10}$ aryl group,
(ii) $C_{3-10}$ cycloalkyl group,
(iii) $C_{8-11}$ spirocyclic cycloalkyl or spirocyclic cycloalkenyl group,
(iv) monocyclic heteroaromatic group wherein the monocyclic heteroaromatic ring consists of carbon atoms and 1 to 4 hetero atoms independently-selected from nitrogen atom, oxygen atom or sulfur atom, and is 3 to 7-membered, or
(v) fused heterocyclic group wherein the fused heterocyclic ring consists of carbon atoms and 1 to 4 hetero atoms independently-selected from nitrogen atom, oxygen atom or sulfur atom, and is 8 to 10-membered;
$R^s$ is a group independently-selected from the following (i) to (vi):
(i) $C_{1-6}$ alkyl group which may be substituted with the same or different 1 to 5 halogen atoms,
(ii) $C_{3-6}$ cycloalkyl group,
(iii) —$OR^{S1}$ wherein $R^{S1}$ is hydrogen atom or $C_{1-12}$ alkyl group which may be substituted with the same or different 1 to 5 halogen atoms,
(iv) halogen atom,
(v) —C(=O)—$OR^{s2}$ wherein $R^{S2}$ is hydrogen atom or $C_{1-6}$ alkyl group, or
(vi) —$SR^{S3}$ wherein $R^{S3}$ is hydrogen atom or $C_{1-6}$ alkyl group; and
q is an integer selected from 0, or 1 to 4;
Group A is selected from the group consisting of the following (a) to (e):
(a) halogen atom,
(b) —$OR^{41}$ wherein $R^{41}$ is hydrogen atom or $C_{1-6}$ alkyl group,
(c) —$NR^{42}R^{43}$ wherein $R^{42}$ and $R^{43}$ are independently selected from hydrogen atom or $C_{1-6}$ alkyl group which may be substituted with
(c1) hydroxyl group, and/or
(c2) —C(=O)—$OR^{44}$ wherein $R^{44}$ is hydrogen atom or $C_{1-6}$ alkyl group,
(d) —C(=O)—$OR^{45}$ wherein $R^{45}$ is hydrogen atom or $C_{1-6}$ alkyl group, and
(e) —C(=O)—$NR^{46}R^{47}$ wherein $R^{46}$ and $R^{47}$ are independently selected from hydrogen atom or $C_{1-6}$ alkyl group which may be substituted with (e1) hydroxyl group, and/or
(e2) —NR$^{A8}$R$^{A9}$ wherein R$^{A8}$ and R$^{A9}$ are independently selected from hydrogen atom or C$_{1-6}$ alkyl group,
or a pharmaceutically acceptable salt or solvate thereof.

[2] The compound according to [1] wherein
R$^b$ is
(1) C$_{1-6}$ alkyl group which may be substituted with the same or different 1 to 5 substituents selected from Group A,
(2) —O—(CH$_2$)$_{n1}$—(O)$_{n2}$—R$^{b1}$,
(3)

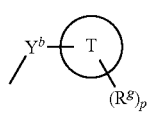
—Y$^c$—O—R$^{b2}$, (4) —CH═CH—C(═O)—R$^{b3}$,
(5) —NR$^{b4}$R$^{b5}$, or
(6)

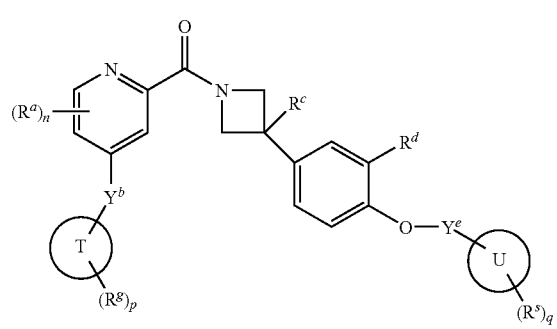

wherein each symbol and Group A are as defined in [1], or a pharmaceutically acceptable salt or solvate thereof.

[3] The compound of formula [II] according to [1] or [2]:

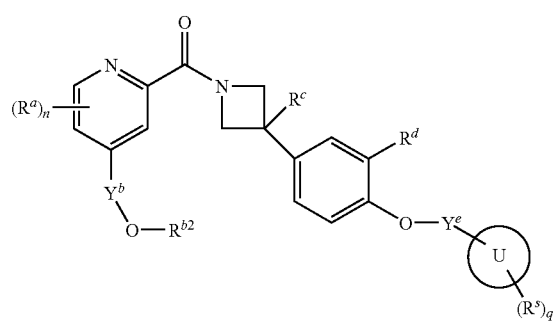
[II]

wherein each symbol is as defined in [1],
or a pharmaceutically acceptable salt or solvate thereof.

[4] The compound of formula [III] according to [1] or [2]:

[III]

wherein each symbol is as defined in [1],
or a pharmaceutically acceptable salt or solvate thereof.

[5] The compound of formula [II-C] according to [1] or [2]:

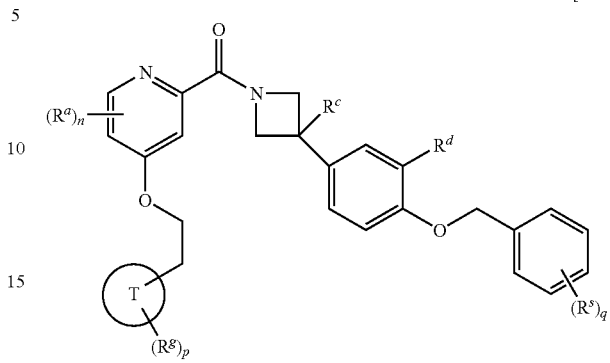
[II-C]

wherein each symbol is as defined in [1],
or a pharmaceutically acceptable salt or solvate thereof.

[6] The compound of formula [III-B] according to [1] or [2]:

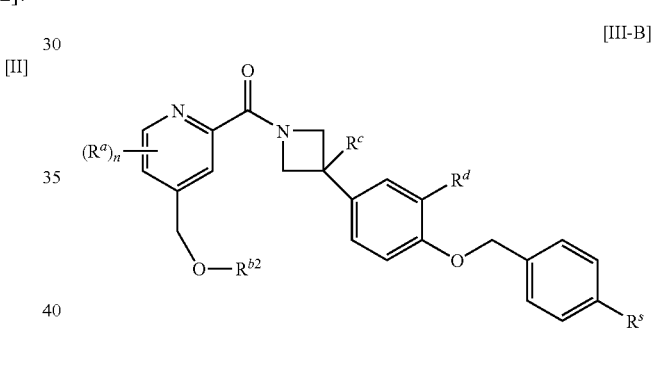
[III-B]

wherein each symbol is as defined in [1],
or a pharmaceutically acceptable salt or solvate thereof.

[7] The compound of formula [IV-A] according to [1] or [2]

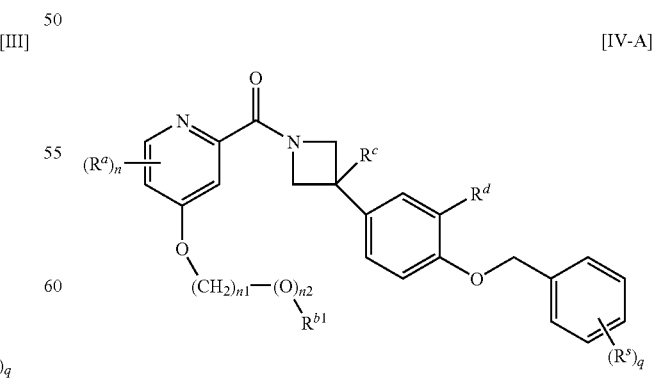
[IV-A]

wherein each symbol is as defined in [1]
or a pharmaceutically acceptable salt or solvate thereof.

[8] The compound according to [1] or [2] which is selected from the group consisting of the following formulas or a pharmaceutically acceptable salt or solvate thereof.
| Structure |
|---|
| 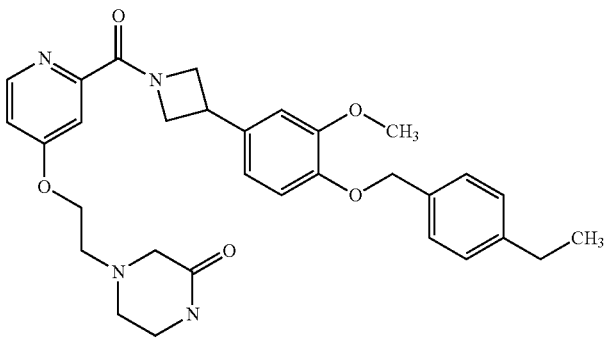 [SMILES: CCc1ccc(COc2ccc(C3CN(C(=O)c4cc(OCCN5CCNC(=O)C5)ccn4)C3)cc2OC)cc1] |
| 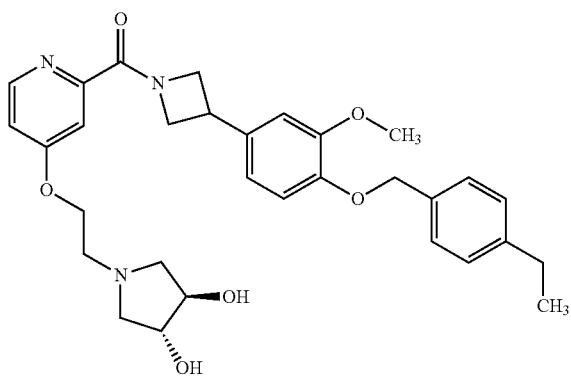 [SMILES: CCc1ccc(COc2ccc(C3CN(C(=O)c4cc(OCCN5C[C@@H](O)[C@H](O)C5)ccn4)C3)cc2OC)cc1] |
| 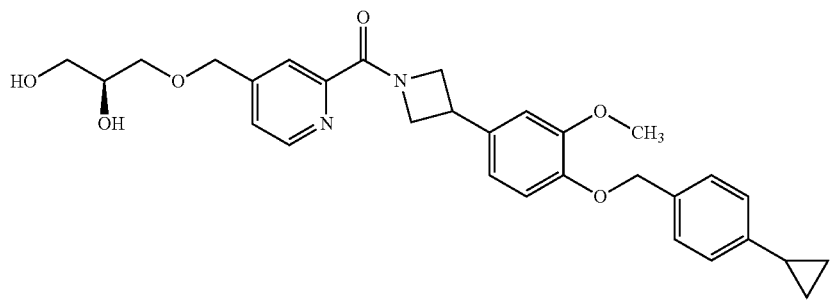 [SMILES: COc1cc(C2CN(C(=O)c3cc(COC[C@@H](O)CO)ccn3)C2)ccc1OCc1ccc(C2CC2)cc1] |
| 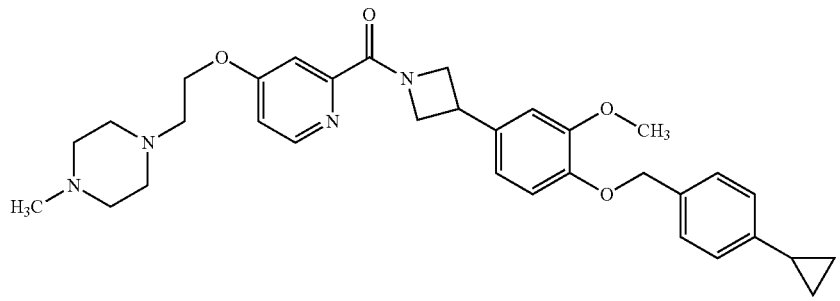 [SMILES: COc1cc(C2CN(C(=O)c3cc(OCCN4CCN(C)CC4)ccn3)C2)ccc1OCc1ccc(C2CC2)cc1] |

| Structure |
|---|
| 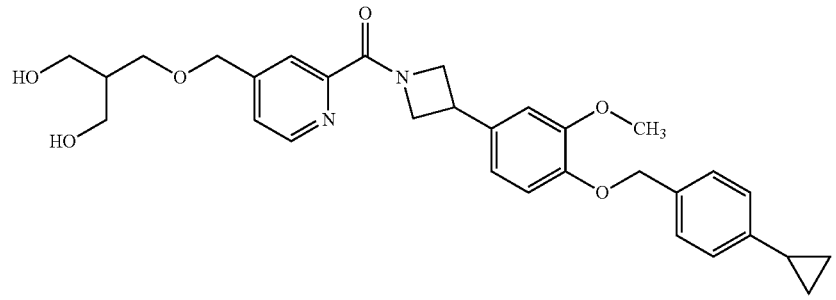 [SMILES: COc1cc(C2CN(C(=O)c3cc(COCC(CO)CO)ccn3)C2)ccc1OCc1ccc(C2CC2)cc1] |
| 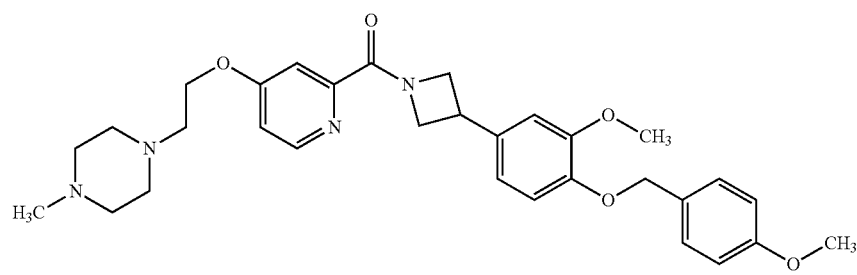 |
| 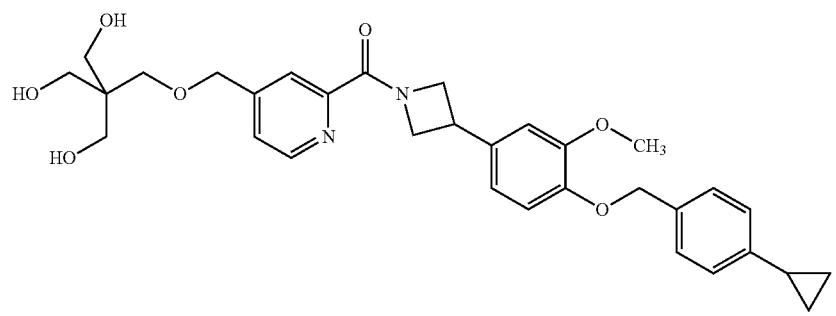 [SMILES: COc1cc(C2CN(C(=O)c3cc(COCC(CO)(CO)CO)ccn3)C2)ccc1OCc1ccc(C2CC2)cc1] |
| 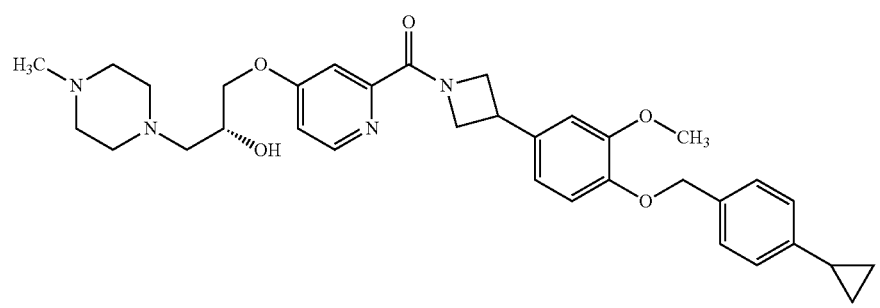 [SMILES: COc1cc(C2CN(C(=O)c3cc(OC[C@H](O)CN4CCN(C)CC4)ccn3)C2)ccc1OCc1ccc(C2CC2)cc1] |
| 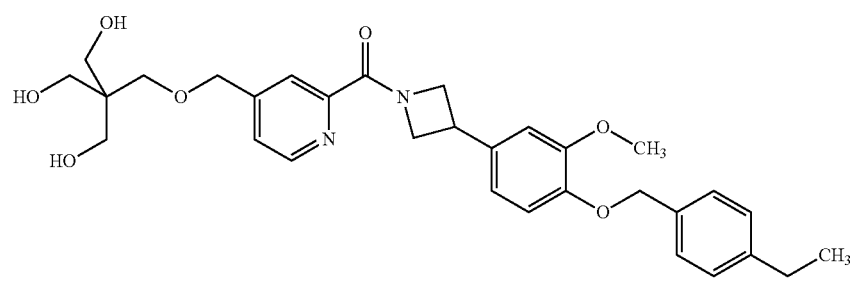 [SMILES: CCc1ccc(COc2ccc(C3CN(C(=O)c4cc(COCC(CO)(CO)CO)ccn4)C3)cc2OC)cc1] |

| Structure |
| --- |
| 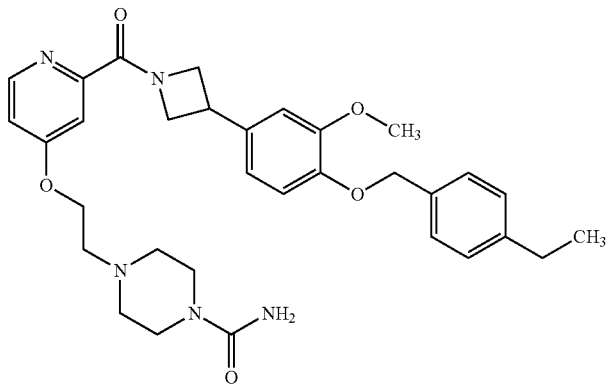 [SMILES: CCc1ccc(COc2ccc(C3CN(C(=O)c4cc(OCCN5CCN(C(N)=O)CC5)ccn4)C3)cc2OC)cc1] |
| 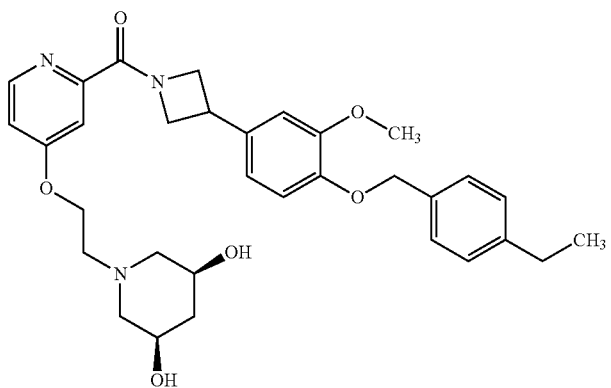 [SMILES: CCc1ccc(COc2ccc(C3CN(C(=O)c4cc(OCCN5C[C@H](O)C[C@H](O)C5)ccn4)C3)cc2OC)cc1] |
| 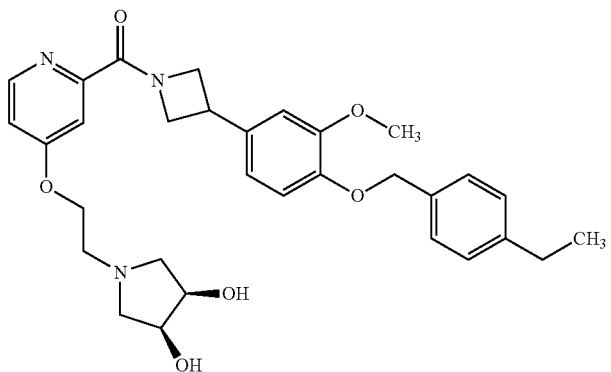 [SMILES: CCc1ccc(COc2ccc(C3CN(C(=O)c4cc(OCCN5C[C@@H](O)[C@@H](O)C5)ccn4)C3)cc2OC)cc1] |
| 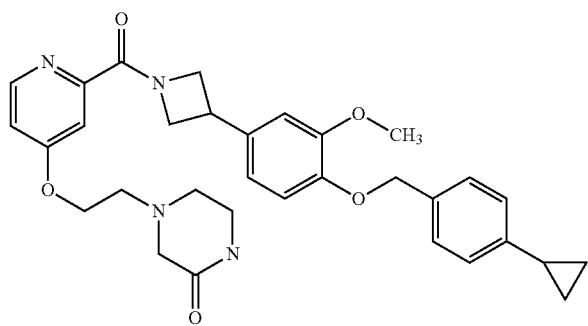 [SMILES: COc1cc(C2CN(C(=O)c3cc(OCCN4CCNC(=O)C4)ccn3)C2)ccc1OCc1ccc(C2CC2)cc1] |

-continued
| Structure |
| --- |
| 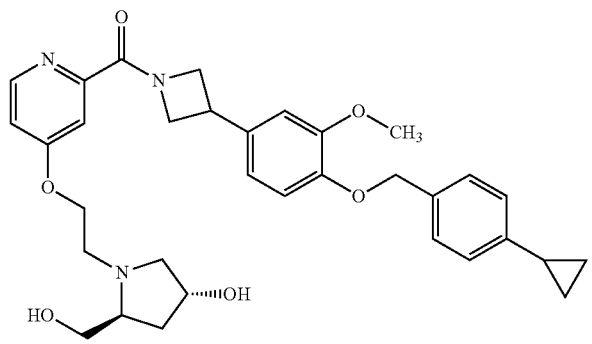 [SMILES: COc1cc(C2CN(C(=O)c3cc(OCCN4C[C@H](O)C[C@H]4CO)ccn3)C2)ccc1OCc1ccc(C2CC2)cc1] |
| 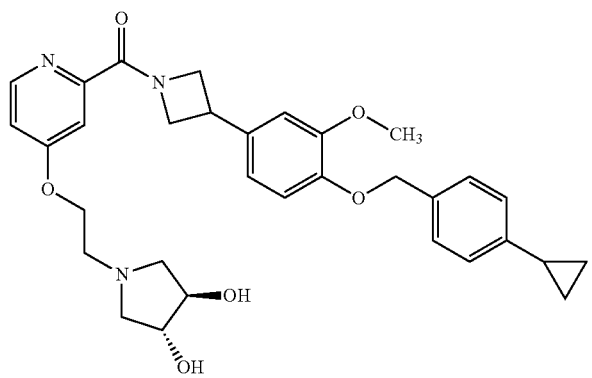 [SMILES: COc1cc(C2CN(C(=O)c3cc(OCCN4C[C@@H](O)[C@H](O)C4)ccn3)C2)ccc1OCc1ccc(C2CC2)cc1] |
| 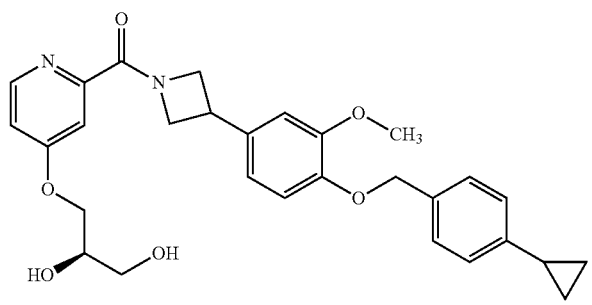 [SMILES: COc1cc(C2CN(C(=O)c3cc(OC[C@H](O)CO)ccn3)C2)ccc1OCc1ccc(C2CC2)cc1] |
| 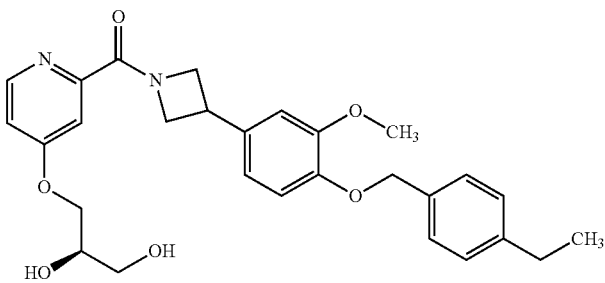 [SMILES: CCc1ccc(COc2ccc(C3CN(C(=O)c4cc(OC[C@H](O)CO)ccn4)C3)cc2OC)cc1] |
| 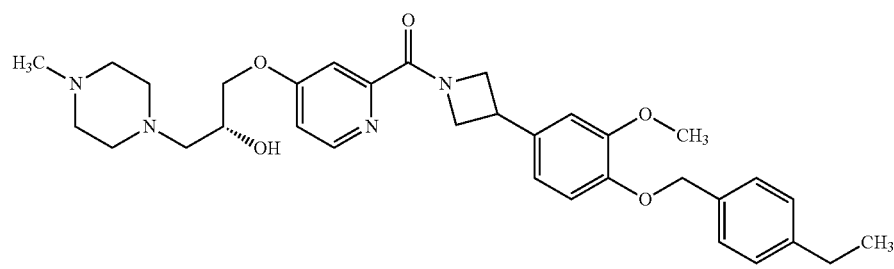 [SMILES: CCc1ccc(COc2ccc(C3CN(C(=O)c4cc(OC[C@H](O)CN5CCN(C)CC5)ccn4)C3)cc2OC)cc1] |

| Structure |
|---|
| 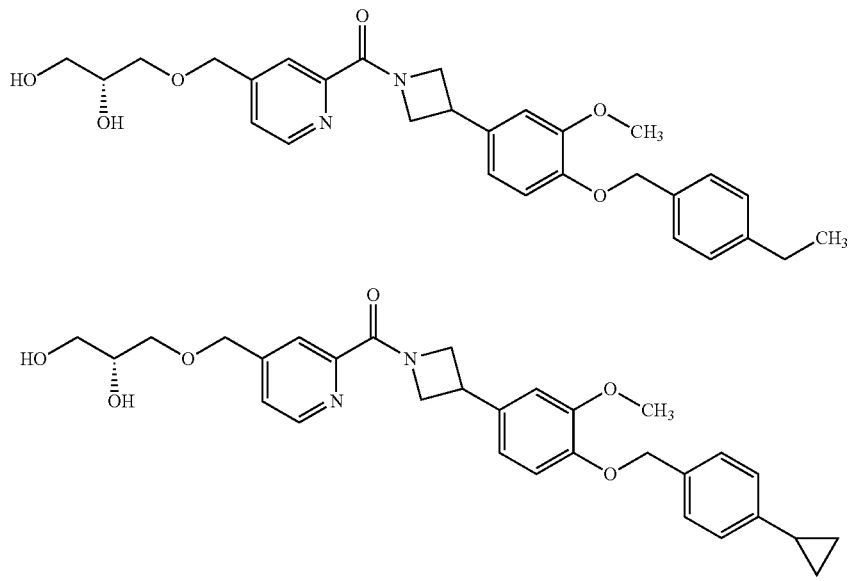 |

[9] A pharmaceutical composition comprising the compound according to any one of [1] to [8] or a pharmaceutically acceptable salt or solvate thereof, and a pharmaceutically acceptable carrier.

[10] An inhibitor of colony-stimulating factor 1 receptor comprising the compound according to any one of [1] to [8] or a pharmaceutically acceptable salt or solvate thereof.

[11] A medicament for treating or preventing autoimmune disease, inflammatory disease, osteoporosis, osteolysis or cancer, comprising the compound according to any one of [1] to [8] or a pharmaceutically acceptable salt or solvate thereof.

[12-1] The medicament according to [11] wherein the autoimmune disease is selected from rheumatoid arthritis, multiple sclerosis, or psoriasis.

[12-2] The medicament according to [12-1] wherein the autoimmune disease is rheumatoid arthritis.

[12-3] The medicament according to [12-2] wherein treating rheumatoid arthritis is done by preventing structural damage of joints.

[13] The medicament according to [11] wherein the inflammatory disease is selected from inflammatory bowel disease, glomerulonephritis, or diabetic nephritis.

[14] The medicament according to [11] wherein the cancer is selected from solid cancer such as prostatic cancer, breast cancer and the like or blood cancer such as myeloid dysplasia, myelocytic leukemia and the like.

The present invention further provides the following aspects.

[15] A medicament for treating or preventing rheumatoid arthritis, multiple sclerosis, osteoporosis, osteolysis, or cancer, comprising the compound according to any one of [1] to [8] or a pharmaceutically acceptable salt or solvate thereof.

[16] A method of inhibiting colony-stimulating factor 1 receptor in a mammal, comprising administering to said mammal a therapeutically effective amount of the compound according to any one of [1] to [8] or a pharmaceutically acceptable salt or solvate thereof.

[17-1] A method of treating or preventing autoimmune disease such as rheumatoid arthritis, multiple sclerosis and psoriasis; inflammatory disease such as inflammatory bowel disease, glomerulonephritis and diabetic nephritis; osteoporosis; osteolysis; or cancer such as solid cancer including prostatic cancer, breast cancer and the like and blood cancer including myeloid dysplasia, myelocytic leukemia and the like in a mammal, comprising administering to said mammal a therapeutically effective amount of the compound according to any one of [1] to [8] or a pharmaceutically acceptable salt or solvate thereof.

[17-2] The method according to [17-1] wherein the autoimmune disease is rheumatoid arthritis.

[17-3] The method according to [17-2] wherein treating rheumatoid arthritis is done by preventing structural damage of joints.

[18] Use of the compound according to any one of [1] to [8] or a pharmaceutically acceptable salt or solvate thereof in the manufacture of an inhibitor of colony-stimulating factor 1 receptor.

[19-1] Use of the compound according to any one of [1] to [8] or a pharmaceutically acceptable salt or solvate thereof in the manufacture of a medicament for treating or preventing autoimmune disease such as rheumatoid arthritis, multiple sclerosis and psoriasis; inflammatory disease such as inflammatory bowel disease, glomerulonephritis and diabetic nephritis; osteoporosis; osteolysis; or cancer such as solid cancer including prostatic cancer, breast cancer and the like and blood cancer including myeloid dysplasia, myelocytic leukemia and the like.

[19-2] The use according to [19-1] wherein the autoimmune disease is rheumatoid arthritis.

[19-3] The use according to [19-2] wherein treating rheumatoid arthritis is done by preventing structural damage of joints.

[20] A combination drug comprising:
(1) the compound according to any one of [1] to [8] or a pharmaceutically acceptable salt or solvate thereof, and
(2) one or more other agents selected from the group consisting of:

an agent for treating and/or preventing rheumatoid arthritis, an agent for treating and/or preventing osteoporosis, an agent for treating and/or preventing diabetic nephropathy and an agent for treating and/or preventing cancer.

[21] The combination drug according to [20] wherein the agent for treating and/or preventing rheumatoid arthritis is selected from the group consisting of leflunomide, methotrexate, sulfasalazine, hydroxychloroquine, tacrolimus and infliximab.

[22] A method of inhibiting colony-stimulating factor receptor in a mammal comprising administering to said mammal a therapeutically effective amount of the combination drug according to [20] or [21].

[23] A method of treating or preventing autoimmune disease, inflammatory disease, osteoporosis, osteolysis or cancer in a mammal, comprising administering to said mammal a therapeutically effective amount of the combination drug according to [20] or [21].

[24] Use of:

(1) the compound according to any one of [1] to [8] or a pharmaceutically acceptable salt or solvate thereof, and (2) one or more other agents selected from the group consisting of:

an agent for treating and/or preventing rheumatoid arthritis, an agent for treating and/or preventing osteoporosis, an agent for treating and/or preventing diabetic nephropathy, and an agent for treating and/or preventing cancer in the manufacture of an inhibitor of colony-stimulating factor 1 receptor.

[25] Use of:

(1) the compound according to any one of [1] to [8] or a pharmaceutically acceptable salt or solvate thereof, and (2) one or more other agents selected from the group consisting of:

an agent for treating and/or preventing rheumatoid arthritis, an agent for treating and/or preventing osteoporosis, an agent for treating and/or preventing diabetic nephropathy, and an agent for treating and/or preventing cancer in the manufacture of an agent for treating or preventing autoimmune disease, inflammatory disease, osteoporosis, osteolysis or cancer.

[26] A commercial package comprising the pharmaceutical composition of [9], and instructions which explain that the pharmaceutical composition can be used to treat and/or prevent a disease selected from autoimmune disease, inflammatory disease, osteoporosis, osteolysis or cancer.

[27] A commercial package comprising the combination drug of [20] and instructions of the combination drug which explain the combination drug can be used to treat and/or prevent a disease selected from rheumatoid arthritis, multiple sclerosis, osteoporosis, osteolysis, cancer, or diabetic nephropathy.

DEFINITIONS

The followings are definitions of terms that may be used in the specification.

The phrase "may be substituted" means to be independently substituted with suitable substituent(s) at any replaceable position(s) or not to be substituted (unsubstituted). The phrase "not substituted" herein means that all replaceable positions are occupied with hydrogen atoms.

For example, the phrase "$C_{1-6}$ alkyl group may be substituted with the same or different 1 to 5 substituents selected from Group A" includes both cases where $C_{1-6}$ alkyl group is substituted with the same or different 1 to 5 substituents selected from Group A at any one or more replaceable positions thereof and where $C_{1-6}$ alkyl group is not substituted.

The term "halogen atom" includes for example, fluorine atom, chlorine atom, bromine atom, iodine atom and the like.

The term "$C_{1-4}$ alkyl group" refers to a straight- or branched-chain saturated hydrocarbon group having 1 to 4 carbon atoms, and includes for example, methyl group, ethyl group, propyl group; isopropyl group, butyl group, isobutyl group, sec-butyl group, tert-butyl group and the like.

The term "$C_{1-6}$ alkyl group" refers to a straight- or branched-chain saturated hydrocarbon group having 1 to 6 carbon atoms, and includes for example, methyl group, ethyl group, propyl group, isopropyl group, butyl group, isobutyl group, sec-butyl group, tert-butyl group, pentyl group, isopentyl group, neopentyl group, 1-ethylpropyl group, hexyl group, isohexyl group, 1,1-dimethylbutyl group, 2,2-dimethylbutyl group, 3,3-dimethylbutyl group, 2-ethylbutyl group and the like. The preferred $C_{1-6}$ alkyl group includes methyl group, ethyl group, propyl group, isopropyl group, butyl group, isobutyl group, sec-butyl group, tert-butyl group, pentyl group, isopentyl group, neopentyl group, hexyl group, isohexyl group, 3,3-dimethylbutyl group and the like.

The term "$C_{1-12}$ alkyl group" refers to a straight- or branched-chain saturated hydrocarbon group having 1 to 12 carbon atoms and includes for example, methyl group, ethyl group, propyl group, isopropyl group, butyl group, isobutyl group, sec-butyl group, tert-butyl group, pentyl group, isopentyl group, neopentyl group, 1-ethylpropyl group, hexyl group, isohexyl group, 1,1-dimethylbutyl group, 2,2-dimethylbutyl group, 3,3-dimethylbutyl group, 2-ethylbutyl group and the like. The preferred $O_{1-12}$ alkyl group includes methyl group, ethyl group, propyl group, isopropyl group, butyl group, isobutyl group, sec-butyl group, tert-butyl group, pentyl group, isopentyl group, neopentyl group, hexyl group, isohexyl group, 3,3-dimethylbutyl group, 5-methyl-hexyl group, 4,4-dimethylpentyl group and the like.

The term "$C_{2-6}$ alkenyl group" refers to a straight- or branched-chain unsaturated hydrocarbon group having 2 to 6 carbon atoms and one or more double bonds, and includes for example, vinyl group, 1-methylvinyl group, 1-propenyl group, allyl group, methylpropenyl group (1-methyl-1-propenyl group, 2-methyl-1-propenyl group and the like), 1-butenyl group, 2-butenyl group, 3-butenyl group, methylbutenyl group (1-methyl-1-butenyl group, 2-methyl-1-butenyl group, 3-methyl-1-butenyl group and the like), pentenyl group, methylpentenyl group, hexenyl group and the like. The preferred $O_{2-6}$ alkenyl group includes vinyl group, 1-methylvinyl group, 1-propenyl group, methylpropenyl group and the like.

The term "$C_{2-6}$ alkynyl group" refers to a straight- or branched-chain unsaturated hydrocarbon group having 2 to 6 carbon atoms and one or more triple bonds and includes for example, ethynyl group, propynyl group (1-propynyl group, 2-propynyl group), butynyl group, pentynyl group, hexynyl group and the like. The preferred $C_{2-6}$ alkynyl group includes ethynyl group, 1-propynyl group and the like.

The term "$C_{1-6}$ alkylene" refers to a divalent group derived from "straight-chain $C_{1-6}$ alkyl" as defined above and includes for example, methylene, ethylene, trimethylene, tetramethylene, pentamethylene, hexamethylene and the like. The preferred $C_{1-6}$ alkylene includes methylene, ethylene, trimethylene and the like.

The term "$C_{2-6}$ alkenylene" refers to a divalent group derived from "$C_{2-6}$ alkenyl group" as defined above and includes for example, vinylene, propenylene, butenylene, pentenylene, hexenylene and the like. The preferred $C_{2-6}$ alkenylene includes vinylene and the like.

The term "$C_{6-10}$ aryl group" refers to an aromatic hydrocarbon group having 6 to 10 carbon atoms and includes for example, phenyl group, 1-naphthyl group, 2-naphthyl group and the like. The preferred $C_{6-10}$ aryl group includes phenyl group.

The term "$C_{3-10}$ cycloalkyl group" refers to a saturated monocyclic hydrocarbon group having 3 to 10 carbon atoms and includes for example, cyclopropyl group, cyclobutyl group, cyclopentyl group, cyclohexyl group, cycloheptyl group, cyclooctyl group and the like. In particular, $C_{3-6}$ cycloalkyl group such as cyclopropyl group, cyclobutyl group, cyclopentyl group, cyclohexyl group and the like is preferred.

The term "$C_{8-11}$ spirocyclic cycloalkyl or spirocyclic cycloalkenyl group" includes spiro[4,4]nonanyl group, spiro[4,4]non-1-enyl group, spiro[4,5]decanyl group, spiro[4,5]dec-6-enyl group, spiro[5,5]undecanyl group, spiro[5,5]undec-1-enyl group and the like.

The term "monocyclic heteroaromatic group" refers to 3 to 7-membered monocyclic heteroaromatic group which contains 1 to 4 hetero atoms independently-selected from nitrogen atom, oxygen atom or sulfur atom in addition to carbon atoms and includes for example, furyl group, thienyl group, pyrrolyl group, oxazolyl group, isooxazolyl group, thiazolyl group, isothiazolyl group, imidazolyl group, pyrazolyl group, oxadiazolyl group (such as 1,2,5-oxadiazolyl group, 1,3,4-oxadiazolyl group and 1,2,4-oxadiazolyl group), thiadiazolyl group (such as 1,2,5-thiadiazolyl group, 1,3,4-thiadiazolyl group and 1,2,4-thiadiazolyl group), triazolyl group (such as 1,2,3-triazolyl group and 1,2,4-triazolyl group), tetrazolyl group, pyridyl group, pyrimidinyl group, pyridazinyl group, pyrazinyl group, triazinyl group and the like. The preferred monocyclic heteroaromatic group includes thienyl group, oxazolyl group, thiazolyl group, imidazolyl group, pyrazolyl group, oxadiazolyl group (such as 1,3,4-oxadiazolyl group and 1,2,4-oxadiazolyl group), triazolyl group (such as 1,2,4-triazolyl group), tetrazolyl group, pyridyl group, pyrimidinyl group and the like.

The term "nonaromatic monocyclic heterocyclic group" refers to 3 to 7-membered saturated or partially-unsaturated monocyclic heterocyclic group which contains 1 to 4 hetero atoms independently-selected from nitrogen atom, oxygen atom or sulfur atom in addition to carbon atoms and includes for example, oxiranyl group, thiolanyl group, aziridinyl group, azetidinyl group, oxetanyl group, pyrrolidinyl group, pyrrolidino group (1-pyrrolidinyl group), tetrahydrofuranyl group, tetrahydrothienyl group, oxazolinyl group, oxazolidinyl group, isooxazolinyl group, isooxazolidinyl group, thiazolinyl group, thiazolidinyl group, isothiazolinyl group, isothiazolidinyl group, imidazolinyl group, imidazolidinyl group, pyrazolinyl group, pyrazolidinyl group, piperidinyl group, piperidino group (1-piperidinyl group), morpholinyl group, morpholino group (4-morpholinyl group), thiomorpholinyl group, thiomorpholino group (4-thiomorpholinyl group), piperazinyl group, piperazino group (1-piperazinyl group), tetrahydro-1,3-oxazinyl group, homomorpholine, homopiperazine and the like.

The group may have 1 to 2 oxo groups. Besides when the group contains a sulfur atom as said hetero atom, the sulfur atom may be mono or dioxided. Moreover, when the group contains nitrogen atom as hetero atom, the nitrogen atom may be a N-oxide derivative thereof and may be quaternized.

In particular, the preferred nonaromatic monocyclic heterocyclic group includes aziridinyl group, azetidinyl group, pyrrolidinyl group, 2-oxopyrrolidinyl group, 2-oxopyrrolidino group, oxazolidinyl group, 2-oxooxazolidinyl group, isothiazolidinyl group, 1,1-dioxoisothiazolidinyl group, imidazolidinyl group, 2-oxoimidazolidinyl group, 2-oxopiperidinyl group, 2-oxopiperidino group, morpholinyl group, morpholino group, 2-oxomorpholino group, piperazinyl group, piperazino group, 2-oxopiperazino group, 3-oxopiperazino group, hexahydro-2-oxo-1,3-oxazinyl group and the like.

The term "fused heterocyclic group" refers to 8 to 10-membered fused ring which contains 1 to 4 hetero atoms independently-selected from nitrogen atom, oxygen atom or sulfur atom in addition to carbon atoms and includes for example, quinolyl, 1,2-dihydroquinolyl, 1,2,3,4-tetrahydroquinolyl, benzofuranyl, 2,3-dihydrobenzofuranyl, 4,5,6,7-tetrahydrobenzofuranyl, benzothienyl, 2,3-dihydrobenzothienyl, 4,5,6,7-tetrahydrobenzothienyl, benzo[1,3]dioxolyl and the like.

The preferred examples of each substituent in the compounds represented by formula [I] (hereinafter called compound [I]) are explained as follows.

$R^a$ is
(1) $C_{1-6}$ alkyl group, or
(2) halogen atom.

The preferred example of $R^a$ includes
(1) methyl group,
(2) fluorine atom, chlorine atom
and the like.

n is an integer selected from 0, or 1 to 3.

The preferred n is an integer selected from 0, 1 or 2 and the like.

The preferred example of $R^b$ is a group selected from the following (1) to (8):
(1) hydrogen atom,
(2) fluorine atom or chlorine atom,
(3) $C_{1-6}$ alkyl group, preferably methyl group, ethyl group, propyl group, isopropyl group, tert-butyl group, n-butyl group, n-pentyl group, isohexyl group which may be substituted with 1 to 5 substituents selected from the following groups:
 (a) halogen atom, preferably fluorine atom,
 (b) hydroxyl group,
 (c) —N($C_{1-6}$ alkyl)$_2$ wherein the alkyl may be substituted with hydroxyl group, preferably dimethylamino group, N-methyl-N-(hydroxyethyl)amino group,
(4) —O—(CH$_2$)$_{n1}$—(O)$_{n2}$—R$^{b1}$ wherein
n1 is 0, 1 or 2,
n2 is 0 or 1, and
R$^{b1}$ is hydrogen atom or $C_{1-6}$ alkyl group which may be substituted with 1 to 5 substituents selected from the following groups:
 (a) halogen atom,
 (b) —OR$^{41}$ wherein R$^{41}$ is hydrogen atom or $C_{1-6}$ alkyl group, preferably hydroxyl group, methyloxy group,
 (c) —NR$^{42}$R$^{43}$ wherein the R$^{42}$ and R$^{43}$ are independently selected from hydrogen atom or $C_{1-6}$ alkyl group which may be substituted with hydroxyl group, —COOH or —COO—$C_{1-6}$ alkyl, preferably N-methyl-N-(hydroxycarbonylmethyl)amino group, di(2-hydroxyethyl)amino group,
 (d) —C(=O)—OR$^{45}$ wherein R$^{45}$ is hydrogen atom or $C_{1-6}$ alkyl group, preferably carboxyl group, methyloxycarbonyl group, ethyloxycarbonyl group,
 (e) —C(=O)—NR$^{46}$R$^{47}$ wherein R$^{46}$ and R$^{47}$ are independently selected from hydrogen atom or $C_{1-6}$ alkyl group which may be substituted with hydroxyl group or —NR$^{48}$R$^{49}$ wherein $R^{A8}$ and $R^{A9}$ are independently selected from hydrogen atom or $C_{1-6}$ alkyl group, preferably 2-(dimethylamino)ethylaminocarbonyl group, dimethylaminocarbonyl group, methylaminocarbonyl group, (5)

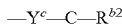

wherein
$Y^c$ is $C_{1-6}$ alkylene which may be substituted with $C_{1-4}$ alkyl group, preferably methylmethylene or methylene,
$R^{b2}$ is $C_{1-6}$ alkyl group which is substituted with the same or different 1 to 5 substituents selected from the following groups:
(a) halogen atom,
(b) hydroxyl group or $C_{1-6}$ alkyloxy group, preferably hydroxyl group or methyloxy group),
(6) —CH=CH—CO—$R^{b3}$ wherein $R^{b3}$ is $C_{1-6}$ alkyl group which may be substituted with 1 to 5 substituents selected from hydroxyl group or $C_{1-6}$ alkyloxycarbonyl group, preferably $R^{b3}$ is 2-hydroxy-3-methyloxycarbonylpropyl group,
(7) —$NR^{b4}R^{b5}$ wherein $R^{b4}$ and $R^{b5}$ are independently selected from hydrogen atom or $C_{1-6}$ alkyl group, preferably amino group,
(8)

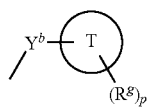

wherein
$Y^b$ is a group selected from the following (i) to (v):
(i) single bond,
(ii) $C_{1-6}$ alkylene which may be substituted with $C_{1-4}$ alkyl group, preferably methylene, methylmethylene, propylene,
(iii)

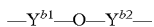

wherein $Y^{b1}$ is single bond or methylene, and $Y^{b2}$ is ethylene or propylene which is substituted with hydroxyl group,
(iv) —O—$(CH_2)_{n4}$—C(=O)— (n4 is 1, 2 or 3),
(v) —O—$(CH_2)_{n5}$—O—C(=O)— (n5 is 2),
cyclic moiety T is nonaromatic monocyclic heterocyclic group selected from morpholinyl, piperidinyl, piperazinyl, 3-oxopiperazinyl, pyrrolidinyl, homomorpholine, homopiperazine, or azetidinyl,
$R^g$ is a group independently-selected from the following (i) to (vi)
(i) halogen atom, preferably fluorine atom,
(ii) $C_{1-6}$ alkyl group which may be substituted with hydroxyl group or carboxyl group, preferably methyl group,
(iii) —C(=O)—$OR^{g2}$ wherein $R^{g2}$ is hydrogen atom or methyl group,
(iv) —C(=O)—$R^{g3}$ wherein $R^{g3}$ is methyl group which is substituted with hydroxyl group,
(v) —$OR^{g6}$ wherein $R^{g6}$ is hydrogen atom or methyl group,
(vi) —$SO_2$—$R^{g7}$ wherein $R^{g7}$ is methyl group,
p is 0, 1 or 2.
$R^c$ is hydrogen atom or hydroxyl group, preferably hydrogen atom.
$R^d$ is
(1) —$OR^{d1}$ wherein $R^{d1}$ is hydrogen atom or $C_{1-6}$ alkyl group, preferably methyl group or ethyl group, which may be substituted with 1 to 3 substituents selected from halogen atoms,
(2) halogen atom, preferably chlorine atom,
(3) —C(=O)—$OR^{d2}$ wherein $R^{d2}$ is methyl group, or (4) $C_{1-6}$ alkyl group which may be substituted with 1 to 5 halogen atoms, preferably ethyl group or trifluoromethyl group,
more preferably $R^d$ is methyloxy group.
m is 0 or 1.
$R^e$ is
$C_{1-12}$ alkyl group, preferably 5-methylhexyl group, or

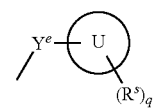

wherein
$Y^e$ is methylene;
cyclic moiety U is
(i) $C_{6-10}$ aryl group, preferably phenyl group,
(ii) $C_{3-10}$ cycloalkyl group, preferably cyclohexyl group,
(iii) $C_{8-11}$ spirocyclic cycloalkyl or spirocyclic cycloalkenyl group, preferably spiro[4.4]non-1-enyl group,
(iv) monocyclic heteroaromatic group selected from pyridyl or thienyl, or
(v) fused heterocyclic group which is benzo[1,3]dioxolyl and the like;
$R^s$ is a group independently-selected from the following (i) to (vi):
(i) $C_{1-6}$ alkyl group which may be substituted with 1 to 5 halogen atoms, preferably ethyl group or trifluoromethyl group,
(ii) $C_{3-6}$ cycloalkyl group, preferably cyclopropyl group,
(iii) —O—$R^{s1}$ wherein $R^{s1}$ is $C_{1-6}$ alkyl group which may be substituted with 1 to 5 halogen atoms, preferably trifluoromethyl group or methyl group,
(iv) halogen atom, preferably fluorine atom, chlorine atom,
(v) —C(=O)—$OR^{s2}$ wherein $R^{s2}$ is alkyl group, preferably methyl group,
(vi) —$SR^{s3}$ wherein $R^{s3}$ is $C_{1-6}$ alkyl group, preferably methyl group;
q is 0, 1 or 2, preferably 1.
The preferred aspect of compounds of formula [I] includes compounds of the following formulae:

[II]

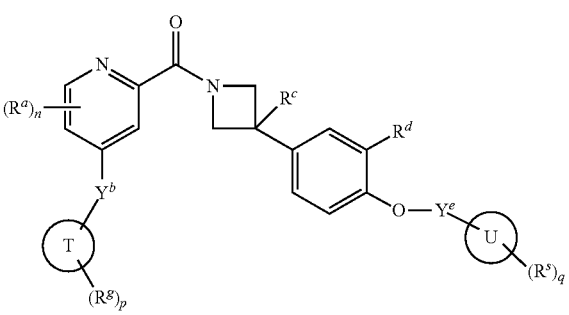

[III]

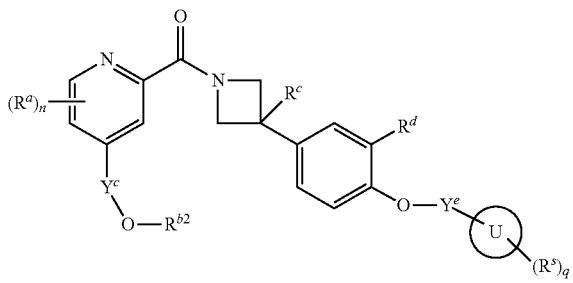

wherein each symbol is as defined in formula [I].

The preferred compound of formula [II] includes compounds of the following formulae [II-A], [II-B], [II-C], [II-D], [II-E] and [II-F]:

[II-A]

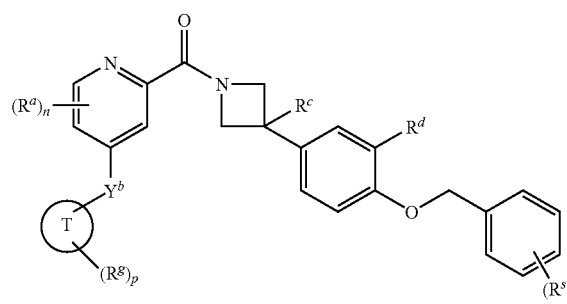

[II-B]

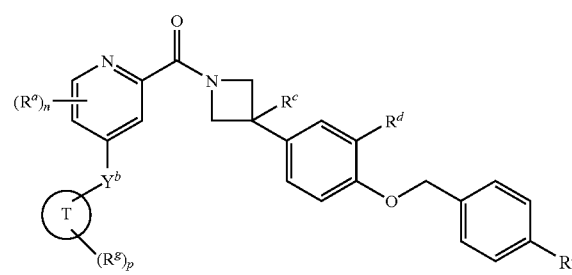

[II-C]

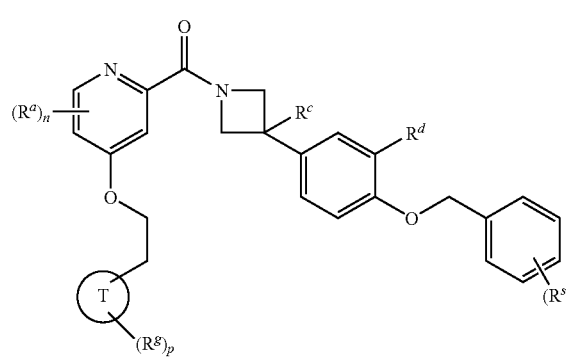

[II-D]

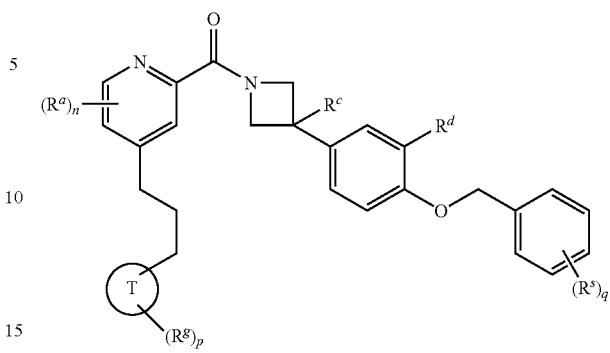

wherein each symbol is as defined in formula [I].
One preferred compound wherein n is 0 (zero) includes the following compound:

[II-E]

[II-F]

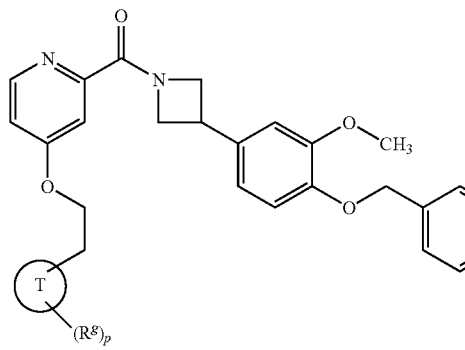

wherein each symbol is as defined in formula [I].

The preferable compounds of the above formulae [II-A], [II-B], [II-C], [II-D], [II-E] and [II-F] include a compound wherein $R^a$ is $C_{1-6}$ alkyl group (preferably methyl group), or halogen atom (preferably fluorine atom or chlorine atom), n is 0 or 1;

$Y^b$ is
(i) single bond,
(ii) $C_{1-6}$ alkylene which may be substituted with $C_{1-4}$ alkyl group, preferably methylene, methylmethylene or propylene,
(iii)

—$Y^{b1}$—O—$Y^{b2}$— wherein $Y^{b1}$ is single bond or methylene, $Y^{b2}$ is ethylene or propylene which is substituted with hydroxyl, (iv) —O—$(CH_2)_{n4}$—C(=O)— (n4 is 1, 2 or 3), (v) —O—$(CH_2)_{n5}$—O—C(=O)— (n5 is 2);

cyclic moiety T is nonaromatic monocyclic heterocyclic group selected from morpholinyl, piperidinyl, piperazinyl, 3-oxopiperazinyl, pyrrolidinyl or azetidinyl;

$R^g$ is (i) halogen atom, preferably fluorine atom, (ii) $C_{1-6}$ alkyl group which may be substituted with hydroxyl group or carboxyl group, preferably methyl group, (iii) —C(=O)—$R^{g1}$ wherein $R^{g1}$ is hydrogen atom or methyl group, (iv) —C(=O)—$OR^{g3}$ wherein $R^{g3}$ is methyl group which is substituted with hydroxyl group, (v) —$OR^{g6}$ wherein $R^{g6}$ is hydrogen atom or methyl group, or (vi) —$SO_2$—$R^{g7}$ wherein $R^{g7}$ is methyl group;

p is 0, 1 or 2;

$R^c$ is hydrogen atom;

$R^d$ is —$OR^{d1}$ wherein $R^{d1}$ is hydrogen atom or $C_{1-6}$ alkyl group which may be substituted with 1 to 3 substituents selected from halogen atoms, preferably methyl group, ethyl group, more preferably $R^d$ is methyloxy group;

$R^s$ is (i) $C_{1-6}$ alkyl group which may be substituted with 1 to 5 halogen atoms, preferably ethyl group, trifluoromethyl group, (ii) $C_{3-6}$ cycloalkyl group, preferably cyclopropyl group, (iii) —O—$R^{s1}$ wherein $R^{s1}$ is $C_{1-6}$ alkyl group which may be substituted with 1 to 5 halogen atoms, preferably methyl group or trifluoromethyl group, (iv) halogen atom, preferably fluorine atom or chlorine atom;

q is 0, 1 or 2.

Besides, the preferred compound of formula [III] includes compounds of formulae [III-A], [III-B] and [III-C]:

[III-A]

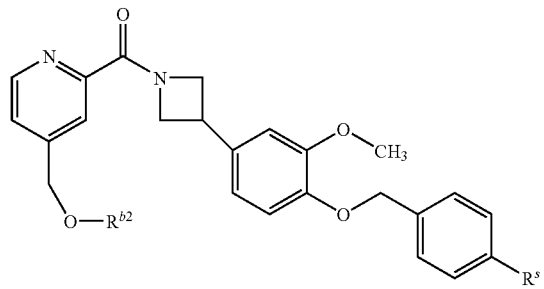

[III-B]

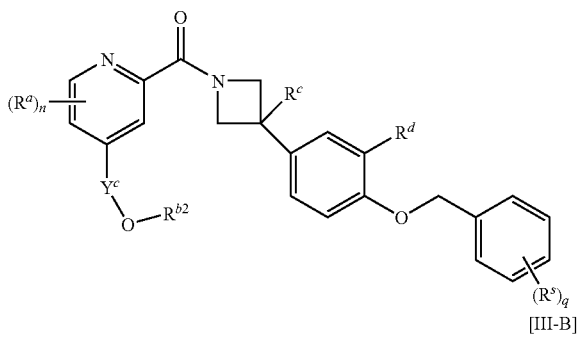

wherein each symbol is as defined in formula [I].

One preferred compound wherein n is 0 (zero) includes the following compound.

[III-C]

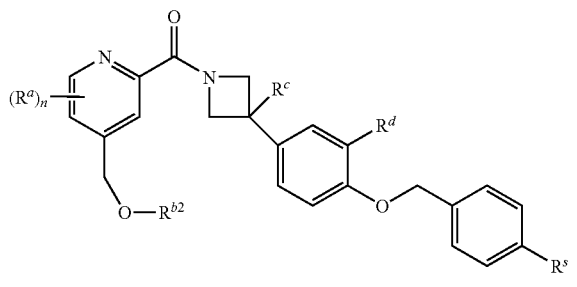

wherein each symbol is as defined in formula [I].

The preferable compounds of the above formulae [III-A], [III-B] and [III-C] include a compound wherein $R^a$ is $C_{1-6}$ alkyl group preferably methyl group, or halogen atom preferably fluorine atom or chlorine atom, is 0 or 1;

$R^c$ is hydrogen atom;

$R^d$ is —$OR^{d1}$ wherein $R^{d1}$ is hydrogen atom or $C_{1-6}$ alkyl group which may be substituted with 1 to 3 substituents selected from halogen atoms, preferably methyl group, ethyl group, more preferably $R^d$ is methyloxy group;

$R^s$ is (i) $C_{1-6}$ alkyl group which may be substituted with 1 to 5 halogen atoms, preferably ethyl group, trifluoromethyl group, (ii) $C_{3-6}$ cycloalkyl group, preferably cyclopropyl group, (iii) —O—$R^{s1}$ wherein $R^{s1}$ is $C_{1-6}$ alkyl group which may be substituted with 1 to 5 halogen atoms, preferably methyl group, or trifluoromethyl group, (iv) halogen atom, preferably fluorine atom or chlorine atom;

q is 0 or 1;

$Y^c$ is methylene or ethylene;

$R^{b2}$ is $C_{1-6}$ alkyl group which is substituted with 1 to 5 substituents selected from the following groups:

(a) halogen atom, (b) hydroxyl group or $C_{1-6}$ alkyloxy group, preferably hydroxyl group or methyloxy group.

The preferred compound of formula [I] includes the following compounds:

[IV]

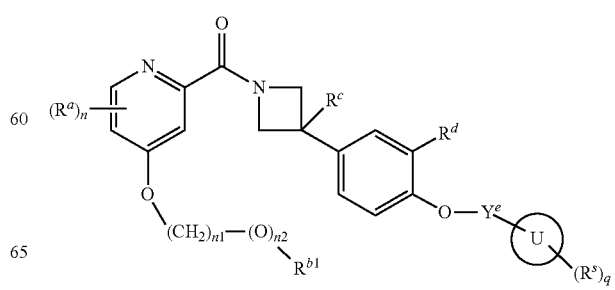

-continued

[IV-A]

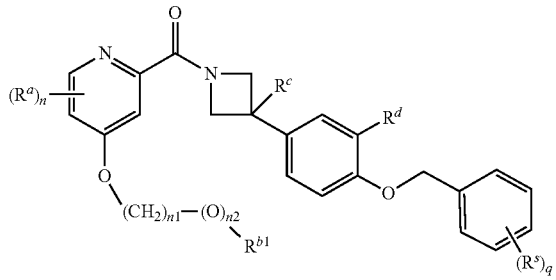

wherein each symbol is as defined in formula [I].

One preferred compound wherein n is 0 (zero) includes the following compound.

[IV-B]

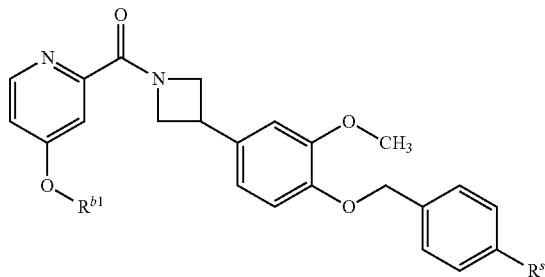

wherein each symbol is as defined in formula [I].

The preferable compounds of the above formulae [IV], [IV-A] and [IV-B] include a compound
wherein
$R^a$ is $C_{1-6}$ alkyl group (preferably methyl group), or halogen atom (preferably fluorine atom or chlorine atom), n is 0 or 1;
$R^c$ is hydrogen atom;
$R^d$ is —$OR^{d1}$ wherein $R^{d1}$ is hydrogen atom or $C_{1-6}$ alkyl group which may be substituted with 1 to 3 substituents selected from halogen atoms, preferably methyl group, ethyl group, more preferably $R^d$ is methyloxy group;
$R^5$ is
(i) $C_{1-6}$ alkyl group which may be substituted with 1 to 5 halogen atoms, preferably ethyl group, trifluoromethyl group,
(ii) $C_{3-6}$ cycloalkyl group, preferably cyclopropyl group,
(iii) —O—$R^{s1}$ wherein $R^{s1}$ is $C_{1-6}$ alkyl group which may be substituted with 1 to 5 halogen atoms, preferably trifluoromethyl group, methyl group,
(iv) halogen atom, preferably fluorine atom or chlorine atom;
q is 0 or 1;
$R^{b1}$ is $C_{1-6}$ alkyl group which may be substituted with the same or different 1 to 5 substituents selected from hydroxyl group, or carboxyl group;
n1 is 0;
n2 is 0.

In the compounds of the present invention, when a chain bonded to a substituent is shown as crossing a bond connecting two atoms in a ring such as pyridine ring, benzene ring, T ring, U ring, such substituent may be bonded to any atom which is a constituent of the rings and is capable of being bonded.

For example, the following aspects are included, which are not to be construed as limitative:

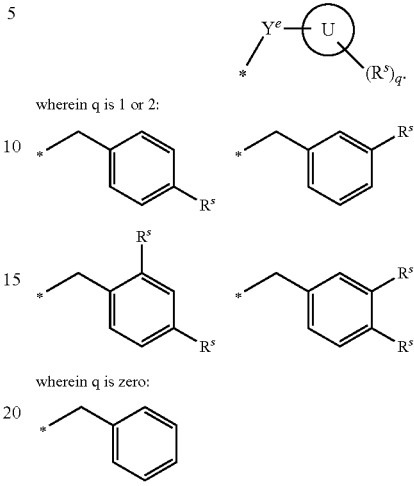

wherein q is 1 or 2:

wherein q is zero:

Pharmaceutically acceptable salts of compounds of formula [I] (hereinafter called "the present invention compound") may be any nontoxic salt of the present invention compound, for example, include salts formed with inorganic acid, organic acid, inorganic base, organic base, amino acid and the like.

The inorganic acid salts include for example, salts formed with hydrochloric acid, nitric acid, sulfuric acid, phosphoric acid, hydrobromic acid and the like.

The organic acid salts include for example, salts formed with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

The salts formed with inorganic base include for example, sodium salt, potassium salt, calcium salt, magnesium salt, ammonium salt and the like.

The salts formed with organic base include for example salts formed with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzyl ethylenediamine, guanidine, pyridine, picoline, choline, cinchonine, meglumine and the like.

The salts formed with amino acid include for example, salts formed with lysine, arginine, aspartic acid, glutamic acid and the like.

Such salts can be formed by reacting compounds of formula [I] with inorganic base, organic base, inorganic acid, organic acid, or amino acid according to conventional methods.

The term "solvate" refers to the compounds of formula [I] or pharmaceutically acceptable salts thereof which coordinate to the solvent molecules, and also includes hydrates. Such solvates are preferably pharmaceutically acceptable solvates. Such solvate includes for example hydrate, ethanol solvate, dimethylsulfoxide-solvate and the like of compounds of formula [I] or pharmaceutically acceptable salts thereof. The specific example includes hemihydrate, monohydrate, dihydrate or mono(ethanol)solvate of compounds of formula [I] or monohydrate of sodium salt of compounds of formula

[I], 2/3(ethanol)solvate of dihydrochloride of the same and the like. Such solvates can be produced according to conventional methods.

In addition, the compounds of formula [I] may have a variety of "isomer". For example, the compounds of formula [I] can exist in E or Z forms as geometric isomers. Moreover, the compounds of formula [I] which have asymmetric carbon atoms include enantiomers and diastereomers as stereoisomers according to said asymmetric carbon atoms. Besides, the compounds of formula [I] which have axial chirality include stereoisomers according to said axial chirality. In some cases, tautomer may be included. Therefore, the present invention includes all of these isomers and mixtures thereof.

In addition, the compound of formula [I] may be labeled with one or more isotopes such as $^3H$, $^{14}C$, $^{35}S$ and the like. Besides, the compound of formula [I] also includes an isotopic compound thereof wherein one or more $^1H$ are replaced with $^2H(D)$.

The compounds of formula [I] or pharmaceutically acceptable salts or solvates thereof are preferably purified to be substantively pure, more preferably 80% or more pure.

According to the present invention, prodrugs of compounds of formula [I] may also be a useful medicine. The "prodrug" as used herein refers to derivatives of the present invention compound having a chemically or metabolically decomposable group, which show the inherent pharmaceutical activity upon hydrolysis, solvolysis, or other decompositions under physiological conditions in vivo, and may also be a complex connected with bonds other than covalent bonds or a salt. Prodrugs can be used for example, for improving absorption of oral administration or targeting the object site. A modified site includes highly reactive functional groups in the present invention compounds, such as hydroxyl group, carboxyl group, amino group, thiol group and the like.

The group that modifies the hydroxyl group includes specifically acetyl group, propionyl group, isobutyryl group, pivaloyl group, palmitoyl group, benzoyl group, 4-methylbenzoyl group, dimethylcarbamoyl group, dimethylaminomethylcarbonyl group, sulfo group, alanyl group, fumary group and the like. In addition, 3-(sodium carboxylate)benzoyl group, 2-(sodium carboxylate)ethylcarbonyl group and the like are also included.

The group that modifies the carboxyl group includes specifically methyl group, ethyl group, propyl group, isopropyl group, butyl group, isobutyl group, tert-butyl group, pivaloyloxymethyl group, carboxymethyl group, dimethylaminomethyl group, 1-(acetyloxy)ethyl group, 1-(ethyloxycarbonyloxy)ethyl group, 1-(isopropyloxycarbonyloxy)ethyl group, 1-(cyclohexyloxycarbonyloxy)ethyl group, (5-methyl-2-oxo-1,3-dioxol-4-yl)methyl group, benzyl group, phenyl group, o-tolyl group, morpholinoethyl group, N,N-diethylcarbamoylmethyl group, phthalidyl group and the like.

The group that modifies the amino group includes specifically tert-butyl group, docosanoyl group, pivaloylmethyloxy group, alanyl group, hexylcarbamoyl group, pentylcarbamoyl group, 3-methylthio-1-(acetylamino)propylcarbonyl group, 1-sulfo-1-(3-ethyloxy-4-hydroxyphenyl)methyl group, (5-methyl-2-oxo-1,3-dioxol-4-yl)methyl group, (5-methyl-2-oxo-1,3-dioxol-4-yl)methyloxycarbonyl group, tetrahydrofuranyl group, pyrrolidylmethyl group and the like.

The term "pharmaceutical composition" includes a mixture comprising one or more active ingredients and one or more pharmaceutically acceptable carriers, for example, preparations such as oral preparations such as tablet, capsule, granule, powder, troche, syrup, emulsion suspension and the like or parenteral preparations such as external preparation, suppository, injection, eye drop, a preparation for transnasal administration and a preparation for lung administration and the like.

Pharmaceutical compositions of the present invention can be prepared for example, by mixing suitably the compounds of formula [I] or pharmaceutically acceptable salts or solvates thereof with at least one pharmaceutically acceptable carrier and the like according to conventional methods in the art of medicinal preparations. Content rate of the compounds of formula [I] or pharmaceutically acceptable salts or solvates thereof in the pharmaceutical composition includes for example, 0.1 to 100%, preferably 0.1 to 70% by weight in the composition while it varies depending on dosage forms, dosage amounts and the like.

The term "pharmaceutically acceptable carriers" includes all sorts of organic or inorganic carriers which are commonly-used as a material for drug formulations, such as excipient, disintegrant, binder, fluidizer, lubricant and the like for solid preparations and solvent, solubilizing agent, suspending agent, tonicity agent, buffering agent, soothing agent and the like for liquid preparations. Such preparations may employ further additives such as preservative, antioxidant, colorant, sweetening agent and the like as necessary.

The term "excipient" includes for example, lactose, white soft sugar, D-mannitol, D-sorbitol, cornstarch, dextrin, microcrystalline cellulose, crystalline cellulose, carmellose, carmellose calcium, sodium carboxymethylstarch, low substituted hydroxypropylcellulose, gum arabic and the like.

The term "disintegrant" includes for example, carmellose, carmellose calcium, carmellose sodium, sodium carboxymethylstarch, croscarmellose sodium, crospovidone, low substituted hydroxypropylcellulose, hydroxypropylmethylcellulose, crystalline cellulose and the like.

The term "binder" includes for example, hydroxypropylcellulose, hydroxypropylmethylcellulose, povidone, crystalline cellulose, white soft sugar, dextrin, starch, gelatin, carmellose sodium, gum arabic and the like.

The term "fluidizer" includes for example, light anhydrous silicic acid, magnesium stearate and the like.

The term "lubricant" includes for example, magnesium stearate, calcium stearate, talc and the like.

The term "solvent" includes for example, purified water, ethanol, propyleneglycol, macrogol, sesame oil, corn oil, olive oil and the like.

The term "solubilizing agent" includes for example, propyleneglycol, D-mannitol, benzyl benzoate, ethanol, triethanolamine, sodium carbonate, sodium citrate and the like.

The term "suspending agent" includes for example, benzalkonium chloride, carmellose, hydroxypropylcellulose, propyleneglycol, povidone, methylcellulose, glyceryl monostearate and the like.

The term "tonicity agent" includes for example, glucose, D-sorbitol, sodium chloride, D-mannitol and the like.

The term "buffering agent" includes for example, disodium hydrogen phosphate, sodium acetate, sodium carbonate, sodium citrate and the like.

The term "soothing agent" includes for example, benzyl alcohol and the like.

The term "preservative" includes for example, methyl parahydroxybenzoate, ethyl parahydroxybenzoate, propyl parahydroxybenzoate, chlorobutanol, benzyl alcohol, sodium dehydroacetate, sorbic acid and the like.

The term "antioxidant" includes for example, sodium sulfite, ascorbic acid and the like.

The term "colorant" includes for example, food dye such as Food Red No. 2 and No. 3, Food Yellow No. 4 and No. 5 and the like, β-carotene and the like.

The term "sweetening agent" includes for example saccharin sodium, dipotassium glycyrrhizate, aspartame and the like.

The pharmaceutical compositions of the present invention can be administered to human as well as mammals other than human such as mice, rat, hamster, guinea pig, rabbit, cat, dog, pig, cattle, horse, sheep, monkey and the like orally or parenterally such as locally, rectally and intravenously. While the dosage amount may vary depending on subject, disease, symptom, dosage form, route of administration and the like, for example when it is administered orally to an adult patient with rheumatoid arthritis (body weight: about 60 kg) the dosage amount of the present invention compound of an active ingredient ranges generally from about 1 mg to about 1 g per day, which can be administered once to several times.

The compounds of formula [I] or pharmaceutically acceptable salts or solvates thereof inhibit colony-stimulating factor 1 receptor thereby are used as a active ingredient of medicaments for treating or preventing the following diseases:

(a) autoimmune disease such as rheumatoid arthritis, multiple sclerosis, psoriasis and the like (b) inflammatory disease such as inflammatory bowel disease, glomerulonephritis, diabetic nephritis and the like (c) osteoporosis including bone loss after ovariectomy and osteolysis, (d) cancer such as solid cancer including prostatic cancer, breast cancer and the like or blood cancer including myeloid dysplasia, myelocytic leukemia and the like.

"Rheumatoid arthritis" includes "structural damage of joints", and "treating rheumatoid arthritis" includes "preventing structural damage of joints"

The phrase "inhibit colony-stimulating factor 1 receptor" means that function of colony-stimulating factor 1 receptor is inhibited specifically and activity thereof disappears or reduces. In addition, it includes for example that function of colony-stimulating factor 1 receptor is inhibited specifically according to biological assay 1 described hereinafter. The preferred "inhibit colony-stimulating factor 1 receptor" is "inhibit human colony-stimulating factor 1 receptor". The preferred "inhibitor of colony-stimulating factor 1 receptors" is "inhibitor of human colony-stimulating factor 1 receptors".

The compounds of formula [I] or pharmaceutically acceptable salts or solvates thereof can be used in combination with other one or more medicament (hereinafter called additional medicament(s)) according to methods commonly-used in the art of medicine, which is hereinafter called combination use.

The timing of administration of the compounds of formula [I] or pharmaceutically acceptable salts or solvates thereof and additional medicament(s) is not limited and they may be administered to a subject in a form of combination drug or may be administered simultaneously or at regular intervals. In addition, the compounds of formula [I] or pharmaceutically acceptable salts or solvates thereof may be used as a kit consisting of the pharmaceutical composition of the present invention and additional medicament(s).

The dosage amount of the additional medicament(s) may follow one employed in clinical practice, and may be determined appropriately depending on subject, disease, symptom, dosage form, route of administration, timing of administration, combination and the like. The mode of additional medicament(s) is not limited as long as the present invention compounds or salts or solvates thereof and the additional medicament(s) are combined.

The additional medicament(s) include for example, (1) an agent for treating and/or preventing rheumatoid arthritis (2) an agent for treating and/or preventing osteoporosis (3) an agent for treating and/or preventing cancer.

(4) an agent for treating and/or preventing diabetic nephropathy.

One to three agents selected from the above (1) to (3) may be employed in combination with the compounds of formula [I] or pharmaceutically acceptable salts or solvates thereof.

The agent for treating and/or preventing rheumatoid arthritis includes for example, leflunomide, methotrexate, sulfasalazine, hydroxychloroquine, tacrolimus, infliximab and the like.

Next, some examples of preparation methods of the compound of the present invention are shown as follows. However, the preparation methods of the present invention compound are not limited to these examples. In a production of compounds of the present invention, the more efficient preparation methods can be afforded. For example, as appropriate, by introducing a protecting group into a functional group followed by deprotection in a subsequent step; by using a precursor of functional group in a step, followed by converting to the desired functional group in a subsequent step; by exchanging the order of preparation methods or steps thereof. The workup after reaction in each step can be applied by a commonly-used method, wherein isolation and purification may be performed by selecting or combining conventional methods as necessary, such as crystallization, recrystallization, distillation, separating, silicagel chromatography, preparative HPLC and the like. In some cases, compounds prepared in each step may be used without purification into next step.

The following abbreviations are employed in the preparation methods and Examples herein:

p-toluenesulfonyl group (Ts), methanesulfonyl group (Ms), tert-butyldimethylsilyl group (TBDMS)

trimethylsilyl group (TMS)

triethylsilyl group (TES)

trifluoromethanesulfonyloxy group (OTf)

tert-butoxycarbonyl group (Boc)

lithium diisopropylamide (LDA)

diisobutylaluminium hydride (DIBAL)

1-ethyl-3-(3-dimethylaminopropyl)carbodiimide hydrochloride (WSC.HCl)

1-hydroxy-1H-benzotriazole monohydrate (HOBt.H$_2$O)

tetrabutylammonium fluoride (TBAF)

1,8-diazabicyclo[5.4.0]undec-7-ene (DBU)

N-bromosuccinimide (NBS)

dimethylsulfoxide (DMSO)

N,N-dimethylformamide (DMF)

tetrahydrofuran (THF).

Preparation Method 1

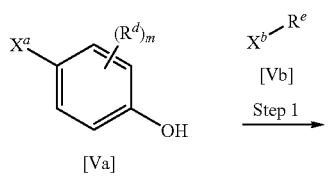

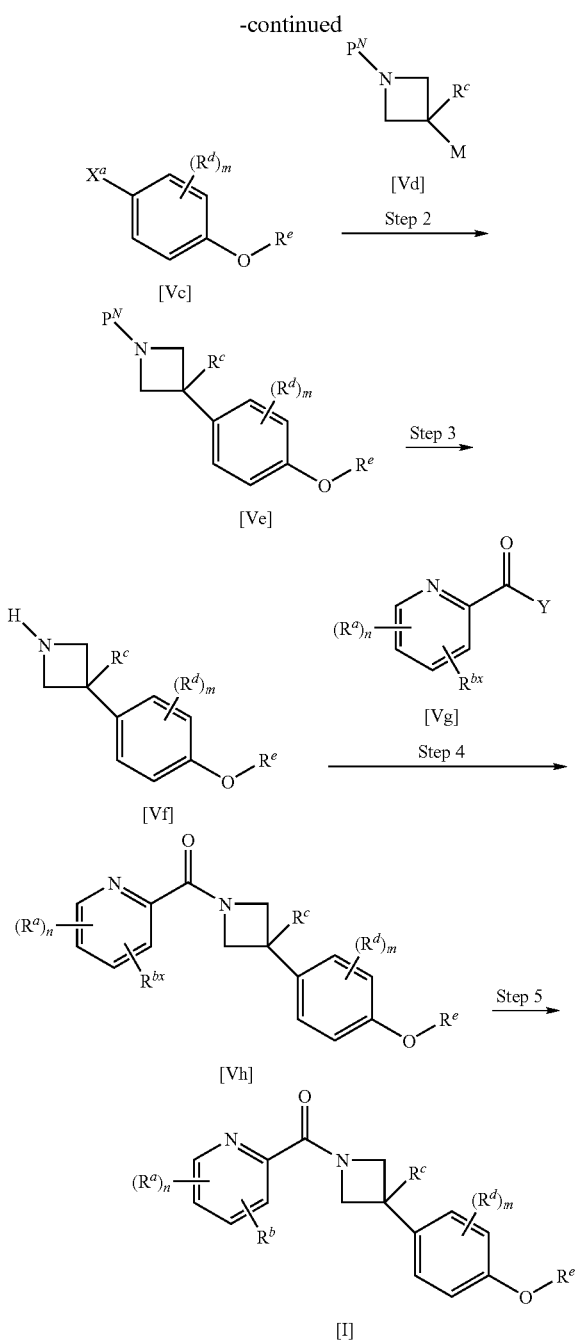

wherein

R$^c$ is hydrogen atom;

X$^a$ is a leaving group such as halogen, trifluoromethanesulfonyloxy, preferably bromo and iodine;

X$^b$ is a leaving group such as halogen, methanesulfonyloxy, preferably chloro, bromo and the like or hydroxyl group;

M is a metal-containing substituent comprising zinc, boron, tin and the like, such as halogeno zinc, boronic acid, trialkyltin and the like, preferably halogeno zinc, more preferably ZnI, ZnBr;

P$^N$ is a protecting group for amine, preferably tert-butoxycarbonyl group;

Y is hydroxyl group, halogen and the like, preferably hydroxyl group;

R$^{bx}$ is a substituent which may be converted to substituent R$^b$ by various reactions or R$^b$ itself; and R$^a$, R$^b$, R$^d$, R$^e$, m and n are as defined in the above formula [I].

Each of the steps in Preparation method 1 as shown above is as follows.

Step 1

(1) For example, the case of that X$^b$ is a leaving group such as halogen, methanesulfonyloxy and the like:

Compound [Vc] can be prepared by binding reaction of Compound [Va] with Compound [Vb] in the presence of a base in a solvent. The solvent used in said reaction includes diethyl ether, tetrahydrofuran, dioxane, 1,2-dimethyloxyethane, benzene, toluene, hexane, methylene chloride, chloroform, 1,2-dichloroethane, ethyl acetate, methyl acetate, acetone, N,N-dimethylformamide, dimethylsulfoxide and the like, which may be used alone or as a mixture of two or more of them. The preferred solvent for the reaction is N,N-dimethylformamide.

The base for the reaction includes for example, triethylamine, pyridine, 4-dimethylaminopyridine, N-methylmorpholine, lithium hydroxide, sodium hydroxide, potassium hydroxide, sodium carbonate, potassium carbonate, sodium hydride, LDA, potassium tert-butoxide, cesium carbonate, sodium bicarbonate and the like, preferably potassium carbonate.

(2) The case of that X$^b$ is hydroxyl group:

Compound [Vc] can be prepared by Mitsunobu reaction of Compound [Va] with Compound [Vb] in the presence of a dialkyl azodicarboxylate such as diethyl azodicarboxylate and diisopropyl azodicarboxylate and triphenylphosphine in a solvent. The solvent for the reaction includes dichloromethane, tetrahydrofuran, toluene, N,N-dimethylformamide and the like, which may be used alone or as a mixture of two or more of them. The preferred solvent for the reaction is tetrahydrofuran.

Step 2

Compound [Ve] can be obtained by Negishi coupling of Compound [Vc] with Compound [Vd] in the presence or absence of a metal catalyst and a ligand in a solvent. The solvent for the reaction includes toluene, tetrahydrofuran, 1,2-dimethyloxyethane, dioxane, N,N-dimethylformamide, N,N-dimethylacetamide, 1-methyl-2-pyrrolidone and the like, which may be used alone or as a mixture of two or more of them. The preferred solvent for the reaction is tetrahydrofuran. The metal catalyst for the reaction includes a catalyst comprising palladium or nickel, preferably a catalyst comprising palladium, more preferably bis(triphenylphosphine)palladium(II) dichloride and palladium(II) acetate.

The ligand for the reaction includes a phosphine such as triphenylphosphine, tributylphosphine, 2-dicyclohexylphosphino-2',6'-dimethyloxybiphenyl and the like, preferably 2-dicyclohexylphosphino-2',6'-dimethyloxybiphenyl.

The amount of the metal catalyst used in the reaction ranges generally about 0.001 to 1 mol, preferably about 0.01 to 0.2 mol per mole of Compound [Vc].

The reaction temperature generally ranges room temperature to about 120° C., preferably room temperature to 50° C. The reaction time generally ranges about 30 minutes to 2 days, preferably about 1 to 24 hr. The term "room temperature" in the Examples means 1 to 40° C.

The amount of Compound [Vd] used in the reaction generally rages about 1 to 5 mol, preferably about 1 to 3 mol per mole of Compound [Vc].

Step 3

Compound [Vf] can be prepared by removal of P$^N$ from Compound [Ve] under the condition of commonly-used amine deprotection reaction. The deprotection reaction may be performed by known methods depending on the employed protecting group. For example, when $P^N$ is tert-butoxycarbonyl group, the treatment with acids such as HCl, trifluoroacetic acid, methanesulfonic acid and the like may be performed in, for example, chloroform, THF, dioxane, ethyl acetate, ethanol water and the like or in a mixture thereof.

Step 4

Compound [Vh] can be obtained by reaction of Compound [Vf] with Reactant [Vg] in the presence of a condensing agent in a solvent under the condition of commonly-used amide bond formation reaction.

The solvent for the reaction includes benzene, toluene, methylene chloride, chloroform, 1,2-dichloroethane, diethyl ether, tetrahydrofuran, dioxane, 1,2-dimethyloxyethane, N,N-dimethylformamide, dimethylsulfoxide and the like, which may be used alone or as a mixture of two or more of them. The preferred solvent for the reaction is N,N-dimethylformamide.

The condensing agent for the reaction includes water-soluble carbodiimide (WSC.HCl: 1-ethyl-3-(3-dimethylaminopropyl)carbodiimide hydrochloride), N,N'-dicyclohexylcarbodiimide (DCC), diphenylphosphoryl azide (DPPA), carbonyldiimidazole (CDI). If needed, 1-hydroxy-1H-benzotriazole monohydrate (HOBt.H$_2$O), 4-dimethylaminopyridine (DMAP) and the like may be used. The preferred condensing agent for the reaction is a mixture of water-soluble carbodiimide (WSC.HCl: 1-ethyl-3-(3-dimethylaminopropyl)carbodiimide hydrochloride) and 1-hydroxy-1H-benzotriazole monohydrate (HOBt.H$_2$O).

Step 5

Compound [I] can be obtained by transformation reaction of each functional group of Compound [Vh] in a solvent.

(1) When $R^b$ is $OR^{b1}$ wherein $R^{b1}$ is as defined in the above formula [I]:

For example, Compound [Vh] wherein $R^{bx}$ is hydroxyl group may be subjected to ether formation reaction followed by a functional group transformation as follows. For example, Compound [I] can be prepared by the following scheme and the like.

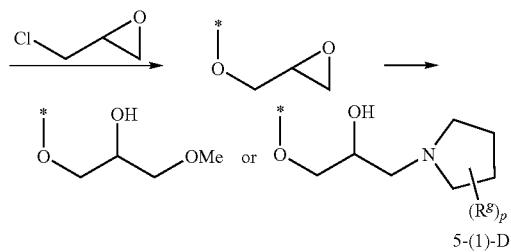

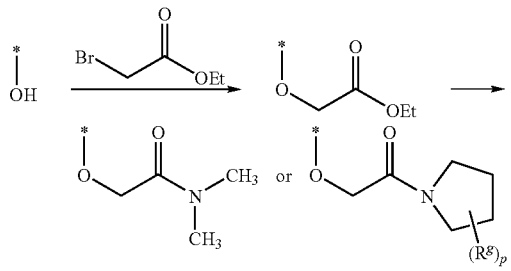

wherein

X is a leaving group such as halogen, methanesulfonyloxy, preferably chloro, bromo and the like, $R^g$ and p are as defined in the above formula [I].

(2) For example, when $R^b$ is $-Y^c-O-R^{b2}$ or

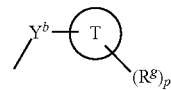

when $R^b$ is
and
$Y^b$ is $-Y^{b1}-O-Y^{b2}-$
and the like, Compound [I] can be prepared by the following scheme.

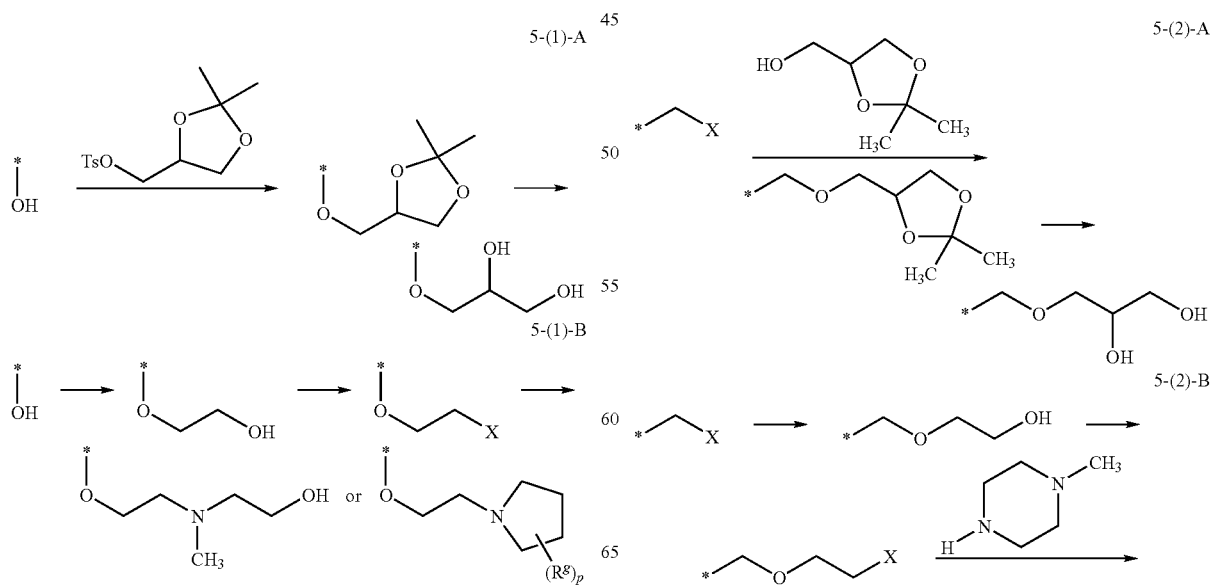

-continued

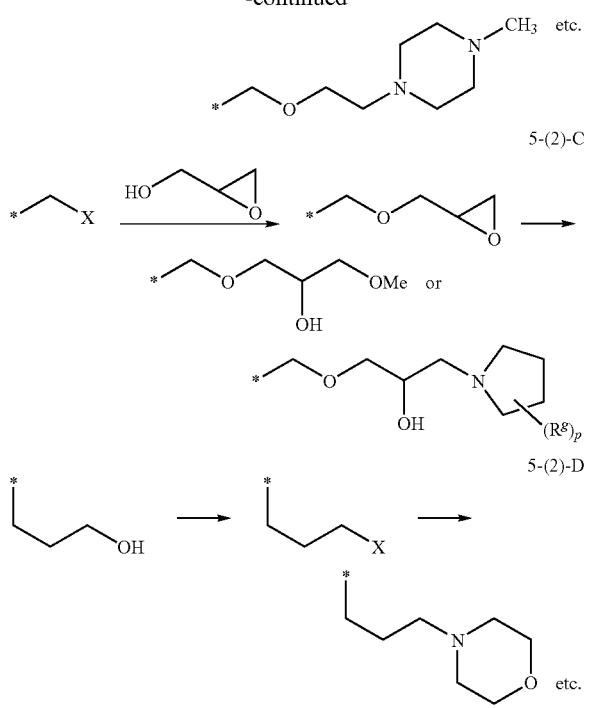

5-(2)-C 5-(2)-D 5-(2)-E 5-(2)-F wherein

X is a leaving group such as halogen, methanesulfonyloxy, preferably chloro, bromo and the like, R$^g$ and p are as defined in the above formula [I].

Reactant [Vg] of the preparation methods described above can be prepared by the following scheme.

Preparation Method 1-2

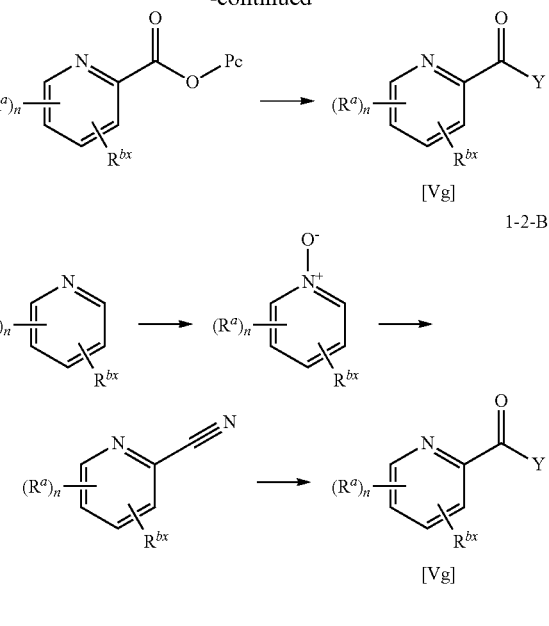

[Vg]
1-2-B wherein each symbol is as defined in Preparation method 1.

Preparation Method 2

Preparation method of the formula [I] wherein R$^c$ is hydroxyl group.

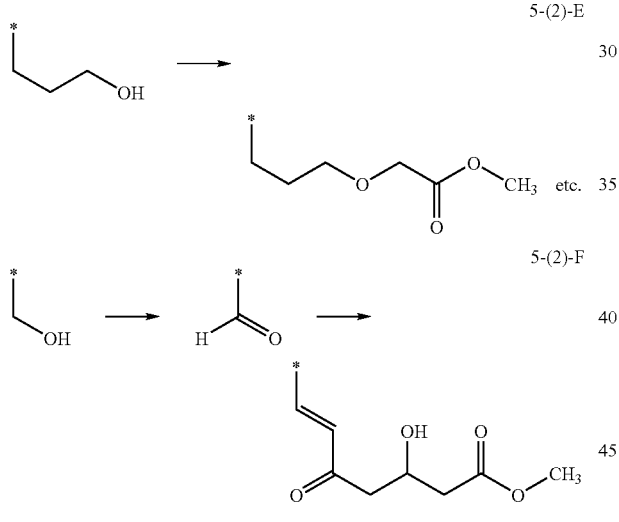

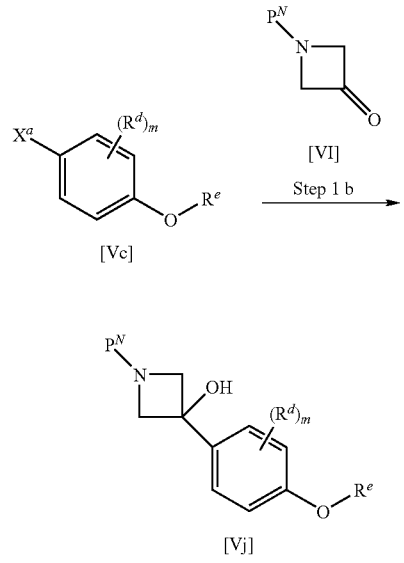

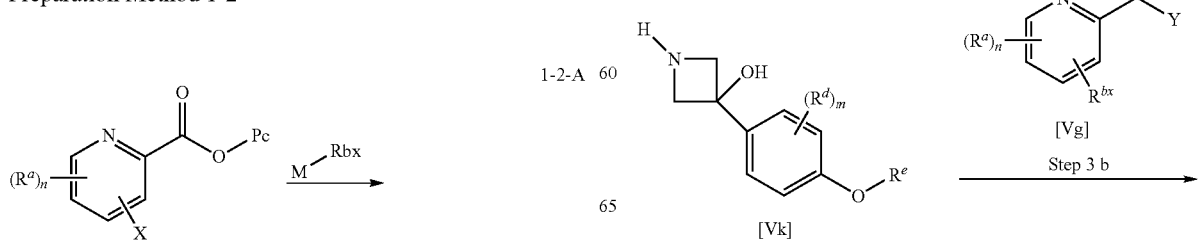

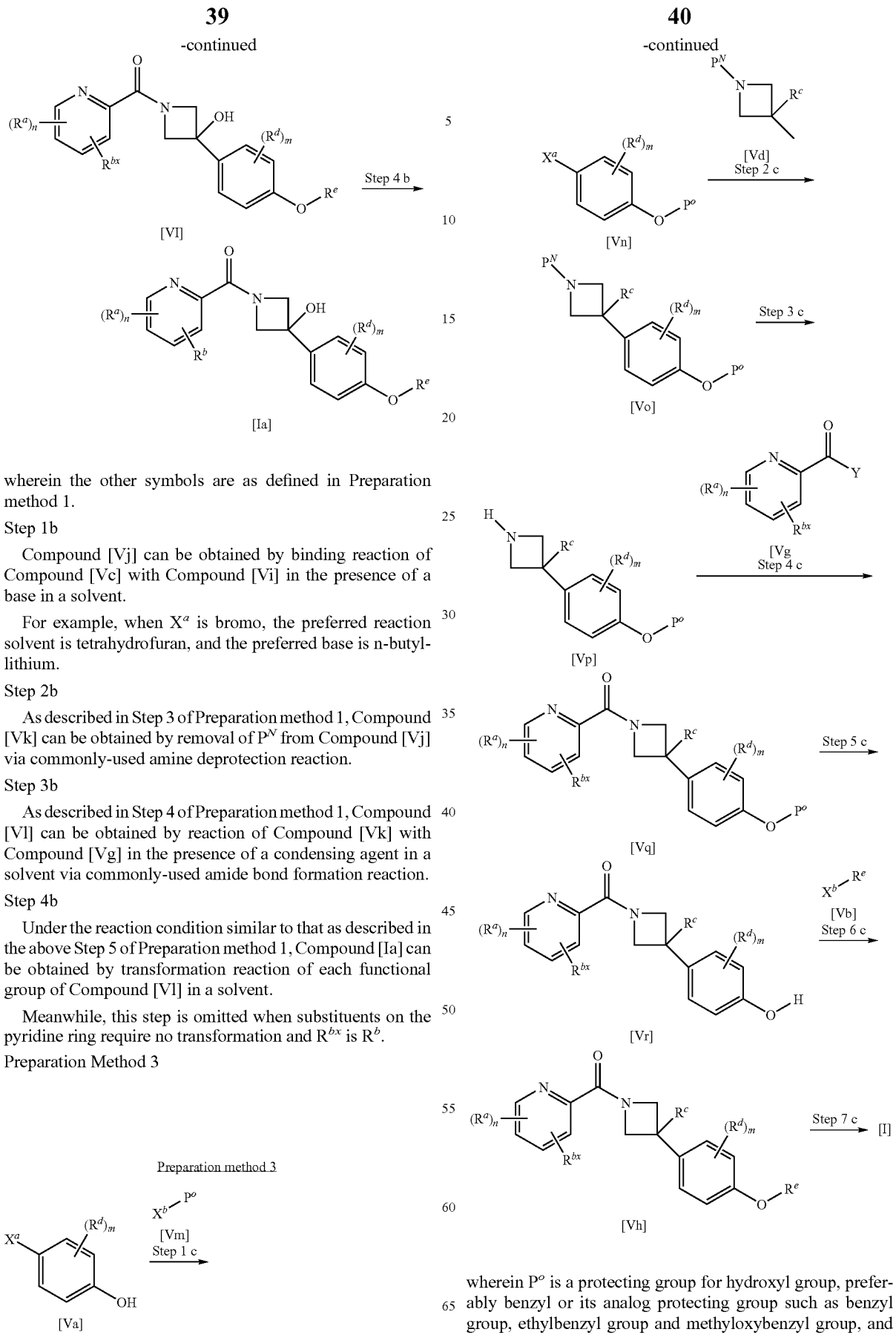

wherein the other symbols are as defined in Preparation method 1.

Step 1b

Compound [Vj] can be obtained by binding reaction of Compound [Vc] with Compound [Vi] in the presence of a base in a solvent.

For example, when $X^a$ is bromo, the preferred reaction solvent is tetrahydrofuran, and the preferred base is n-butyllithium.

Step 2b

As described in Step 3 of Preparation method 1, Compound [Vk] can be obtained by removal of $P^N$ from Compound [Vj] via commonly-used amine deprotection reaction.

Step 3b

As described in Step 4 of Preparation method 1, Compound [Vl] can be obtained by reaction of Compound [Vk] with Compound [Vg] in the presence of a condensing agent in a solvent via commonly-used amide bond formation reaction.

Step 4b

Under the reaction condition similar to that as described in the above Step 5 of Preparation method 1, Compound [Ia] can be obtained by transformation reaction of each functional group of Compound [Vl] in a solvent.

Meanwhile, this step is omitted when substituents on the pyridine ring require no transformation and $R^{bx}$ is $R^b$.

Preparation Method 3 wherein $P^o$ is a protecting group for hydroxyl group, preferably benzyl or its analog protecting group such as benzyl group, ethylbenzyl group and methyloxybenzyl group, and the other symbols are as defined in Preparation method 1.

Step 1c

For example, when $X^b$ is a leaving group such as halogen, methanesulfonyloxy and the like, Compound [Vn] can be obtained by binding reaction of Compound [Va] with Compound [Vm] in the presence of a base in a solvent, as described in Step 1 of Preparation method 1.

Besides, when $X^b$ is hydroxyl group, Compound [Vn] can be obtained by Mitsunobu reaction of Compound [Va] with Compound [Vm] in the presence of a dialkyl azodicarboxylate such as diethyl azodicarboxylate and diisopropyl azodicarboxylate and triphenylphosphine in a solvent.

Step 2c

As described in Step 2 of Preparation method 1, Compound [Vo] can be obtained by Negishi coupling of Compound [Vn] with Compound [Vd] in the presence of a metal catalyst and a ligand in a solvent.

Step 3c

As described in Step 3 of Preparation method 1, Compound [Vp] can be obtained by removal of $P^N$ from Compound [Vo] via commonly-used amine deprotection reaction.

Step 4c

As described in Step 4 of Preparation method 1, Compound [Vq] can be obtained by reaction of Compound [Vp] with Compound [Vg] in the presence of a condensing agent in a solvent via commonly-used amide bond formation reaction.

Step 5c

Compound [Vr] can be obtained by removal of $P^o$ from Compound [Vq] via commonly-used phenol deprotection reaction. The deprotection reaction may be performed by known methods depending on the employed protecting group. For example, in case that $P^o$ is a benzyl or its analog protecting group, the deprotection reaction may be performed by hydrogenation reaction in the presence of a catalyst such as palladium on carbon and the like, in a solvent such as chloroform, THF, ethyl acetate, ethanol, methanol, and water or a mixture thereof.

Step 6c

For example, $X^b$ is a leaving group such as halogen, methanesulfonyloxy and the like, Compound [Vh] can be obtained by binding reaction of Compound [Vr] with [Vb] in the presence of a base in a solvent, as described in Step 1 of Preparation method 1. Besides, when $X^b$ is hydroxyl group, Compound [Vh] can be obtained by Mitsunobu reaction of Compound [Vr] with Compound [Vb] in the presence of a dialkyl azodicarboxylate such as diethyl azodicarboxylate and diisopropyl azodicarboxylate and triphenylphosphine in a solvent.

Step 7c

Under the reaction condition similar to that described in Step 5 of Preparation method 1, Compound [I] can be obtained by transformation reaction of each functional group of Compound [Vh] in a solvent.

Meanwhile, this step is omitted when substituents on the pyridine ring require no transformation and $R^{bx}$ is $R^b$.

Effects of the Invention

Compounds [I] of the present invention have CSF-1R inhibitory activity, and are useful as a medicament of preventing or treating autoimmune disease, inflammatory disease, osteoporosis, osteolysis or cancer.

BEST MODE FOR CARRYING OUT THE INVENTION

The following working Examples serve to illustrate the present invention more specifically, which dose not intend to limit the present invention.

EXAMPLE

Example 1

{3-[4-(4-Cyclopropylbenzyloxy)-3-methoxyphenyl]azetidin-1-yl}-[4-((S)-2,3-dihydroxypropoxymethyl)pyridin-2-yl]-methanone (1) 4-Cyclopropylbenzaldehyde

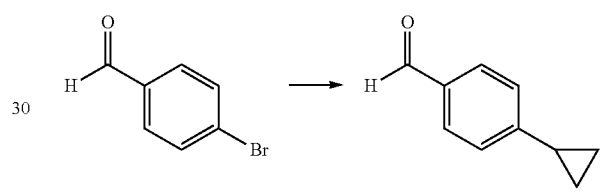

To a solution of 4-bromobenzaldehyde (94 g) in toluene (470 mL) were added potassium fluoride (95 g), cyclo-propylboronic acid (48 g) and bis(triphenylphosphine)-palladium (II) dichloride (3.6 g) under nitrogen atmosphere. The reaction mixture was stirred at 110° C. for 24 hr under nitrogen atmosphere. The reaction mixture was filtered using Celite. The filtrate was concentrated in vacuo to give the crude title compound.

(2) (4-Cyclopropylphenyl)methanol

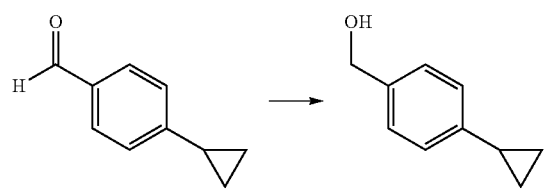 [SMILES: O=Cc1ccc(C2CC2)cc1 ; OCc1ccc(C2CC2)cc1]

To a solution of NaBH$_4$ (15 g) in ethanol (180 mL) was added the crude 4-cyclopropylbenzaldehyde prepared in (1) at 0° C. under nitrogen atmosphere. The reaction mixture was stirred at 0° C. for 1 hr. To the reaction mixture was added 6 N hydrochloric acid (90 mL) at 0° C. The reaction mixture was stirred for 30 min and then concentrated in vacuo. Water was added to the residue and the mixture was extracted with toluene. The solvent was removed under reduced pressure. The resulting residue was distilled under reduced pressure to give the title compound (60 g, 79%).

¹H-NMR (400 MHz, DMSO-d₆) δ: 7.17 (2H, d, J=8.12 Hz), 7.01 (2H, d, J=8.12 Hz), 5.06 (1H, t, J=5.68 Hz), 4.42 (2H, d, J=5.57 Hz), 1.91-1.85 (1H, m), 0.94-0.89 (2H, m), 0.64-0.60 (2H, m).

(3) 1-(4-Cyclopropylbenzyloxy)-4-iodo-2-methoxybenzene

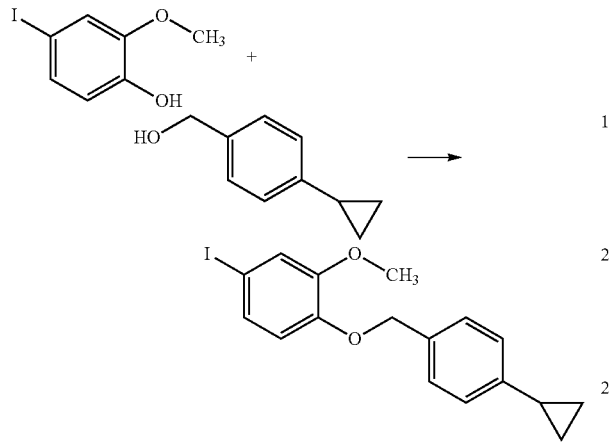

To a solution of (4-cyclopropylphenyl)methanol (4.5 g) prepared in (2) and 4-iodo-2-methoxyphenol (7.5 g) in THF (40 mL) were added triphenylphosphine (8.7 g) and diisopropyl azodicarboxylate (6.5 mL) at 0° C. The reaction mixture was stirred at RT for 22 hr. The solvent was removed under reduced pressure. The residue was purified by silica-gel chromatography (Developing solvent: hexane/ethyl acetate=9/1) to give the title compound (5.3 g, 46%).

¹H-NMR (400 MHz, DMSO-d₆) δ: 7.28 (2H, d, J=8.12 Hz), 7.21-7.18 (2H, m), 7.08 (2H, d, J=8.12 Hz), 6.83 (1H, d, J=8.35 Hz), 4.99 (2H, s), 3.75 (3H, s), 1.94-1.87 (1H, m), 0.96-0.92 (2H, m), 0.68-0.64 (2H, m).

(4) tert-Butyl 3-[4-(4-cyclopropylbenzyloxy)-3-methoxyphenyl]azetidine-1-carboxylate

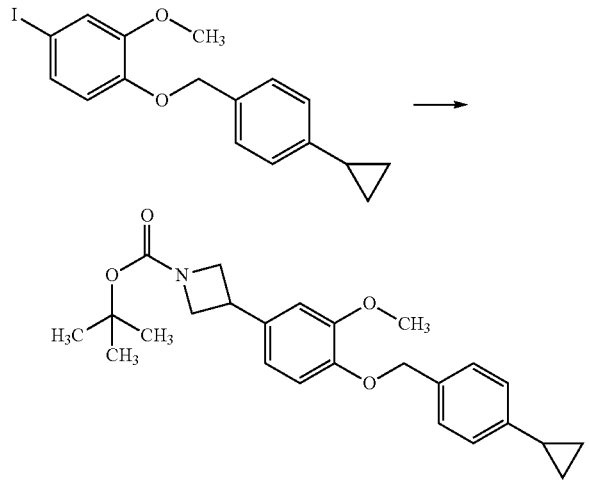

To a suspension of zinc (3.0 g) and lithium chloride (1.5 g) in THF (25 mL) were added dibromoethane (0.30 mL) and chlorotrimethylsilane (0.44 mL) at 70° C. under argon atmosphere. The mixture was stirred at 70° C. for 10 min. A solution of 1-Boc-3-iodoazetidine (9.8 g) in THF (10 mL) was added dropwise to the mixture at RT. The mixture was stirred at RT for 1 hr. To the mixture were added a solution of 1-(4-cyclopropylbenzyloxy)-4-iodo-2-methoxybenzene (5.3 g) prepared in (3) in THF (15 mL) and bis(triphenylphosphine)palladium (II) dichloride (0.49 g). The reaction mixture was stirred at RT for 3 hr. The reaction mixture was quenched with saturated aqueous NH₄Cl and extracted with ethyl acetate. The organic layer was dried over MgSO₄. The solvent was removed under reduced pressure. The residue was purified by silica-gel chromatography (Developing solvent: hexane/ethyl acetate=9/1 to 4/1) to give the title compound.

¹H-NMR (400 MHz, DMSO-d₆) δ: 7.29 (2H, d, J=8.12 Hz), 7.08 (2H, d, J=8.12 Hz), 6.97 (1H, d, J=8.35 Hz), 6.90 (1H, d, J=2.09 Hz), 6.80 (1H, dd, J=8.35, 1.86 Hz), 4.99 (2H, s), 4.20 (2H, t, J=8.12 Hz), 3.82 (2H, t, J=6.84 Hz), 3.77 (3H, s), 3.74-3.69 (1H, m), 1.94-1.88 (1H, m), 1.40 (9H, s), 0.96-0.92 (2H, m), 0.68-0.64 (2H, m).

(5) 3-[4-(4-Cyclopropylbenzyloxy)-3-methoxyphenyl]-azetidine monohydrochloride

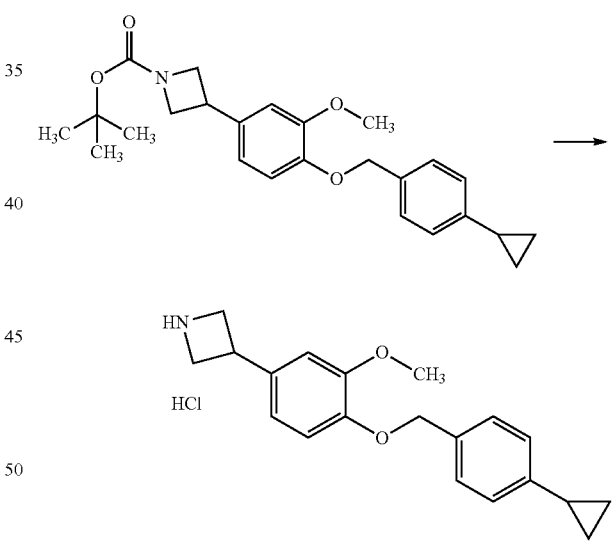

To a solution of tert-butyl 3-[4-(4-cyclopropylbenzyloxy)-3-methoxyphenyl]azetidine-1-carboxylate prepared in (4) in ethyl acetate (30 mL) was added 4 N HCl/ethyl acetate (30 mL) at 0° C. The reaction mixture was stirred at 0° C. for 10 min and then at RT for 30 min. The reaction mixture was stirred in an ice-bath. The precipitated solid was collected on a filter and dried to give the title compound (2.61 g, 54%).

¹H-NMR (400 MHz, DMSO-d₆) δ: 8.73 (2H, br s), 7.29 (2H, d, J=8.12 Hz), 7.09-7.06 (3H, m), 7.00 (1H, d, J=8.12 Hz), 6.87 (1H, dd, J=8.23, 1.97 Hz), 5.01 (2H, s), 4.25-4.17 (2H, m), 4.06-4.00 (3H, m), 3.80 (3H, s), 1.94-1.88 (1H, m), 0.96-0.92 (2H, m), 0.67-0.63 (2H, m).

(6) {3-[4-(4-Cyclopropylbenzyloxy)-3-methoxyphenyl]-azetidin-1-yl}-(4-hydroxymethylpyridin-2-yl)-methanone

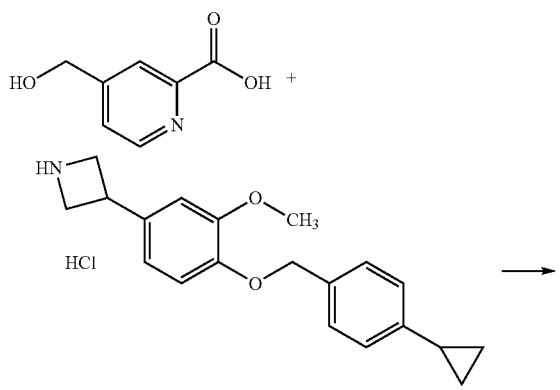

To a solution of 3-[4-(4-cyclopropylbenzyloxy)-3-methoxyphenyl]azetidine monohydrochloride (5.0 g) prepared in (5), 4-hydroxymethylpyridine-2-calboxylic acid (2.2 g), WSC.HCl (3.3 g) and HOBt.H$_2$O (2.7 g) in DMF (50 mL) was added triethylamine (3.0 mL). The reaction mixture was stirred at RT for 21 hr. Water was added to the reaction mixture and the mixture was extracted with a mixed solvent of ethyl acetate/THF. The organic layer was washed with water and aqueous 1 N NaOH, and then dried over MgSO$_4$. The solvent was removed under reduced pressure. Hexane was added to the residue. The precipitated solid was collected on a filter and dried to give the title compound (4.0 g, 62%).

$^1$H-NMR (400 MHz, DMSO-d$_6$) δ: 8.54 (1H, d, J=4.85 Hz), 7.95 (1H, s), 7.45-7.44 (1H, m), 7.30 (2H, d, J=8.16 Hz), 7.08 (2H, d, J=8.16 Hz), 6.99-6.97 (2H, m), 6.87 (1H, dd, J=8.38, 1.98 Hz), 5.52 (1H, t, J=5.84 Hz), 4.99 (2H, s), 4.97 (1H, t, J=9.26 Hz), 4.60 (2H, d, J=5.73 Hz), 4.55 (1H, dd, J=10.26, 6.29 Hz), 4.45 (1H, t, J=9.04 Hz), 4.08 (1H, dd, J=9.92, 6.62 Hz), 3.93-3.85 (1H, m), 3.77 (3H, s), 1.94-1.88 (1H, m), 0.96-0.92 (2H, m), 0.68-0.64 (2H, m).

(7) 2-{3-[4-(4-Cyclopropylbenzyloxy)-3-methoxyphenyl]-azetidine-1-carbonyl}pyridin-4-ylmethyl methanesulfonate

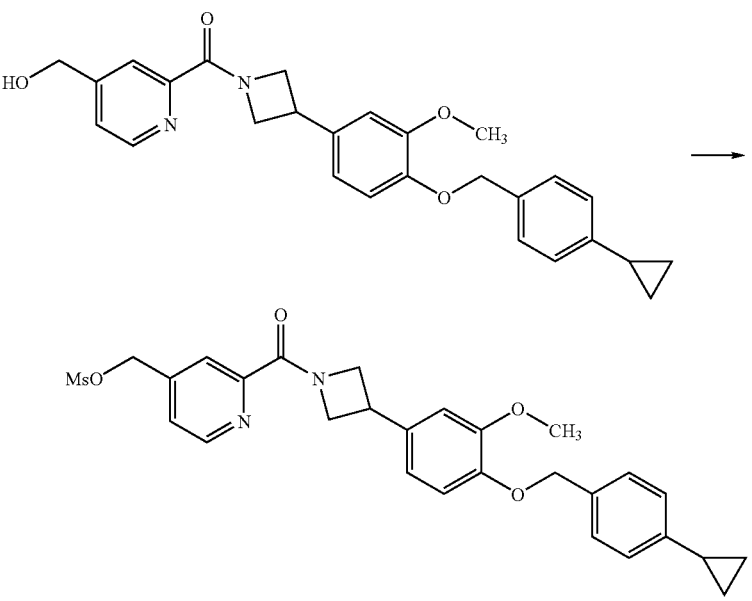

To a solution of {3-[4-(4-cyclopropylbenzyloxy)-3-methoxyphenyl]azetidin-1-yl}-(4-hydroxymethylpyridin-2-yl)-methanone (4.0 g) prepared in (6) in chloroform (80 mL) were added triethylamine (3.0 mL) and methanesulfonyl chloride (1.5 mL) at 0° C. The reaction mixture was stirred at RT for 30 min. Water was added to the reaction mixture and the mixture was extracted with chloroform. The organic layer was dried over MgSO$_4$. The solvent was removed under reduced pressure. Hexane was added to the residue. The precipitated solid was collected on a filter and dried to give the title compound (4.6 g, 99%).

$^1$H-NMR (400 MHz, DMSO-d$_6$) δ: 8.66 (1H, d, J=5.10 Hz), 8.02 (1H, s), 7.57 (1H, dd, J=5.10, 1.16 Hz), 7.30 (2H, d, J=7.88 Hz), 7.08 (2H, d, J=8.12 Hz), 6.99-6.97 (2H, m), 6.87 (1H, dd, J=8.12, 1.86 Hz), 5.42 (2H, s), 4.99-4.95 (3H, m), 4.56 (1H, dd, J=9.97, 6.49 Hz), 4.47 (1H, t, J=9.62 Hz), 4.09 (1H, dd, J=9.97, 6.49 Hz), 3.94-3.86 (1H, m), 3.77 (3H, s), 3.32 (3H, s), 1.94-1.88 (1H, m), 0.96-0.92 (2H, m), 0.68-0.64 (2H, m).

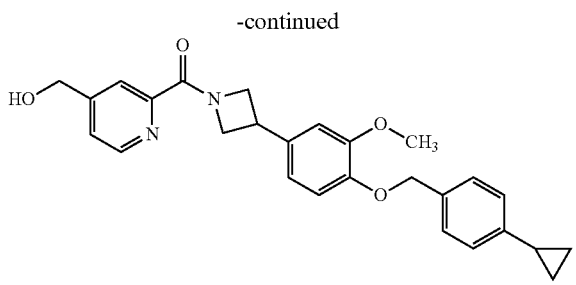

(8) {3-[4-(4-Cyclopropylbenzyloxy)-3-methoxyphenyl]-azetidin-1-yl}-[4-((R)-2,2-dimethyl-[1,3]dioxolan-4-yl-methoxymethyl)pyridin-2-yl]-methanone

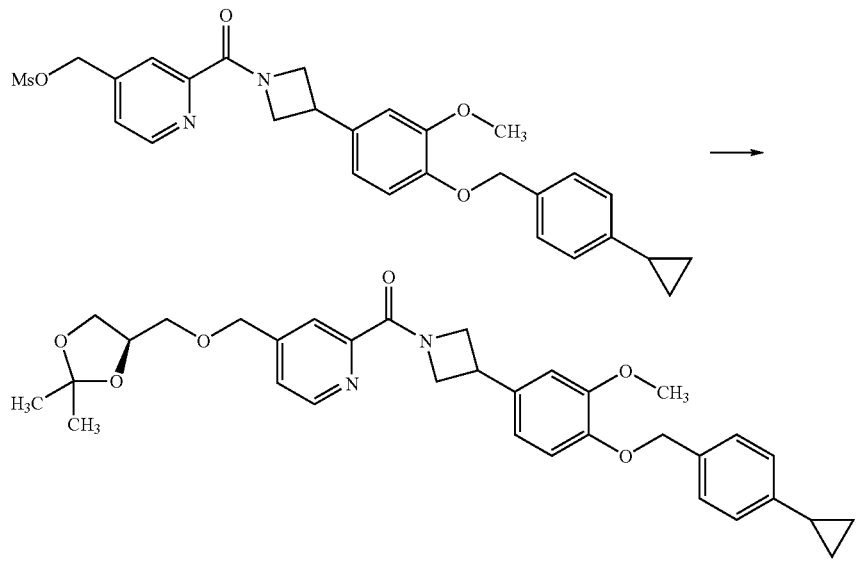

To a solution of (R)-(−)-2,2-dimethyl-1,3-dioxolan-4-methanol (0.42 mL) in DMF (10 mL) was added NaH (0.14 g). The mixture was stirred at RT for 1 hr. To the mixture was added 2-{3-[4-(4-cyclopropylbenzyloxy)-3-methoxyphenyl]azetidine-1-carbonyl}pyridin-4-ylmethyl methanesulfonate (0.80 g) prepared in (7). The reaction mixture was stirred for at RT for 1 hr. Water was added to the reaction mixture and the mixture was extracted with ethyl acetate. The organic layer was washed with water, reduced pressure to give the crude title compound.

(9) {3-[4-(4-Cyclopropylbenzyloxy)-3-methoxyphenyl]-azetidin-1-yl}-[4-((S)-2,3-dihydroxypropoxymethyl)pyridin-2-yl]-methanone

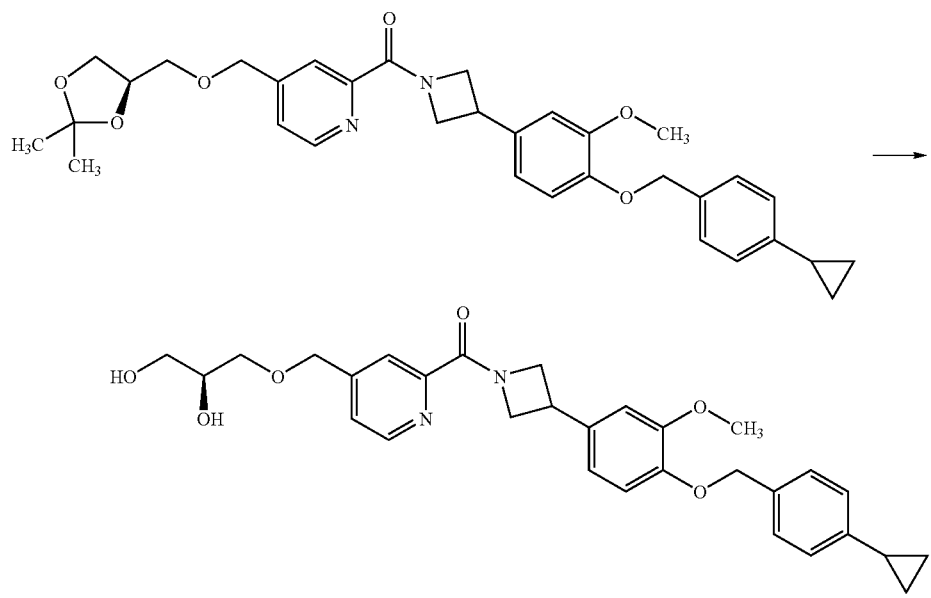

To a solution of the crude {3-[4-(4-cyclopropylbenzyloxy)-3-methoxyphenyl]azetidin-1-yl}-[4-((R)-2,2-dimethyl-[1,3]dioxolan-4-ylmethoxymethyl)pyridin-2-yl]-methanone prepared in (8) in THF (10 mL) was added 1 N hydrochloric acid (5 mL). The reaction mixture was stirred at RT for 3 hr. The reaction mixture was quenched with aqueous 1 N NaOH and saturated aqueous NaHCO$_3$. The mixture was extracted with ethyl acetate. The organic layer was dried over MgSO$_4$. The solvent was removed under reduced pressure. The residue was purified by preparative thin-layer chromatography (Developing solvent: chloroform/methanol=8/1) to give the title compound (0.30 g, 38%).

$^1$H-NMR (400 MHz, DMSO-d$_6$) δ: 8.57 (1H, d, J=4.87 Hz), 7.94 (1H, s), 7.49 (1H, dd, J=4.87, 1.16 Hz), 7.30 (2H, d, J=8.12 Hz), 7.08 (2H, d, J=8.12 Hz), 6.98 (2H, dd, J=4.99, 3.13 Hz), 6.87 (1H, dd, J=8.35, 1.86 Hz), 4.99-4.94 (3H, m), 4.77 (1H, d, J=5.10 Hz), 4.62 (2H, s), 4.57-4.53 (2H, m), 4.46 (1H, t, J=9.74 Hz), 4.08 (1H, dd, J=10.09, 6.38 Hz), 3.93-3.85 (1H, m), 3.77 (3H, s), 3.69-3.62 (1H, m), 3.52 (1H, dd, J=9.86, 4.52 Hz), 3.42-3.35 (3H, m), 1.94-1.88 (1H, m), 0.95-0.93 (2H, m), 0.68-0.64 (2H, m).

MASS 519 (M+1).

Example 2

{3-[4-(4-Cyclopropylbenzyloxy)-3-methoxyphenyl]azetidin-1-yl}-[4-((R)-2,3-dihydroxypropoxy)pyridin-2-yl]-methanone (1) {3-[4-(4-cyclopropylbenzyloxy)-3-methoxyphenyl]-azetidin-1-yl}-[4-((S)-2,2-dimethyl-[1,3]dioxolan-4-ylmethoxy)pyridin-2-yl]-methanone

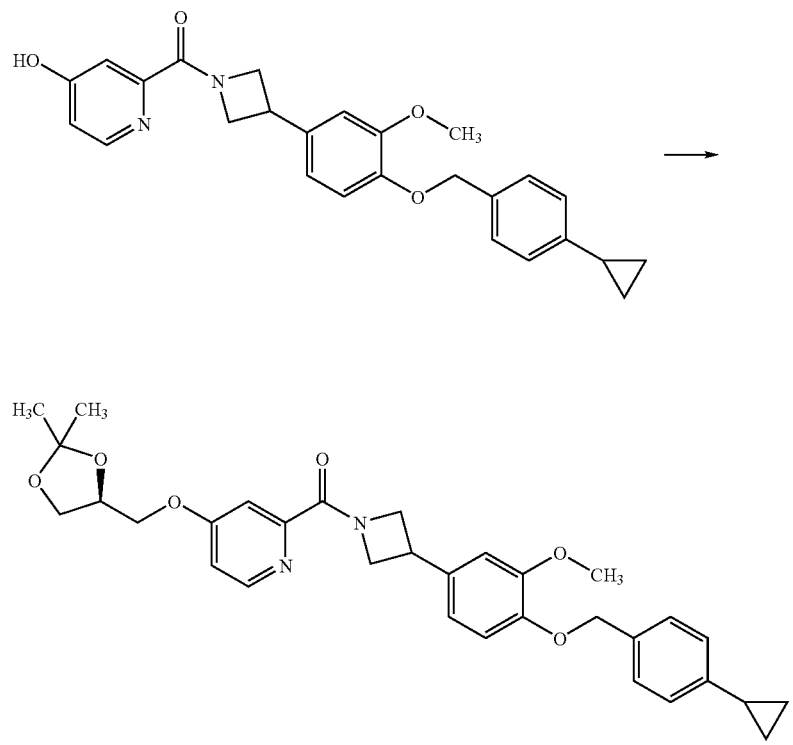

To a suspension of {3-[4-(4-cyclopropylbenzyloxy)-3-methoxyphenyl]-azetidin-1-yl}-(4-hydroxypyridin-2-yl)-methanone (0.45 g) prepared in a manner similar to Example (6) using 4-hydroxypyridine-2-calboxylic acid and K$_2$CO$_3$ (0.21 g) in DMF (8.0 mL) was added (R)-2,2-dimethyl-[1,3]dioxolan-4-ylmethyl toluene-4-sulfonate (0.33 g). The reaction mixture was stirred at 100° C. for 13 hr. Water was added to the reaction mixture and the mixture was extracted with ethyl acetate. The organic layer was washed with water and brine, and then dried over MgSO$_4$. The solvent was removed under reduced pressure. The residue was purified by silica gel chromatography (Developing solvent: hexane/ethyl acetate=1/2) to give the title compound (0.27 g, 49%).

(2) {3-[4-(4-Cyclopropylbenzyloxy)-3-methoxyphe-
nyl]-azetidin-1-yl}-[4-((R)-2,3-dihydroxypropoxy)
pyridin-2-yl]-methanone

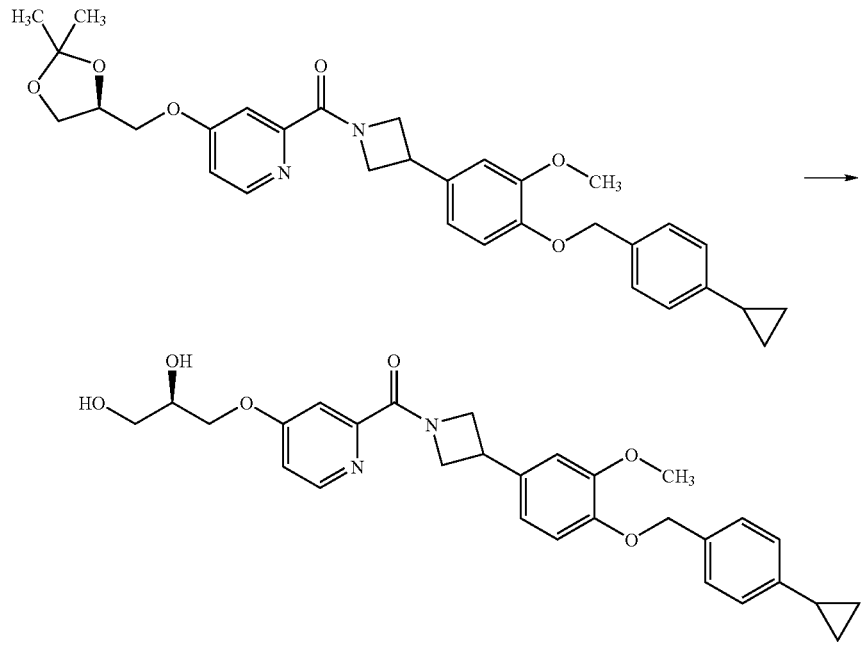

To a solution of {{3-[4-(4-cyclopropylbenzyloxy)-3-methoxyphenyl]azetidin-1-yl}-[4-((S)-2,2-dimethyl-[1,3]dioxolan-4-ylmethoxy)pyridin-2-yl]-methanone prepared in (1) (0.27 g) in THF (4.0 mL) was added 1 N hydrochloric acid (2.0 mL). The reaction mixture was stirred at 60° C. for 2 hr. To the reaction mixture was added aqueous 1 N NaOH (2.0 mL) and the mixture was extracted with ethyl acetate. The solvent was removed under reduced pressure. A mixed solvent of hexane/ethyl acetate (1/1) was added to the residue. The precipitated solid was collected on a filter and dried to give the title compound (0.23 g, 93%).

$^1$H-NMR (400 MHz, DMSO-$d_6$) δ: 8.42 (1H, d, J=5.64 Hz), 7.49 (1H, d, J=2.62 Hz), 7.30 (2H, d, J=8.26 Hz), 7.10-7.07 (3H, m), 6.99-6.97 (2H, m), 6.86 (1H, dd, J=8.46, 1.81 Hz), 5.04 (1H, d, J=5.04 Hz), 4.99 (2H, s), 4.95 (1H, t, J=9.27 Hz), 4.73 (1H, t, J=5.64 Hz), 4.54 (1H, dd, J=10.17, 6.55 Hz), 4.44 (1H, t, J=9.37 Hz), 4.16 (1H, dd, J=10.17, 3.73 Hz), 4.09-3.99 (2H, m), 3.92-3.79 (2H, m), 3.77 (3H, s), 3.47-3.42 (2H, m), 1.94-1.88 (1H, m), 0.96-0.92 (2H, m), 0.68-0.64 (2H, m).

MASS 505 (M+1).

Example 3

{3-[4-(4-Cyclopropylbenzyloxy)-3-methoxyphenyl]
azetidin-1-yl}-[4-(3-hydroxy-2,2-bis-hydroxymethylpropoxymethyl)-pyridin-2-yl]-methanone (1) {3-[4-(4-Cyclopropylbenzyloxy)-3-methoxyphenyl]-azetidin-1-yl}-[4-(5-hydroxymethyl-2-phenyl-[1,3]dioxan-5-ylmethoxymethyl)pyridin-2-yl]-methanone

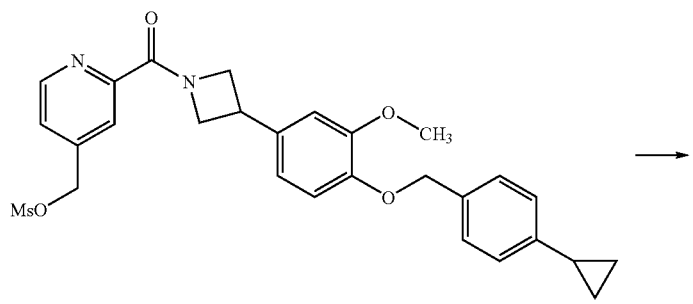

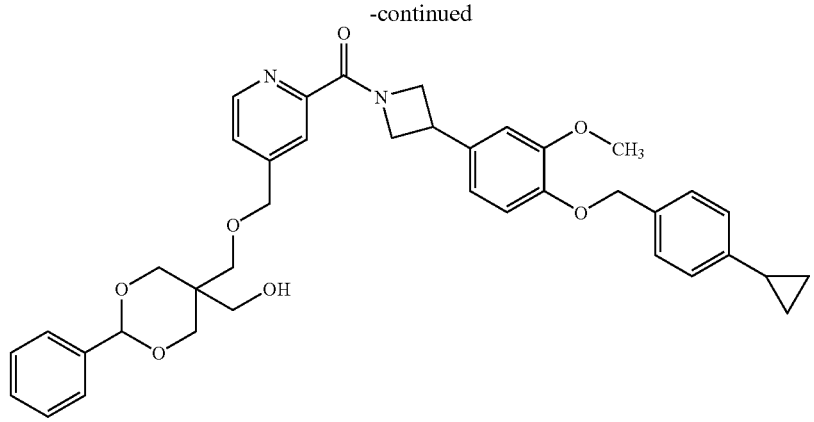

To a solution of (5-hydroxymethyl-2-phenyl-[1,3]dioxan-5-yl)methanol (0.66 g) in DMF (10 mL) was added NaH (0.12 g). The mixture was stirred at RT for 1 hr. To the mixture was added 2-{3-[4-(4-cyclopropylbenzyloxy)-3-methoxyphenyl] azetidine-1-carbonyl}pyridin-4-ylmethyl methanesulfonate (0.7 g) prepared in Example 1 (7). The reaction mixture was stirred at RT for 1 hr. Water was added to the reaction mixture and the mixture was extracted with ethyl acetate. The organic layer was washed with water, and then dried over $MgSO_4$. The solvent was removed under reduced pressure to give the crude title compound.

(2) {3-[4-(4-Cyclopropylbenzyloxy)-3-methoxyphenyl]-azetidin-1-yl}-[4-(3-hydroxy-2,2-bis-hydroxymethylpropoxy-methyl)pyridin-2-yl]-methanone To a solution of the crude {3-[4-(4-cyclopropylbenzyloxy)-3-methoxyphenyl]azetidin-1-yl}-[4-(5-hydroxymethyl-2-phenyl-[1,3]dioxan-5-ylmethoxymethyl)-pyridin-2-yl]-methanone prepared in (1) in THF (10 mL) was added 1 N hydrochloric acid (5.0 mL). The reaction mixture was stirred at RT for 24 hr. To the reaction mixture were added aqueous 1 N NaOH and saturated aqueous $NaHCO_3$ and then the mixture was extracted with ethyl acetate. The organic layer was dried over $MgSO_4$. The solvent was removed under reduced pressure. The residue was purified by silica gel chromatography (Developing solvent: chloroform/methanol=5/1) to give the title compound (0.33 g, 44%).

$^1$H-NMR (400 MHz, DMSO-$d_6$) δ: 8.57 (1H, d, J=4.87 Hz), 7.92 (1H, s), 7.47 (1H, dd, J=4.99, 1.51 Hz), 7.30 (2H, d, J=8.12 Hz), 7.08 (2H, d, J=8.12 Hz), 6.98 (2H, dd, J=5.10, 3.25 Hz), 6.87 (1H, dd, J=8.35, 1.86 Hz), 4.99-4.94 (3H, m), 4.57-4.53 (3H, m), 4.45 (1H, t, J=9.51 Hz), 4.28 (3H, t, J=5.33

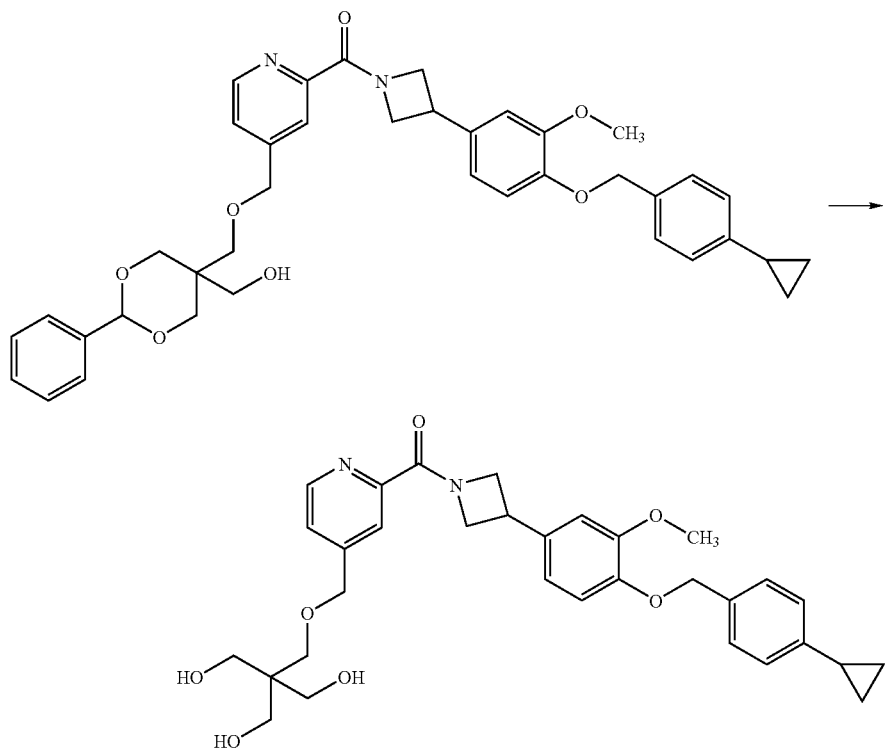

Hz), 4.07 (1H, dd, J=10.09, 6.61 Hz), 3.93-3.85 (1H, m), 3.77 (3H, s), 3.43-3.41 (8H, m), 1.94-1.88 (1H, m), 0.96-0.92 (2H, m), 0.68-0.64 (2H, m).

MASS 563 (M+1).

Example 4

{3-[4-(4-Ethylbenzyloxy)-3-methoxyphenyl]azetidin-1-yl}-[4-(2-hydroxyethoxy)pyridin-2-yl]-methanone (1) 1-(4-Ethylbenzyloxy)-4-iodo-2-methoxybenzene

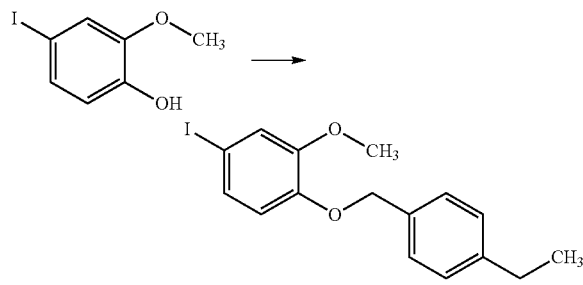

To a solution of 4-iodo-2-methoxyphenol (90 g) in DMF (450 mL) were added $K_2CO_3$ (60 g) and 4-ethylbenzyl chloride (58 g) at RT. The reaction mixture was stirred at 80° C. for 3 hr. Water (900 mL) was added to the reaction mixture. The precipitated solid was collected on a filter and dried under reduced pressure. The suspension of this solid in heptane (520 mL) was stirred at RT. The precipitated solid was collected on a filter and dried under reduced pressure to give the title compound (115 g, 87%).

$^1$H-NMR (400 MHz, DMSO-$d_6$) δ: 7.32 (2H, d, =8.16 Hz), 7.23-7.18 (4H, m), 6.84 (1H, d, J=8.38 Hz), 5.01 (2H, s), 3.76 (3H, s), 2.60 (2H, q, J=7.57 Hz), 1.17 (3H, t, J=7.61 Hz).

(2) tert-Butyl 3-[4-(4-ethylbenzyloxy)-3-methoxyphenyl]-azetidine-1-carboxylate

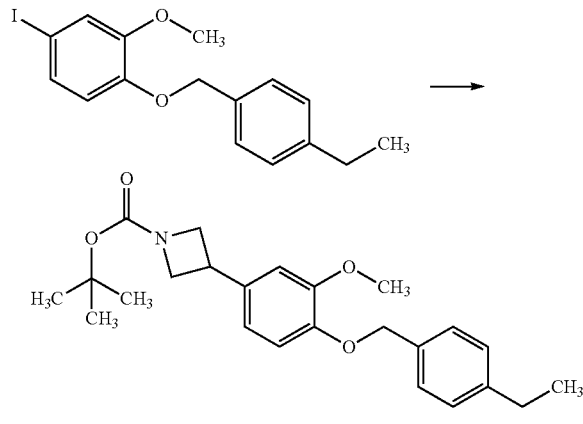

To a suspension of zinc (20.7 g) and lithium chloride (10 g) in THF (120 mL) were added dibromoethane (2 mL) and chlorotrimethylsilane (3 mL) at 70° C. under argon atmosphere. The mixture was stirred at 70° C. for 10 min. A solution of 1-Boc-3-iodoazetidine (67 g) in THF (120 mL) was added dropwise to the mixture at RT. The reaction mixture was stirred for 1 hr. To the mixture were added a solution of 1-(4-ethylbenzyloxy)-4-iodo-2-methoxybenzene (58.1 g) prepared in (1) in THF (120 mL) and bis(triphenylphosphine)palladium (II) dichloride (0.49 g). The reaction mixture was stirred at RT for 3 hr. Saturated aqueous $NH_4Cl$ was added to the reaction mixture and the mixture was extracted with ethyl acetate. The organic layer was dried over $MgSO_4$. The solvent was removed under reduced pressure. The residue was purified by silica gel chromatography (Developing solvent: hexane/ethyl acetate=4/1) to give the title compound (32.4 g, 52%).

$^1$H-NMR (400 MHz, DMSO-$d_6$) δ: 7.29 (2H, d, J=8.35 Hz), 7.08 (2H, d, J=8.12 Hz), 6.97 (1H, d, J=8.12 Hz), 6.90 (1H, d, J=2.09 Hz), 6.80 (1H, dd, J=8.35, 1.86 Hz), 4.99 (2H, s), 4.20 (2H, t, J=8.12 Hz), 3.82 (2H, t, J=6.84 Hz), 3.77 (3H, s), 3.74-3.69 (1H, m), 1.40 (9H, s), 2.59 (2H, q, J=7.58 Hz), 1.17 (3H, t, J=7.54 Hz).

(3) 3-[4-(4-Ethylbenzyloxy)-3-methoxyphenyl]azetidine methanesulfonate

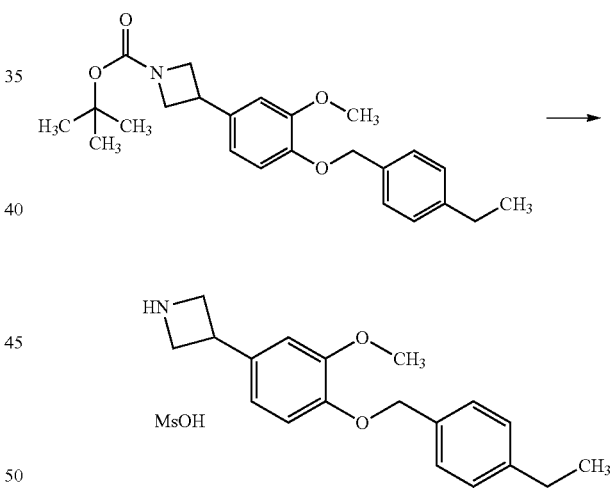

To a solution of tert-butyl 3-[4-(4-ethylbenzyloxy)-3-methoxyphenyl]azetidine-1-carboxylate (32.4 g) prepared in (2) in ethanol (160 mL) was added methanesulfonic acid (6.3 mL). The reaction mixture was stirred at 80° C. for 3 hr. Ethyl acetate (320 mL) was added to the reaction mixture. The precipitated solid was collected on a filter and dried to give the title compound (24.3 g, 77%).

$^1$H-NMR (400 MHz, DMSO-$d_6$) δ: 8.79 (1H, br s), 8.51 (1H, br s), 7.35 (2H, d, J=7.65 Hz), 7.23 (2H, d, J=7.65 Hz), 7.07-7.02 (2H, m), 6.89 (1H, d, J=8.12 Hz), 5.05 (2H, s), 4.30-4.14 (2H, m), 4.13-3.97 (3H, m), 3.81 (3H, s), 2.62 (2H, q, J=7.58 Hz), 2.33 (2H, d, J=3.71 Hz), 1.19 (3H, t, J=7.54 Hz).

(4) {3-[4-(4-Ethylbenzyloxy)-3-methoxyphenyl]azetidin-1-yl}-(4-hydroxypyridin-2-yl)-methanone

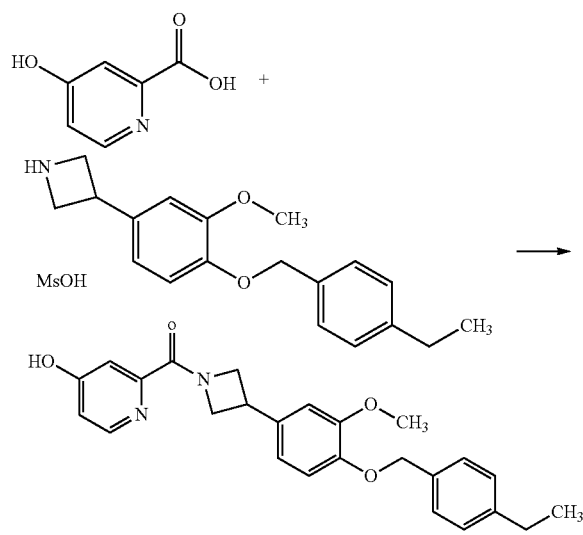

To a solution of 3-[4-(4-ethylbenzyloxy)-3-methoxyphenyl]azetidine methanesulfonate (61.3 g) prepared in (3), 4-hydroxypyridine-2-calboxylic acid (22.8 g), WSC.HCl (36 g) and HOBt.H$_2$O (29 g) in DMF (300 mL) was added triethylamine (23 mL). The reaction mixture was stirred at RT for 5 hr. Ethyl acetate, THF and water were added to the reaction mixture. The organic layer was washed with saturated aqueous NaHCO$_3$ and water, and then pressure. Ethyl acetate (300 mL) was added to the residue and then the precipitated solid was collected on a filter and dried to give the title compound (51 g, 78%).

$^1$H-NMR (400 MHz, DMSO-d$_6$) δ: 10.89 (1H, s), 8.30 (1H, d, =5.29 Hz), 7.37 (1H, s), 7.34 (2H, d, J=8.16 Hz), 7.22 (2H, d, J=8.16 Hz), 6.99 (2H, d, J=8.38 Hz), 6.86 (2H, d, J=7.72 Hz), 5.01 (2H, s), 4.94 (1H, t, J=9.59 Hz), 4.53 (1H, dd, J=10.14, 6.40 Hz), 4.42 (1H, t, J=9.48 Hz), 4.04 (1H, dd, J=9.92, 6.62 Hz), 3.91-3.83 (1H, m), 3.78 (3H, s), 2.60 (2H, q, J=7.72 Hz), 1.17 (3H, t, J=7.61 Hz).

MASS 419 (M+1).

Example 5

{3-[4-(4-Ethylbenzyloxy)-3-methoxyphenyl]azetidin-1-yl}-[4-(2-hydroxyethoxy)pyridin-2-yl]-methanone {3-[4-(4-Ethylbenzyloxy)-3-methoxyphenyl]azetidin-1-yl}-[4-(2-hydroxyethoxy)pyridin-2-yl]-methanone

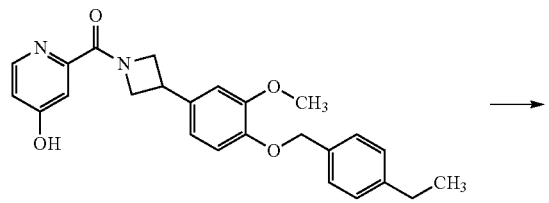

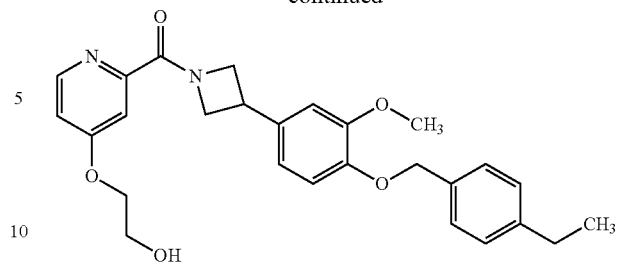

To a suspension of {3-[4-(4-ethylbenzyloxy)-3-methoxyphenyl]azetidin-1-yl}-(4-hydroxypyridin-2-yl)-methanone (9.6 g) prepared in Example 4 (4) and K$_2$CO$_3$ (40 g) in DMF (90 mL) was added 2-bromoethanol (9.6 mL). The reaction mixture was stirred at 80° C. for 11 hr. Water was added to the reaction mixture and the mixture was extracted with ethyl acetate. The organic layer was dried over Na$_2$SO$_4$. The solvent was removed under reduced pressure. Diisopropyl ether was added to the residue. The precipitated solid was collected on a filter and dried to give the title compound (8.4 g, 80%).

$^1$H-NMR (400 MHz, CDCl$_3$) δ: 8.38 (1H, d, J=5.51 Hz), 7.69 (1H, d, J=2.43 Hz), 7.34 (2H, d, J=7.94 Hz), 7.19 (2H, d, J=8.16 Hz), 6.91-6.81 (4H, m), 5.11 (2H, s), 5.08 (1H, t, J=9.70 Hz), 4.69 (1H, dd, J=10.81, 6.40 Hz), 4.59 (1H, t, J=9.70 Hz), 4.26 (1H, dd, J=10.59, 6.62 Hz), 4.20 (2H, t, J=4.52 Hz), 4.03-3.99 (2H, m), 3.89 (3H, s), 3.86-3.80 (1H, m), 2.64 (2H, q, J=7.57 Hz), 2.01 (1H, t, J=6.18 Hz), 1.23 (3H, t, J=7.57 Hz).

MASS 464 (M+1).

Example 6

{4-[2-((3R,4R)-3,4-Dihydroxypyrrolidin-1-yl)-ethoxy]-pyridin-2-yl}-{3-[4-(4-ethylbenzyloxy)-3-methoxyphenyl]-azetidin-1-yl}-methanone (1) 2-(2-{3-[4-(4-Ethylbenzyloxy)-3-methoxyphenyl]-azetidine-1-carbonyl}pyridin-4-yloxy)ethyl methanesulfonate

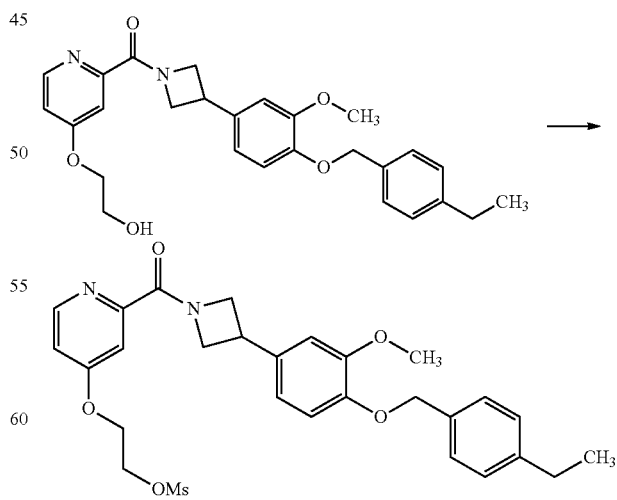

To a solution of {3-[4-(4-ethylbenzyloxy)-3-methoxyphenyl]azetidin-1-yl}-[4-(2-hydroxyethoxy)pyridin-2-yl]-methanone (8.49 g) prepared in Example 5 in THF (45 mL)

were added triethylamine (2.8 mL) and methanesulfonyl chloride (1.5 mL) at 0° C. The reaction mixture was stirred at RT for 30 min. Water was added to the reaction mixture and the mixture was extracted with ethyl acetate. The organic layer was washed with water and brine, and then dried over Na₂SO₄. The solvent was removed under reduced pressure. Diisopropyl ether was added to the residue. The precipitated solid was collected on a filter and dried to give the title compound (9.5 g, 97%).

¹H-NMR (400 MHz, DMSO-d₆) δ: 8.45 (1H, d, J=5.73 Hz), 7.52 (1H, d, J=2.65 Hz), 7.34 (2H, d, J=8.16 Hz), 7.22 (2H, d, J=8.16 Hz), 7.15 (1H, dd, J=5.73, 2.65 Hz), 7.05-6.95 (2H, m), 6.87 (1H, dd, J=8.38, 1.98 Hz), 5.01 (2H, s), 4.96 (1H, t, J=9.59 Hz), 4.57-4.52 (3H, m), 4.50-4.40 (3H, m), 4.09-4.04 (1H, m), 3.93-3.85 (1H, m), 3.78 (3H, s), 3.26 (3H, d, J=8.16 Hz), 2.60 (2H, q, J=7.57 Hz), 1.17 (3H, t, J=7.61 Hz).

(2) {4-[2-((3R,4R)-3,4-Dihydroxypyrrolidin-1-yl)ethoxy]-pyridin-2-yl}-{3-[4-(4-ethylbenzyloxy)-3-methoxyphenyl]-azetidin-1-yl}-methanone

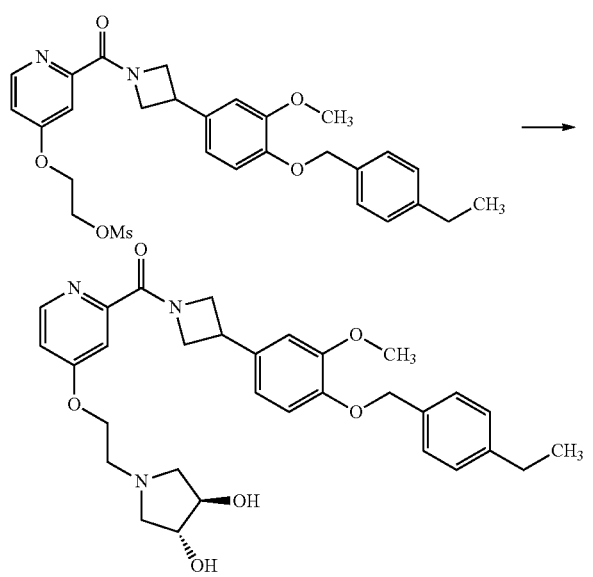

To a mixed solution of (3R,4R)-pyrrolidine-3,4-diol monohydrochloride (2.1 g) in 1-propanol (60 mL)/water (2.0 mL) was added Na₂CO₃ (4.0 g). The mixture was stirred at 60° C. for 1 hr. To the mixture was added 2-(2-{3-[4-(4-ethylbenzyloxy)-3-methoxyphenyl]azetidine-1-carbonyl}pyridin-4-yloxy)ethyl methanesulfonate (6.7 g) prepared in (1). The reaction mixture was stirred at 100° C. for 10 hr. Water was added to the reaction mixture and the mixture was extracted with ethyl acetate. The organic layer was washed with water and brine, and then dried over Na₂SO₄. The solvent was removed under reduced pressure. The residue was purified by silica gel chromatography (Developing solvent: chloroform/methanol=40/1 to 5/1) to give the title compound (4.7 g, 70%).

¹H-NMR (400 MHz, DMSO-d₆) δ: 8.41 (1H, d, J=5.57 Hz), 7.47 (1H, d, J=2.55 Hz), 7.33 (2H, d, J=8.12 Hz), 7.21 (2H, d, J=8.35 Hz), 7.09 (1H, dd, J=5.68, 2.67 Hz), 6.98 (1H, d, J=10.44 Hz), 6.97 (1H, s), 6.86 (1H, dd, J=8.35, 2.09 Hz), 5.00 (2H, s), 4.95 (1H, t, J=9.39 Hz), 4.84 (2H, d, J=4.41 Hz), 4.53 (1H, dd, J=10.09, 6.61 Hz), 4.44 (1H, t, J=9.62 Hz), 4.16 (2H, t, J=5.68 Hz), 4.06 (1H, dd, J=10.09, 6.61 Hz), 3.91-3.81 (3H, m), 3.77 (3H, s), 2.85 (2H, dd, J=9.51, 5.80 Hz), 2.79-2.73 (2H, m), 2.59 (2H, q, J=7.58 Hz), 2.41 (2H, dd, J=9.74, 4.17 Hz), 1.17 (3H, t, J=7.65 Hz).

MASS 548 (M+1).

Example 7

4-[2-(2-{3-[4-(4-ethylbenzyloxy)-3-methoxyphenyl]azetidine-1-carbonyl}pyridin-4-yloxy)ethyl]piperazin-2-one 4-[2-(2-{3-[4-(4-ethylbenzyloxy)-3-methoxyphenyl]-azetidine-1-carbonyl}pyridin-4-yloxy)ethyl]piperazin-2-one

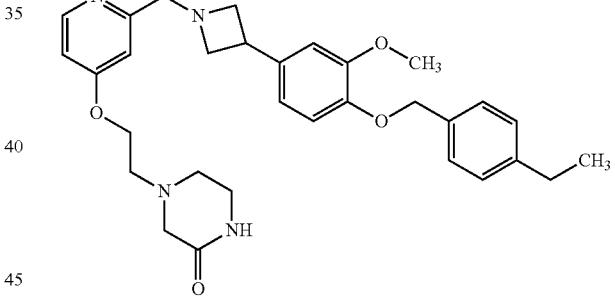

To a solution of 2-(2-{3-[4-(4-ethylbenzyloxy)-3-methoxyphenyl]azetidine-1-carbonyl}-pyridin-4-yloxy)ethyl methanesulfonate (0.4 g) prepared in Example 6 (1) in 1-propanol (5.0 mL) was added 2-piperazinone (0.22 g). The reaction mixture was stirred at 100° C. for 18 hr. The reaction mixture was concentrated in vacuo. The residue was purified by silica gel chromatography (Developing solvent: chloroform/methanol=8/1 to 7/1) to give the title compound (0.3 g, 76%).

¹H-NMR (400 MHz, CDCl₃) δ: 8.38 (1H, d, J=5.57 Hz), 7.68 (1H, d, J=2.55 Hz), 7.35 (2H, d, J=8.12 Hz), 7.20 (2H, d, J=8.12 Hz), 6.90-6.82 (4H, m), 5.86 (1H, br s), 5.12 (2H, s), 5.09 (1H, t, J=9.74 Hz), 4.70 (1H, dd, J=10.67, 6.72 Hz), 4.60 (1H, t, J=9.74 Hz), 4.26 (1H, dd, J=10.67, 6.72 Hz), 4.24 (2H, t, J=5.33 Hz), 3.90 (3H, s), 3.89-3.81 (1H, m), 3.43-3.40 (2H, m), 3.31 (2H, s), 2.93 (2H, t, J=5.33 Hz), 2.83 (2H, t, J=5.45 Hz), 2.65 (2H, q, J=7.65 Hz), 1.23 (3H, t, J=7.65 Hz).

MASS 545 (M+1).

Example 8

{4-[2-((3S,4S)-3,4-Dihydroxypyrrolidin-1-yl)ethoxy]pyridin-2-yl}-{3-[4-(4-ethylbenzyloxy)-3-methoxyphenyl]azetidin-1-yl}-methanone {4-[2-((3S,4S)-3,4-Dihydroxypyrrolidin-1-yl)ethoxy]pyridin-2-yl}-{3-[4-(4-ethylbenzyloxy)-3-methoxyphenyl]azetidin-1-yl}-methanone

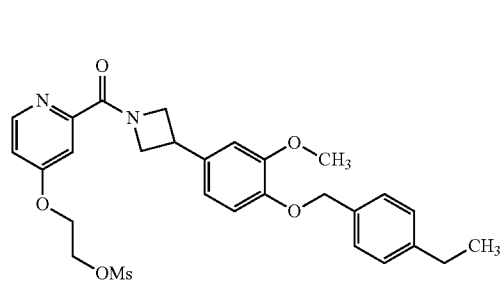

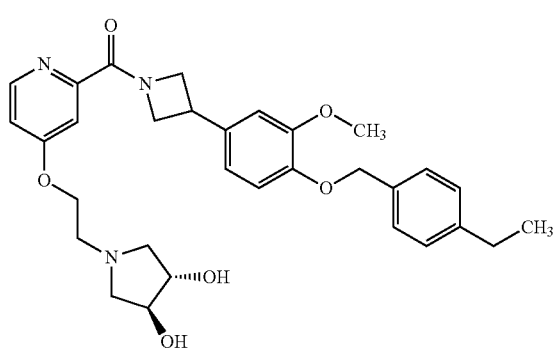

a solution of (3S,4S)-pyrrolidine-3,4-diol monohydrochloride (0.14 g) in 1-propanol (3.0 mL) was added aqueous 4 N NaOH (0.25 mL). The mixture was stirred at RT for 1 hr. To the mixture was added 2-(2-{3-[4-(4-ethylbenzyloxy)-3-methoxyphenyl]azetidine-1-carbonyl}pyridin-4-yloxy)ethyl methanesulfonate (0.1 g) prepared in Example 6 (1). The reaction mixture was stirred at 100° C. for 5 hr. Water was added to the reaction mixture. The precipitated solid was collected on a filter and dried to give the title compound (0.05 g, 50%).

$^1$H-NMR (400 MHz, DMSO-$d_6$) δ: 8.41 (1H, d, J=5.57 Hz), 7.47 (1H, d, J=2.55 Hz), 7.33 (2H, d, J=8.12 Hz), 7.21 (2H, d, J=8.35 Hz), 7.09 (1H, dd, J=5.68, 2.67 Hz), 6.98 (1H, d, J=10.44 Hz), 6.97 (1H, s), 6.86 (1H, dd, J=8.35, 2.09 Hz), 5.00 (2H, s), 4.95 (1H, t, J=9.39 Hz), 4.84 (2H, d, J=4.41 Hz), 4.53 (1H, dd, J=10.09, 6.61 Hz), 4.44 (1H, t, J=9.62 Hz), 4.16 (2H, t, J=5.68 Hz), 4.06 (1H, dd, J=10.09, 6.61 Hz), 3.91-3.81 (3H, m), 3.77 (3H, s), 2.85 (2H, dd, J=9.51, 5.80 Hz), 2.79-2.73 (2H, m), 2.59 (2H, q, J=7.58 Hz), 2.41 (2H, dd, J=9.74, 4.17 Hz), 1.17 (3H, t, J=7.65 Hz).

MASS 548 (M+1).

Example 9

{3-[4-(4-Cyclopropylbenzyloxy)-3-methoxyphenyl]azetidin-1-yl}-{4-[(R)-2-hydroxy-3-(4-methylpiperazin-1-yl)propoxy]-pyridin-2-yl}-methanone (1) {3-[4-(4-Cyclopropylbenzyloxy)-3-methoxyphenyl]-azetidin-1-yl}-[4-((R)-1-oxiranylmethoxy)pyridin-2-yl]-methanone

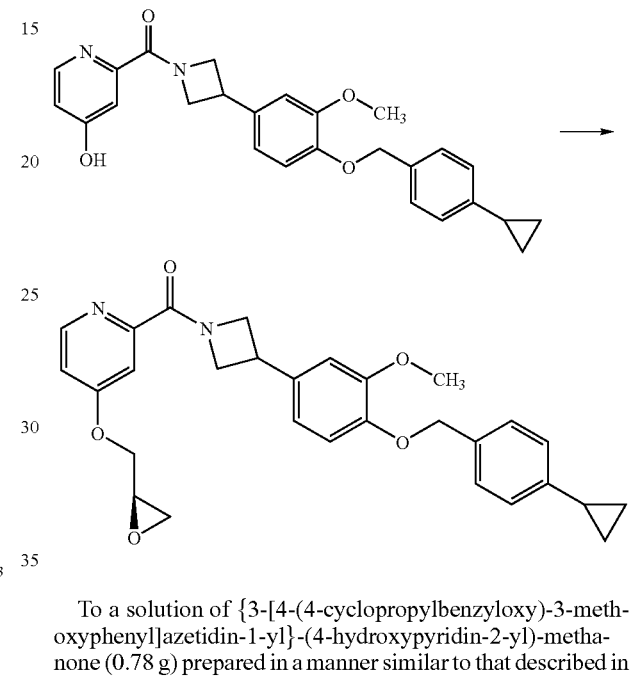

To a solution of {3-[4-(4-cyclopropylbenzyloxy)-3-methoxyphenyl]azetidin-1-yl}-(4-hydroxypyridin-2-yl)-methanone (0.78 g) prepared in a manner similar to that described in Example 4 (4) using 3-[4-(4-cyclopropylbenzyloxy)-3-methoxyphenyl]azetidine monohydrochloride in DMSO (15 mL) were added (R)-(−)-glycidyl nosylate (0.70 g) and $K_2CO_3$ (0.38 g). The reaction mixture was stirred at RT for 12 hr. Water was added to the reaction mixture and the mixture was extracted with ethyl acetate. The organic layer was dried over $MgSO_4$. The solvent was removed under reduced pressure. The residue was purified by silica gel chromatography (Developing solvent: chloroform/methanol=97/3) to give the title compound (0.83 g, 94%).

(2) {3-[4-(4-Cyclopropylbenzyloxy)-3-methoxyphenyl]-azetidin-1-yl}-{4-[(R)-2-hydroxy-3-(4-methylpiperazin-1-yl)propoxy]pyridin-2-yl}-methanone

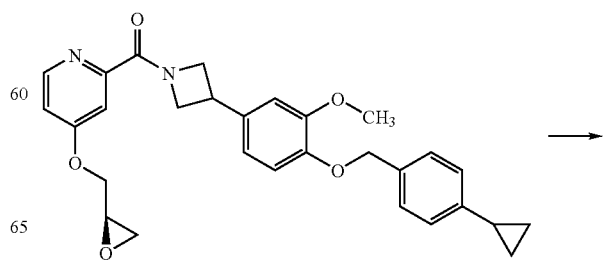

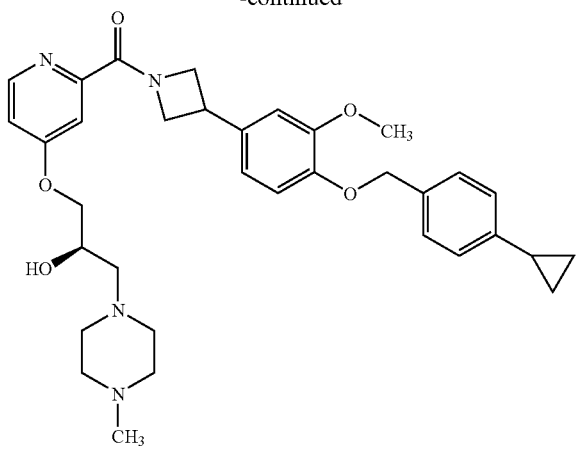

To a mixed solution of {3-[4-(4-cyclopropylbenzyloxy)-3-methoxyphenyl]azetidin-1-yl}-[4-((R)-1-oxiranylmethoxy)-pyridin-2-yl]-methanone (0.45 g) prepared in (1) in acetonitrile (4.0 mL)/water (1.0 mL) was added 1-methylpiperazine (1.0 mL). The reaction mixture was stirred at RT for 12 hr. The reaction mixture was concentrated in vacuo. The residue was purified by silica gel chromatography (Developing solvent: chloroform/methanol=9/1) to give the title compound (0.43 g, 80%).

$^1$H-NMR (400 MHz, DMSO-d$_6$) δ: 8.41 (1H, d, J=5.80 Hz), 7.49 (1H, d, J=2.55 Hz), 7.29 (2H, d, J=8.12 Hz), 7.10-7.07 (3H, m), 6.99-6.97 (2H, m), 6.86 (1H, dd, J=8.35, 1.86 Hz), 4.99 (2H, s), 4.98-4.93 (2H, m), 4.54 (1H, dd, J=10.20, 6.49 Hz), 4.44 (1H, t, J=9.51 Hz), 4.13 (1H, dd, J=9.74, 2.78 Hz), 4.08-3.98 (3H, m), 3.92-3.84 (1H, m), 3.77 (3H, s), 2.46-2.25 (10H, br m), 2.13 (3H, s), 1.94-1.88 (1H, m), 0.96-0.92 (2H, m), 0.68-0.64 (2H, m).

MASS 587 (M+1).

Example 10

{3-[4-(4-Ethylbenzyloxy)-3-methoxyphenyl]-3-hydroxyazetidin-1-yl}pyridin-2-yl-methanone (1)
4-Bromo-1-(4-ethylbenzyloxy)-2-methoxybenzene

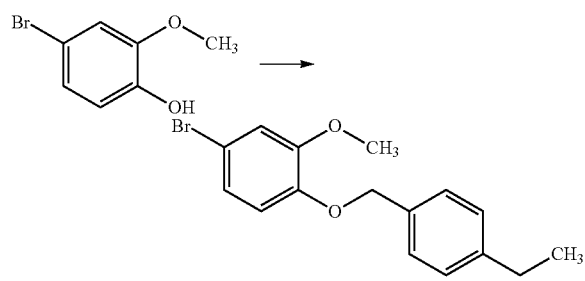

To a solution of 4-bromo-2-methoxyphenol (7.0 g) and ethylbenzyl chloride (5.6 g) in DMF (35 mL) was added K$_2$CO$_3$ (5.7 g). The reaction mixture was stirred at 80° C. for 1 hr. Water was added to the reaction mixture. The precipitated solid was collected on a filter and dried to give the title compound (11 g, 99%).

$^1$H-NMR (400 MHz, DMSO-d$_6$) δ: 7.33 (2H, d, J=8.12 Hz), 7.22 (2H, d, J=8.12 Hz), 7.12 (1H, d, J=2.32 Hz), 7.03 (1H, dd, J=8.58, 2.32 Hz), 6.97 (1H, d, J=8.58 Hz), 5.02 (2H, s), 3.77 (3H, s), 2.60 (2H, q, J=7.58 Hz), 1.17 (3H, t, J=7.65 Hz).

(2) tert-Butyl 3-[4-(4-ethylbenzyloxy)-3-methoxyphenyl]-3-hydroxyazetidine-1-carboxylate

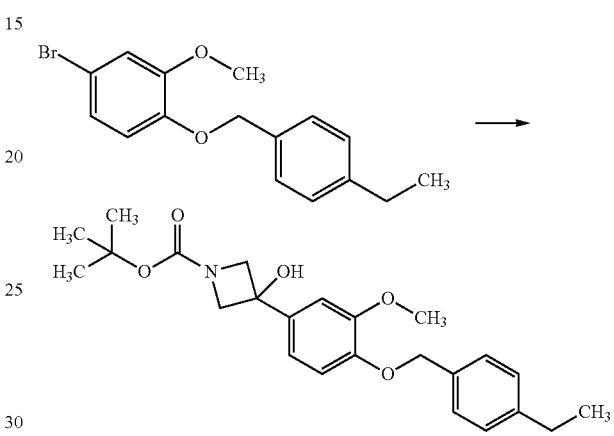

To a solution of 4-bromo-1-(4-ethylbenzyloxy)-2-methoxybenzene (1.2 g) prepared in (1) in THF (6.0 mL) was added dropwise 1.6 N n-butyllithium/hexane (2.8 mL) at −78° C. under argon atmosphere. The mixture was stirred at −78° C. for 30 min. A solution of 1-Boc-azetidin-3-one (0.64 g) in THF (6.0 mL) was added dropwise over 10 min to the mixture at −78° C. The reaction mixture was allowed to warm to RT and then stirred for 14 hr. Water was added to the reaction mixture and the mixture was extracted with ethyl acetate. The organic layer was dried over MgSO$_4$. The solvent was removed under reduced pressure. The residue was purified by silica gel chromatography (Developing solvent: hexane/ethyl acetate=3/1 to 1/1) to give the title compound (0.88 g, 57%).

$^1$H-NMR (400 MHz, DMSO-d$_6$) δ: 7.34 (2H, d, J=7.88 Hz), 7.22 (2H, d, J=8.12 Hz), 7.04-7.00 (2H, m), 6.96 (1H, dd, J=8.35, 2.09 Hz), 6.22 (1H, s), 5.03 (2H, s), 4.06-3.97 (4H, m), 3.77 (3H, s), 2.60 (2H, q, J=7.58 Hz), 1.40 (9H, s), 1.18 (3H, t, J=7.54 Hz).

(3) 3-[4-(4-Ethylbenzyloxy)-3-methoxyphenyl]-azetidin-3-ol hydrochloride

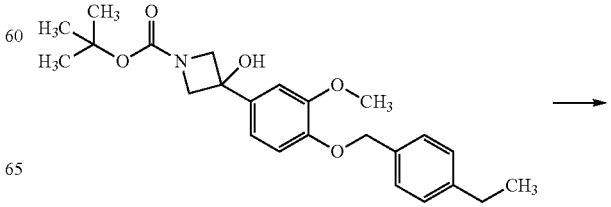

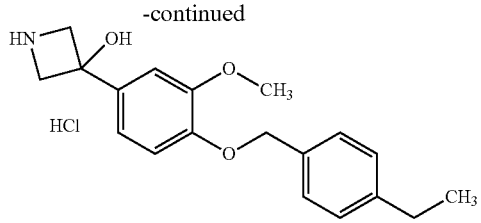

To a solution of tert-butyl 3-[4-(4-ethylbenzyloxy)-3-methoxyphenyl]-3-hydroxyazetidine-1-carboxylate (0.88 g) prepared in (2) in ethyl acetate (4.0 mL) was added a solution of 4 N HCl/ethyl acetate (4.0 mL) at 0° C. The reaction mixture was stirred at 0° C. for 3 hr. Ethyl acetate was added to the reaction mixture. The precipitated solid was collected on a filter and dried to give the title compound (0.53 g, 71%).

$^1$H-NMR (400 MHz, DMSO-$d_6$) δ: 9.23 (1H, br s), 9.01 (1H, br s), 7.34 (2H, d, J=8.12 Hz), 7.22 (2H, d, J=8.12 Hz), 7.14 (1H, s), 7.09-6.99 (2H, m), 6.58 (1H, s), 5.08-5.06 (2H, m), 4.32-4.26 (2H, m), 4.06-4.01 (2H, m), 3.81 (3H, s), 2.60 (2H, q, J=7.65 Hz), 1.17 (3H, t, J=7.54 Hz).

(4) {3-[4-(4-Ethylbenzyloxy)-3-methoxyphenyl]-3-hydroxyazetidin-1-yl}-pyridin-2-ylmethanone

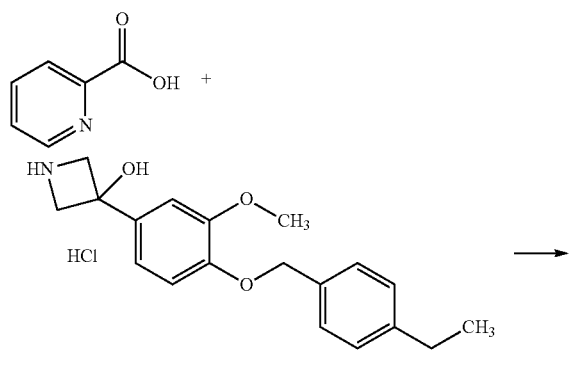

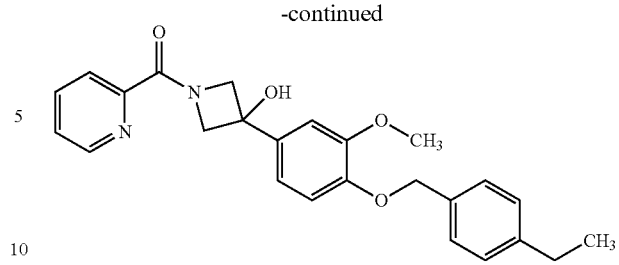

To a solution of 3-[4-(4-ethylbenzyloxy)-3-methoxyphenyl]-azetidin-3-ol hydrochloride (0.50 g) prepared in (3), 2-pyridinecalboxylic acid (0.070 g), WSC.HCl (0.12 g) and HOBt.H$_2$O (0.092 g) in DMF (3.0 mL) was added triethylamine (0.070 mL). The reaction mixture was stirred at RT for 15 hr. Water was added to the reaction mixture and the mixture was extracted with ethyl acetate. The organic layer was dried over MgSO$_4$. The solvent was removed under reduced pressure. A mixed solvent of chloroform/hexane was added the residue. The precipitated solid was collected on a filter and dried to give the title compound (0.15 g, 74%).

$^1$H-NMR (400 MHz, DMSO-$d_6$) δ: 8.64-8.61 (1H, m), 8.01-7.95 (2H, m), 7.56-7.53 (1H, m), 7.34 (2H, d, J=8.12 Hz), 7.22 (2H, d, J=8.12 Hz), 7.11 (1H, s), 7.02-7.01 (2H, m), 6.31 (1H, s), 5.03 (2H, s), 4.80 (1H, d, J=11.59 Hz), 4.68 (1H, d, J=10.67 Hz), 4.34 (1H, d, J=11.59 Hz), 4.19 (1H, d, J=10.67 Hz), 3.78 (3H, s), 2.60 (2H, q, J=7.58 Hz), 1.17 (3H, t, J=7.54 Hz).

MASS 419 (M+1).

Example 11

[4-(2-Hydroxyethoxy)pyridin-2-yl]-{3-[3-methoxy-4-(spiro[4.4]-non-1-en-2-ylmethoxy)phenyl]azetidin-1-yl}-methanone (1) [3-(4-Hydroxy-3-methoxyphenyl)azetidin-1-yl]-{4-[2-(tetrahydropyran-2-yloxy)ethoxy]pyridin-2-yl}-methanone

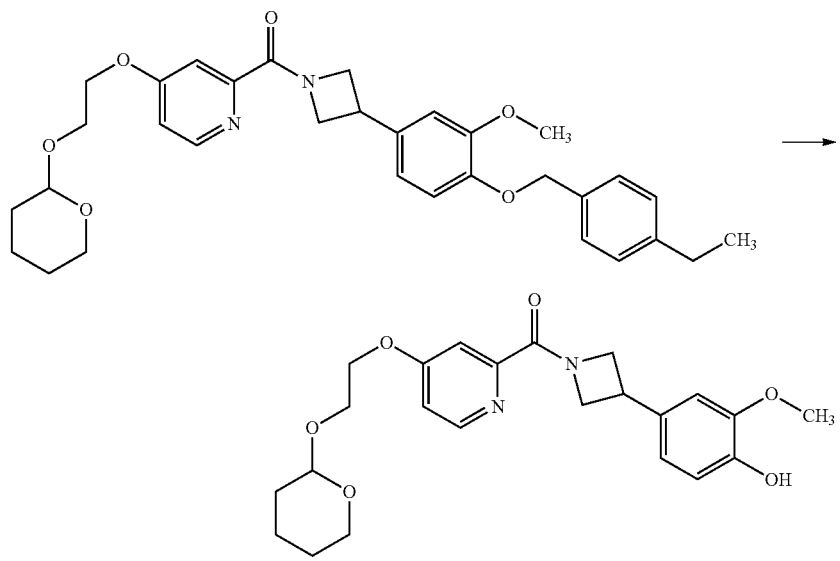

To a solution of {3-[4-(4-ethylbenzyloxy)-3-methoxyphenyl]azetidin-1-yl}-{4-[2-(tetrahydropyran-2-yloxy)ethoxy]pyridin-2-yl}-methanone (1.5 g) obtained in a manner similar to Example 5 in THF (5 mL)/methanol (5 mL) was added 10% palladium carbon (50% wet with water) (0.15 g). The reaction mixture was stirred under hydrogen atmosphere at RT for 22 hr. The reaction mixture was filtered using Celite. The filtrate was concentrated in vacuo to give the crude title compound.

(2) [4-(2-Hydroxyethoxy)pyridin-2-yl]-[3-(4-hydroxy-3-methoxyphenyl)azetidin-1-yl]-methanone

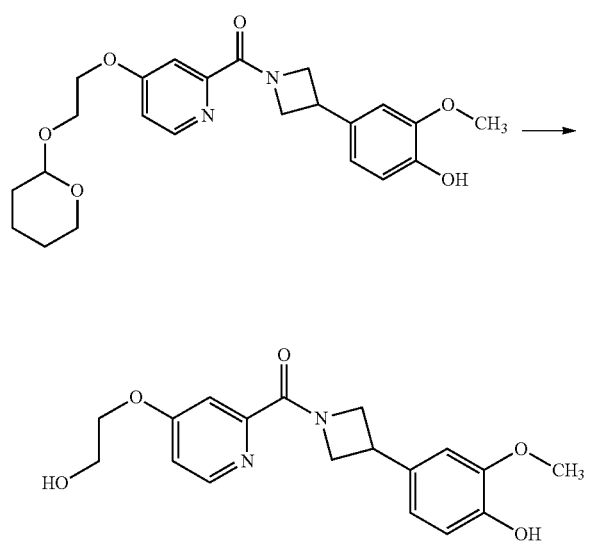

To a solution of the crude [3-(4-hydroxy-3-methoxyphenyl)azetidin-1-yl]-{4-[2-(tetrahydropyran-2-yloxy)ethoxy]pyridin-2-yl}-methanone prepared in (1) in THF (5.0 mL) was added 1 N hydrochloric acid (5.0 mL). The reaction mixture was stirred at RT for 13 hr. To the reaction mixture were added aqueous 1 N NaOH and saturated aqueous NaHCO$_3$ and then the mixture was extracted with ethyl acetate. The organic layer was dried over MgSO$_4$. The solvent was removed under reduced pressure. The residue was purified by silica gel chromatography (Developing solvent: chloroform/methanol=9/1) to give the title compound (0.70 g, 75%).

$^1$H-NMR (400 MHz, DMSO-d$_6$) δ: 8.87 (1H, s), 8.42 (1H, d, J=5.57 Hz), 7.49 (1H, d, J=2.55 Hz), 7.10 (1H, dd, J=5.68, 2.67 Hz), 6.92 (1H, d, J=1.86 Hz), 6.78-6.73 (2H, m), 4.94 (2H, t, J=9.28 Hz), 4.52 (1H, dd, J=10.20, 6.49 Hz), 4.43 (1H, t, J=9.51 Hz), 4.14 (2H, t, J=4.87 Hz), 4.04 (1H, dd, J=10.09, 6.61 Hz), 3.88-3.80 (1H, m), 3.77 (3H, s), 3.74 (2H, q, J=4.72 Hz).

(3) [4-(2-Hydroxyethoxy)pyridin-2-yl]-{3-[3-methoxy-4-(spiro[4.4]non-1-en-2-ylmethoxy)phenyl]azetidin-1-yl}-methanone

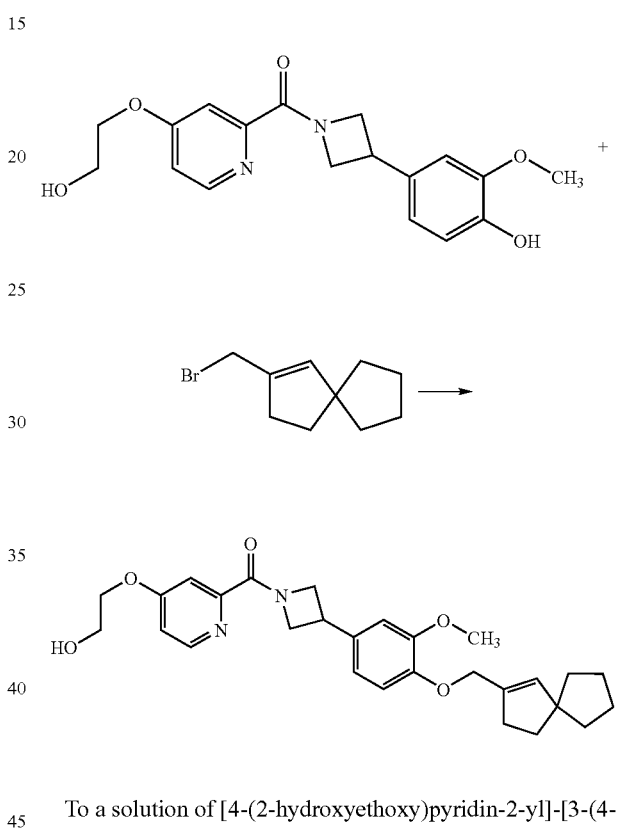

To a solution of [4-(2-hydroxyethoxy)pyridin-2-yl]-[3-(4-hydroxy-3-methoxyphenyl)azetidin-1-yl]-methanone (0.090 g) prepared in (2) and 2-bromomethylspiro[4.4]-1-nonene (0.056 g) in DMF (3.0 mL) were added K$_2$CO$_3$ (0.043 g) and potassium iodide (0.0010 g). The reaction mixture was stirred at RT for 13 hr. Water was added to the reaction mixture and the mixture was extracted with ethyl acetate. The organic layer was dried over MgSO$_4$. The solvent was removed under reduced pressure. Diethyl ether was added to the residue. The precipitated solid was collected on a filter and dried to give the title compound (0.054 g, 43%).

$^1$H-NMR (400 MHz, DMSO-d$_6$) δ: 8.42 (1H, d, J=5.80 Hz), 7.49 (1H, d, J=2.55 Hz), 7.10 (1H, dd, J=5.68, 2.67 Hz), 6.97-6.92 (2H, m), 6.86 (1H, dd, J=8.35, 1.86 Hz), 5.57 (1H, s), 4.98-4.93 (2H, m), 4.55 (1H, t, J=5.10 Hz), 4.51 (2H, s), 4.45 (1H, t, J=9.62 Hz), 4.14 (2H, t, J=4.75 Hz), 4.06 (1H, dd, J=10.09, 6.61 Hz), 3.92-3.84 (1H, m), 3.78 (3H, s), 3.74 (2H, q, J=5.02 Hz), 2.34 (2H, t, J=6.49 Hz), 1.74 (2H, t, J=7.19 Hz), 1.62-1.56 (4H, br m), 1.52-1.43 (4H, br m).

MASS 479 (M+1)

Example 12

{3-[3-Methoxy-4-(spiro[4.4]non-1-en-2-ylmethoxy)phenyl]-azetidin-1-yl}-{4-[2-(4-methylpiperazin-1-yl)ethoxy]-pyridin-2-yl}-methanone (1) 2-(2-{3-[3-Methoxy-4-(spiro[4.4]non-1-en-2-ylmethoxy)-phenyl]azetidine-1-carbonyl}pyridin-4-yloxy)ethyl methanesulfonate

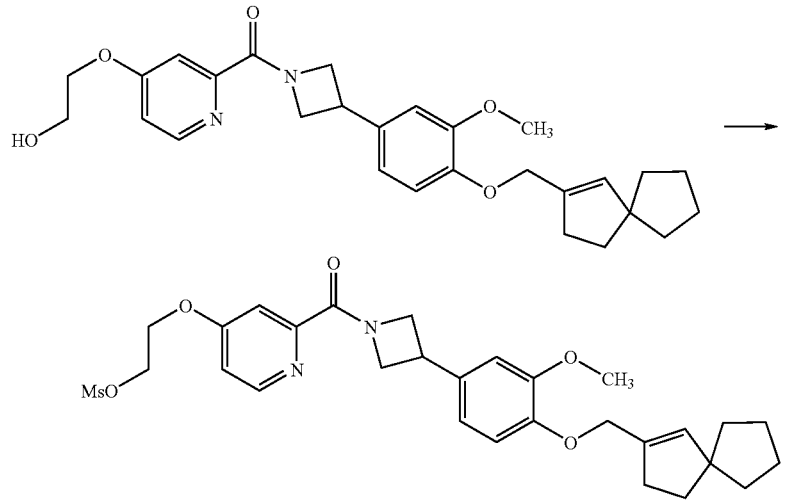

To a solution of [4-(2-hydroxyethoxy)-pyridin-2-yl]-{3-[3-methoxy-4-(spiro[4.4]non-1-en-2-ylmethoxy)phenyl]-azetidin-1-yl}-methanone (0.040 g) prepared in Example 11 (3) in chloroform (3.0 mL) were added triethylamine (0.028 mL) and methanesulfonyl chloride (0.014 mL). The reaction mixture was stirred at RT for 30 minutes. Water was added to the reaction mixture. The organic layer was dried over MgSO$_4$. The solvent was removed under reduced pressure to give the crude title compound.

(2) {3-[3-Methoxy-4-(spiro[4.4]-1-nonen-2-ylmethoxy)phenyl]azetidin-1-yl}-{4-[2-(4-methylpiperazin-1-yl)ethoxy]pyridin-2-yl}-methanone

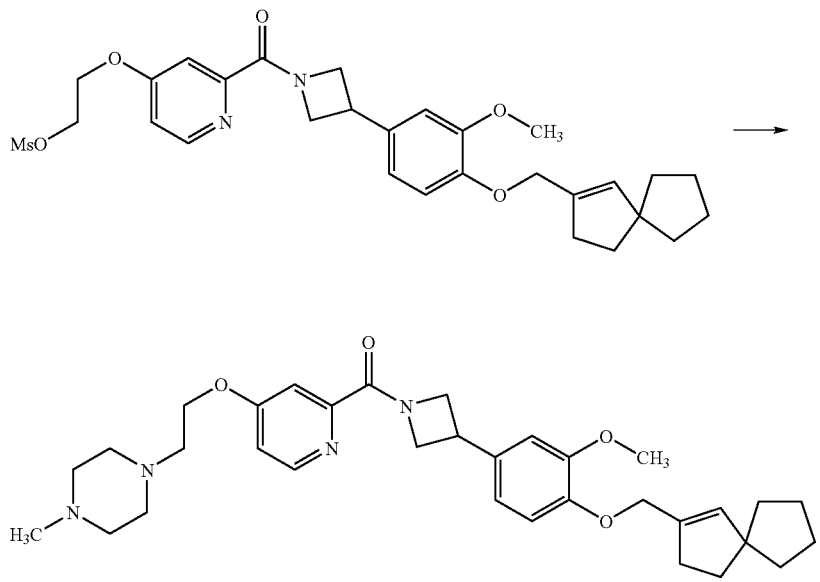

To a solution of the crude 2-(2-{3-[3-methoxy-4-(spiro[4.4]non-1-en-2-ylmethoxy)phenyl]azetidine-1-carbonyl}pyridin-4-yloxy)ethyl methanesulfonate prepared in (1) in ethanol (3.0 mL) was added 1-methylpiperazine (1.0 mL). The reaction mixture was stirred at 80° C. for 2 hr. The solvent was removed under reduced pressure. The residue was purified by preparative thin-layer chromatography (Developing solvent: chloroform/methanol=5/1) to give the title compound (0.034 g, 73%).

$^1$H-NMR (400 MHz, DMSO-$d_6$) δ: 8.42 (1H, d, J=5.80 Hz), 7.49 (1H, d, J=2.55 Hz), 7.10 (1H, dd, J=5.68, 2.67 Hz), 6.96 (1H, d, J=2.09 Hz), 6.93 (1H, d, J=8.12 Hz), 6.86 (1H, dd, J=8.35, 1.86 Hz), 5.57 (1H, s), 4.98-4.93 (2H, m), 4.56-4.53 (1H, m), 4.51 (2H, s), 4.45 (1H, t, J=9.62 Hz), 4.14 (2H, t, J=4.75 Hz), 4.06 (1H, dd, J=10.09, 6.61 Hz), 3.92-3.84 (1H, m), 3.78 (3H, s), 3.74 (2H, q, J=5.02 Hz), 2.34 (2H, t, J=6.49 Hz), 1.74 (2H, t, J=7.19 Hz), 1.62-1.55 (4H, m), 1.52-1.43 (4H, m).

MASS 561 (M+1).

In addition, 2-bromomethyl-spiro[4,4]non-1-ene was prepared as follows.

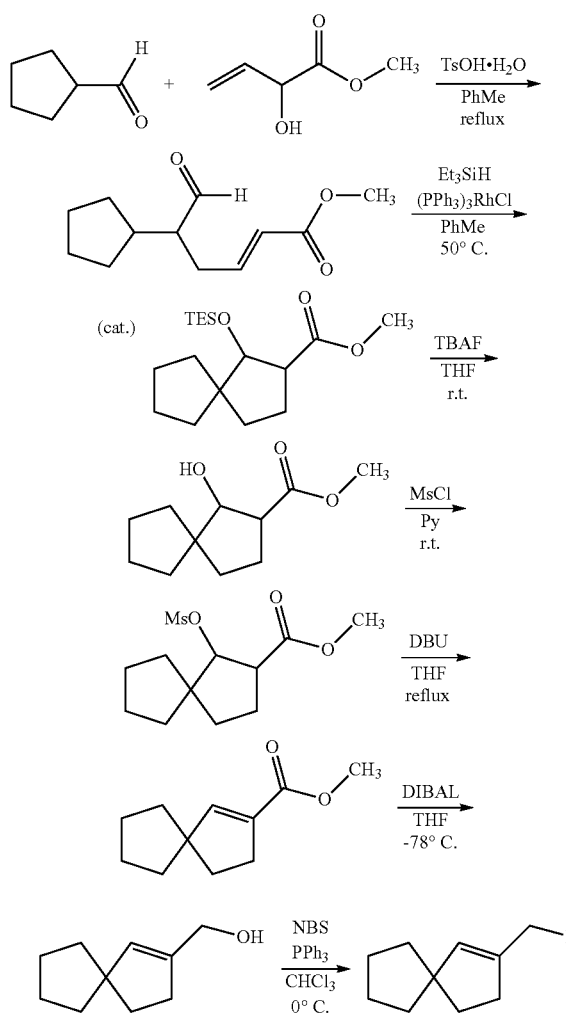

Example 13

[4-(2,3-Dihydroxypropyl)pyridin-2-yl]-{3-[4-(4-ethylbenzyloxy)-3-methoxyphenyl]azetidin-1-yl}-methanone (1) Ethyl 4-allylpyridin-2-carboxylate

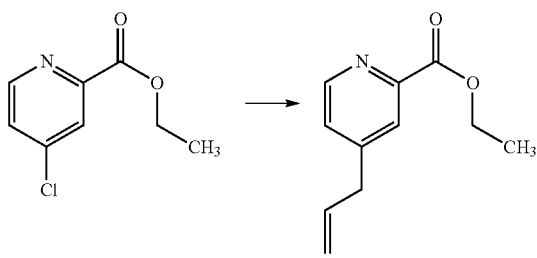

To a solution of ethyl 4-chloropyridin-2-carboxylate (0.37 g) and allyltributyltin (IV) (0.86 mL) in toluene (5.0 mL) was added tetrakis(triphenylphosphine)palladium (0) (0.12 g). The reaction mixture was stirred under nitrogen atmosphere at 120° C. for 12 hr. The solvent of the reaction mixture was removed under reduced pressure. The residue was purified by silica gel chromatography (Developing solvent: hexane/ethyl acetate=3/2) to give the title compound (0.28 g, 73%).

$^1$H-NMR (400 MHz, CDCl$_3$) δ: 8.66 (1H, d, J=5.10 Hz), 8.00-7.99 (1H, m), 7.32-7.31 (1H, br m), 6.00-5.90 (1H, m), 5.23-5.12 (2H, m), 4.49 (2H, q, J=7.19 Hz), 3.47 (2H, d, J=6.72 Hz), 1.46 (3H, t, J=7.19 Hz).

(2) Ethyl 4-(2,3-dihydroxypropyl)pyridin-2-carboxylate

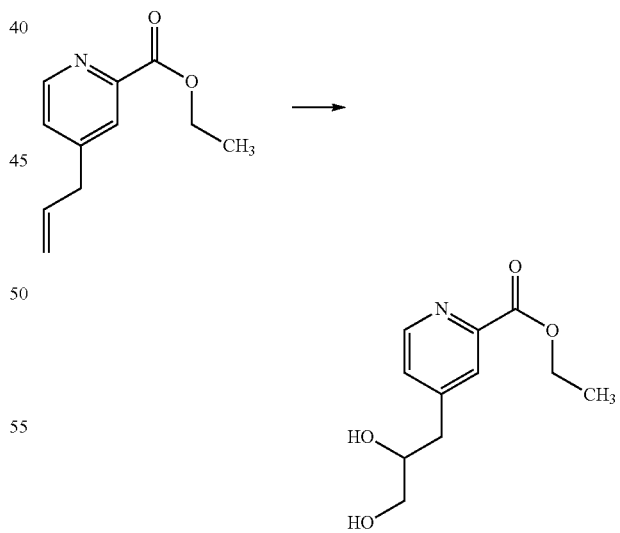

To a mixed solution of ethyl 4-allylpyridin-2-carboxylate (0.28 g) prepared in (1) in acetonitrile (9.0 mL)/water (3.0 mL) were added 4-methylmorpholine N-oxide (0.34 g) and aqueous 4% osmium tetraoxide (0.40 mL). The reaction mixture was stirred at RT for 12 hr. An excess amount of saturated aqueous Na$_2$S$_2$O$_3$ was added to the reaction mixture and the mixture was extracted with ethyl acetate. The organic layer was dried over Na₂SO₄. The solvent was removed under reduced pressure. The residue was purified by silica gel chromatography (Developing solvent: ethyl acetate/methanol=10/1) to give the title compound (0.25 g, 77%).

¹H-NMR (400 MHz, CDCl₃) δ: 8.65 (1H, d, J=4.85 Hz), 8.03-8.01 (1H, m), 7.38-7.37 (1H, br m), 4.48 (2H, q, J=7.06 Hz), 4.07-4.00 (1H, br m), 3.75-3.72 (1H, m), 3.56-3.53 (1H, m), 2.91-2.82 (2H, m), 2.42 (1H, d, J=4.41 Hz), 2.03 (1H, t, J=5.51 Hz), 1.45 (3H, t, J=7.06 Hz).

(3) 4-(2,3-Dihydroxypropyl)pyridine-2-calboxylic acid

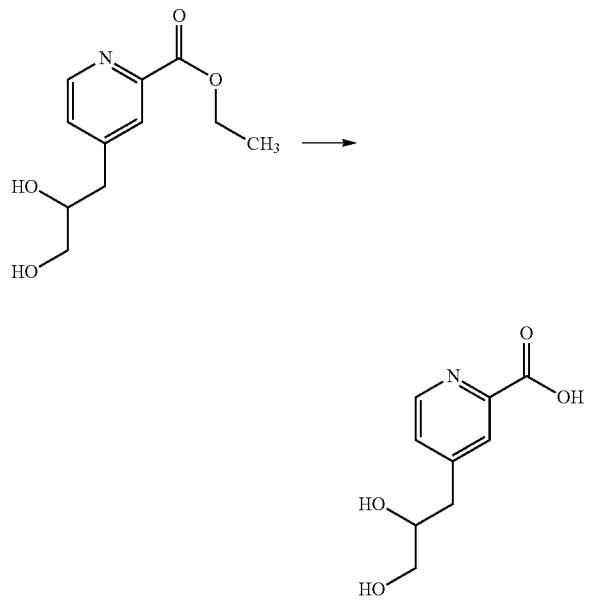

To a solution of ethyl 4-(2,3-dihydroxypropyl)-pyridine-2-carboxylate (0.040 g) prepared in (2) in methanol (1.0 mL) was added aqueous 1 N NaOH (1.0 mL). The reaction mixture was stirred at RT for 12 hr. The reaction mixture was adjusted to pH 5 using 6 N hydrochloric acid. The solvent was removed under reduced pressure to give the crude title compound.

(4) [4-(2,3-Dihydroxypropyl)pyridin-2-yl]-{3-[4-(4-ethylbenzyloxy)-3-methoxyphenyl]azetidin-1-yl}-methanone

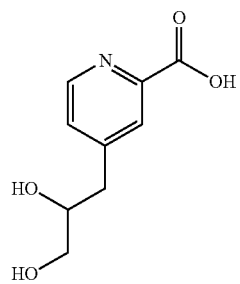

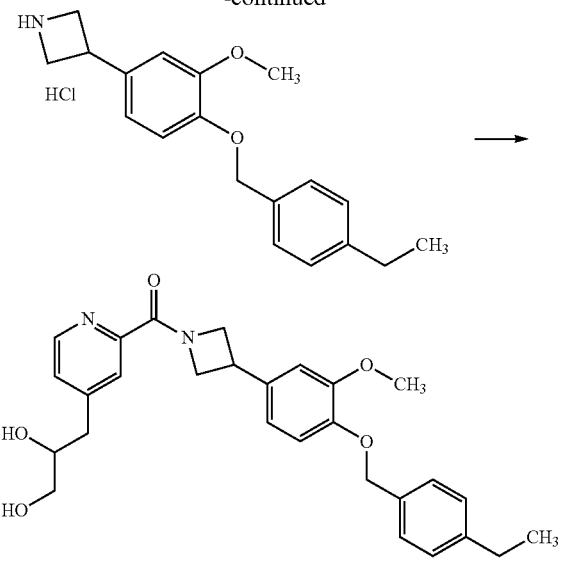

To a suspension of the crude 4-(2,3-dihydroxypropyl)-pyridine-2-calboxylic acid prepared in (3), 3-[4-(4-ethylbenzyloxy)-3-methoxyphenyl]azetidine hydrochloride (0.057 g) obtained in a similar manner to Example 4, WSC.HCl (0.036 g) and HOBt.H₂O (0.029 g) in DMF (1.5 mL) was added triethylamine (0.035 mL). The reaction mixture was stirred at RT for 12 hr. To the reaction mixture was added 1 N hydrochloric acid and the mixture was extracted with ethyl acetate. The organic layer was washed with water, saturated aqueous NaHCO₃ and brine, and then dried over MgSO₄. The solvent was removed under reduced pressure. A mixed solvent of hexane/ethyl acetate was added to the residue. The precipitated solid was collected on a filter and dried to give the title compound (0.29 g, 35%).

¹H-NMR (400 MHz, DMSO-d₆) δ: 8.48 (1H, d, J=4.85 Hz), 7.87 (1H, br s), 7.38 (1H, dd, J=4.85, 1.54 Hz), 7.34 (2H, d, J=7.94 Hz), 7.22 (2H, d, J=7.94 Hz), 6.99 (2H, d, J=8.16 Hz), 6.87 (1H, dd, J=8.38, 1.98 Hz), 5.01 (2H, s), 4.96 (1H, t, J=9.37 Hz), 4.71 (1H, d, J=5.29 Hz), 4.66 (1H, t, J=5.62 Hz), 4.55 (1H, dd, J=10.26, 6.73 Hz), 4.45 (1H, t, J=9.48 Hz), 4.07 (1H, dd, J=10.03, 6.51 Hz), 3.92-3.85 (1H, m), 3.78 (3H, s), 3.67 (1H, td, J=9.04, 5.37 Hz), 3.38-3.32 (1H, m), 3.29-3.23 (1H, m), 2.89 (1H, dd, J=13.67, 3.75 Hz), 2.61-2.59 (3H, m), 1.17 (3H, t, J=7.61 Hz).

MASS 476 (M+1).

Example 14

{3-[4-(4-Ethylbenzyloxy)-3-methoxyphenyl]azetidin-1-yl}-[4-(5-hydroxy-4-hydroxymethylpentyl)pyridin-2-yl]-methanone

(1) 4-(3-chloropropyl)pyridine

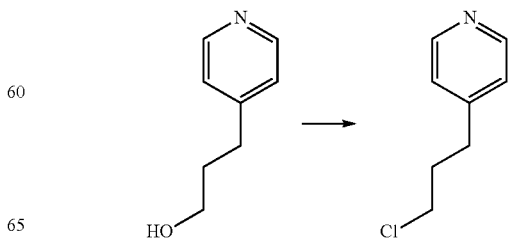

To a solution of 3-pyridin-4-yl-propan-1-ol (3.1 g) in pyridine (8 mL) was added 4-methylbenzenesulfonyl chloride (5.0 g) at 0° C. The reaction mixture was stirred at RT for 12 hr. The reaction mixture was concentrated in vacuo. Saturated aqueous NaHCO₃ was added to the residue and the mixture was extracted with ethyl acetate. The organic layer was washed with water and brine, and then dried over Na₂SO₄. The solvent was removed under reduced pressure. The residue was purified by silica gel chromatography (Developing solvent: hexane/ethyl acetate=1/2) to give the title compound (2.1 g, 61%).

¹H-NMR (400 MHz, CDCl₃) δ: 8.52 (2H, dd, J=4.41, 1.54 Hz), 7.14 (2H, dd, J=4.41, 1.54 Hz), 3.53 (2H, t, J=6.40 Hz), 2.79 (2H, t, J=7.50 Hz), 2.11 (2H, tt, J=7.50, 6.40 Hz).

(2) Diethyl 2-(3-pyridin-4-yl-propyl)malonate

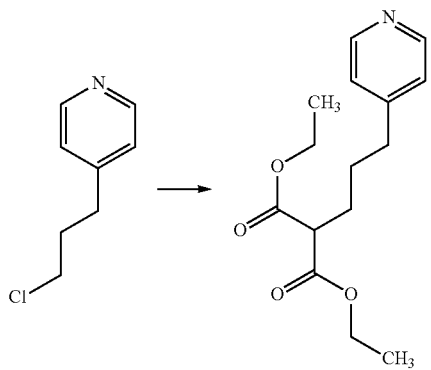 [SMILES: ClCCCc1ccncc1 ; CCOC(=O)C(CCCc1ccncc1)C(=O)OCC]

To a suspension of NaH (0.4 g) in DMF (8 mL) was added diethyl malonate (0.16 g) at 0° C. The mixture was stirred at RT for 30 min. To the mixture was added a solution of 4-(3-chloropropyl)pyridine (1.2 g) prepared in (1) in DMF (4 mL). The reaction mixture was stirred at 80° C. for 10 hr. Water was added to the reaction mixture and the mixture was extracted with ethyl acetate. The organic layer was washed with water and brine, and then dried over Na₂SO₄. The solvent was removed under reduced pressure. The residue was purified by silica gel chromatography (Developing solvent: hexane/ethyl acetate=1/1) to give the title compound (1.3 g, 60%).

¹H-NMR (400 MHz, CDCl₃) δ: 8.49 (2H, dd, J=4.23, 1.61 Hz), 7.10 (2H, dd, J=4.43, 1.61 Hz), 4.25-4.14 (4H, m), 3.34 (1H, t, J=7.45 Hz), 2.64 (2H, t, J=7.76 Hz), 1.97-1.91 (2H, m), 1.72-1.66 (2H, m), 1.26 (6H, t, J=7.05 Hz).

(3) 2-(3-Pyridin-4-yl-propyl)propane-1,3-diol

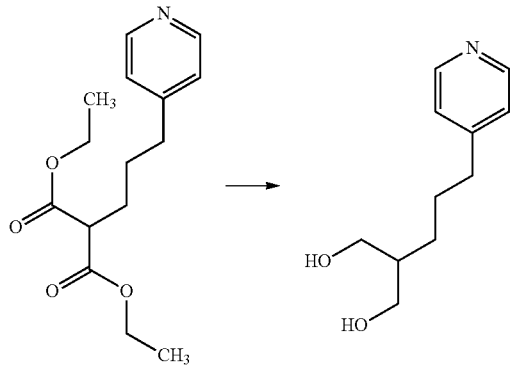 [SMILES: CCOC(=O)C(CCCc1ccncc1)C(=O)OCC ; OCC(CO)CCCc1ccncc1]

To a suspension of LiAlH₄ (0.34 g) in THF (10 mL) was added a solution of diethyl 2-(3-pyridin-4-yl-propyl)malonate (1.23 g) prepared in (2) in THF (5 mL) at 0° C. The reaction mixture was stirred at RT for 3 hr and at 50° C. for 2 hr. To the reaction mixture were added water (0.34 mL), aqueous 4 N NaOH (0.34 mL) and then water (1 mL) at 0° C. The mixture was stirred at RT for 30 min. Celite and Na₂SO₄ were added to the mixture. The mixture was filtered using Celite. The filtrate was concentrated in vacuo. The residue was purified by silica gel chromatography (Developing solvent: chloroform/methanol=9/1) to give the title compound (0.21 g, 24%).

¹H-NMR (400 MHz, CDCl₃) δ: 8.48 (2H, dd, J=4.43, 1.61 Hz), 7.10 (2H, dd, J=4.43, 1.61 Hz), 3.82 (2H, dd, J=10.68, 3.83 Hz), 3.67 (2H, dd, J=10.68, 7.25 Hz), 2.62 (2H, t, J=7.76 Hz), 2.29 (2H, br s), 1.83-1.75 (1H, m), 1.73-1.65 (2H, m), 1.36-1.30 (2H, m).

(4) 4-[5-(tert-Butyldimethylsilanyloxy)-4-(tert-butyldimethylsilanyloxymethyl)-pentyl]pyridine

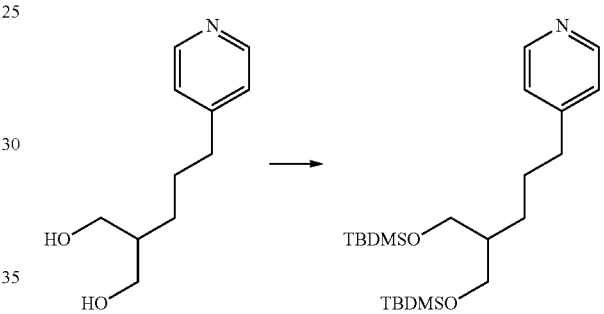

To a solution of 2-(3-pyridin-4-yl-propyl)propane-1,3-diol (0.208 g) prepared in (3) in DMF (3 mL) were added imidazole (0.218 g) and tert-butyldimethylchlorosilane (0.401 g). The reaction mixture was stirred at RT for 12 hr. Water was added to the reaction mixture and the mixture was extracted with ethyl acetate. The organic layer was washed with water and brine, and then dried over Na₂SO₄. The solvent was removed under reduced pressure. The residue was purified by silica gel chromatography (Developing solvent: hexane/ethyl acetate=9/1) to give the title compound (0.43 g, 96%).

(5) 4-[5-(tert-Butyldimethylsilanyloxy)-4-(tert-butyldimethylsilanyloxymethyl)-pentyl]pyridin-1-oxide

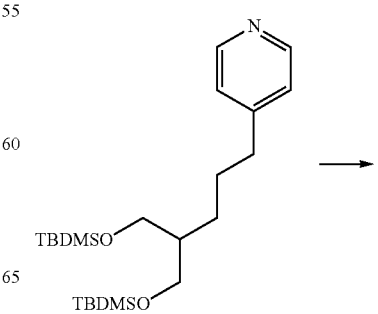

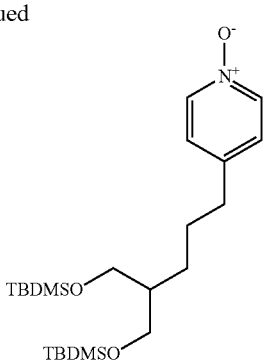

To a solution of 4-[5-(tert-butyldimethylsilanyloxy)-4-(tert-butyldimethylsilanyloxymethyl)-pentyl]pyridine (0.43 g) prepared in (4) in chloroform (5.0 mL) were added methyltrioxorhenium (VII) (0.0030 g) and aqueous 30% hydrogen peroxide (0.21 mL). The reaction mixture was stirred at RT for 4 hr. An appropriate amount of manganese dioxide (IV) was added to the reaction mixture. The mixture was stirred for 1 hr. Water was added to the mixture and the mixture was extracted with chloroform. The organic layer was dried over $Na_2SO_4$. The solvent was removed under reduced pressure to obtain the crude title compound.

(6) 4-[5-(tert-Butyldimethylsilanyloxy)-4-(tert-butyldimethylsilanyloxymethyl)-pentyl]pyridine-2-carbonitrile

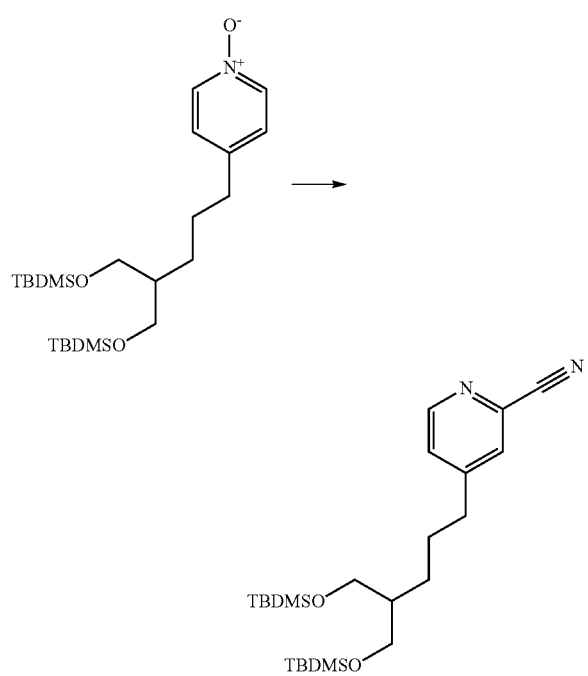

To a solution of the crude 4-[5-(tert-butyldimethylsilanyloxy)-4-(tert-butyldimethylsilanyloxy-methyl)-pentyl]pyridine 1-oxide (0.43 g) prepared in (5) in chloroform (5 mL) were added trimethylsilyl cyanide (0.17 mL) and N,N-dimethylcarbamoyl chloride (0.12 mL). The reaction mixture was stirred at RT for 12 hr. Saturated aqueous $NaHCO_3$ was added to the reaction mixture and the mixture was extracted with chloroform. The organic layer was dried over $Na_2SO_4$. The solvent was removed under reduced pressure. The residue was purified by silica gel chromatography (Developing solvent: hexane/ethyl acetate=9/1) to give the title compound (0.40 g, 87%).

(7) 4-(5-Hydroxy-4-hydroxymethylpentyl)pyridine-2-calboxylic acid

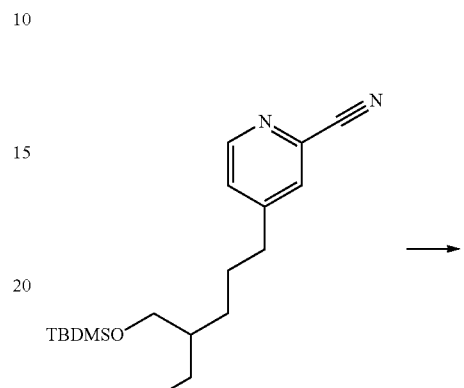

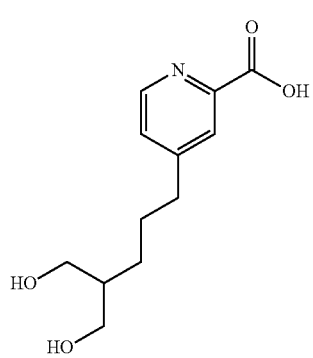

To 4-[5-(tert-butyldimethylsilanyloxy)-4-(tert-butyl-dimethylsilanyloxymethyl)-pentyl]pyridine-2-carbonitrile (0.089 g) prepared in (6) was added 6 N hydrochloric acid (2.0 mL). The reaction mixture was stirred at 110° C. for 12 hr. The solvent was removed under reduced pressure to give the crude title compound.

(8) {3-[4-(4-Ethylbenzyloxy)-3-methoxyphenyl]azetidin-1-yl}-[4-(5-hydroxy-4-hydroxymethylpentyl)pyridin-2-yl]-methanone -continued

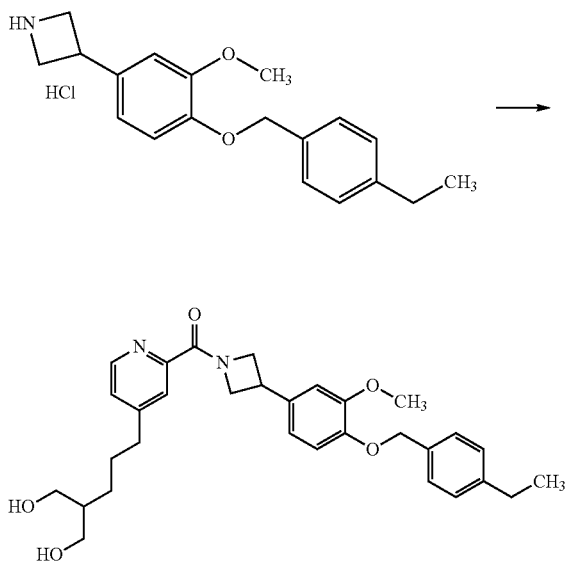

Using the crude 4-(5-hydroxy-4-hydroxymethyl-pentyl)pyridine-2-calboxylic acid prepared in (7), the title compound (0.074 g, 80%) was obtained in a similar manner to that described in Example 13 (4).

$^1$H-NMR (400 MHz, CDCl$_3$) δ: 8.44 (1H, dd, J=4.94, 0.71 Hz), 7.96 (1H, d, J=1.01 Hz), 7.34 (2H, d, J=8.26 Hz), 7.20-7.16 (3H, m), 6.88-6.81 (3H, m), 5.11 (2H, s), 5.08 (1H, t, J=9.67 Hz), 4.69 (1H, dd, J=10.58, 6.35 Hz), 4.60 (1H, t, J=9.67 Hz), 4.26 (1H, dd, J=10.38, 6.35 Hz), 3.89 (3H, s), 3.86-3.80 (3H, m), 3.69-3.65 (2H, m), 2.71-2.61 (4H, m), 2.27 (2H, br s), 1.79-1.68 (3H, m), 1.37-1.31 (2H, m), 1.23 (3H, t, J=7.66 Hz).

MASS 519 (M+1).

Example 15

[4-(3,4-Dihydroxybutyl)pyridin-2-yl]-{3-[4-(4-ethyl-benzyl-oxy)-3-methoxyphenyl]azetidin-1-yl}-methanone (1) 4-But-3-enyl-pyridine-2-carbonitrile

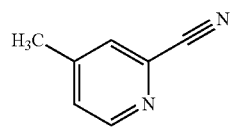

To a solution of 4-methylpyridine-2-carbonitrile (2.0 g) in THF (60 mL) was added 2.0 M LDA in heptane/THF/ethylbenzene (10.2 mL) at −78° C. The mixture was stirred at −78° C. for 2 hr. Allyl bromide (2.4 g) was added to the mixture at −78° C. The reaction mixture was stirred at −78° C. for 2.5 hr and at RT for 12 hr. Water was added to the reaction mixture and the mixture was extracted with ethyl acetate. The organic layer was dried over Na$_2$SO$_4$. The solvent was removed under reduced pressure. The residue was purified by silica gel chromatography (Developing solvent: hexane/ethyl acetate=9/1) to give the title compound (0.34 g, 12%).

$^1$H-NMR (400 MHz, CDCl$_3$) δ: 8.59 (1H, dd, J=5.07, 0.66 Hz), 7.53 (1H, dd, J=1.54, 0.66 Hz), 7.33 (1H, dd, J=5.07, 1.76 Hz), 5.83-5.73 (1H, m), 5.06-5.01 (2H, m), 2.78 (2H, t, J=7.61 Hz), 2.44-2.38 (2H, m).

(2) 4-(3,4-Dihydroxybutyl)pyridine-2-carbonitrile

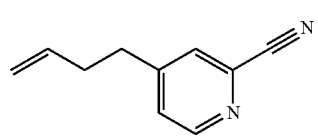

To a mixed solution of 4-but-3-enyl-pyridine-2-carbonitrile (0.17 g) prepared in (1) in acetone (4 mL)/water (2 mL) were added 4-methylmorpholine N-oxide (0.37 g) and aqueous 4% osmium tetraoxide (0.67 g). The reaction mixture was stirred at RT for 12 hr. Saturated aqueous Na$_2$S$_2$O$_3$ was added to the reaction mixture and the mixture was extracted with ethyl acetate. The organic layer was washed with brine, and then dried over Na$_2$SO$_4$. The solvent was removed under reduced pressure. The residue was purified by silica gel chromatography (Developing solvent: chloroform/methanol=15/1) to give the title compound (0.15 g, 72%).

$^1$H-NMR (400 MHz, CDCl$_3$) δ: 8.60 (1H, d, J=5.07 Hz), 7.57 (1H, d, J=1.54 Hz), 7.38 (1H, dd, J=5.07, 1.76 Hz), 3.73-3.68 (2H, m), 3.52-3.48 (1H, m), 2.96-2.88 (1H, m), 2.83-2.75 (1H, m), 2.33 (1H, br s), 1.87 (1H, br s), 1.84-1.71 (2H, m).

(3) [4-(3,4-Dihydroxybutyl)pyridin-2-yl]-{3-[4-(4-ethyl-benzyloxy)-3-methoxyphenyl]azetidin-1-yl}-methanone

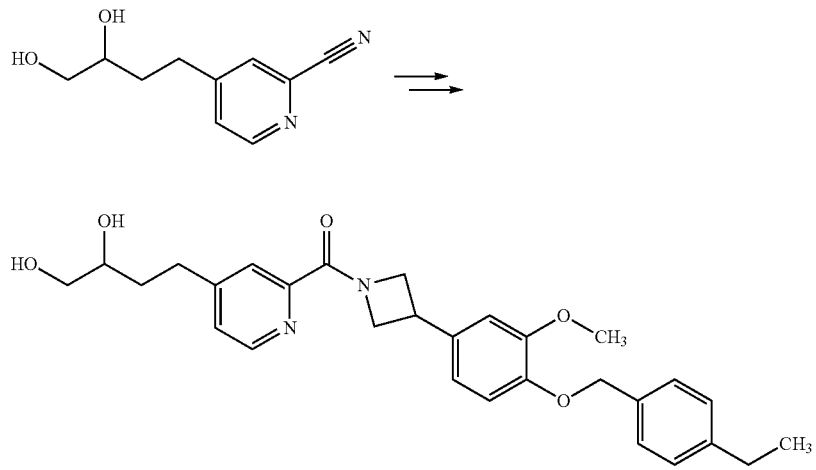

Using 4-(3,4-dihydroxybutyl)-pyridine-2-carbonitrile (0.069 g) prepared in (2), the title compound (0.13 g, 90%) was obtained in a similar manner to that described in Example 14.

$^1$H-NMR (400 MHz, DMSO-$d_6$) δ: 8.49 (1H, d, J=4.85 Hz), 7.84 (1H, d, J=0.88 Hz), 7.37 (1H, dd, J=4.96, 1.65 Hz), 7.34 (2H, d, J=7.94 Hz), 7.22 (2H, d, J=8.16 Hz), 7.00-6.98 (2H, m), 6.87 (1H, dd, J=8.38, 1.98 Hz), 5.01 (2H, s), 4.96 (1H, t, J=9.48 Hz), 4.59-4.42 (4H, m), 4.07 (1H, dd, J=10.03, 6.73 Hz), 3.92-3.85 (1H, m), 3.78 (3H, s), 3.41-3.22 (3H, m), 2.85-2.66 (2H, m), 2.60 (2H, q, J=7.57 Hz), 1.82-1.73 (1H, m), 1.59-1.50 (1H, m), 1.17 (3H, t, J=7.50 Hz).

MASS 491 (M+1).

Example 16

[4-(1,1-Difluoro-2-hydroxyethyl)pyridin-2-yl]-{3-[4-(4-ethylbenzyloxy)-3-methoxyphenyl]azetidin-1-yl}-methanone (1) Ethyl pyridin-4-yl-difluoroacetate

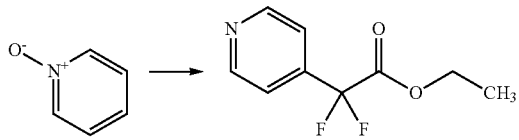

Preparation of Reformatsky Reagent

To a suspension of zinc (4.9 g) and lithium chloride (3.2 g) in THF (60 mL) were added 1,2-dibromoethane (0.65 mL) and chlorotrimethylsilane (0.95 mL) under argon atmosphere at 70° C. The mixture was stirred at 70° C. for 20 min. and at RT for 2 hr. Ethyl bromodifluoroacetate (11 mL) was added dropwise over 10 min to the mixture at 0° C. The reaction mixture was stirred at 0° C. for 30 min. and at RT for 1 hr to give Reformatsky reagent.

To a solution of pyridine N-oxide (5.1 g) in THF (90 mL) was added N,N-dimethylcarbamoyl chloride (5.0 mL) under argon atmosphere. The mixture was stirred at RT for 20 min. The Reformatsky reagent prepared previously was added dropwise over 10 min. to the mixture at RT. The reaction mixture was stirred at RT for 18 hr. Water was added to the reaction mixture and the mixture was extracted with ethyl acetate. The organic layer was dried over MgSO$_4$. The solvent was removed under reduced pressure. The residue was purified by silica gel chromatography (Developing solvent: hexane/ethyl acetate=4/1) to give the title compound.

(2) 2,2-Difluoro-2-(pyridin-4-yl)-ethanol

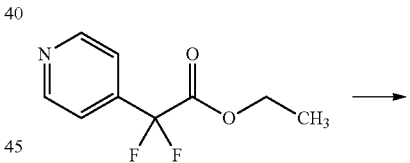

To a solution of ethyl pyridin-4-yl-difluoroacetate (0.59 g) prepared in (1) in ethanol (10 mL) was added NaBH$_4$ (0.11 g) at 0° C. The reaction mixture was stirred at RT for 2 hr. The solvent was removed under reduced pressure. Water was added to the residue and the mixture was extracted with ethyl acetate. The organic layer was washed with saturated aqueous NaHCO$_3$, and then dried over MgSO$_4$. The solvent was removed under reduced pressure. The residue was purified by silica gel chromatography (Developing solvent: ethyl acetate) to give the title compound (0.082 g, 1%).

$^1$H-NMR (400 MHz, DMSO-$d_6$) δ: 8.73 (2H, dd, J=4.41, 1.62 Hz), 7.53 (2H, dd, J=4.52, 1.51 Hz), 5.71 (1H, t, J=6.26 Hz), 3.88 (2H, td, J=13.91, 6.26 Hz).

(3) 4-[2-(tert-Butyldimethylsilanyloxy)-1,1-difluoro-ethyl]pyridine

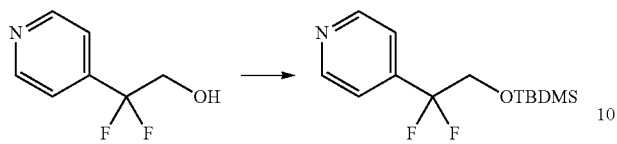

To a solution of 2,2-difluoro-2-(pyridin-4-yl)-ethanol (0.15 g) prepared in (2) in DMF (3.0 mL) were added imidazole (0.076 g) and tert-butyldimethylchlorosilane (0.15 g). The reaction mixture was stirred at RT for 2 hr. Water was added to the reaction mixture and the mixture was extracted with ethyl acetate. The organic layer was dried over $MgSO_4$. The solvent was removed under reduced pressure. The residue was purified by silica gel chromatography (Developing solvent: ethyl acetate) to give the title compound.

(4) 4-[2-(tert-Butyldimethylsilanyloxy)-1,1-difluoro-ethyl]-pyridine-1-oxide

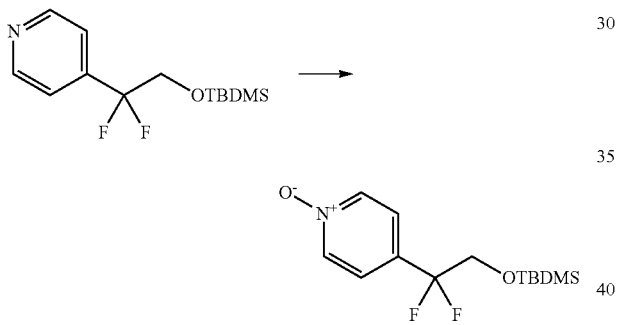

To a solution of 4-[2-(tert-butyldimethylsilanyloxy)-1,1-difluoroethyl]pyridine (0.14 g) prepared in (3) in chloroform (3 mL) were added methyltrioxorhenium (VII) (0.0010 g) and aqueous 30% hydrogen peroxide (0.11 mL). The reaction mixture was stirred at RT for 4 hr. To the mixture was added manganese (IV) oxide. The reaction mixture was stirred at RT for 1 hr. Water was added to the reaction mixture and the mixture was extracted with ethyl acetate. The organic layer was dried over $MgSO_4$. The solvent was removed under reduced pressure to give the crude title compound.

(5) 4-[2-(tert-Butyldimethylsilanyloxy)-1,1-difluoro-ethyl]pyridine-2-carbonitrile

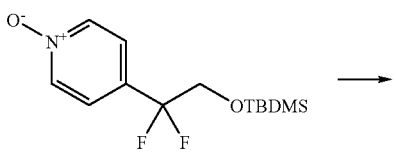

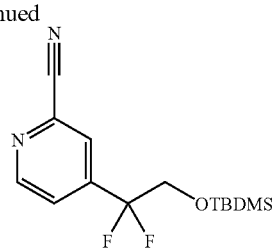

The title compound was obtained from the crude 4-[2-(tert-butyldimethylsilanyloxy)-1,1-difluoroethyl]pyridine 1-oxide prepared in (4) in a similar manner to that described in Example 14 (6).

$^1$H-NMR (400 MHz, DMSO-$d_6$) δ: 8.94 (1H, d, J=5.10 Hz), 8.26 (1H, s), 7.91 (1H, dd, J=5.10, 1.62 Hz), 4.16 (2H, t, J=13.10 Hz), 0.77 (9H, s), −0.02 (6H, t, J=3.13 Hz).

(6) [4-(1,1-Difluoro-2-hydroxyethyl)pyridin-2-yl]-{3-[4-(4-ethylbenzyloxy)-3-methoxyphenyl]azetidin-1-yl}-methanone

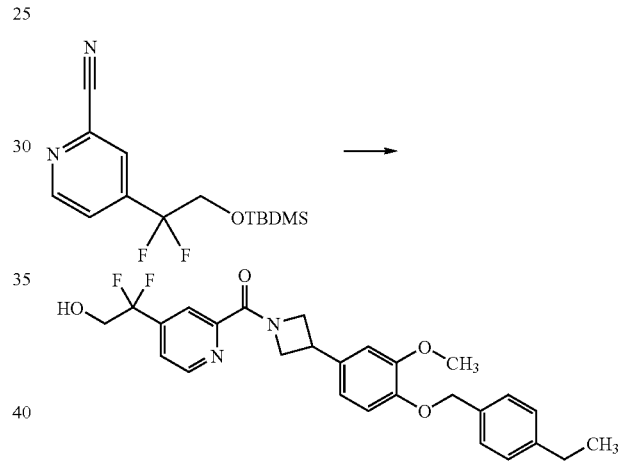

Using 4-[2-(tert-butyldimethylsilanyloxy)-1,1-difluoroethyl]-pyridine-2-carbonitrile prepared in (5), the title compound was obtained in a similar manner to that described in Example 14.

$^1$H-NMR (400 MHz, DMSO-$d_6$) δ: 8.78 (1H, d, J=5.10 Hz), 8.06 (1H, s), 7.68 (1H, dd, J=5.10, 1.62 Hz), 7.34 (2H, d, J=8.12 Hz), 7.22 (2H, d, J=7.88 Hz), 7.00-6.98 (2H, m), 6.88 (1H, dd, J=8.23, 1.97 Hz), 5.76 (1H, t, J=6.26 Hz), 5.01-4.97 (3H, m), 4.58 (1H, dd, J=10.09, 6.61 Hz), 4.48 (1H, t, J=9.62 Hz), 4.11 (1H, dd, J=10.09, 6.61 Hz), 3.92 (3H, td, J=13.62, 6.34 Hz), 3.78 (3H, s), 2.60 (2H, q, J=7.65 Hz), 1.17 (3H, t, J=7.54 Hz).

MASS 483 (M+1).

Example of Crystallization

As described in Example 1, {3-[4-(cyclopropylbenzyloxy)-3-methoxyphenyl]azetidin-1-yl}-[4-((S)-2,3-dihydroxypropoxymethyl)-pyridin-2-yl]-methanone was prepared and purified by silica gel chromatography (Developing solvent: chloroform/methanol=9/1). The solvent was removed under reduced pressure. A mixed solvent of ethyl acetate/heptane was added to the residue. The precipitated solid was collected on a filter and dried under reduced pressure. To a solution of the resulting solid (32 g) in methanol (160 mL) was added activated carbon (3.2 g). The mixture was heated with stirring at 80° C. for 3 hr. The mixture was filtered to remove the activated carbon. The filtrate was concentrated in vacuo. Ethyl acetate (320 mL) was added to the residue. This mixture was heated with stirring at 100° C. for 2 hr. Heptane (320 mL) was added to this mixture. This suspension was stirred in an ice-bath for 1 hr. The precipitated solid was collected on a filter and dried under reduced pressure to give the crude crystal. The resulting crude crystal (0.1 g) was dissolved in ethyl acetate (2.0 mL) in an oil-bath (at 95° C.). The solution was gradually cooled to RT with stirring in the oil-bath. Solids were precipitated under cooling. The suspension was stirred at RT overnight. The precipitated solid was collected on a filter. The resulting solid was dried at RT under reduced pressure to give the crystal (0.078 g).

As described in Example 6, {4-[2-((3R,4R)-3,4-dihydroxypyrrolidin-1-yl)ethoxy]pyridin-2-yl}-{3-[4-(4-ethylbenzyloxy)-3-methoxyphenyl]azetidin-1-yl}-methanone was prepared and purified by silica gel chromatography (Developing solvent: chloroform/methanol=15/1 to 7/1). The solvent was removed under reduced pressure. Ethanol (400 mL) was added to the residue (38 g). Activated carbon (3.8 g) was added to this mixture. This mixture was heated with stirring at 90° C. for 1 hr. The mixture was filtered to remove the activated carbon. The filtrate was concentrated in vacuo. Ethyl acetate (400 mL) was added to the residue. This suspension was stirred at 80° C. for 2 hr. The suspension was cooled to RT and then the precipitated solid was collected on a filter. The resulting solid was dried under reduced pressure to give the crude crystal. The resulting crude crystal (0.1 g) was dissolved in isobutyl acetate (0.3 mL) at 120° C. in an oil-bath. The solution was gradually cooled to RT with stirring in the oil-bath. Solids were precipitated under cooling. The suspension was stirred at RT overnight. The precipitated solid was collected on a filter. The resulting solid was dried under reduced pressure at RT to give the crystal (0.089 g).

As described in Example 7, 4-[2-(2-{3-[4-(4-ethylbenzyloxy)-3-methoxyphenyl]azetidine-1-carbonyl}-pyridin-4-yloxy)ethyl]piperazin-2-one was prepared and purified by silica gel chromatography (Developing solvent: chloroform/methanol=96/4). The solvent was removed under reduced pressure. Ethanol (190 mL) was added to the residue (38 g). Water (380 mL) was added to this mixture at 80° C. This mixture was heated at 80° C. with stirring for 2 hr. The mixture was cooled to RT and then the precipitated solid was collected on a filter. A suspension of the resulting solid in ethyl acetate (730 mL) was heated at 70° C. for 2 hr with stirring. The suspension was cooled to RT and then the precipitated solid was collected on a filter. The resulting solid was dried under reduced pressure to give the crude crystal. The resulting crude crystal (0.1 g) was dissolved in THF (0.6 mL) in an oil-bath (at 75° C.). The solution was gradually cooled to RT with stirring in the oil-bath. Solid was precipitated under cooling. The suspension was stirred at RT overnight. The precipitated solid was collected on a filter. The resulting solid was dried under reduced pressure at RT to give crystal (0.063 g).

As described in Examples 1 to 16, compounds listed in Tables 1-1 to 1-42 were obtained.

TABLE 1-1

| Example No. | Structure | NMR |
|---|---|---|
| 17 | (structure) | 1H-NMR (400 MHz, CDCl3) δ: 8.57 (1H, ddd, J = 4.63, 2.32, 1.16 Hz), 8.14 (1H, d, J = 7.94 Hz), 7.83-7.79 (1H, m), 7.37-7.33 (3H, m), 7.19 (2H, d, J = 8.16 Hz), 6.89-6.81 (3H, m), 5.11 (2H, s), 5.09 (1H, t, J = 9.70 Hz), 4.70 (1H, dd, J = 10.70, 6.51 Hz), 4.61 (1H, t, J = 9.92 Hz), 4.27 (1H, dd, J = 10.48, 6.51 Hz), 3.89 (3H, s), 3.87-3.81 (1H, m), 2.64 (2H, q, J = 7.65 Hz), 1.23 (3H, t, J = 7.61 Hz). |
| 18 | (structure) | 1H-NMR (400 MHz, CDCl3) δ: 8.40 (1H, ddd, J = 4.63, 1.54, 0.66 Hz), 7.57 (1H, ddd, J = 7.94, 1.76, 0.66 Hz), 7.34 (2H, d, J = 8.16 Hz), 7.23 (1H, dd, J = 7.72, 4.85 Hz), 7.19 (2H, d, J = 8.38 Hz), 6.87-6.85 (2H, m), 6.80 (1H, dd, J = 8.16, 1.98 Hz), 5.11 (2H, s), 4.65-4.57 (2H, m), 4.29-4.24 (2H, m), 3.90 (3H, s), 3.86-3.78 (1H, m), 2.64 (2H, q, J = 7.72 Hz), 2.53 (3H, s), 1.23 (3H, t, J = 7.72 Hz). |
| 19 | (structure) | 1H-NMR (400 MHz, CDCl3) δ: 8.42 (1H, d, J = 4.85 Hz), 7.96-7.95 (1H, m), 7.34 (2H, d, J = 8.16 Hz), 7.20-7.16 (3H, m), 6.88-6.81 (3H, m), 5.10 (2H, s), 5.07 (1H, t, J = 9.70 Hz), 4.67 (1H, did, J = 10.59, 6.40 Hz), 4.60 (1H, t, J = 9.70 Hz), 4.26 (1H, dd, J = 10.37, 6.40 Hz), 3.89 (3H, s), 3.88-3.80 (1H, m), 2.64 (2H, q, J = 7.57 Hz), 2.41 (3H, s), 1.23 (3H, t, J = 7.50 Hz). |

TABLE 1-1-continued

| Example No. | Structure | NMR |
|---|---|---|
| 20 | 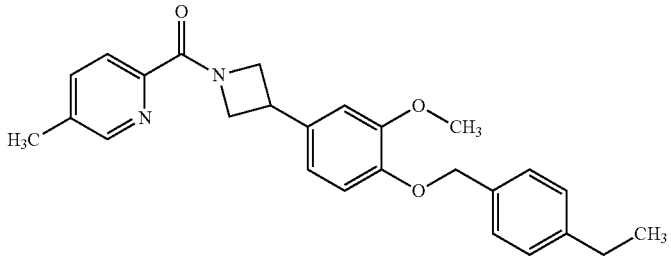 [SMILES: CCc1ccc(COc2ccc(C3CN(C(=O)c4ccc(C)cn4)C3)cc2OC)cc1] | 1H-NMR (400 MHz, CDCl3) δ: 8.39 (1H, d, J = 2.21 Hz), 8.03 (1H, d, J = 8.16 Hz), 7.60 (1H, ddd, J = 8.16, 2.21, 0.66 Hz), 7.34 (2H, d, J = 7.94 Hz), 7.19 (2H, d, J = 8.16 Hz), 6.88-6.81 (3H, m), 5.11 (2H, s), 5.07 (1H, t, J = 9.70 Hz), 4.68 (1H, dd, J = 10.59, 6.40 Hz), 4.59 (1H, t, J = 9.70 Hz), 4.26 (1H, dd, J = 10.48, 6.29 Hz), 3.89 (3H, s), 3.87-3.80 (1H, m), 2.64 (2H, q, J = 7.65 Hz), 2.38 (3H, s), 1.23 (3H, t, J = 7.72 Hz). |

TABLE 1-2

| | | |
|---|---|---|
| 21 | 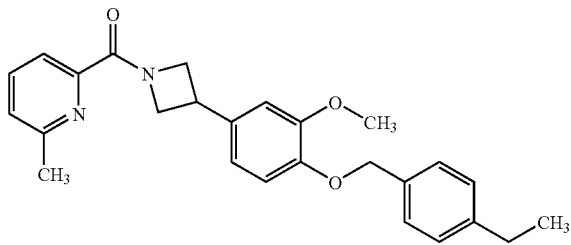 [SMILES: CCc1ccc(COc2ccc(C3CN(C(=O)c4cccc(C)n4)C3)cc2OC)cc1] | 1H-NMR (400 MHz, CDCl3) δ: 7.94 (1H, d, J = 7.42 Hz), 7.70 (1H, t, J = 7.77 Hz), 7.36 (2H, d, J = 8.12 Hz), 7.23-7.19 (3H, m), 6.91-6.83 (3H, m), 5.15-5.10 (3H, m), 4.69 (1H, dd, J = 10.44, 6.49 Hz), 4.60 (1H, t, J = 9.74 Hz), 4.28 (1H, dd, J = 10.44, 6.49 Hz), 3.91 (3H, s), 3.90-3.81 (1H, m), 2.65 (2H, q, J = 7.65 Hz), 2.54 (3H, s), 1.23 (3H, t, J = 7.65 Hz). |
| 22 | 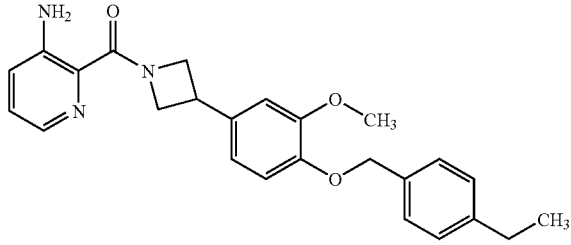 [SMILES: CCc1ccc(COc2ccc(C3CN(C(=O)c4ncccc4N)C3)cc2OC)cc1] | 1H-NMR (400 MHz, CDCl3) δ: 7.88 (1H, dd, J = 4.30, 1.43 Hz), 7.35 (2H, d, J = 7.94 Hz), 7.19 (2H, d, J = 7.94 Hz), 7.09 (1H, dd, J = 8.38, 4.41 Hz), 6.98 (1H, dd, J = 8.27, 1.43 Hz), 6.89-6.81 (3H, m), 5.85 (2H, br s), 5.11 (2H, s), 5.06 (1H, t, J = 9.70 Hz), 4.68 (1H, dd, J = 10.70, 6.51 Hz), 4.55 (1H, t, J = 9.70 Hz), 4.21 (1H, dd, J = 10.37, 6.40 Hz), 3.90 (3H, s), 3.84-3.76 (1H, m), 2.64 (2H, q, J = 7.65 Hz), 1.23 (3H, t, J = 7.65 Hz). |
| 23 | 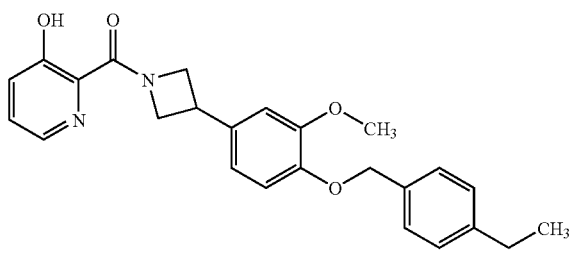 [SMILES: CCc1ccc(COc2ccc(C3CN(C(=O)c4ncccc4O)C3)cc2OC)cc1] | 1H-NMR (400 MHz, CDCl3) δ: 12.63 (1H, s), 8.08 (1H, dd, J = 3.43, 2.32 Hz), 7.35 (2H, d, J = 8.26 Hz), 7.29-7.26 (2H, m), 7.19 (2H, d, J = 8.26 Hz), 6.89-6.82 (3H, m), 5.20 (1H, t, J = 9.87 Hz), 5.12 (2H, s), 4.81 (2H, dd, J = 10.88, 6.65 Hz), 4.62 (1H, t, J = 9.87 Hz), 4.27 (1H, dd, J = 10.68, 6.85 Hz), 3.90 (3H, s), 3.89-3.84 (1H, m), 2.64 (2H, q, J = 7.59 Hz), 1.23 (3H, t, J = 7.66 Hz). |
| 24 | 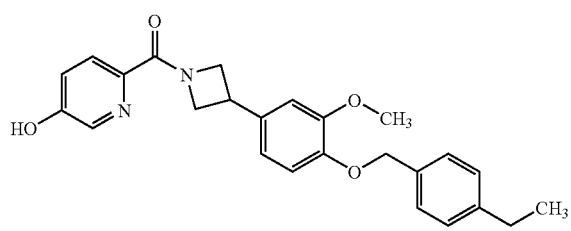 [SMILES: CCc1ccc(COc2ccc(C3CN(C(=O)c4ccc(O)cn4)C3)cc2OC)cc1] | 1H-NMR (400 MHz, CDCl3) δ: 8.20 (1H, d, J = 2.62 Hz), 8.00 (1H, d, J = 8.66 Hz), 7.34 (2H, d, J = 8.26 Hz), 7.24 (1H, dd, J = 8.56, 2.92 Hz), 7.19 (2H, d, J = 8.06 Hz), 6.86-6.81 (3H, m), 5.10 (2H, s), 5.06 (1H, d, J = 9.27 Hz), 4.70 (1H, dd, J = 10.68, 6.45 Hz), 4.61 (1H, dd, J = 18.74, 8.46 Hz), 4.26 (1H, dd, J = 10.48, 6.45 Hz), 3.88 (3H, t, J = 7.45 Hz), 3.84 (1H, dd, J = 10.68, 4.43 Hz), 2.64 (2H, q, J = 7.59 Hz), 1.22 (3H, t, J = 7.66 Hz). |

TABLE 1-3

| 25 | 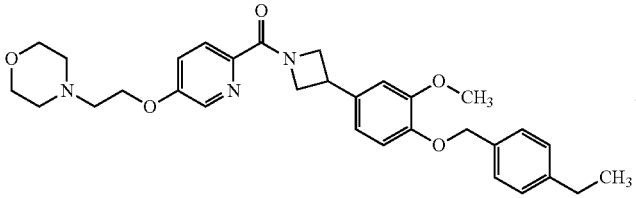 [SMILES: CCc1ccc(COc2ccc(C3CN(C(=O)c4ccc(OCCN5CCOCC5)cn4)C3)cc2OC)cc1] | 1H-NMR (400 MHz, CDCl3) δ: 8.40-8.33 (1H, m), 8.18-8.09 (1H, m), 7.58-7.49 (1H, m), 7.36-7.32 (2H, m), 7.21-7.17 (2H, m), 6.92-6.80 (4H, m), 5.10 (2H, s), 5.05-4.93 (1H, m), 4.85-4.75 (2H, m), 4.69-4.57 (2H, m), 4.33-4.20 (3H, m), 4.07-3.95 (2H, m), 3.89 (3H, s), 3.21-3.07 (2H, m), 2.68-2.55 (3H, m), 1.30-1.19 (3H, m). |
|---|---|---|
| 26 | 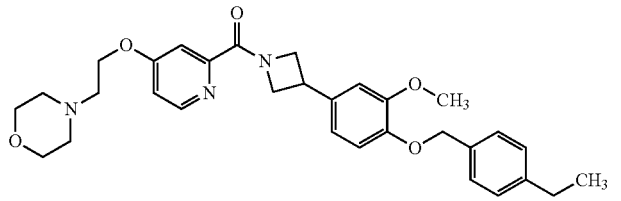 [SMILES: CCc1ccc(COc2ccc(C3CN(C(=O)c4cc(OCCN5CCOCC5)ccn4)C3)cc2OC)cc1] | 1H-NMR (400 MHz, CDCl3) δ: 8.36 (1H, d, J = 5.51 Hz), 7.68 (1H, d, J = 2.65 Hz), 7.34 (2H, d, J = 8.16 Hz), 7.19 (2H, d, J = 8.16 Hz), 6.89-6.80 (4H, m), 5.11 (2H, s), 5.08 (1H, t, J = 9.92 Hz), 4.68 (1H, dd, J = 10.59, 6.40 Hz), 4.59 (1H, t, J = 9.92 Hz), 4.25 (1H, dd, J = 10.37, 6.18 Hz), 4.22 (2H, t, J = 5.62 Hz), 3.89 (3H, s), 3.88-3.80 (1H, m), 3.73 (4H, t, J = 4.63 Hz), 2.82 (2H, t, J = 5.62 Hz), 2.64 (2H, q, J = 7.57 Hz), 2.57 (4H, t, J = 4.63 Hz), 1.23 (3H, t, J = 7.61 Hz). |
| 27 | 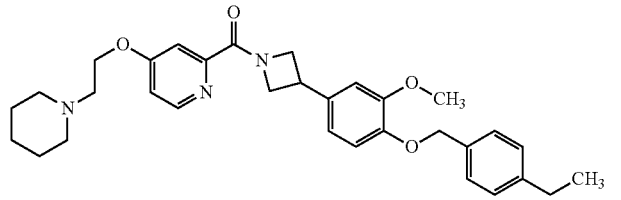 [SMILES: CCc1ccc(COc2ccc(C3CN(C(=O)c4cc(OCCN5CCCCC5)ccn4)C3)cc2OC)cc1] | 1H-NMR (400 MHz, CDCl3) δ: 8.35 (1H, d, J = 5.44 Hz), 7.67 (1H, d, J = 2.42 Hz), 7.34 (2H, d, J = 8.06 Hz), 7.19 (2H, d, J = 8.06 Hz), 6.89-6.80 (4H, m), 5.11 (2H, s), 5.07 (1H, t, J = 9.77 Hz), 4.68 (1H, dd, J = 10.68, 6.45 Hz), 4.59 (1H, t, J = 9.77 Hz), 4.25 (1H, dd, J = 10.58, 6.55 Hz), 4.21 (2H, t, J = 5.94 Hz), 3.89 (3H, s), 3.87-3.80 (1H, m), 2.80 (2H, t, J = 5.84 Hz), 2.64 (2H, q, J = 7.59 Hz), 2.51 (4H, br s), 1.62-1.58 (4H, br m), 1.48-1.42 (2H, m), 1.23 (3H, t, J = 7.59 Hz). |
| 28 | 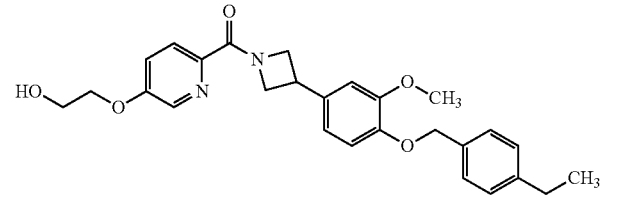 [SMILES: CCc1ccc(COc2ccc(C3CN(C(=O)c4ccc(OCCO)cn4)C3)cc2OC)cc1] | 1H-NMR (400 MHz, CDCl3) δ: 8.29-8.20 (1H, m), 8.16-8.06 (1H, m), 7.41-7.31 (2H, m), 7.32-7.28 (1H, m), 7.22-7.10 (2H, m), 6.91-6.81 (3H, m), 5.16-4.99 (3H, m), 4.72-4.64 (1H, m), 4.64-4.53 (1H, m), 4.31-4.22 (1H, m), 4.17 (1H, br s), 4.01 (2H, br s), 3.90 (3H, s), 3.87-3.75 (1H, m), 2.73-2.58 (2H, m), 2.08-1.92 (1H, m), 1.28-1.19 (3H, m). |

TABLE 1-4

| 29 | 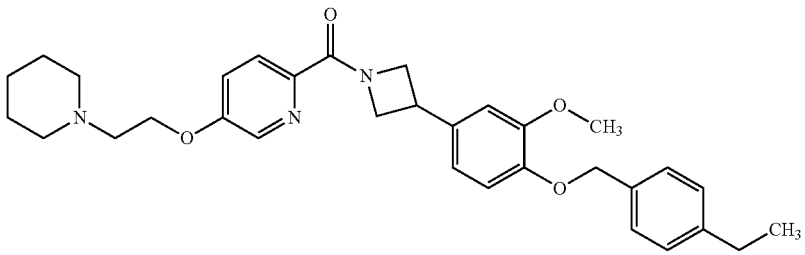 [SMILES: CCc1ccc(COc2ccc(C3CN(C(=O)c4ccc(OCCN5CCCCC5)cn4)C3)cc2OC)cc1] | 1H-NMR (400 MHz, CDCl3) δ: 8.23 (1H, d, J = 2.62 Hz), 8.10 (1H, d, J = 8.66 Hz), 7.35 (2H, d, J = 8.06 Hz), 7.29-7.24 (1H, m), 7.19 (2H, d, J = 7.86 Hz), 6.90-6.80 (3H, m), 5.11 (2H, s), 5.10-5.03 (1H, m), 4.70-4.54 (2H, m), 4.28-4.15 (3H, m), 3.89 (3H, s), 3.87-3.78 (1H, m), 2.80 (2H, t, J = 6.85 Hz), 2.66 (2H, d, J = 7.66 Hz), 2.64 (2H, q, J = 7.45 Hz), 2.57-2.46 (4H, m), 1.68-1.58 (6H, m), 1.23 (3H, t, J = 7.45 Hz). |
|---|---|---|
| 30 | 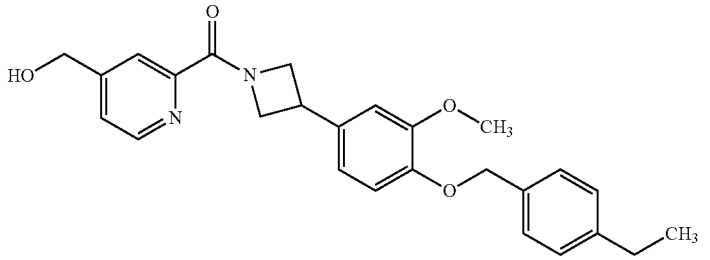 [SMILES: CCc1ccc(COc2ccc(C3CN(C(=O)c4cc(CO)ccn4)C3)cc2OC)cc1] | 1H-NMR (400 MHz, DMSO-d6) δ: 8.54 (1H, dd, J = 4.87, 0.46 Hz), 7.96 (1H, d, J = 0.70 Hz), 7.45 (1H, dd, J = 4.87, 0.46 Hz), 7.34 (2H, d, J = 7.88 Hz), 7.22 (2H, d, J = 8.12 Hz), 7.00-6.98 (2H, m), 6.87 (1H, dd, J = 8.23, 1.97 Hz), 5.52 (1H, t, J = 5.68 Hz), 5.01 (2H, s), 4.97 (1H, t, J = 9.51 Hz), 4.60 (2H, d, J = 5.57 Hz), 4.55 (1H, dd, J = 10.20, 6.49 Hz), 4.46 (1H, t, J = 9.62 Hz), 4.08 (1H, dd, J = 9.97, 6.49 Hz), 3.93-3.85 (1H, m), 3.78 (3H, s), 2.60 (2H, q, J = 7.58 Hz), 1.17 (3H, t, J = 7.65 Hz). |

TABLE 1-4-continued

| 31 | 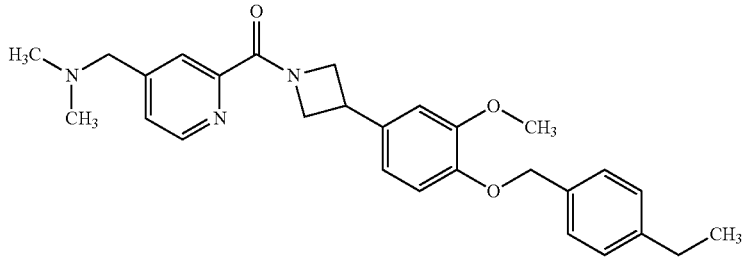 [SMILES: CCc1ccc(COc2ccc(C3CN(C(=O)c4cc(CN(C)C)ccn4)C3)cc2OC)cc1] | 1H-NMR (400 MHz, DMSO-d6) δ: 8.55 (1H, d, J = 4.87 Hz), 7.93 (1H, d, J = 0.70 Hz), 7.44 (1H, dd, J = 4.99, 1.74 Hz), 7.34 (2H, d, J = 8.12 Hz), 7.22 (2H, d, J = 8.12 Hz), 6.99 (2H, t, J = 4.17 Hz), 6.87 (1H, dd, J = 8.23, 1.97 Hz), 5.01 (2H, s), 4.98 (1H, t, J = 9.51 Hz), 4.56 (1H, dd, J = 10.09, 6.61 Hz), 4.45 (1H, t, J = 9.51 Hz), 4.08 (1H, dd, J = 9.97, 6.49 Hz), 3.93-3.85 (1H, m), 3.78 (3H, s), 3.49 (2H, s), 2.60 (2H, q, J = 7.58 Hz), 2.17 (6H, s), 1.17 (3H, t, J = 7.65 Hz). |
|---|---|---|
| 32 | 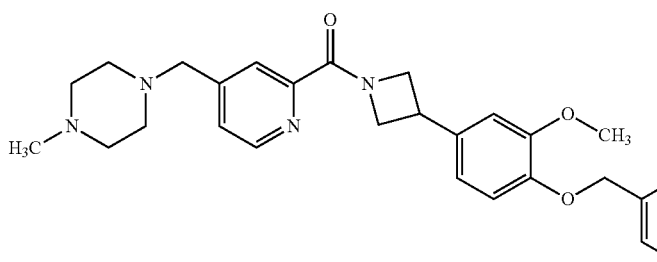 | 1H-NMR (400 MHz, DMSO-d6) δ: 8.54 (1H, d, J = 4.87 Hz), 7.92 (1H, d, J = 0.70 Hz), 7.44 (1H, dd, J = 4.87, 1.62 Hz), 7.34 (2H, d, J = 8.12 Hz), 7.22 (2H, d, J = 8.12 Hz), 6.99 (2H, t, J = 4.06 Hz), 6.87 (1H, dd, J = 8.35, 2.09 Hz), 5.01 (2H, s), 4.97 (1H, t, J = 9.51 Hz), 4.55 (1H, dd, J = 10.09, 6.61 Hz), 4.45 (1H, t, J = 9.51 Hz), 4.07 (1H, dd, J = 9.97, 6.49 Hz), 3.92-3.85 (1H, m), 3.78 (3H, s), 3.56 (2H, s), 3.09 (1H, t, J = 4.99 Hz), 2.60 (2H, q, J = 7.58 Hz), 2.42-2.30 (7H, br m), 2.16 (3H, s), 1.17 (3H, t, J = 7.54 Hz). |

TABLE 1-5

| 33 | 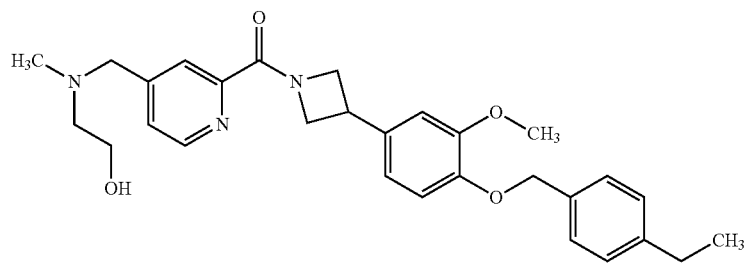 [SMILES: CCc1ccc(COc2ccc(C3CN(C(=O)c4cc(CN(C)CCO)ccn4)C3)cc2OC)cc1] | 1H-NMR (400 MHz, DMSO-d6) δ: 8.54 (1H, d, J = 4.87 Hz), 7.94 (1H, s), 7.47 (1H, dd, J = 4.99, 1.51 Hz), 7.34 (2H, d, J = 8.12 Hz), 7.22 (2H, d, J = 8.12 Hz), 7.01-6.98 (2H, m), 6.87 (1H, dd, J = 8.35, 1.86 Hz), 5.01 (2H, s), 4.97 (1H, t, J = 9.39 Hz), 4.56 (1H, dd, J = 10.20, 6.49 Hz), 4.48-4.43 (2H, m), 4.08 (1H, dd, J = 9.97, 6.49 Hz), 3.93-3.85 (1H, m), 3.78 (3H, s), 3.61 (2H, s), 3.53 (2H, q, J = 5.95 Hz), 2.60 (2H, q, J = 7.58 Hz), 2.46 (2H, t, J = 6.38 Hz), 2.18 (3H, s), 1.17 (3H, t, J = 7.65 Hz). |
|---|---|---|
| 34 | 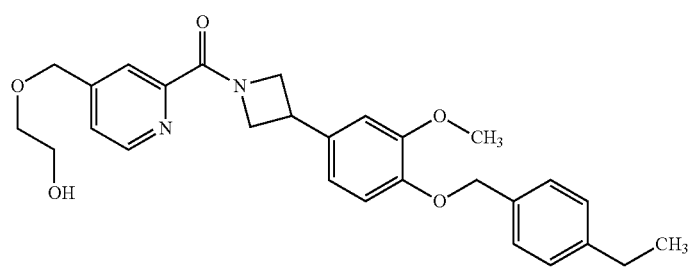 [SMILES: CCc1ccc(COc2ccc(C3CN(C(=O)c4cc(COCCO)ccn4)C3)cc2OC)cc1] | 1H-NMR (400 MHz, DMSO-d6) δ: 8.57 (1H, d, J = 4.87 Hz), 7.95 (1H, d, J = 0.93 Hz), 7.49-7.48 (1H, m), 7.34 (2H, d, J = 8.12 Hz), 7.22 (2H, d, J = 7.88 Hz), 7.00-6.98 (2H, m), 6.87 (1H, dd, J = 8.23, 1.97 Hz), 5.01 (2H, s), 4.97 (1H, t, J = 9.39 Hz), 4.70 (1H, t, J = 5.45 Hz), 4.63 (2H, s), 4.56 (1H, dd, J = 10.20, 6.49 Hz), 4.46 (1H, t, J = 9.74 Hz), 4.08 (1H, dd, J = 9.97, 6.49 Hz), 3.93-3.85 (1H, m), 3.78 (3H, s), 3.60-3.56 (2H, m), 3.54-3.51 (2H, m), 2.60 (2H, q, J = 7.58 Hz), 1.17 (3H, t, J = 7.54 Hz). |
| 35 | 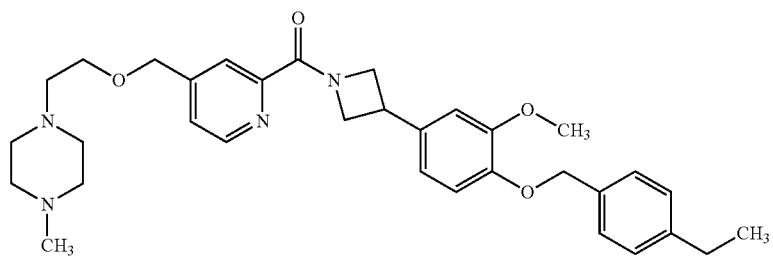 [SMILES: CCc1ccc(COc2ccc(C3CN(C(=O)c4cc(COCCN5CCN(C)CC5)ccn4)C3)cc2OC)cc1] | 1H-NMR (400 MHz, DMSO-d6) δ: 8.57 (1H, d, J = 4.87 Hz), 7.93 (1H, d, J = 0.70 Hz), 7.46-7.45 (1H, m), 7.34 (2H, d, J = 8.12 Hz), 7.22 (2H, d, J = 8.12 Hz), 7.00-6.98 (2H, m), 6.87 (1H, dd, J = 8.35, 2.09 Hz), 5.01 (2H, s), 4.97 (1H, t, J = 9.39 Hz), 4.60 (2H, s), 4.55 (1H, dd, J = 10.20, 6.49 Hz), 4.46 (1H, t, J = 9.62 Hz), 4.08 (1H, dd, J = 10.20, 6.49 Hz), 3.93-3.85 (1H, m), 3.78 (3H, s), 3.59 (2H, t, J = 5.80 Hz), 3.09 (1H, t, J = 4.99 Hz), 2.60 (2H, q, J = 7.58 Hz), 2.53 (2H, t, J = 5.80 Hz), 2.46-2.26 (8H, br m), 2.15 (3H, s), 1.17 (3H, t, J = 7.54 Hz). |

TABLE 1-5-continued

| 36 | 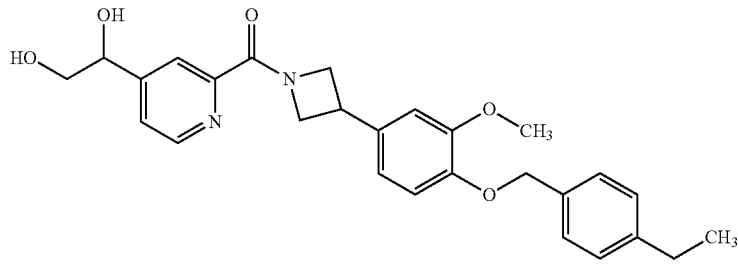 [SMILES: CCc1ccc(COc2ccc(C3CN(C(=O)c4cc(C(O)CO)ccn4)C3)cc2OC)cc1] | 1H-NMR (400 MHz, DMSO-d6) δ: 8.53 (1H, d, J = 4.87 Hz), 7.98 (1H, d, J = 0.70 Hz), 7.48 (1H, dd, J = 5.10, 1.39 Hz), 7.34 (2H, d, J = 8.12 Hz), 7.22 (2H, d, J = 8.12 Hz), 6.99 (2H, d, J = 8.12 Hz), 6.87 (1H, dd, J = 8.23, 1.97 Hz), 5.57 (1H, d, J = 4.64 Hz), 5.01 (2H, s), 4.97 (1H, t, J = 9.39 Hz), 4.83 (1H, t, J = 5.80 Hz), 4.62 (1H, q, J = 5.41 Hz), 4.55 (1H, dd, J = 10.32, 6.38 Hz), 4.45 (1H, t, J = 9.51 Hz), 4.08 (1H, dd, J = 10.09, 6.61 Hz), 3.93-3.85 (1H, m), 3.78 (3H, s), 3.55-3.43 (2H, m), 2.60 (2H, q, J = 7.58 Hz), 1.17 (3H, t, J = 7.65 Hz). |

TABLE 1-6

| 37 | 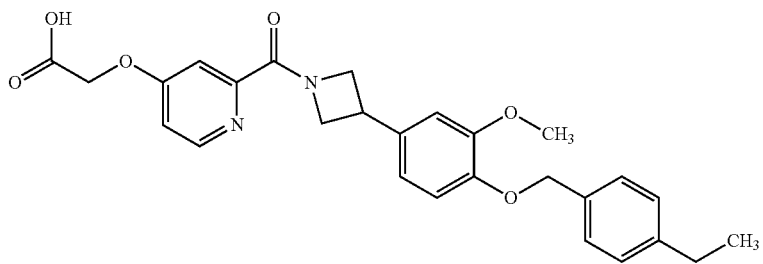 [SMILES: CCc1ccc(COc2ccc(C3CN(C(=O)c4cc(OCC(=O)O)ccn4)C3)cc2OC)cc1] | 1H-NMR (400 MHz, CDCl3) δ: 8.42-8.35 (1H, m), 7.70-7.61 (1H, m), 7.34 (2H, d, J = 7.45 Hz), 7.00-6.94 (1H, m), 6.89-6.76 (3H, m), 5.14-5.05 (3H, m), 4.82 (2H, s), 4.76-4.67 (1H, m), 4.59 (1H, t, J = 9.97 Hz), 4.29-4.22 (1H, m), 3.93-3.80 (1H, m), 3.87 (2H, s), 2.64 (2H, q, J = 7.59 Hz), 1.22 (3H, t, J = 7.66 Hz). |
| 38 | 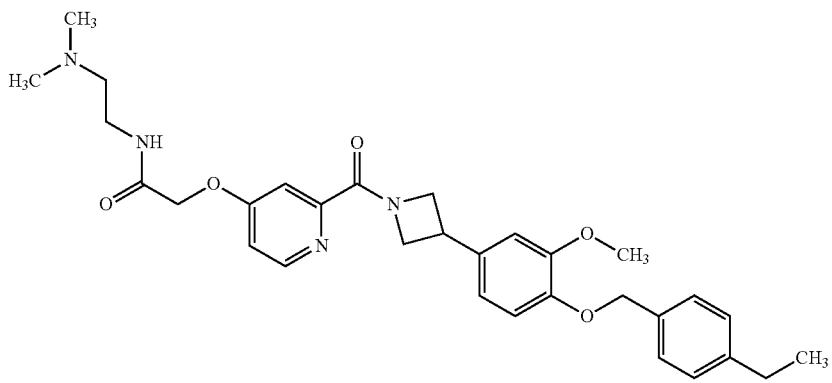 [SMILES: CCc1ccc(COc2ccc(C3CN(C(=O)c4cc(OCC(=O)NCCN(C)C)ccn4)C3)cc2OC)cc1] | 1H-NMR (400 MHz, CDCl3) δ: 8.42 (1H, d, J = 5.64 Hz), 7.71 (1H, d, J = 2.62 Hz), 7.37 (1H, br s), 7.34 (2H, d, J = 8.06 Hz), 7.19 (2H, d, J = 7.86 Hz), 6.98 (1H, dd, J = 5.64, 2.62 Hz), 6.89-6.79 (3H, m), 5.10 (2H, s), 5.08-5.03 (1H, m), 4.72-4.65 (1H, m), 4.61 (2H, s), 4.60-4.56 (1H, m), 4.30-4.21 (1H, m), 3.89 (3H, s), 3.88-3.78 (1H, m), 3.52 (2H, q, J = 5.64 Hz), 2.65 (3H, t, J = 7.66 Hz), 2.41 (6H, br s). |
| 39 | 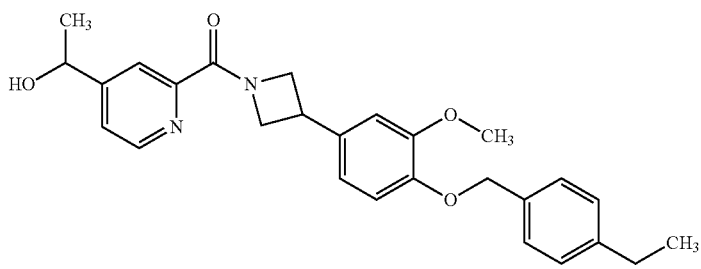 [SMILES: CCc1ccc(COc2ccc(C3CN(C(=O)c4cc(C(C)O)ccn4)C3)cc2OC)cc1] | 1H-NMR (400 MHz, DMSO-d6) δ: 8.53 (1H, d, J = 5.07 Hz), 7.97 (1H, s), 7.48 (1H, d, J = 4.85 Hz), 7.34 (2H, d, J = 7.94 Hz), 7.22 (2H, d, J = 7.94 Hz), 6.99 (2H, d, J = 8.38 Hz), 6.87 (1H, t, J = 4.08 Hz), 5.48 (1H, d, J = 4.41 Hz), 5.01 (2H, s), 4.96 (1H, t, J = 9.59 Hz), 4.80 (1H, t, J = 5.73 Hz), 4.55 (1H, dd, J = 10.03, 6.51 Hz), 4.45 (1H, t, J = 9.37 Hz), 4.08 (1H, dd, J = 10.03, 6.29 Hz), 3.89 (1H, t, J = 6.62 Hz), 3.78 (3H, s), 2.60 (2H, q, J = 7.57 Hz), 1.34 (3H, d, J = 6.40 Hz), 1.17 (3H, t, J = 7.61 Hz). |

TABLE 1-6-continued

| 40 | 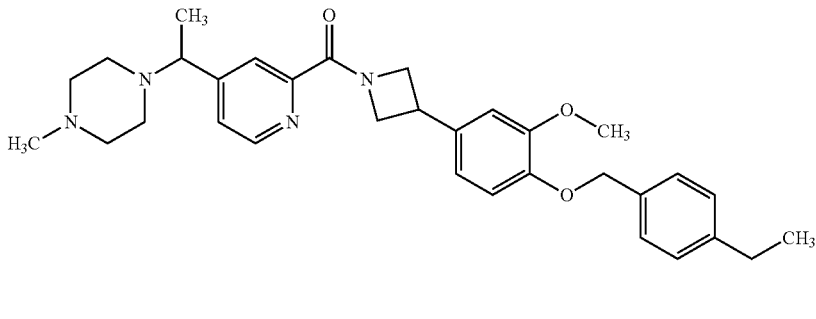 [SMILES: CCc1ccc(COc2ccc(C3CN(C(=O)c4cc(C(C)N5CCN(C)CC5)ccn4)C3)cc2OC)cc1] | 1H-NMR (400 MHz, DMSO-d6) δ: 8.55 (1H, d, J = 4.87 Hz), 7.92 (1H, s), 7.45 (1H, dd, J = 5.10, 1.62 Hz), 7.34 (2H, d, J = 8.12 Hz), 7.22 (2H, d, J = 7.88 Hz), 7.00-6.98 (2H, m), 6.87 (1H, dd, J = 8.35, 1.86 Hz), 5.01 (2H, s), 4.97 (1H, t, J = 9.51 Hz), 4.56 (1H, dd, J = 9.97, 6.49 Hz), 4.45 (1H, t, J = 9.51 Hz), 4.07 (1H, dd, J = 10.20, 6.49 Hz), 3.92-3.85 (1H, m), 3.78 (3H, s), 3.56-3.50 (1H, m), 2.60 (2H, q, J = 7.58 Hz), 2.31 (8H, s), 2.15 (3H, s), 1.27 (3H, d, J = 6.72 Hz), 1.17 (3H, t, J = 7.65 Hz). |

TABLE 1-7

| 41 | 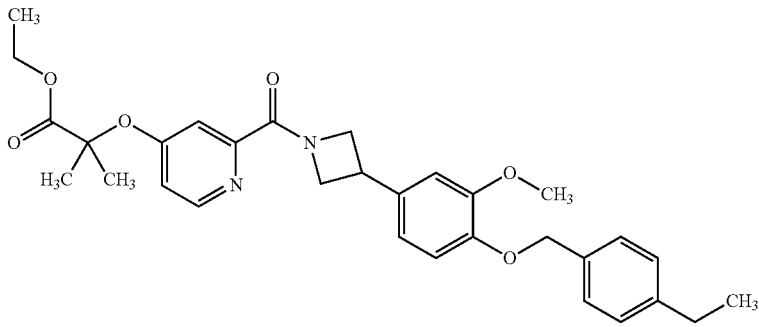 [SMILES: CCOC(=O)C(C)(C)Oc1ccnc(C(=O)N2CC(c3ccc(OCc4ccc(CC)cc4)c(OC)c3)C2)c1] | 1H-NMR (400 MHz, CDCl3) δ: 8.36-8.29 (1H, m), 7.54-7.47 (1H, m), 7.38-7.30 (2H, m), 7.22-7.13 (2H, m), 6.92-6.68 (4H, m), 5.15-4.99 (3H, m), 4.72-4.50 (2H, m), 4.30-4.19 (3H, m), 3.89 (3H, s), 3.86-3.73 (1H, m), 2.64 (2H, q, J = 7.45 Hz), 1.68 (6H, s), 1.23 (6H, q, J = 7.52 Hz). |
| 42 | 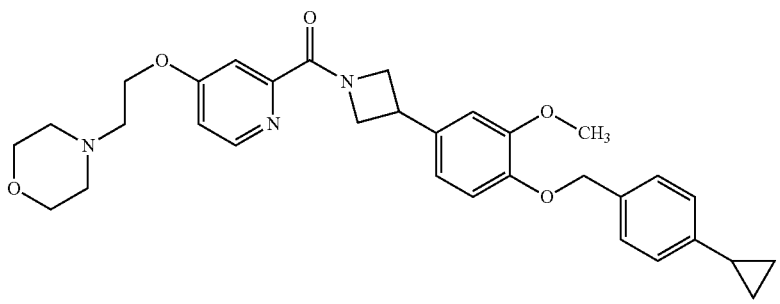 [SMILES: COc1cc(C2CN(C(=O)c3cc(OCCN4CCOCC4)ccn3)C2)ccc1OCc1ccc(C2CC2)cc1] | 1H-NMR (400 MHz, DMSO-d6) δ: 8.41 (1H, d, J = 5.73 Hz), 7.49 (1H, d, J = 2.65 Hz), 7.29 (2H, d, J = 7.94 Hz), 7.11-7.06 (3H, m), 6.98 (2H, d, J = 8.60 Hz), 6.86 (1H, dd, J = 8.27, 1.87 Hz), 4.99 (2H, s), 4.95 (1H, t, J = 9.48 Hz), 4.53 (1H, dd, J = 10.14, 6.40 Hz), 4.44 (1H, t, J = 9.59 Hz), 4.24 (2H, t, J = 5.51 Hz), 4.06 (1H, dd, J = 10.03, 6.51 Hz), 3.92-3.84 (1H, m), 3.77 (3H, s), 3.57 (4H, t, J = 4.63 Hz), 3.30 (3H, s), 2.71 (2H, t, J = 5.51 Hz), 2.47 (4H, t, J = 4.63 Hz), 1.94-1.87 (1H, m), 0.96-0.91 (2H, m), 0.68-0.63 (2H, m). |
| 43 | 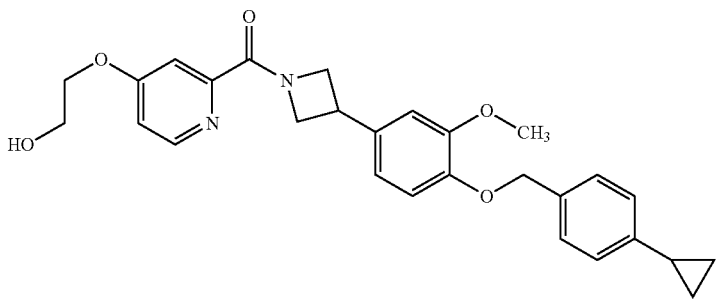 [SMILES: COc1cc(C2CN(C(=O)c3cc(OCCO)ccn3)C2)ccc1OCc1ccc(C2CC2)cc1] | 1H-NMR (400 MHz, DMSO-d6) δ: 8.42 (1H, d, J = 5.51 Hz), 7.48 (1H, d, J = 2.65 Hz), 7.29 (2H, d, J = 8.16 Hz), 7.10-7.07 (3H, m), 8.99-6.97 (2H, m), 6.86 (1H, dd, J = 8.38, 1.98 Hz), 4.99 (2H, s), 4.97-4.92 (2H, m), 4.54 (1H, dd, J = 10.03, 6.51 Hz), 4.44 (1H, t, J= 9.70 Hz), 4.14 (2H, t, J = 4.85 Hz), 4.06 (1H, dd, J = 10.37, 6.62 Hz), 3.92-3.84 (1H, m), 3.77 (3H, s), 3.74 (2H, t, J = 4.74 Hz), 1.94-1.88 (1H, m), 0.96-0.91 (2H, m), 0.68-0.64 (2H, m). |

TABLE 1-7-continued

| 44 | 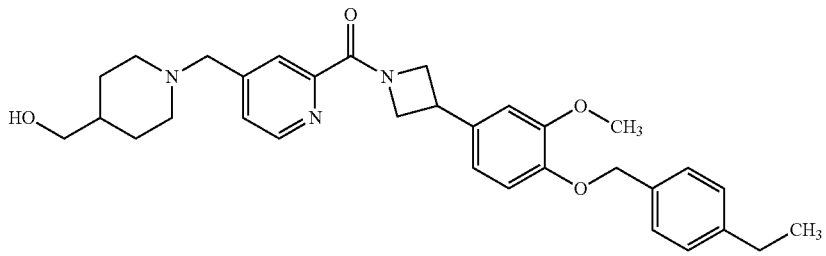 [SMILES: CCc1ccc(COc2ccc(C3CN(C(=O)c4cc(CN5CCC(CO)CC5)ccn4)C3)cc2OC)cc1] | 1H-NMR (400 MHz, DMSO-d6) δ: 8.54 (1H, d, J = 4.87 Hz), 7.92 (1H, s), 7.44 (1H, d, J = 4.41 Hz), 7.34 (2H, d, J = 7.88 Hz), 7.22 (2H, d, J = 8.12 Hz), 7.00-6.98 (2H, m), 6.87 (1H, dd, J = 8.23, 1.97 Hz), 5.01 (2H, s), 4.97 (1H, t, J = 9.51 Hz), 4.56 (1H, dd, J = 9.97, 6.49 Hz), 4.48-4.40 (2H, m), 4.07 (1H, dd, J = 9.97, 6.49 Hz), 3.93-3.85 (1H, m), 3.78 (3H, s), 3.54 (2H, s), 3.25 (2H, t, J = 5.80 Hz), 2.77 (2H, d, J = 10.20 Hz), 2.60 (2H, q, J = 7.58 Hz), 1.95 (2H, t, J = 11.02 Hz), 1.63 (2H, d, J = 11.36 Hz), 1.33 (1H, s), 1.19-1.11 (5H, m). |
|---|---|---|

TABLE 1-8

| 45 | 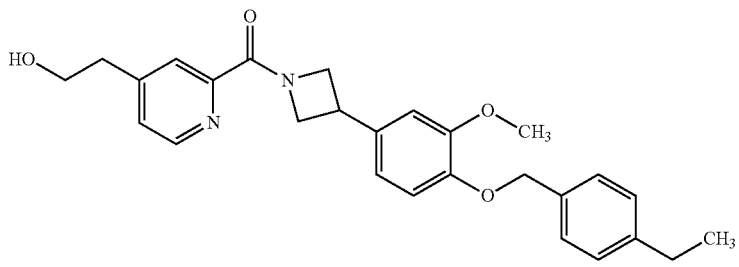 [SMILES: CCc1ccc(COc2ccc(C3CN(C(=O)c4cc(CCO)ccn4)C3)cc2OC)cc1] | 1H-NMR (400 MHz, DMSO-d6) δ: 8.49 (1H, d, J = 4.87 Hz), 7.86 (1H, s), 7.39 (1H, dd, J = 4.87, 1.62 Hz), 7.34 (2H, d, J = 7.88 Hz), 7.22 (2H, d, J = 8.12 Hz), 7.00-6.98 (2H, m), 6.87 (1H, dd, J = 8.35, 1.86 Hz), 5.01 (2H, s), 4.96 (1H, t, J = 9.51 Hz), 4.72 (1H, t, J = 5.22 Hz), 4.54 (1H, dd, J= 10.20, 6.49 Hz), 4.45 (1H, t, J = 9.62 Hz), 4.07 (1H, dd, J = 9.97, 6.49 Hz), 3.91-3.86 (1H, m), 3.78 (3H, s), 3.67 (2H, dd, J = 11.59, 6.26 Hz), 2.81 (2H, t, J = 6.38 Hz), 2.60 (2H, q, J = 7.58 Hz), 1.17 (3H, t, J = 7.54 Hz). |
|---|---|---|
| 46 | 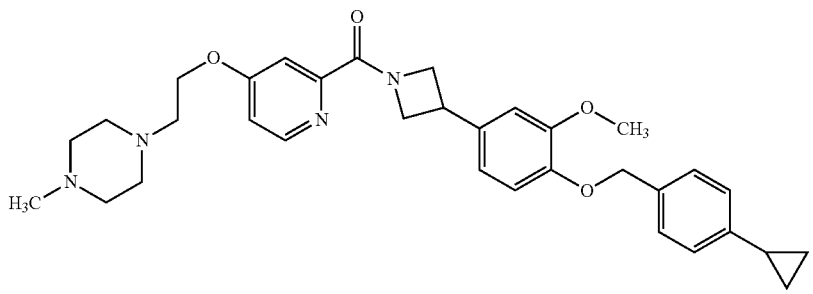 [SMILES: COc1cc(C2CN(C(=O)c3cc(OCCN4CCN(C)CC4)ccn3)C2)ccc1OCc1ccc(C2CC2)cc1] | 1H-NMR (400 MHz, CDCl3) δ: 8.35 (1H, d, J = 5.51 Hz), 7.67 (1H, d, J = 2.43 Hz), 7.31 (2H, d, J = 8.16 Hz), 7.06 (2H, d, J = 8.16 Hz), 6.88-6.79 (4H, m), 5.09 (2H, s), 5.07 (1H, t, J = 9.48 Hz), 4.68 (1H, dd, J = 10.70, 6.51 Hz), 4.59 (1H, t, J = 9.81 Hz), 4.25 (1H, dd, J = 10.70, 6.51 Hz), 4.21 (2H, t, J = 5.51 Hz), 3.89 (3H, s), 3.87-3.79 (1H, m), 2.84 (2H, t, J = 5.62 Hz), 2.64 (3H, br s), 2.52 (3H, br s), 2.32 (3H, s), 1.92-1.85 (1H, m), 0.97-0.92 (2H, m), 0.70-0.66 (2H, m). |
| 47 | 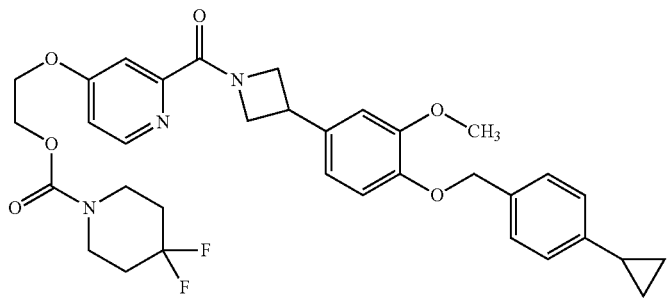 [SMILES: COc1cc(C2CN(C(=O)c3cc(OCCOC(=O)N4CCC(F)(F)CC4)ccn3)C2)ccc1OCc1ccc(C2CC2)cc1] | 1H-NMR (400 MHz, CDCl3) δ: 8.38 (1H, d, J = 5.51 Hz), 7.69 (1H, d, J = 2.65 Hz), 7.31 (2H, d, J = 8.38 Hz), 7.06 (2H, d, J = 8.38 Hz), 6.89-6.80 (4H, m), 5.09 (2H, s), 5.07 (1H, t, J = 9.60 Hz), 4.68 (1H, dd, J = 10.59, 6.40 Hz), 4.59 (1H, t, J = 9.70 Hz), 4.47 (2H, t, J = 4.85 Hz), 4.31 (2H, t, J = 4.85 Hz), 4.25 (1H, dd, J = 10.48, 6.51 Hz), 3.89 (3H, s), 3.86-3.80 (1H, m), 3.60 (4H, br s), 2.02-1.85 (5H, br m), 0.97-0.92 (2H, m), 0.70-0.66 (2H, m). |
| 48 | 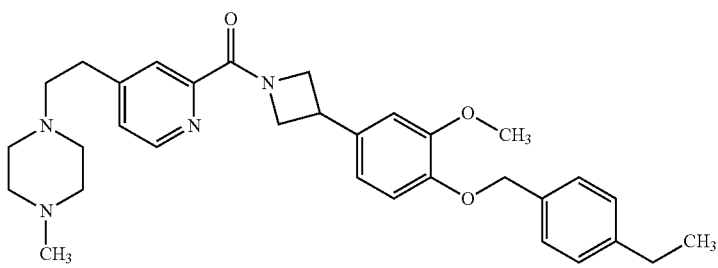 [SMILES: CCc1ccc(COc2ccc(C3CN(C(=O)c4cc(CCN5CCN(C)CC5)ccn4)C3)cc2OC)cc1] | 1H-NMR (400 MHz, DMSO-d6) δ: 8.49 (1H, d, J = 4.87 Hz), 7.86 (1H, s), 7.41 (1H, dd, J = 5.10, 1.62 Hz), 7.34 (2H, d, J = 8.12 Hz), 7.22 (2H, d, J = 8.12 Hz), 7.00-6.98 (2H, m), 6.87 (1H, dd, J = 8.23, 1.97 Hz), 5.01 (2H, s), 4.96 (1H, t, J = 9.51 Hz), 4.54 (1H, dd, J = 10.09, 6.61 Hz), 4.45 (1H, t, J = 9.51 Hz), 4.07 (1H, dd, J = 9.97, 6.49 Hz), 3.92-3.85 (1H, m), 3.78 (3H, s), 3.09 (1H, t, J = 4.99 Hz), 2.82 (2H, t, J = 7.42 Hz), 2.61 (2H, t, J = 7.65 Hz), 2.55 (2H, t, J = 7.54 Hz), 2.43-2.30 (7H, m), 2.15 (3H, s), 1.17 (3H, t, J = 7.65 Hz). |

TABLE 1-9

| 49 | 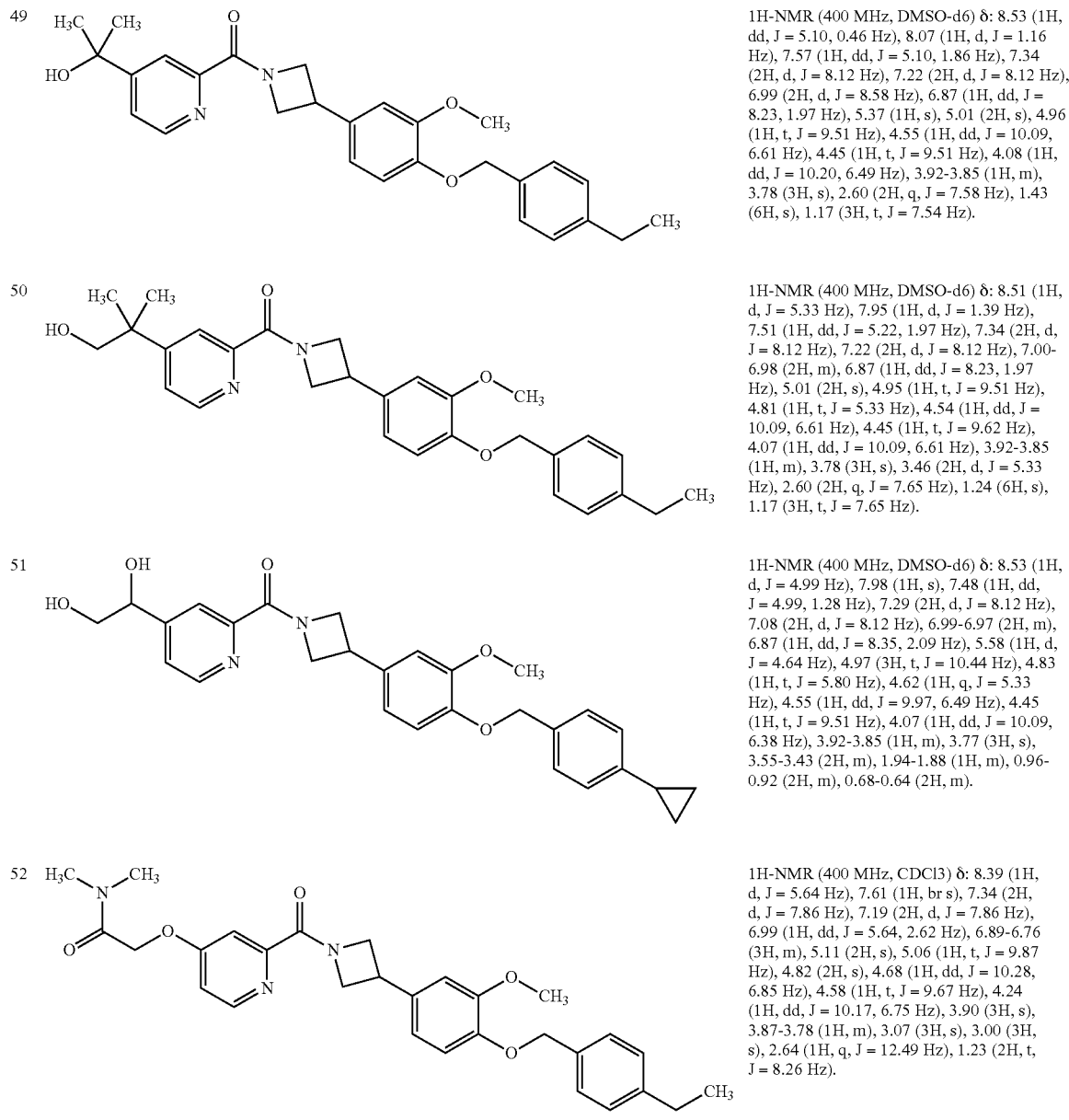 | 1H-NMR (400 MHz, DMSO-d6) δ: 8.53 (1H, dd, J = 5.10, 0.46 Hz), 8.07 (1H, d, J = 1.16 Hz), 7.57 (1H, dd, J = 5.10, 1.86 Hz), 7.34 (2H, d, J = 8.12 Hz), 7.22 (2H, d, J = 8.12 Hz), 6.99 (2H, d, J = 8.58 Hz), 6.87 (1H, dd, J = 8.23, 1.97 Hz), 5.37 (1H, s), 5.01 (2H, s), 4.96 (1H, t, J = 9.51 Hz), 4.55 (1H, dd, J = 10.09, 6.61 Hz), 4.45 (1H, t, J = 9.51 Hz), 4.08 (1H, dd, J = 10.20, 6.49 Hz), 3.92-3.85 (1H, m), 3.78 (3H, s), 2.60 (2H, q, J = 7.58 Hz), 1.43 (6H, s), 1.17 (3H, t, J = 7.54 Hz). |
|---|---|---|
| 50 | | 1H-NMR (400 MHz, DMSO-d6) δ: 8.51 (1H, d, J = 5.33 Hz), 7.95 (1H, d, J = 1.39 Hz), 7.51 (1H, dd, J = 5.22, 1.97 Hz), 7.34 (2H, d, J = 8.12 Hz), 7.22 (2H, d, J = 8.12 Hz), 7.00-6.98 (2H, m), 6.87 (1H, dd, J = 8.23, 1.97 Hz), 5.01 (2H, s), 4.95 (1H, t, J = 9.51 Hz), 4.81 (1H, t, J = 5.33 Hz), 4.54 (1H, dd, J = 10.09, 6.61 Hz), 4.45 (1H, t, J = 9.62 Hz), 4.07 (1H, dd, J = 10.09, 6.61 Hz), 3.92-3.85 (1H, m), 3.78 (3H, s), 3.46 (2H, d, J = 5.33 Hz), 2.60 (2H, q, J = 7.65 Hz), 1.24 (6H, s), 1.17 (3H, t, J = 7.65 Hz). |
| 51 | | 1H-NMR (400 MHz, DMSO-d6) δ: 8.53 (1H, d, J = 4.99 Hz), 7.98 (1H, s), 7.48 (1H, dd, J = 4.99, 1.28 Hz), 7.29 (2H, d, J = 8.12 Hz), 7.08 (2H, d, J = 8.12 Hz), 6.99-6.97 (2H, m), 6.87 (1H, dd, J = 8.35, 2.09 Hz), 5.58 (1H, d, J = 4.64 Hz), 4.97 (3H, t, J = 10.44 Hz), 4.83 (1H, t, J = 5.80 Hz), 4.62 (1H, q, J = 5.33 Hz), 4.55 (1H, dd, J = 9.97, 6.49 Hz), 4.45 (1H, t, J = 9.51 Hz), 4.07 (1H, dd, J = 10.09, 6.38 Hz), 3.92-3.85 (1H, m), 3.77 (3H, s), 3.55-3.43 (2H, m), 1.94-1.88 (1H, m), 0.96-0.92 (2H, m), 0.68-0.64 (2H, m). |
| 52 | | 1H-NMR (400 MHz, CDCl3) δ: 8.39 (1H, d, J = 5.64 Hz), 7.61 (1H, br s), 7.34 (2H, d, J = 7.86 Hz), 7.19 (2H, d, J = 7.86 Hz), 6.99 (1H, dd, J = 5.64, 2.62 Hz), 6.89-6.76 (3H, m), 5.11 (2H, s), 5.06 (1H, t, J = 9.87 Hz), 4.82 (2H, s), 4.68 (1H, dd, J = 10.28, 6.85 Hz), 4.58 (1H, t, J = 9.67 Hz), 4.24 (1H, dd, J = 10.17, 6.75 Hz), 3.90 (3H, s), 3.87-3.78 (1H, m), 3.07 (3H, s), 3.00 (3H, s), 2.64 (1H, q, J = 12.49 Hz), 1.23 (2H, t, J = 8.26 Hz). |

TABLE 1-10

| 53 | 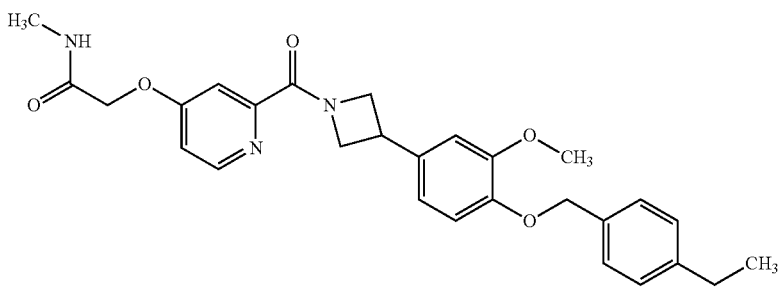 [SMILES: CCc1ccc(COc2ccc(C3CN(C(=O)c4cc(OCC(=O)NC)ccn4)C3)cc2OC)cc1] | 1H-NMR (400 MHz, CDCl3) δ: 8.44 (1H, d, J = 5.64 Hz), 7.73 (1H, d, J = 2.42 Hz), 7.34 (2H, d, J = 7.86 Hz), 7.19 (2H, d, J = 8.06 Hz), 6.93-6.80 (4H, m), 6.51 (1H, br s), 5.11 (2H, s), 5.09-5.04 (1H, m), 4.73-4.66 (1H, m), 4.64-4.57 (3H, m), 4.30-4.22 (1H, m), 3.89 (3H, s), 3.88-3.79 (3H, m), 2.93 (3H, d, J = 5.04 Hz), 2.64 (2H, q, J = 7.66 Hz), 1.23 (3H, t, J = 7.66 Hz). |
|---|---|---|

TABLE 1-10-continued

| 54 | 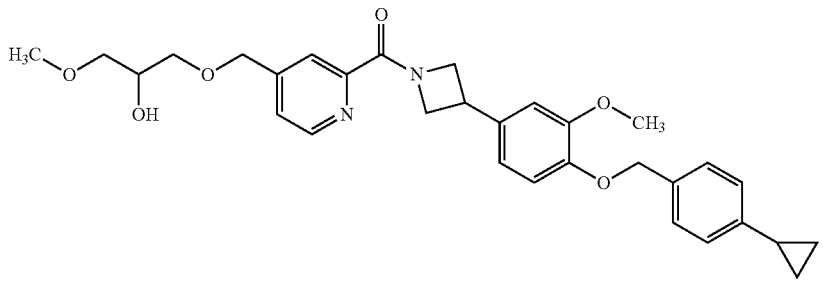 [SMILES: COCC(O)COCc1ccnc(C(=O)N2CC(c3ccc(OCc4ccc(C5CC5)cc4)c(OC)c3)C2)c1] | 1H-NMR (400 MHz, CDCl3) δ: 8.53 (1H, d, J = 5.07 Hz), 8.06 (1H, s), 7.36 (1H, d, J = 5.07 Hz), 7.31 (2H, d, J = 8.16 Hz), 7.06 (2H, d, J = 8.16 Hz), 6.88-6.80 (3H, m), 5.09 (2H, s), 5.08 (1H, t, J = 9.70 Hz), 4.68 (1H, dd, J = 10.48, 6.51 Hz), 4.63 (2H, s), 4.60 (1H, t, J = 9.70 Hz), 4.26 (1H, dd, J = 10.59, 6.40 Hz), 4.02 (1H, br s), 3.89 (3H, s), 3.86-3.80 (1H, m), 3.65-3.44 (4H, m), 3.40 (3H, s), 2.46 (1H, d, J = 3.75 Hz), 1.92-1.85 (1H, m), 0.97-0.92 (2H, m), 0.70-0.65 (2H, m). |
| --- | --- | --- |
| 55 | 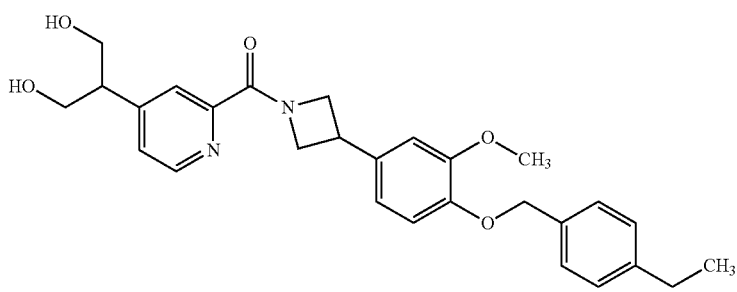 [SMILES: CCc1ccc(COc2ccc(C3CN(C(=O)c4cc(C(CO)CO)ccn4)C3)cc2OC)cc1] | 1H-NMR (400 MHz, DMSO-d6) δ: 8.49 (1H, d, J = 5.10 Hz), 7.86 (1H, d, J = 1.16 Hz), 7.40 (1H, dd, J = 4.99, 1.74 Hz), 7.34 (2H, d, J = 8.12 Hz), 7.21 (2H, d, J = 8.12 Hz), 7.00-6.98 (2H, m), 6.87 (1H, dd, J = 8.35, 1.86 Hz), 5.01 (2H, s), 4.96 (1H, t, J = 9.39 Hz), 4.65 (2H, t, J = 5.10 Hz), 4.54 (1H, dd, J = 9.97, 6.26 Hz), 4.45 (1H, t, J = 9.51 Hz), 4.07 (1H, dd, J = 9.97, 6.49 Hz), 3.92-3.85 (1H, m), 3.78 (3H, s), 3.73-3.68 (2H, m), 3.66-3.60 (2H, m), 3.16-3.12 (1H, m), 2.94-2.88 (1H, m), 2.60 (2H, q, J = 7.58 Hz), 1.85-1.82 (1H, m), 1.17 (3H, t, J = 7.65 Hz). |
| 56 | 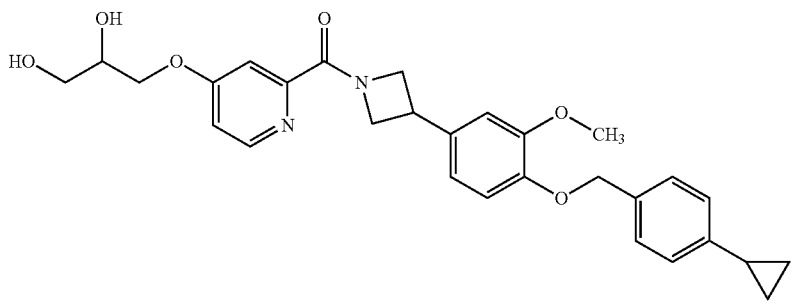 [SMILES: COc1cc(C2CN(C(=O)c3cc(OCC(O)CO)ccn3)C2)ccc1OCc1ccc(C2CC2)cc1] | 1H-NMR (400 MHz, DMSO-d6) δ: 8.42 (1H, d, J = 5.64 Hz), 7.49 (1H, d, J = 2.62 Hz), 7.29 (2H, d, J = 8.06 Hz), 7.10-7.07 (3H, m), 6.99-6.97 (3H, m), 6.86 (1H, dd, J = 8.36, 1.91 Hz), 5.04 (1H, d, J = 5.04 Hz), 4.99 (2H, s), 4.95 (1H, t, J = 9.27 Hz), 4.72 (1H, t, J = 5.64 Hz), 4.54 (1H, dd, J = 10.38, 6.35 Hz), 4.44 (1H, t, J = 9.87 Hz), 4.16 (1H, dd, J = 10.17, 3.73 Hz), 4.08-3.99 (2H, m), 3.92-3.79 (2H, m), 3.77 (3H, s), 3.46-3.42 (2H, m), 1.94-1.88 (1H, m), 0.96-0.92 (2H, m), 0.68-0.64 (2H, m). |

TABLE 1-11

| 57 | 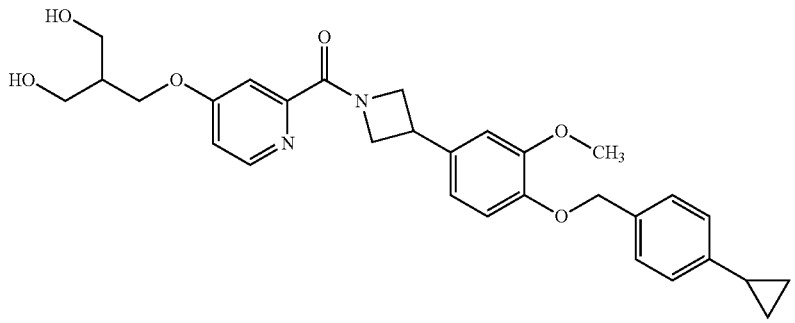 [SMILES: COc1cc(C2CN(C(=O)c3cc(OCC(CO)CO)ccn3)C2)ccc1OCc1ccc(C2CC2)cc1] | 1H-NMR (400 MHz, DMSO-d6) δ: 8.42 (1H, d, J = 5.64 Hz), 7.49 (1H, d, J = 2.62 Hz), 7.29 (2H, d, J = 8.06 Hz), 7.10-7.07 (3H, m), 8.99-6.97 (2H, m), 6.86 (1H, dd, J = 8.26, 1.81 Hz), 4.99 (2H, s), 4.95 (1H, t, J = 9.57 Hz), 4.64-4.51 (3H, br m), 4.44 (1H, t, J = 9.47 Hz), 4.12 (2H, d, J = 6.04 Hz), 4.06 (1H, dd, J = 9.97, 6.55 Hz), 3.92-3.84 (1H, m), 3.77 (3H, s), 3.56-3.47 (4H, m), 2.03-1.97 (1H, m), 1.94-1.88 (1H, m), 0.96-0.91 (2H, m), 0.68-0.64 (2H, m). |
| --- | --- | --- |

TABLE 1-11-continued

| 58 | 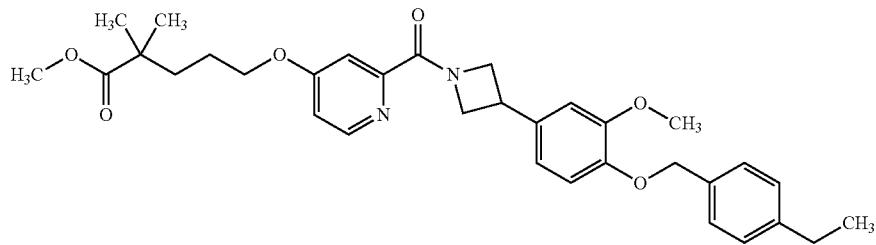 [SMILES: CCc1ccc(COc2ccc(C3CN(C(=O)c4cc(OCCCC(C)(C)C(=O)OC)ccn4)C3)cc2OC)cc1] | 1H-NMR (400 MHz, CDCl3) δ: 8.35 (1H, d, J = 5.44 Hz), 7.64 (1H, d, J = 2.42 Hz), 7.34 (2H, d, J = 8.06 Hz), 7.19 (2H, d, J = 7.86 Hz), 6.89-6.80 (4H, m), 5.11 (2H, s), 5.10-5.03 (1H, m), 4.71-4.65 (1H, m), 4.63-4.55 (1H, m), 4.38-4.33 (1H, m), 4.28-4.22 (1H, m), 4.07-4.02 (2H, m), 3.89 (3H, s), 3.67 (3H, s), 2.67-2.61 (2H, m), 1.94-1.86 (1H, m), 1.79-1.66 (5H, m), 1.31 (3H, s), 1.25-1.19 (6H, m). |
| --- | --- | --- |
| 59 | 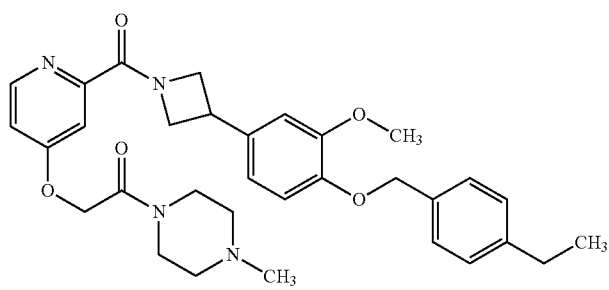 [SMILES: CCc1ccc(COc2ccc(C3CN(C(=O)c4cc(OCC(=O)N5CCN(C)CC5)ccn4)C3)cc2OC)cc1] | 1H-NMR (400 MHz, CDCl3) δ: 8.46-8.37 (1H, m), 7.64 (1H, s), 7.35 (2H, d, J = 7.66 Hz), 7.19 (2H, d, J = 7.66 Hz), 7.04-6.95 (1H, m), 6.93-6.74 (3H, m), 5.11 (2H, s), 5.09-5.01 (1H, m), 4.98-4.87 (1H, m), 4.81 (2H, s), 4.73-4.65 (1H, m), 4.63-4.55 (1H, m), 4.29-4.21 (1H, m), 3.90 (3H, s), 3.88-3.80 (1H, m), 3.70-3.62 (2H, m), 3.57-3.46 (6H, m), 2.70-2.59 (2H, m), 2.31 (3H, s), 1.29-1.20 (3H, m). |
| 60 | 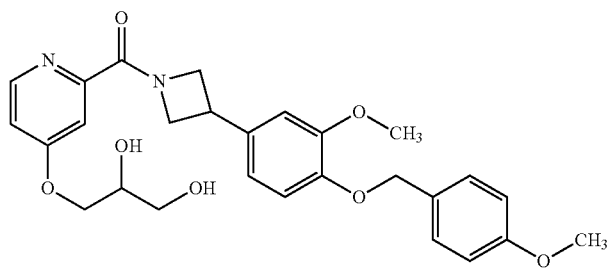 [SMILES: COc1ccc(COc2ccc(C3CN(C(=O)c4cc(OCC(O)CO)ccn4)C3)cc2OC)cc1] | 1H-NMR (400 MHz, DMSO-d6) δ: 8.42 (1H, d, J = 5.73 Hz), 7.49 (1H, d, J = 2.65 Hz), 7.35 (2H, d, J = 8.82 Hz), 7.09 (1H, dd, J = 5.62, 2.76 Hz), 7.01-6.93 (4H, m), 6.87 (1H, dd, J = 8.16, 2.21 Hz), 5.03 (1H, d, J = 5.07 Hz), 4.97 (2H, s), 4.96 (1H, t, J = 9.48 Hz), 4.72 (1H, t, J = 5.73 Hz), 4.54 (1H, dd, J = 10.14, 6.84 Hz), 4.45 (1H, t, J = 9.70 Hz), 4.16 (1H, dd, J = 10.03, 3.86 Hz), 4.09-3.98 (2H, m), 3.92-3.79 (2H, m), 3.77 (3H, s), 3.75 (3H, s), 3.45 (2H, t, J = 5.29 Hz). |

TABLE 1-12

| 61 | 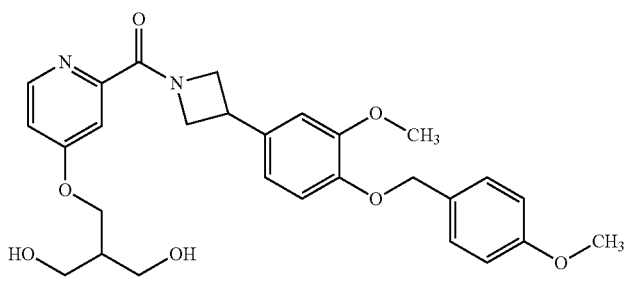 [SMILES: COc1ccc(COc2ccc(C3CN(C(=O)c4cc(OCC(CO)CO)ccn4)C3)cc2OC)cc1] | 1H-NMR (400 MHz, DMSO-d6) δ: 8.41 (1H, d, J = 5.73 Hz), 7.49 (1H, d, J = 2.65 Hz), 7.35 (2H, d, J = 8.60 Hz), 7.09 (1H, dd, J = 5.73, 2.65 Hz), 7.00-6.92 (4H, m), 6.87 (1H, dd, J = 8.27, 1.87 Hz), 4.97 (2H, s), 4.95 (1H, t, J = 9.70 Hz), 4.58-4.52 (3H, m), 4.45 (1H, t, J = 9.48 Hz), 4.12 (2H, d, J = 5.73 Hz), 4.09-4.02 (1H, m), 3.92-3.84 (1H, m), 3.77 (3H, s), 3.75 (3H, s), 3.57-3.47 (4H, m), 2.03-1.97 (1H, m). |
| --- | --- | --- |

TABLE 1-12-continued

| | | |
|---|---|---|
| 62 | 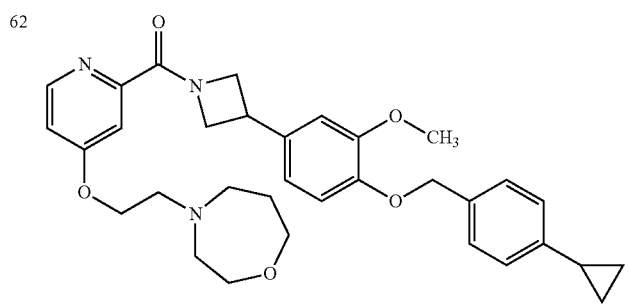 | 1H-NMR (400 MHz, CDCl3) δ: 8.35 (1H, d, J = 5.73 Hz), 7.67 (1H, d, J = 2.65 Hz), 7.31 (2H, d, J = 8.16 Hz), 7.06 (2H, d, J = 7.94 Hz), 6.88-6.80 (4H, m), 5.09 (2H, s), 5.07 (1H, t, J = 9.48 Hz), 4.68 (1H, dd, J = 10.70, 6.51 Hz), 4.59 (1H, t, J = 10.03 Hz), 4.25 (1H, dd, J = 10.48, 6.51 Hz), 4.19 (2H, t, J = 5.84 Hz), 3.89 (3H, s), 3.87-3.82 (1H, m), 3.80 (2H, t, J = 6.06 Hz), 3.74 (2H, t, J = 4.74 Hz), 3.01 (2H, t, J = 5.84 Hz), 2.87-2.83 (4H, m), 1.94-1.85 (3H, m), 0.97-0.92 (2H, m), 0.70-0.66 (2H, m). |
| 63 | 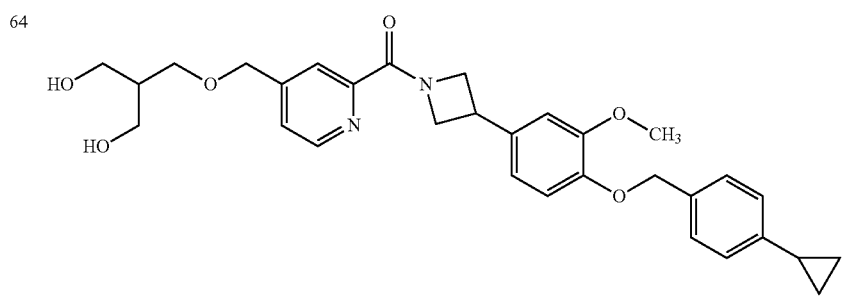 | 1H-NMR (400 MHz, CDCl3) δ: 7.66-7.62 (1H, m), 7.30 (2H, d, J = 7.86 Hz), 7.05 (2H, d, J = 7.86 Hz), 6.88-6.78 (4H, m), 5.10-5.02 (3H, m), 4.72-4.64 (1H, m), 4.62-4.54 (1H, m), 4.29-4.21 (1H, m), 4.10-4.02 (2H, m), 3.89 (3H, s), 3.86-3.78 (2H, m), 2.12-2.02 (1H, m), 1.91-1.61 (5H, m), 1.23 (6H, s), 0.97-0.90 (2H, m), 0.70-0.64 (2H, m). |
| 64 | 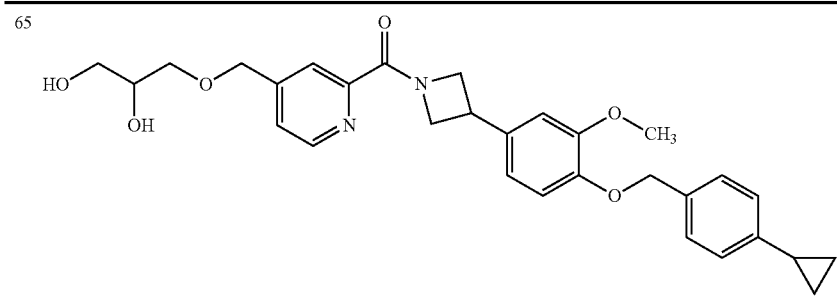 | 1H-NMR (400 MHz, DMSO-d6) δ: 8.57 (1H, d, J = 5.10 Hz), 7.92 (1H, s), 7.46 (1H, d, J = 6.49 Hz), 7.30 (2H, d, J = 8.12 Hz), 7.08 (2H, d, J = 8.12 Hz), 6.98 (2H, dd, J = 5.22, 3.13 Hz), 6.87 (1H, dd, J = 8.35, 1.86 Hz), 4.99 (2H, s), 4.96 (1H, d, J = 9.51 Hz), 4.55 (3H, dd, J = 9.74, 6.03 Hz), 4.48-4.40 (3H, m), 4.08 (1H, dd, J = 10.09, 6.61 Hz), 3.93-3.85 (1H, m), 3.77 (3H, s), 3.50-3.45 (6H, m), 1.94-1.88 (1H, m), 1.86-1.81 (1H, m), 0.95-0.93 (2H, m), 0.68-0.64 (2H, m). |

TABLE 1-13

| | | |
|---|---|---|
| 65 | 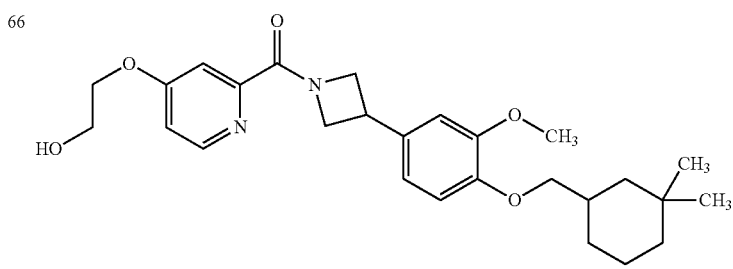 | 1H-NMR (400 MHz, DMSO-d6) δ: 8.57 (1H, d, J = 5.33 Hz), 7.94 (1H, s), 7.48 (1H, dd, J = 4.99, 1.51 Hz), 7.30 (2H, d, J = 8.12 Hz), 7.08 (2H, d, J = 8.12 Hz), 6.98 (2H, dd, J = 5.10, 3.25 Hz), 6.87 (1H, dd, J = 8.35, 1.86 Hz), 4.99-4.94 (3H, m), 4.77 (1H, d, J = 5.10 Hz), 4.62 (2H, s), 4.57-4.53 (2H, m), 4.46 (1H, t, J = 9.51 Hz), 4.08 (1H, dd, J = 10.09, 6.61 Hz), 3.93-3.85 (1H, m), 3.77 (3H, s), 3.67-3.64 (1H, m), 3.52 (1H, dd, J = 9.74, 4.41 Hz), 3.42-3.35 (3H, m), 1.94-1.88 (1H, m), 0.96-0.92 (2H, m), 0.68-0.64 (2H, m). |
| 66 | | 1H-NMR (400 MHz, DMSO-d6) δ: 8.42 (1H, d, J = 5.57 Hz), 7.49 (1H, d, J = 2.55 Hz), 7.10 (1H, dd, J = 5.68, 2.67 Hz), 6.95 (1H, d, J = 1.62 Hz), 6.91-6.85 (2H, m), 4.98-4.93 (2H, m), 4.54 (1H, dd, J = 10.20, 6.49 Hz), 4.44 (1H, t, J = 9.51 Hz), 4.14 (2H, t, J = 4.75 Hz), 4.06 (1H, dd, J = 10.09, 6.61 Hz), 3.91-3.84 (1H, m), 3.77 (3H, s), 3.76-3.66 (4H, m), 1.93-1.81 (2H, m), 1.56-1.34 (4H, m), 1.12-1.04 (1H, m), 0.92-0.80 (8H, m). |

| | | |
|---|---|---|
| 67 | 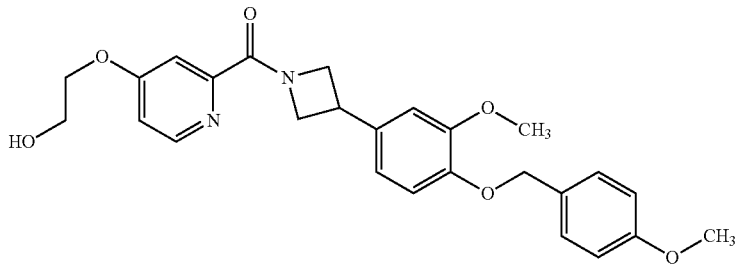 [SMILES: COc1ccc(COc2ccc(C3CN(C(=O)c4cc(OCCO)ccn4)C3)cc2OC)cc1] | 1H-NMR (400 MHz, DMSO-d6) δ: 8.42 (1H, d, J = 5.57 Hz), 7.49 (1H, d, J = 2.78 Hz), 7.36 (2H, d, J = 8.58 Hz), 7.10 (1H, dd, J = 5.68, 2.67 Hz), 7.01-6.97 (2H, m), 6.95-6.92 (2H, m), 6.87 (1H, dd, J = 8.35, 1.86 Hz), 4.95 (4H, dd, J = 10.67, 5.33 Hz), 4.54 (1H, dd, J = 10.09, 6.61 Hz), 4.45 (1H, t, J = 9.62 Hz), 4.14 (2H, t, J = 4.75 Hz), 4.06 (1H, dd, J = 9.97, 6.49 Hz), 3.92-3.84 (1H, m), 3.77 (3H, s), 3.75-3.72 (5H, m). |
| 68 | 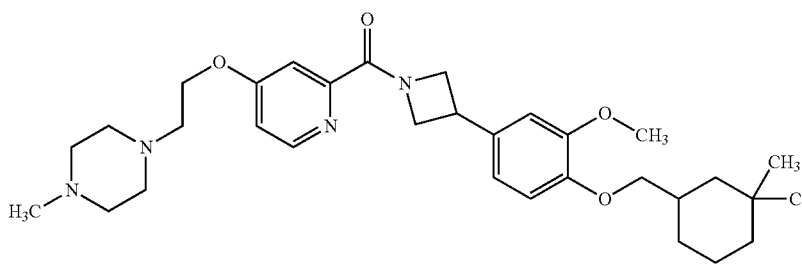 | 1H-NMR (400 MHz, DMSO-d6) δ: 8.42 (1H, d, J = 5.80 Hz), 7.48 (1H, d, J = 2.78 Hz), 7.10 (1H, dd, J = 5.80, 2.55 Hz), 6.95 (1H, d, J = 1.86 Hz), 6.89-6.86 (2H, m), 4.95 (1H, t, J = 9.39 Hz), 4.53 (1H, dd, J = 10.09, 6.38 Hz), 4.44 (1H, t, J = 9.51 Hz), 4.22 (2H, t, J = 5.57 Hz), 4.06 (1H, dd, J = 10.09, 6.61 Hz), 3.91-3.85 (1H, m), 3.77 (3H, s), 3.73-3.66 (2H, m), 3.09 (1H, t, J = 4.87 Hz), 2.71 (2H, t, J = 5.68 Hz), 2.55-2.45 (4H, br m), 2.40-2.32 (3H, br m), 2.18 (3H, s), 1.91-1.82 (2H, m), 1.56-1.34 (4H, m), 1.08 (1H, td, J = 13.10, 4.02 Hz), 0.91-0.79 (8H, m). |

TABLE 1-14

| | | |
|---|---|---|
| 69 | 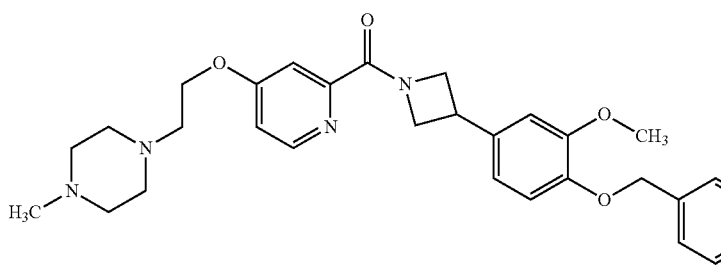 | 1H-NMR (400 MHz, DMSO-d6) δ: 8.41(1H, d, J = 5.57 Hz), 7.48 (1H, d, J = 2.55 Hz), 7.35(2H, d, J = 8.58 Hz), 7.10(1H, dd, J = 5.68, 2.67 Hz), 7.00-6.97(H, m), 6.95-6.92(2H, m), 6.86(1H, dd, J = 8.35, 1.86 Hz), 4.97-4.93(3H, m), 4.53(1H, dd, J = 10.09, 6.61 Hz), 4.44(1H, t, J = 9.39 Hz), 4.21(2H, t, J = 5.68 Hz), 4.06(1H, dd, J = 10.09, 6.61 Hz), 3.93-3.84(1H, m), 3.77(3H, s), 3.75(3H, s), 3.09 (1H, t, J = 4.87 Hz), 2.70(2H, t, J = 5.68 Hz), 2.47(3H, br s), 2.38(1H, t, J = 4.87 Hz), 2.30(3H, br s), 2.14(3H, s). |
| 70 | 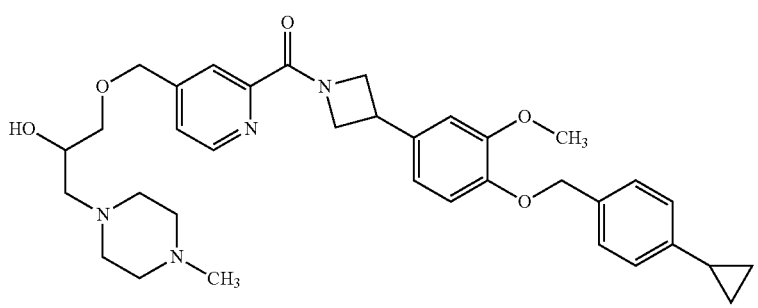 [SMILES: COc1cc(C2CN(C(=O)c3cc(COCC(O)CN4CCN(C)CC4)ccn3)C2)ccc1OCc1ccc(C2CC2)cc1] | 1H-NMR (400 MHz, DMSO-d6) δ: 8.57(1H, d, J = 4.87 Hz), 7.94 (1H, s), 7.49(1H, d, J = 4.87 Hz), 7.29(2H, d, J = 8.35 Hz), 7.06(2H, d, J = 8.12 Hz), 6.99-6.97(2H, m), 6.87(1H, dd, J = 8.35, 1.86 Hz), 4.99-4.94(3H, m), 4.66-4.62(3H, m), 4.58-4.53(1H, m), 4.46(1H, t, J = 9.51 Hz), 4.08(1H, dd, J = 9.97, 6.72 Hz), 3.93-3.85(1H, m), 3.81-3.79(1H, m), 3.77(3H, s), 3.48(1H,dd, J = 9.97, 4.17 Hz), 3.39(1H, dd, J = 9.86, 5.91 Hz), 2.44-2.20(10H, br m), 2.12(3H, s), 1.94-1.88(1H, m), 0.96-0.92(2H, m), 0.68-0.64(2H, m). |

TABLE 1-14-continued

71 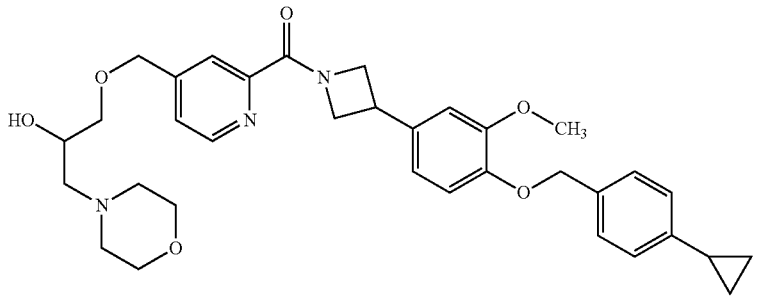 [SMILES: COc1cc(C2CN(C(=O)c3cc(COCC(O)CN4CCOCC4)ccn3)C2)ccc1OCc1ccc(C2CC2)cc1]

1H-NMR (400 MHz, DMSO-d6) δ: 8.58(1H, d, J = 4.87 Hz), 7.94 (1H, d, J = 0.70 Hz), 7.49(1H, dd, J = 4.87, 1.62 Hz), 7.30(2H, d, J = 8.12 Hz), 7.08(2H, d, J = 8.12 Hz), 6.99-6.97(2H, m), 6.87(1H, dd, J = 8.35, 1.86 Hz), 4.97(3H, t, J = 9.74 Hz), 4.69(1H, d, J = 4.87 Hz), 4.63(2H, d, J = 2.32 Hz), 4.55(1H, dd, J = 10.20, 6.49 Hz), 4.46(1H, t, J = 9.51 Hz), 4.08(1H, dd, J = 10.20, 6.49 Hz), 3.93-3.80(2H, m), 3.77(3H, s), 3.55-3.48(5H, br m), 3.43-3.37 (1H, m), 2.40-2.34(5H, br m), 2.30-2.25(1H, m), 1.94-1.88(1H, m), 0.96-0.92(2H, m), 0.68-0.64(2H, m).

72 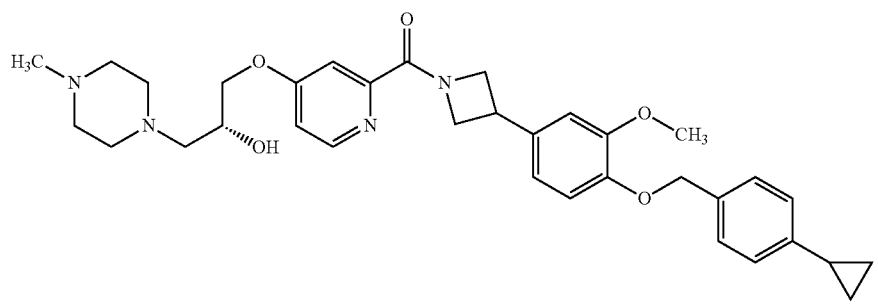 [SMILES: COc1cc(C2CN(C(=O)c3cc(OC[C@H](O)CN4CCN(C)CC4)ccn3)C2)ccc1OCc1ccc(C2CC2)cc1]

1H-NMR (400 MHz, DMSO-d6) δ: 8.41(1H, d, J = 5.80 Hz), 7.49(1H, d, J = 2.55 Hz), 7.29(2H, d, J = 8.12 Hz), 7.10-7.07(3H, m), 6.99-6.97(2H, m), 6.86(1H, dd, J = 8.35, 1.86 Hz), 4.99(2H, s), 4.98-4.93 (2H, m), 4.54(1H, dd, J = 10.20, 6.49 Hz), 4.44(1H, t, J = 9.51 Hz), 4.13(1H, dd, J = 9.74, 2.78 Hz), 4.08-3.98(3H, m), 3.92-3.84 (1H, m), 3.77(3H, s), 2.46-2.25 (10H, br m), 2.13(3H, s), 1.94-1.88 (1H, m), 0.96-0.92(2H, m), 0.68-0.64(2H, m).

TABLE 1-15

73 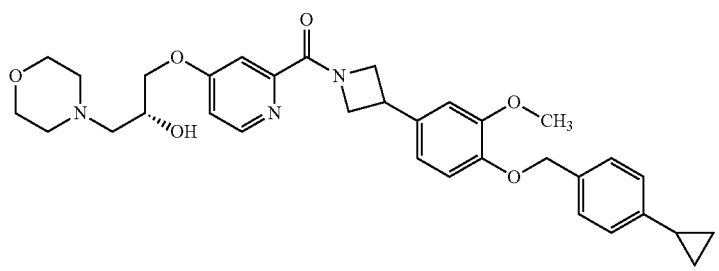 [SMILES: COc1cc(C2CN(C(=O)c3cc(OC[C@H](O)CN4CCOCC4)ccn3)C2)ccc1OCc1ccc(C2CC2)cc1]

1H-NMR (400 MHz, DMSO-d6) δ: 8.42(1H, d, J = 5.80 Hz), 7.50(1H, d, J = 2.55 Hz), 7.30(2H, d, J = 8.12 Hz), 7.11-7.07(3H, m), 6.99-6.97(2H, m), 6.86(1H, dd, J = 8.35,1.86 Hz), 4.99(2H, s), 4.96(2H, t, J = 10.55 Hz), 4.54(1H, dd, J = 10.20, 6.49 Hz), 4.44(1H, t, J = 9.51 Hz), 4.16(1H, dd, J = 9.39, 2.67 Hz), 4.08-3.96(3H, m), 3.92-3.84(1H, m), 3.77(3H, s), 3.56 (4H, t, J = 4.64 Hz), 2.47-2.34(6H, m),1.94-1.88(1H, m), 0.96-0.92(2H, m), 0.68-0.64(2H, m).

74 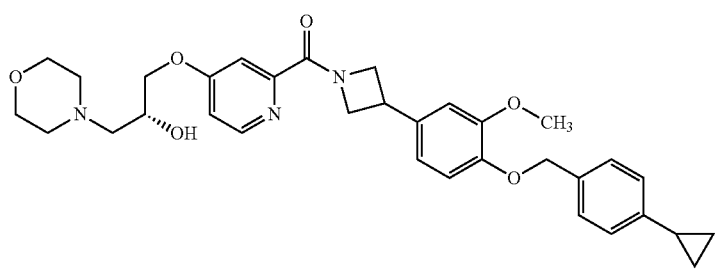 [SMILES: COc1cc(C2CN(C(=O)c3cc(OC[C@H](O)CN4CCOCC4)ccn3)C2)ccc1OCc1ccc(C2CC2)cc1]

1H-NMR (400 MHz, DMSO-d6) δ: 8.42(1H, d, J = 5.80 Hz), 7.50(1H, d, J = 2.55 Hz), 7.30(2H, d, J = 8.12 Hz), 7.11-7.07(3H, m), 6.99-6.97(2H, m), 6.86(1H, dd, J = 8.35, 1.86 Hz), 4.99(2H, s), 4.96(2H, t, J = 10.20 Hz), 4.54(1H, dd, J = 10.09, 6.38 Hz), 4.44(1H, t, J = 9.51 Hz), 4.16(1H, dd, J = 9.39, 2.67 Hz), 4.08-3.96(3H, m), 3.92-3.84(1H, m), 3.77 (3H, s), 3.56(4H, t, J = 4.52 Hz), 2.46-2.33(6H, m), 1.94-1.88(1H, m), 0.96-0.92(2H, m), 0.68-0.64 (2H, m).

TABLE 1-15-continued

| 75 | 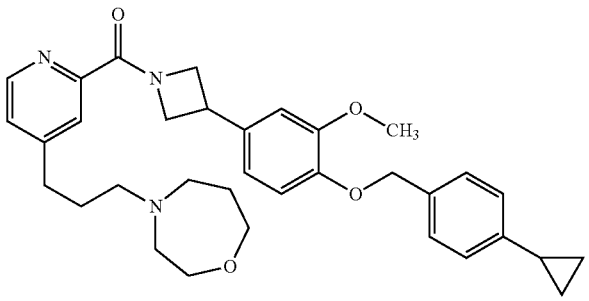 | 1H-NMR (400 MHz, CDCl3) δ: 8.44(1H, d, J = 5.44 Hz), 7.98(1H, d, J = 1.01 Hz), 7.31(2H, d, J = 8.26 Hz), 7.19(1H, dd, J = 4.94, 1.71 Hz), 7.06(2H, d, J = 8.06 Hz), 6.88-6.80 (3H, m), 5.08(2H, s), 5.08(1H, t, J = 9.67 Hz), 4.68(1H, dd, J = 10.48, 6.45 Hz), 4.60(1H, t, J = 9.67 Hz), 4.26(1H, dd, J = 10.58, 6.55 Hz), 3.89(3H, s), 3.88-3.82(1H, m), 3.80(2H, t, J = 6.04 Hz), 3.73(2H, t, J = 4.63 Hz), 2.73-2.67 (6H, m), 2.52(2H, t, J = 7.15 Hz), 1.93-1.80(5H, m), 0.97-0.92(2H, m), 0.70-0.66(2H, m). |
| --- | --- | --- |
| 76 | 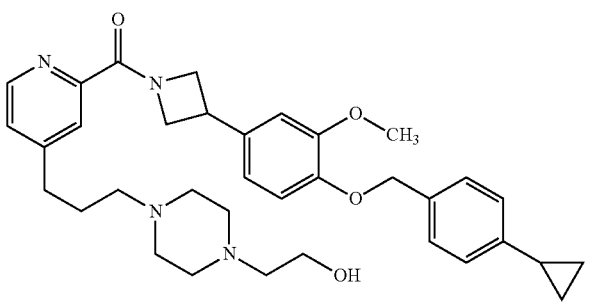 [SMILES: COc1cc(C2CN(C(=O)c3cc(CCCN4CCN(CCO)CC4)ccn3)C2)ccc1OCc1ccc(C2CC2)cc1] | 1H-NMR (400 MHz, CDCl3) δ: 8.44(1H, dd, J = 4.94, 0.71 Hz), 7.98(1H, d, J = 1.01 Hz), 7.31(2H, d, J = 8.06 Hz), 7.18(1H, dd, J = 4.94, 1.71 Hz), 7.06(2H, d, J = 8.26 Hz), 6.87-6.80(3H, m), 5.09(2H, s), 5.08 (1H, t, J = 9.87 Hz), 4.68(1H, dd, J = 10.48, 6.45 Hz), 4.60(1H, t, J = 9.77 Hz), 4.26(1H, dd, J = 10.58, 8.55 Hz), 3.89(3H, s), 3.88-3.80(1H, m), 3.61(2H, t, J = 5.44 Hz), 3.41(1H, t, J = 5.04 Hz), 2.70(2H, t, J = 7.66 Hz), 2.61-2.44(10H, m), 3.86(2H, t, J = 7.35 Hz), 1.92-1.81(3H, m), 0.97-0.92(2H, m), 0.70-0.66(2H, m). |

TABLE 1-16

| 77 | 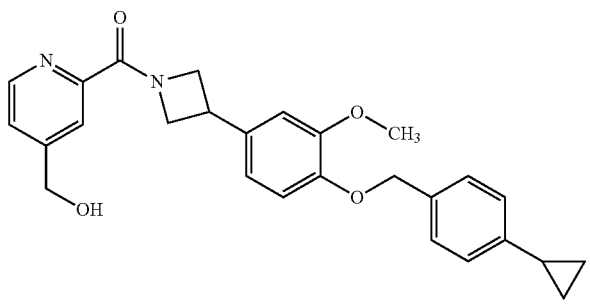 [SMILES: COc1cc(C2CN(C(=O)c3cc(CO)ccn3)C2)ccc1OCc1ccc(C2CC2)cc1] | 1H-NMR (400 MHz, DMSO-d6) δ: 8.54(1H, dd, J = 5.04, 0.60 Hz), 7.95(1H, dd, J = 1.61, 0.81 Hz), 7.45-7.44(1H, m), 7.29(2H, d, J = 8.26 Hz), 7.08 (2H, d, J = 8.06 Hz), 7.00-6.96(2H, m), 6.87(1H, dd, J = 8.36, 1.91 Hz), 5.52(1H, t, J = 5.84 Hz), 4.99(2H, s), 4.97(1H, t, J = 9.47 Hz), 4.60(2H, d, J = 5.84 Hz), 4.55(1H, dd, J = 10.07, 6.45 Hz), 4.45 (1H, t, J = 9.77 Hz), 4.07(1H, dd, J = 10.07, 6.65 Hz), 3.93-3.85(1H, m), 3.77(3H, s), 1.94-1.86(1H, m), 0.96-0.91(2H, m), 0.68-0.64(2H, m). |
| --- | --- | --- |
| 78 | 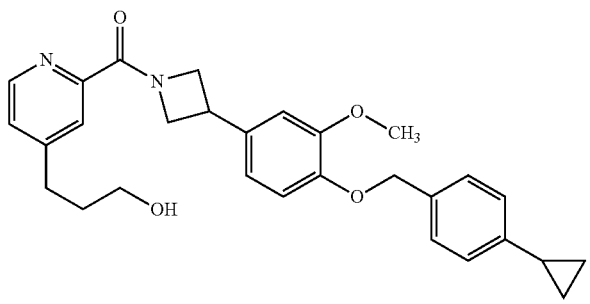 [SMILES: COc1cc(C2CN(C(=O)c3cc(CCCO)ccn3)C2)ccc1OCc1ccc(C2CC2)cc1] | 1H-NMR (400 MHz, CDCl3) δ: 8.46(1H, d, J = 4.87 Hz), 8.00(1H, d, J = 0.93 Hz), 7.32(2H, d, J = 8.35 Hz), 7.22(1H, dd, J = 4.99, 1.74 Hz), 7.07(2H, d, J = 8.12 Hz), 6.89-6.81(3H, m), 5.10(2H, s), 5.08 (1H, t, J = 9.51 Hz), 4.69(1H, dd, J = 10.67, 6.26 Hz), 4.61(1H, t, J = 9.74 Hz), 4.27(1H, dd, J = 10.44, 6.26 Hz), 3.90(3H, s), 3.89-3.81(1H, m), 3.72-3.67(2H, m), 2.80(2H, t, J = 7.77 Hz), 1.97-1.86(3H, m), 1.39(1H, t, J = 5.22 Hz), 0.98-0.93 (2H, m), 0.71-0.67(2H, m). |

TABLE 1-16-continued

| | | |
|---|---|---|
| 79 | 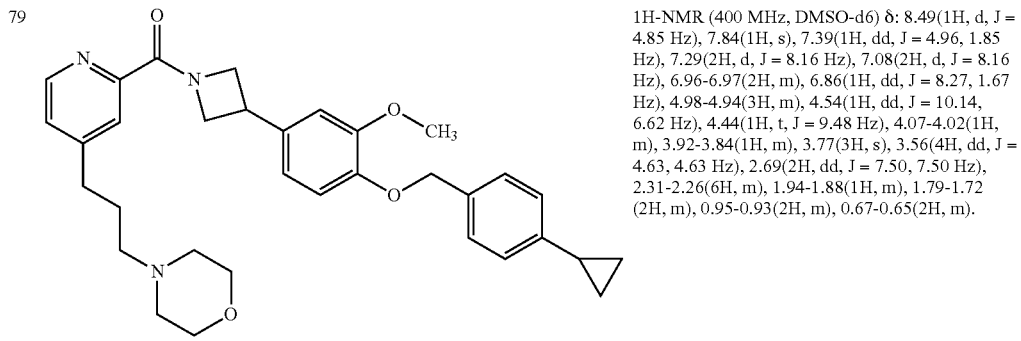 | 1H-NMR (400 MHz, DMSO-d6) δ: 8.49(1H, d, J = 4.85 Hz), 7.84(1H, s), 7.39(1H, dd, J = 4.96, 1.85 Hz), 7.29(2H, d, J = 8.16 Hz), 7.08(2H, d, J = 8.16 Hz), 6.96-6.97(2H, m), 6.86(1H, dd, J = 8.27, 1.67 Hz), 4.98-4.94(3H, m), 4.54(1H, dd, J = 10.14, 6.62 Hz), 4.44(1H, t, J = 9.48 Hz), 4.07-4.02(1H, m), 3.92-3.84(1H, m), 3.77(3H, s), 3.56(4H, dd, J = 4.63, 4.63 Hz), 2.69(2H, dd, J = 7.50, 7.50 Hz), 2.31-2.26(6H, m), 1.94-1.88(1H, m), 1.79-1.72 (2H, m), 0.95-0.93(2H, m), 0.67-0.65(2H, m). |
| 80 | 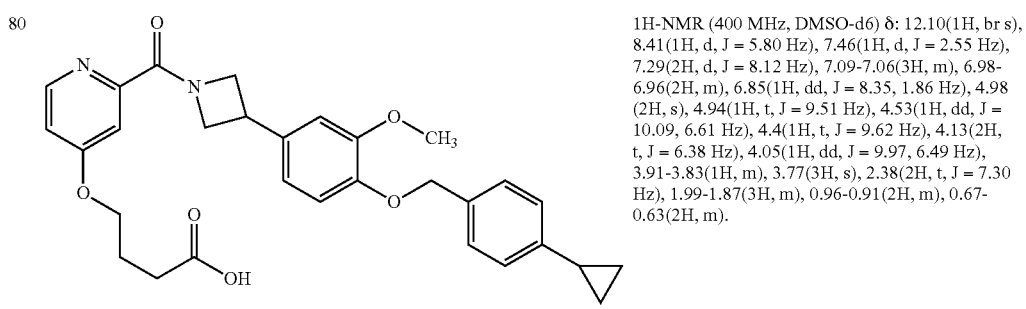 | 1H-NMR (400 MHz, DMSO-d6) δ: 12.10(1H, br s), 8.41(1H, d, J = 5.80 Hz), 7.46(1H, d, J = 2.55 Hz), 7.29(2H, d, J = 8.12 Hz), 7.09-7.06(3H, m), 6.98-6.96(2H, m), 6.85(1H, dd, J = 8.35, 1.86 Hz), 4.98 (2H, s), 4.94(1H, t, J = 9.51 Hz), 4.53(1H, dd, J = 10.09, 6.61 Hz), 4.4(1H, t, J = 9.62 Hz), 4.13(2H, t, J = 6.38 Hz), 4.05(1H, dd, J = 9.97, 6.49 Hz), 3.91-3.83(1H, m), 3.77(3H, s), 2.38(2H, t, J = 7.30 Hz), 1.99-1.87(3H, m), 0.96-0.91(2H, m), 0.67-0.63(2H, m). |

TABLE 1-17

| | | |
|---|---|---|
| 81 | 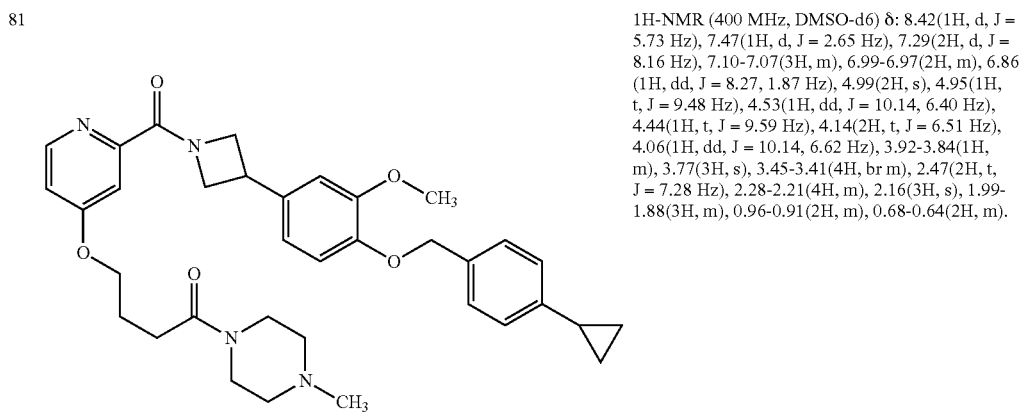 | 1H-NMR (400 MHz, DMSO-d6) δ: 8.42(1H, d, J = 5.73 Hz), 7.47(1H, d, J = 2.65 Hz), 7.29(2H, d, J = 8.16 Hz), 7.10-7.07(3H, m), 6.99-6.97(2H, m), 6.86 (1H, dd, J = 8.27, 1.87 Hz), 4.99(2H, s), 4.95(1H, t, J = 9.48 Hz), 4.53(1H, dd, J = 10.14, 6.40 Hz), 4.44(1H, t, J = 9.59 Hz), 4.14(2H, t, J = 6.51 Hz), 4.06(1H, dd, J = 10.14, 6.62 Hz), 3.92-3.84(1H, m), 3.77(3H, s), 3.45-3.41(4H, br m), 2.47(2H, t, J = 7.28 Hz), 2.28-2.21(4H, m), 2.16(3H, s), 1.99-1.88(3H, m), 0.96-0.91(2H, m), 0.68-0.64(2H, m). |
| 82 | 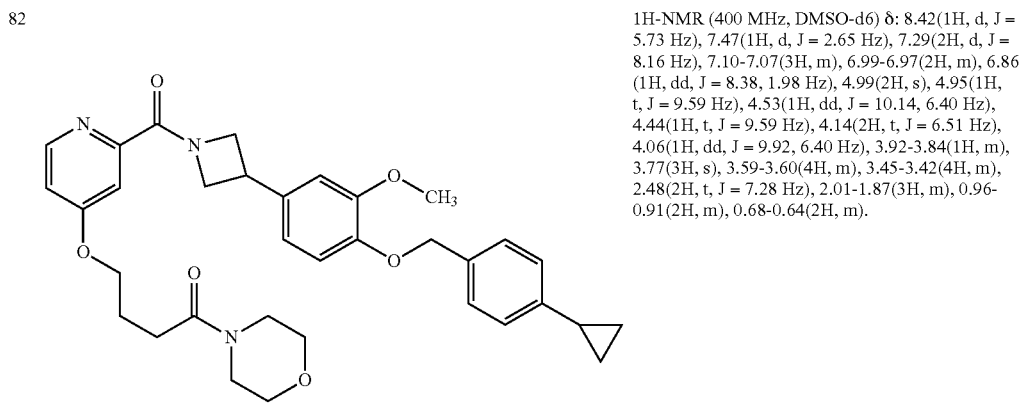 | 1H-NMR (400 MHz, DMSO-d6) δ: 8.42(1H, d, J = 5.73 Hz), 7.47(1H, d, J = 2.65 Hz), 7.29(2H, d, J = 8.16 Hz), 7.10-7.07(3H, m), 6.99-6.97(2H, m), 6.86 (1H, dd, J = 8.38, 1.98 Hz), 4.99(2H, s), 4.95(1H, t, J = 9.59 Hz), 4.53(1H, dd, J = 10.14, 6.40 Hz), 4.44(1H, t, J = 9.59 Hz), 4.14(2H, t, J = 6.51 Hz), 4.06(1H, dd, J = 9.92, 6.40 Hz), 3.92-3.84(1H, m), 3.77(3H, s), 3.59-3.60(4H, m), 3.45-3.42(4H, m), 2.48(2H, t, J = 7.28 Hz), 2.01-1.87(3H, m), 0.96-0.91(2H, m), 0.68-0.64(2H, m). |

TABLE 1-17-continued

| 83 | 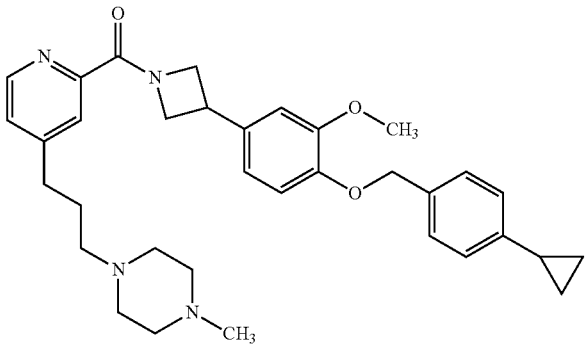 [SMILES: COc1cc(C2CN(C(=O)c3cc(CCCN4CCN(C)CC4)ccn3)C2)ccc1OCc1ccc(C2CC2)cc1] | 1H-NMR (400 MHz, DMSO-d6) δ: 8.48(1H, dd, J = 5.01, 0.55 Hz), 7.83(1H, d, J = 0.88 Hz), 7.38(1H, dd, J = 5.01, 1.76 Hz), 7.29(2H, d, J = 8.16 Hz), 7.08(2H, d, J = 8.16 Hz), 6.99-6.96(2H, m), 6.86 (1H, dd, J = 8.38, 1.98 Hz), 5.00-4.92(3H, m), 4.54 (1H, dd, J = 10.14, 6.62 Hz), 4.44(1H, dd, J = 9.37, 9.37 Hz), 4.06(1H, dd, J = 10.14, 6.40 Hz0, 3.92-3.84(1H, m), 3.77(3H, s), 2.67(2H, t, J = 7.61 Hz), 2.45-2.21(10H, m), 2.13(3H, s), 1.95-1.87(1H, m), 1.78-1.70(2H, m), 0.97-0.91(2H, m), 0.68-0.64(2H, m). |
|---|---|---|
| 84 | 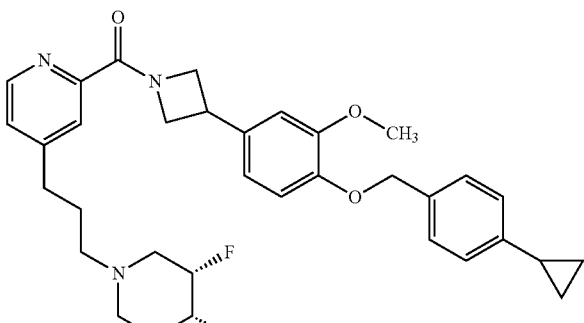 | 1H-NMR (400 MHz,CDCl3) δ: 8.4(1H, dd, J = 5.04, 0.60 Hz), 7.98(1H, d, J = 1.01 Hz), 7.31(2H, d, J = 8.26 Hz), 7.19(1H, dd, J = 4.84, 1.81 Hz), 7.06(2H, d, J = 8.06 Hz), 6.88-6.80(3H, m), 5.09 (2H, s), 5.07(1H, t, J = 9.67 Hz), 4.73-4.57(3H, m), 4.26(1H, dd, J = 10.58, 6.55 Hz), 3.89(3H, s), 3.88-3.80(2H, m), 2.88-2.79(1H, br m), 2.70(2H, t, J = 7.56 Hz), 2.64-2.45(2H, br m), 2.40(2H, t, J = 7.25 Hz), 2.29-2.23(1H, br m), 1.93-1.78(6H, br m), 0.97-0.92(2H, m), 0.70-0.66(2H, m). |

TABLE 1-18

| 85 | 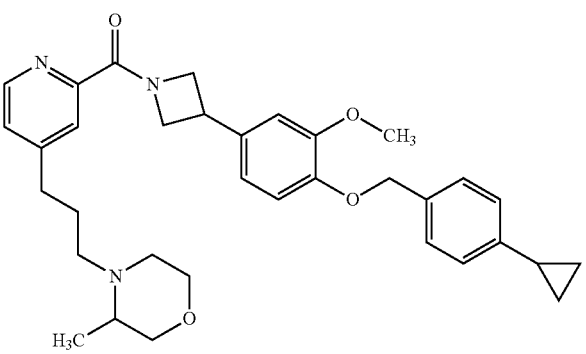 [SMILES: COc1cc(C2CN(C(=O)c3cc(CCCN4CCOCC4C)ccn3)C2)ccc1OCc1ccc(C2CC2)cc1] | 1H-NMR (400 MHz, DMSO-d6) δ: 8.48(1H, d, J = 4.87 Hz), 7.83(1H, d, J = 8.58 Hz), 7.40-7.36(1H, m), 7.29(2H, d, J = 8.12 Hz), 7.07(2H, d, J = 8.12 Hz), 6.99-6.95 (2H, m), 6.85(1H, d, J = 8.46 Hz), 4.96-4.93(3H, m), 4.56-4.51(2H, m), 4.44(1H, dd, J = 9.39, 9.39 Hz), 4.06 (1H, dd, J = 9.39, 6.49 Hz), 3.91-3.84 (1H, m), 3.76(3H, s), 3.68-3.62(1H, m), 3.58-3.53(1H, m), 3.48-3.24(2H, m), 3.10-3.04(1H, m), 2.72-2.61(4H, m), 2.30-2.25(1H, m), 2.16-2.09(1H, m), 1.94-1.87(1H, m), 1.76-1.70(2H, m), 0.96-0.90(2H, m), 0.84(2H, d, J = Hz), 0.67-0.63(2H, m). |
|---|---|---|
| 86 | 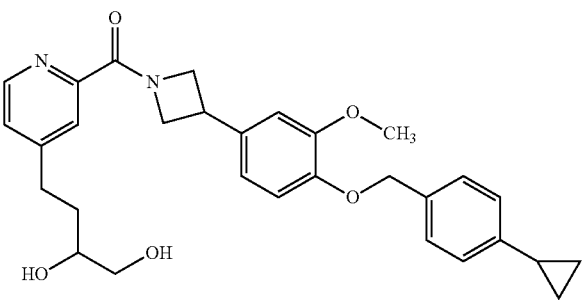 [SMILES: COc1cc(C2CN(C(=O)c3cc(CCC(O)CO)ccn3)C2)ccc1OCc1ccc(C2CC2)cc1] | 1H-NMR (400 MHz, CDCl3) δ: 8.45(1H, dd, J = 4.84, 0.60 Hz), 7.99 (1H, d, J = 1.01 Hz), 7.31(2H, d, J = 8.26 Hz), 7.21(1H, dd, J = 5.04, 1.81 Hz), 7.06(2H, d, J = 8.06 Hz), 6.87-6.80(3H, m), 5.09 (2H, s), 5.07(1H, t, J = 9.87 Hz), 4.71-4.66(1H, m), 4.60(1H, t, J = 9.77 Hz), 4.26(1H, dd, J = 10.38, 6.35 Hz), 3.89(3H, s), 3.88-3.80(1H, m), 3.73-3.65(2H, m), 3.51-3.45(1H, m), 2.93-2.74(2H, m), 2.38 (1H, br s), 1.94(1H, br s), 1.91-1.76(3H, m), 0.97-0.92(2H, m), 0.70-0.66(2H, m). |

TABLE 1-18-continued

| 87 | 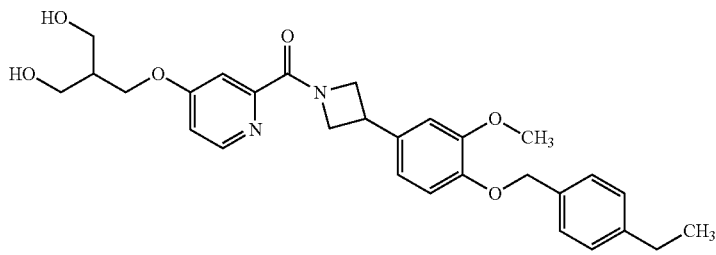 [SMILES: CCc1ccc(COc2ccc(C3CN(C(=O)c4cc(OCC(CO)CO)ccn4)C3)cc2OC)cc1] | 1H-NMR (400 MHz, DMSO-d6) δ: 8.41(1H, d, J = 5.62 Hz), 7.49(1H, d, J = 2.61 Hz), 7.33(2H, d, J = 8.12 Hz), 7.21(2H, d, J = 8.12 Hz), 7.09(1H, dd, J = 5.62, 2.61 Hz), 7.00-6.96(2H, m), 6.87-6.85(1H, m), 5.00-4.92(4H, m), 4.59-4.51(3H, m), 4.44(1H, dd, J = 9.51, 9.51 Hz), 4.13-4.01(2H, m), 3.91-3.83 (1H, m), 3.77(3H, s), 3.55-3.47(4H, m), 2.59(2H, q, J = 7.61 Hz), 2.02-1.97(1H, m), 1.17(3H, t, J = 7.61 Hz). |
| --- | --- | --- |
| 88 | 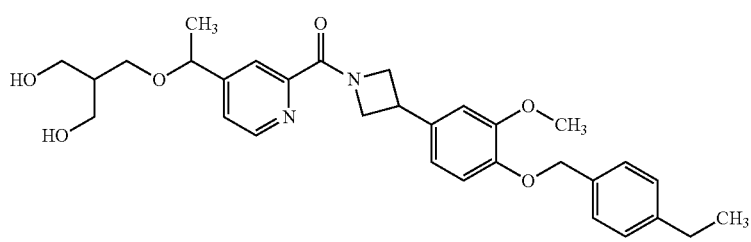 [SMILES: CCc1ccc(COc2ccc(C3CN(C(=O)c4cc(C(C)OCC(CO)CO)ccn4)C3)cc2OC)cc1] | 1H-NMR (400 MHz, DMSO-d6) δ: 8.58(1H, d, J = 5.07 Hz), 7.92(1H, s), 7.46(1H, d, J = 5.07 Hz), 7.34(2H, d, J = 7.94 Hz), 7.22(2H, d, J = 7.94 Hz), 7.01-6.98(2H, m), 6.89-6.86(1H, m), 5.02-4.96(3H, m), 4.58-4.43(3H, m), 4.35(2H, dd, J = 5.18, 5.18 Hz), 4.06(1H, dd, J = 10.14, 6.62 Hz), 3.92-3.86(1H, m), 3.78(3H, s), 3.45-3.25(5H, m), 2.60 (2H, q, J = 7.59 Hz), 1.80-1.74(1H, m), 1.33(3H, d, J = 6.40 Hz), 1.17(3H, t, J = 7.59 Hz). |

TABLE 1-19

| 89 | 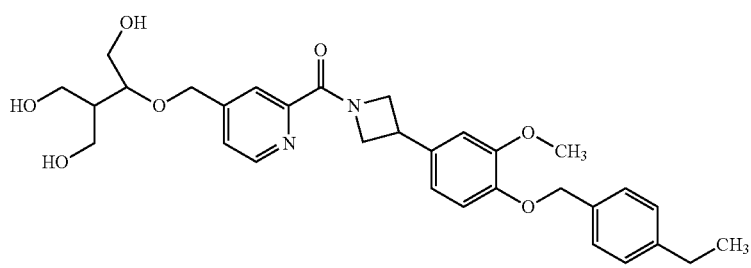 [SMILES: CCc1ccc(COc2ccc(C3CN(C(=O)c4cc(COC(CO)C(CO)CO)ccn4)C3)cc2OC)cc1] | 1H-NMR (400 MHz, DMSO-d6) δ: 8.57(1H, d, J = 4.87 Hz), 7.92(1H, s), 7.47(1H, d, J = 3.48 Hz), 7.34(1H, d, J = 7.88 Hz), 7.22(2H, d, J = 8.12 Hz), 7.00-6.98(2H, m), 6.87(1H, dd, J = 8.35, 1.86 Hz), 5.01(2H, s), 4.97(1H, t, J = 9.51 Hz), 4.61-4.54(3H, m), 4.46(1H, t, J = 9.62 Hz), 4.28(3H, t, J = 5.33 Hz), 4.06(1H, dd, J = 10.09, 6.61 Hz) ,3.91-3.87(1H, m), 3.78 (3H, s), 3.43-3.41(8H, m), 2.60 (2H, q, J = 7.58 Hz), 1.17(3H, t, J = 7.54 Hz). |
| --- | --- | --- |
| 90 | 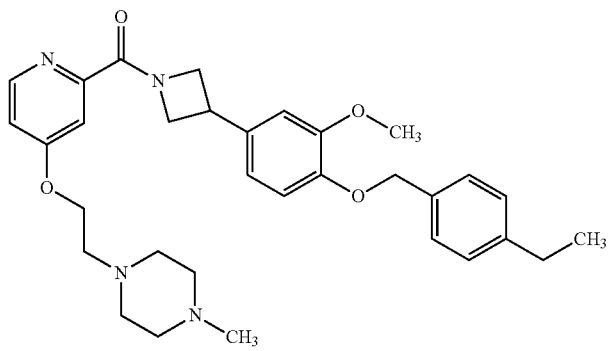 [SMILES: CCc1ccc(COc2ccc(C3CN(C(=O)c4cc(OCCN5CCN(C)CC5)ccn4)C3)cc2OC)cc1] | 1H-NMR (400 MHz, CDCl3) δ: 8.36(1H, d, J = 5.57 Hz), 7.58(1H, d, J = 2.55 Hz), 7.35 (2H, d, J = 8.35Hz), 7.20(2H, d, J = 8.35 Hz), 6.89-6.81(4H, m), 5.12(2H, s), 5.08(1H, t, J = 9.74 Hz), 4.59(1H, dd, J = 10.67, 6.72 Hz), 4.80(1H, t, J = 9.74 Hz), 4.26(1H, dd, J = 10.44, 6.49 Hz), 4.22(2H, t, J = 5.88Hz), 3.90(3H, s), 3.88-3.81(1H, m), 2.65(2H, t, J = 5.68 Hz) ,2.68-2.58(8H, br m), 2.49(4H, br s), 2.30 (3H, s), 1.23(3H, t, J = 7.54 Hz). |

TABLE 1-19-continued

| 91 | 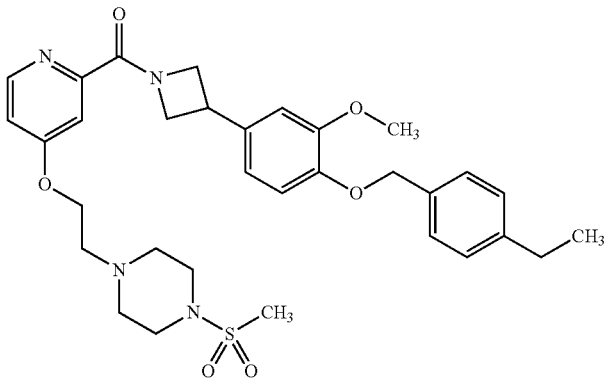 [SMILES: CCc1ccc(COc2ccc(C3CN(C(=O)c4cc(OCCN5CCN(S(C)(=O)=O)CC5)ccn4)C3)cc2OC)cc1] | 1H-NMR (400 MHz, CDCl3) δ: 8.38(1H, d, J = 5.80 Hz), 7.69(1H, d, J = 2.55 Hz), 7.35(2H, d, J = 8.12 Hz), 7.20(2H, d, J = 8.35 Hz), 6.89-6.82(4H, m), 5.12(2H, s), 5.09 (1H, t, J = 9.74 Hz), 4.70(1H, dd, J = 10.78, 6.61 Hz), 4.60(1H, t, J = 9.74 Hz), 4.26(1H, dd, J = 10.67, 6.49 Hz), 4.22(2H, t, J = 5.45 Hz), 3.90(3H, s), 3.89-3.81 (1H, m), 3.28(4H, t J = 4.87 Hz), 2.89(2H, t, J = 5.45 Hz), 2.79(3H, s), 2.70(4H, t, J = 4.67 Hz), 2.65(2H, q, J = 7.58 Hz), 1.24(3H, t, J = 7.65 Hz). |
|---|---|---|
| 92 | 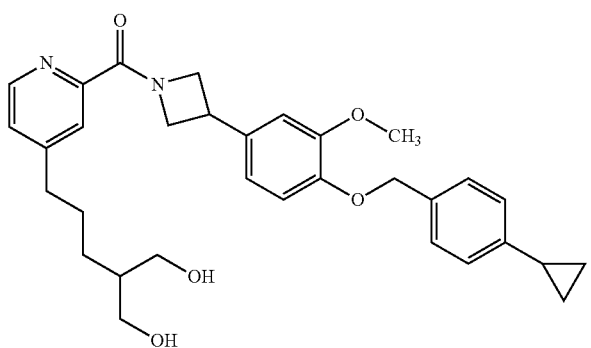 [SMILES: COc1cc(C2CN(C(=O)c3cc(CCCC(CO)CO)ccn3)C2)ccc1OCc1ccc(C2CC2)cc1] | 1H-NMR (400 MHz, CDCl3) δ: 8.44(1H, dd, J = 4.84, 0.60 Hz), 7.96(1H, d, J = 1.01 Hz), 7.31(2H, d, J = 8.26 Hz), 7.17(1H, dd, J = 5.04, 1.81 Hz), 7.06(2H, d, J = 8.06 Hz), 6.87-6.80(3H, m), 5.09(2H, s), 5.08(1H, t, J = 9.67 Hz), 4.69(1H, dd, J = 10.48, 6.85 Hz), 4.60(1H, t, J = 9.77 Hz), 4.26 (1H, dd, J = 10.48, 6.45 Hz), 3.89(3H, s), 3.86-3.80(3H, m), 3.69-3.65(2H, m), 2.68(2H, t, J = 7.66 Hz), 2.28(2H, br s), 1.92-1.85(1H, m), 1.80-1.68(3H, m), 1.37-1.31(2H, m), 0.97-0.92(2H, m), 0.70-0.66 (2H, m). |

TABLE 1-20

| 93 | 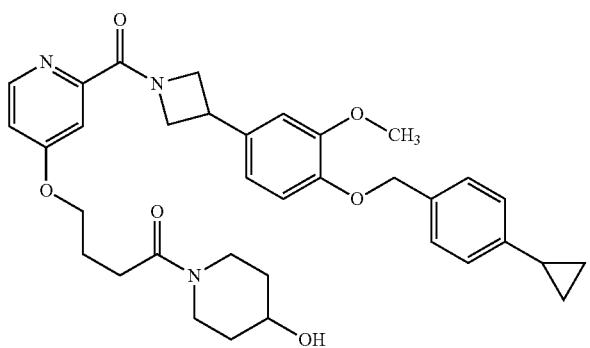 [SMILES: COc1cc(C2CN(C(=O)c3cc(OCCCC(=O)N4CCC(O)CC4)ccn3)C2)ccc1OCc1ccc(C2CC2)cc1] | 1H-NMR (400 MHz, DMSO-d6) δ: 8.41(1H, d, J = 5.80 Hz), 7.47(1H, d, J = 2.55 Hz), 7.29(2H, d, J = 8.12 Hz), 7.10-7.06(3H, m), 6.97(2H, t, J = 4.06 Hz), 6.85(1H, dd, J = 8.46, 1.97 Hz), 4.98(2H, s), 494(1H, t, J = 8.51 Hz), 4.71(1H, d, J = 4.17 Hz), 4.53(1H, dd, J = 10.09, 6.61 Hz), 4.43(1H, t, J = 9.62 Hz), 4.13(2H, t, J = 6.49 Hz), 4.05(1H, dd, J = 9.97, 6.49 Hz), 3.91-3.87(2H, m), 3.77(3H, s), 3.69-3.66(2H, m), 3.16-3.10(1H, m), 3.02-2.95 (1H, m), 2.46-2.44(2H, m), 1.96-1.90(3H, m), 1.71-1.66(2H, m), 1.34-1.17(2H, m), 0.94-0.92(2H, m), 0.67-0.63(2H, m). |
|---|---|---|
| 94 | 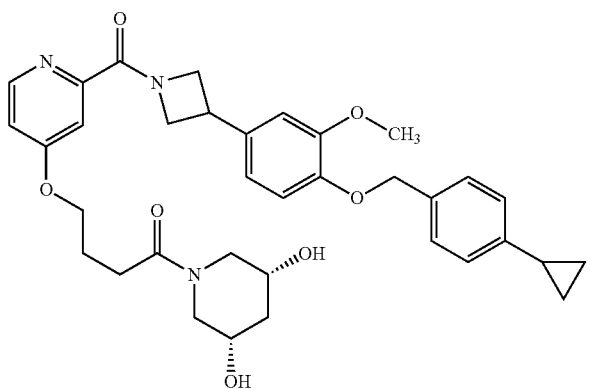 [SMILES: COc1cc(C2CN(C(=O)c3cc(OCCCC(=O)N4C[C@H](O)C[C@H](O)C4)ccn3)C2)ccc1OCc1ccc(C2CC2)cc1] | 1H-NMR (400 MHz, DMSO-d6) δ: 8.41(1H, d, J = 5.80 Hz), 7.47(1H, d, J = 2.55 Hz), 7.29(2H, d, J = 8.12 Hz), 7.10-7.06(3H, m), 6.98-6.97(2H, m), 6.85 (1H, dd, J = 8.35, 1.86 Hz), 4.97-4.93(5H, m), 4.53 (1H, dd, J = 10.09, 6.61 Hz), 4.43(1H, t, J = 9.51 Hz), 4.32(1H, dd, J = 12.06, 4.41 Hz), 4.13(2H, t, J = 6.49 Hz), 4.05(1H, dd, J = 10.20, 6.49 Hz), 3.91-3.83(1H, m), 3.76-3.74(4H, m), 3.47-3.38(1H, m), 2.63(1H, dd, J = 12.87, 10.09 Hz), 2.47-2.39(2H, m), 2.24(1H, d, J = 11.13 Hz), 2.12-2.09(1H, m), 1.98-1.87(3H, m), 1.20(1H, dd, J = 22.49, 10.67 Hz), 0.94-0.92(2H, m), 0.67-0.63(2H, m). |

TABLE 1-20-continued

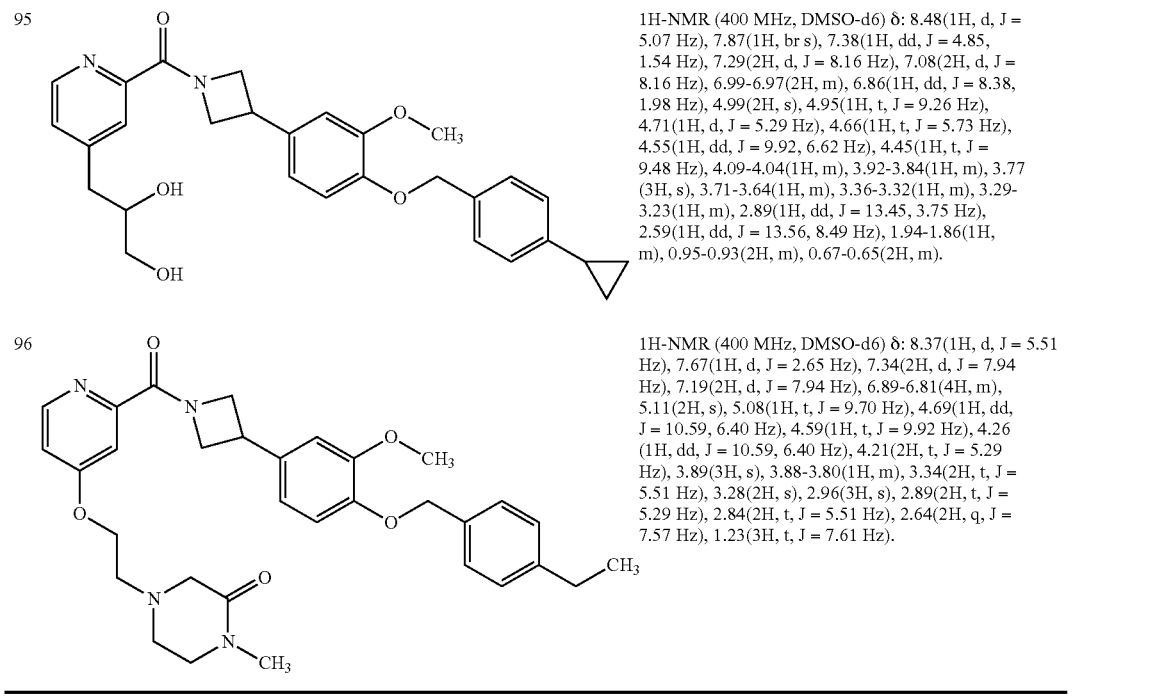

| 95 | 1H-NMR (400 MHz, DMSO-d6) δ: 8.48(1H, d, J = 5.07 Hz), 7.87(1H, br s), 7.38(1H, dd, J = 4.85, 1.54 Hz), 7.29(2H, d, J = 8.16 Hz), 7.08(2H, d, J = 8.16 Hz), 6.99-6.97(2H, m), 6.86(1H, dd, J = 8.38, 1.98 Hz), 4.99(2H, s), 4.95(1H, t, J = 9.26 Hz), 4.71(1H, d, J = 5.29 Hz), 4.66(1H, t, J = 5.73 Hz), 4.55(1H, dd, J = 9.92, 6.62 Hz), 4.45(1H, t, J = 9.48 Hz), 4.09-4.04(1H, m), 3.92-3.84(1H, m), 3.77(3H, s), 3.71-3.64(1H, m), 3.36-3.32(1H, m), 3.29-3.23(1H, m), 2.89(1H, dd, J = 13.45, 3.75 Hz), 2.59(1H, dd, J = 13.56, 8.49 Hz), 1.94-1.86(1H, m), 0.95-0.93(2H, m), 0.67-0.65(2H, m). |
| --- | --- |
| 96 | 1H-NMR (400 MHz, DMSO-d6) δ: 8.37(1H, d, J = 5.51 Hz), 7.67(1H, d, J = 2.65 Hz), 7.34(2H, d, J = 7.94 Hz), 7.19(2H, d, J = 7.94 Hz), 6.89-6.81(4H, m), 5.11(2H, s), 5.08(1H, t, J = 9.70 Hz), 4.69(1H, dd, J = 10.59, 6.40 Hz), 4.59(1H, t, J = 9.92 Hz), 4.26(1H, dd, J = 10.59, 6.40 Hz), 4.21(2H, t, J = 5.29 Hz), 3.89(3H, s), 3.88-3.80(1H, m), 3.34(2H, t, J = 5.51 Hz), 3.28(2H, s), 2.96(3H, s), 2.89(2H, t, J = 5.29 Hz), 2.84(2H, t, J = 5.51 Hz), 2.64(2H, q, J = 7.57 Hz), 1.23(3H, t, J = 7.61 Hz). |

TABLE 1-21

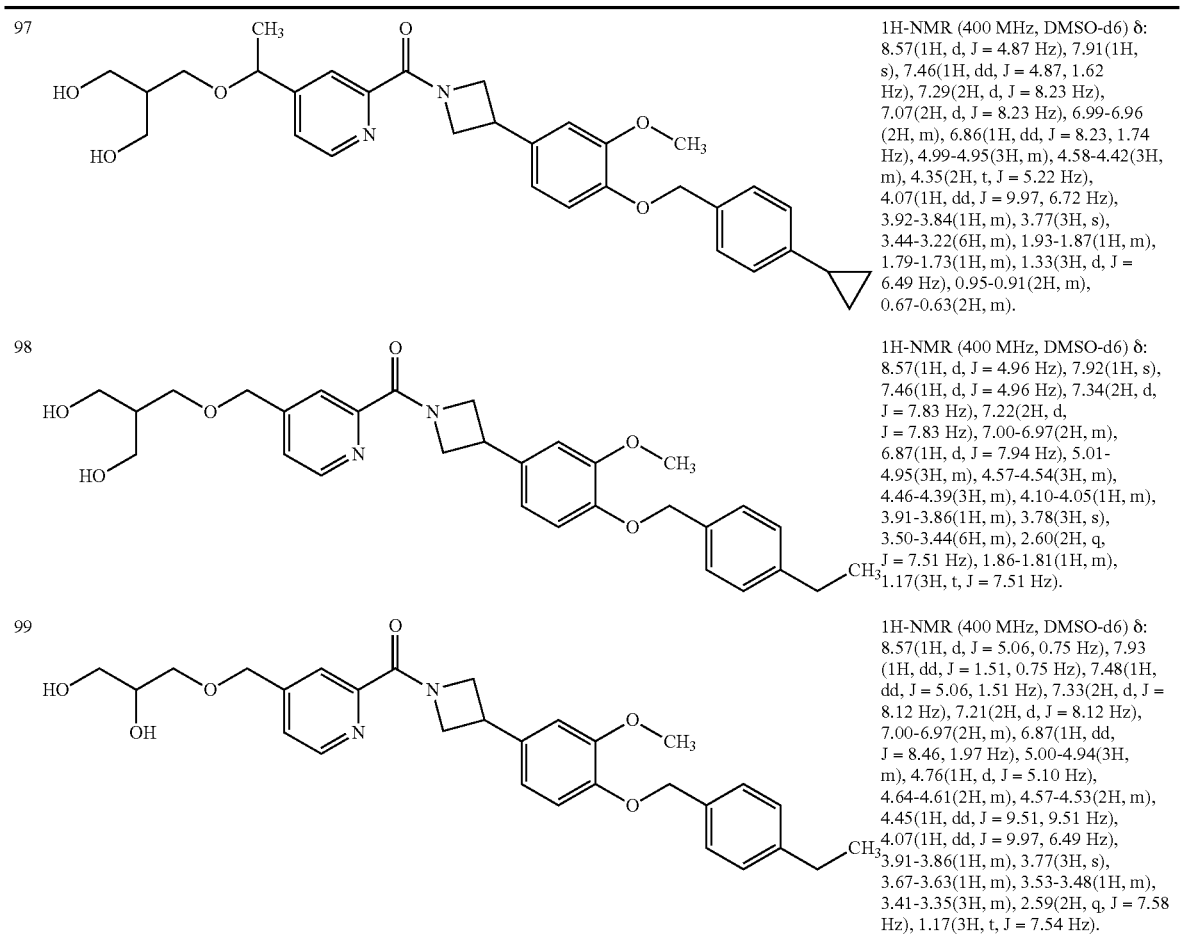

| 97 | 1H-NMR (400 MHz, DMSO-d6) δ: 8.57(1H, d, J = 4.87 Hz), 7.91(1H, s), 7.46(1H, dd, J = 4.87, 1.62 Hz), 7.29(2H, d, J = 8.23 Hz), 7.07(2H, d, J = 8.23 Hz), 6.99-6.96(2H, m), 6.86(1H, dd, J = 8.23, 1.74 Hz), 4.99-4.95(3H, m), 4.58-4.42(3H, m), 4.35(2H, t, J = 5.22 Hz), 4.07(1H, dd, J = 9.97, 6.72 Hz), 3.92-3.84(1H, m), 3.77(3H, s), 3.44-3.22(6H, m), 1.93-1.87(1H, m), 1.79-1.73(1H, m), 1.33(3H, d, J = 6.49 Hz), 0.95-0.91(2H, m), 0.67-0.63(2H, m). |
| --- | --- |
| 98 | 1H-NMR (400 MHz, DMSO-d6) δ: 8.57(1H, d, J = 4.96 Hz), 7.92(1H, s), 7.46(1H, d, J = 4.96 Hz), 7.34(2H, d, J = 7.83 Hz), 7.22(2H, d, J = 7.83 Hz), 7.00-6.97(2H, m), 6.87(1H, d, J = 7.94 Hz), 5.01-4.95(3H, m), 4.57-4.54(3H, m), 4.46-4.39(3H, m), 4.10-4.05(1H, m), 3.91-3.86(1H, m), 3.78(3H, s), 3.50-3.44(6H, m), 2.60(2H, q, J = 7.51 Hz), 1.86-1.81(1H, m), 1.17(3H, t, J = 7.51 Hz). |
| 99 | 1H-NMR (400 MHz, DMSO-d6) δ: 8.57(1H, d, J = 5.06, 0.75 Hz), 7.93(1H, dd, J = 1.51, 0.75 Hz), 7.48(1H, dd, J = 5.06, 1.51 Hz), 7.33(2H, d, J = 8.12 Hz), 7.21(2H, d, J = 8.12 Hz), 7.00-6.97(2H, m), 6.87(1H, dd, J = 8.46, 1.97 Hz), 5.00-4.94(3H, m), 4.76(1H, d, J = 5.10 Hz), 4.64-4.61(2H, m), 4.57-4.53(2H, m), 4.45(1H, dd, J = 9.51, 9.51 Hz), 4.07(1H, dd, J = 9.97, 6.49 Hz), 3.91-3.86(1H, m), 3.77(3H, s), 3.67-3.63(1H, m), 3.53-3.48(1H, m), 3.41-3.35(3H, m), 2.59(2H, q, J = 7.58 Hz), 1.17(3H, t, J = 7.54 Hz). |

TABLE 1-21-continued

| 100 | 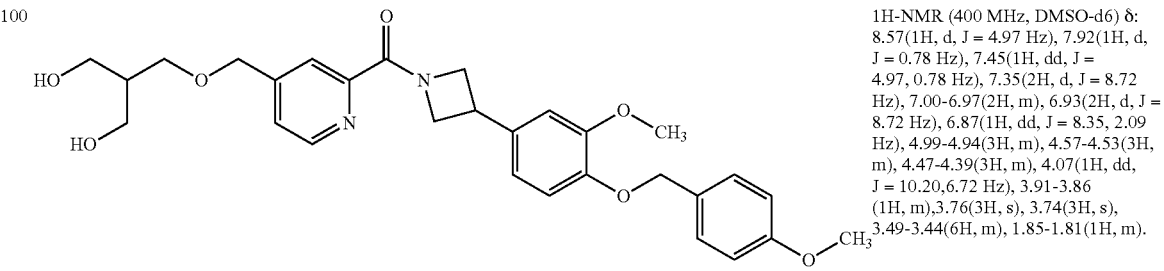 | 1H-NMR (400 MHz, DMSO-d6) δ: 8.57(1H, d, J = 4.97 Hz), 7.92(1H, d, J = 0.78 Hz), 7.45(1H, dd, J = 4.97, 0.78 Hz), 7.35(2H, d, J = 8.72 Hz), 7.00-6.97(2H, m), 6.93(2H, d, J = 8.72 Hz), 6.87(1H, dd, J = 8.35, 2.09 Hz), 4.99-4.94(3H, m), 4.57-4.53(3H, m), 4.47-4.39(3H, m), 4.07(1H, dd, J = 10.20, 6.72 Hz), 3.91-3.86 (1H, m), 3.76(3H, s), 3.74(3H, s), 3.49-3.44(6H, m), 1.85-1.81(1H, m). |

TABLE 1-22

| 101 | 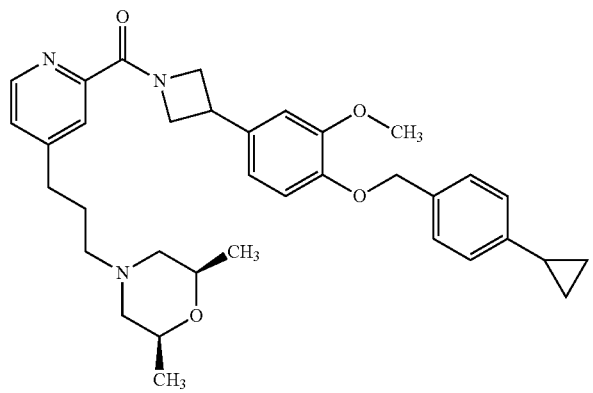 [SMILES: COc1cc(C2CN(C(=O)c3cc(CCCN4C[C@@H](C)O[C@@H](C)C4)ccn3)C2)ccc1OCc1ccc(C2CC2)cc1] | 1H-NMR (400 MHz, DMSO-d6) δ: 8.48(1H, d, J = 4.87 Hz), 7.63(1H, s), 7.38(1H, dd, J = 4.87, 1.86 Hz), 7.29(2H, d, J = 8.12 Hz), 7.07(2H, d, J = 8.12 Hz), 6.99-6.96(2H, m), 6.85(1H, dd, J = 8.46, 1.97 Hz), 4.99-4.92(3H, m), 4.55-4.51(1H, m), 4.44(1H, dd, J = 9.51, 9.51 Hz), 4.08-4.03(1H, m), 3.90-3.85 (1H, m), 3.76(3H, s), 3.54-3.46(2H, m), 2.71-2.65 (4H, m), 2.23(2H, dd, J = 7.19, 7.19 Hz), 1.93-1.87 (1H, m), 1.79-1.71(2H, m), 1.53(2H, dd, J = 10.67, 10.67 Hz), 1.02(6H, d, J = 6.26 Hz), 0.95-0.91(2H, m), 0.67-0.63(2, m). |
| 102 | 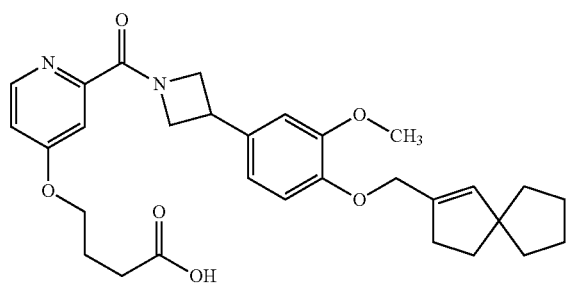 [SMILES: COc1cc(C2CN(C(=O)c3cc(OCCCC(=O)O)ccn3)C2)ccc1OCC1=CC2(CCCC2)CC1] | 1H-NMR (400 MHz, DMSO-d6) δ: 8.42(1H, d, J = 5.73 Hz), 7.47(1H, d, J = 2.21 Hz), 7.10-7.06(1H, m), 6.95-6.93(2H, m), 6.86(1H, d, J = 8.38 Hz), 5.57(1H, s), 4.95(1H, t, J = 9.59 Hz), 4.54-4.52 (1H, m), 4.51(2H, s), 4.44(1H, t, J = 9.81 Hz), 4.14 (2H, t, J = 6.18 Hz), 4.08-4.04(1H, m), 3.91-3.85 (1H, m), 3.77(3H, s), 2.36-2.35(4H, m), 1.99-1.94 (2H, m), 1.74(2H, t, J = 7.17 Hz), 1.63-1.61(4H, m), 1.50-1.47(4H, m). |
| 103 | 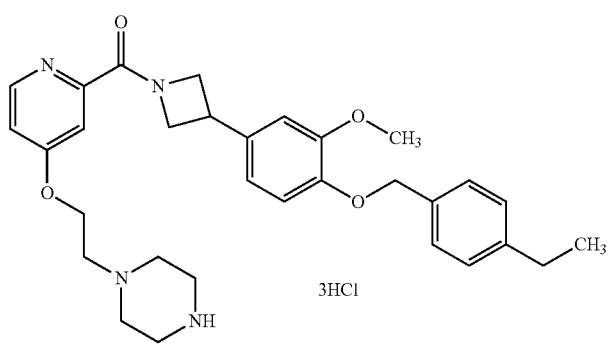 [SMILES: CCc1ccc(COc2ccc(C3CN(C(=O)c4cc(OCCN5CCNCC5)ccn4)C3)cc2OC)cc1] | 1H-NMR (400 MHz, DMSO-d6) δ: 9.73(2H, br s), 8.51(1H, d, J = 6.03 Hz), 7.59(1H, s), 7.33(2H, d, J = 7.88 Hz), 7.23-7.20(3H, m), 7.00-6.97(2H, m), 6.87(1H, d, J = 8.12 Hz), 5.01(2H, s), 4.95(1H, dd, J = 9.51, 9.51 Hz), 4.73-4.32(12H, m), 4.10-4.05(1H, m), 3.92-3.86(1H, m), 3.77(3H, s), 3.66 (2H, s), 2.59(2H, q, J = 7.66 Hz), 1.17(3H, t, J = 7.65 Hz). |

TABLE 1-22-continued

| 104 | 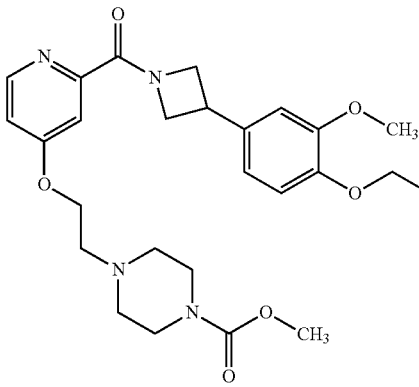 | 1H-NMR (400 MHz, DMSO-d6) δ: 8.41(1H, d, J = 5.74 Hz), 7.49(1H, d, J = 2.61 Hz), 7.33(2H, d, J = 8.12 Hz), 7.21(2H, d, J = 8.12 Hz), 7.10(1H, dd, J = 5.74, 2.61 Hz), 6.99-6.96(2H, m), 6.86(1H, dd, J = 8.35, 1.86 Hz), 5.00(2H, s), 4.94(1H, dd, J = 9.56, 9.56 Hz), 4.53(1H, dd, J = 10.09, 6.61 Hz), 4.43(1H, dd, J = 9.56, 9.56 Hz), 4.23(2H, dd, J = 5.57, 5.57 Hz), 4.06(1H, dd, J = 10.09, 6.81 Hz), 3.89-3.85(1H, m), 3.77(3H, s), 3.58(3H, s), 3.36-3.33(4H, m), 2.74(2H, dd, J = 5.57, 5.57 Hz), 2.59(2H, q, J = 7.52 Hz), 2.46-2.43(4H, m), 1.17(3H, t, J = 7.52 Hz). |

TABLE 1-23

| 105 | 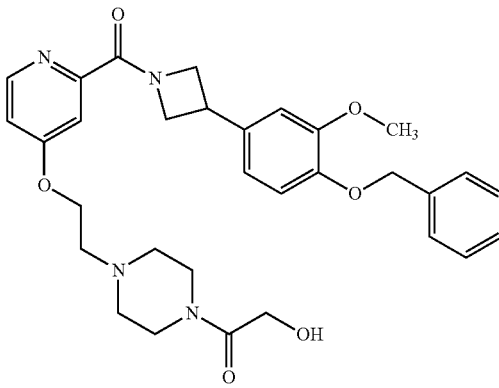 | 1H-NMR (400 MHz, DMSO-d6) δ: 8.41(1H, d, J = 5.80 Hz), 7.49(1H, d, J = 2.65 Hz), 7.33(2H, d, J = 8.12 Hz), 7.21(2H, d, J = 8.12 Hz), 7.10(1H, dd, J = 5.80, 2.65 Hz), 7.00-6.96(2H, m), 6.86(1H, dd, J = 8.23, 1.97 Hz), 5.00(2H, s), 4.94(1H, dd, J = 9.63, 9.63 Hz), 4.55-4.51(2H, m), 4.44(1H, dd, J = 9.63, 9.63 Hz), 4.24(2H, dd, J = 5.45, 5.45 Hz), 4.08-4.04(3H, m), 3.91-3.85(1H, m), 3.77(3H, s), 3.45(2H, br s), 3.33-3.29(2H, m), 2.74(2H, dd, J = 5.45, 5.45 Hz), 2.59(2H, q, J = 7.61 Hz), 2.49-2.45(4H, m), 1.17(3H, t, J = 7.61 Hz). |
| 106 | 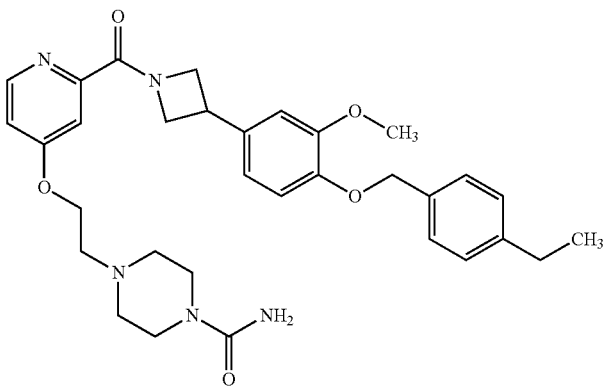 [SMILES: CCc1ccc(COc2ccc(C3CN(C(=O)c4cc(OCCN5CCN(C(N)=O)CC5)ccn4)C3)cc2OC)cc1] | 1H-NMR (400 MHz, DMSO-d6) δ: 8.41(1H, d, J = 5.62 Hz), 7.49(1H, d, J = 2.61 Hz), 7.33(2H, d, J = 8.23 Hz), 7.21(2H, d, J = 8.23 Hz), 7.10(1H, dd, J = 5.62, 2.61 Hz), 6.99-6.96(2H, m), 6.86(1H, dd, J = 8.35, 1.86 Hz), 5.94(2H, s), 5.00(2H, s), 4.94(1H, dd, J = 9.39, 9.39 Hz), 4.53(1H, dd, J = 10.20, 6.49 Hz), 4.44(1H, dd, J = 9.51, 9.51 Hz), 4.23(2H, t, J = 5.57 Hz), 4.06(1H, dd, J = 10.20, 6.49 Hz), 3.90-3.85(1H, m), 3.77(3H, s), 3.27-3.24(4H, m), 2.72(2H, t, J = 5.57 Hz), 2.59(2H, q, J = 7.58 Hz), 2.42-2.39(4H, m), 1.17(3H, t, J = 7.54 Hz). |
| 107 | 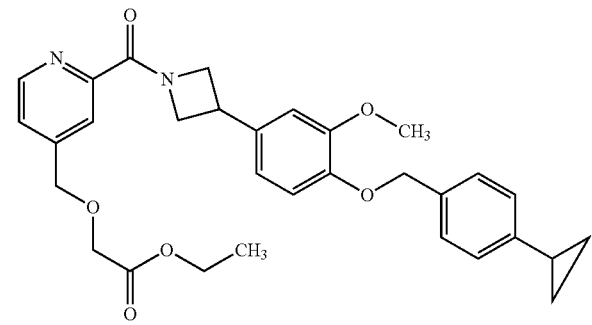 [SMILES: CCOC(=O)COCc1ccnc(C(=O)N2CC(c3ccc(OCc4ccc(C5CC5)cc4)c(OC)c3)C2)c1] | 1H-NMR (400 MHz, DMSO-d6) δ: 8.55(1H, d, J = 2.42 Hz), 8.07(1H, s), 7.44(1H, d, J = 2.82 Hz), 7.31(2H, d, J = 7.66 Hz), 7.06(2H, d, J = 7.86 Hz), 6.89-6.78(3H, m), 5.10(2H, s), 5.07(1H, t, J = 9.87 Hz), 4.71(2H, s), 4.69(1H, t, J = 9.07 Hz), 4.61(1H, t, J = 9.77 Hz), 4.31-4.19(4H, m), 4.18-4.15(2H, m), 4.15-4.06(1H, m), 3.89(3H, s), 3.84(1H, t, J = 7.76 Hz), 1.93-1.83(1H, m), 1.33-1.23(3H, m), 0.99-0.92(2H, m), 0.72-0.65(2H, m). |

TABLE 1-23-continued

| 108 | 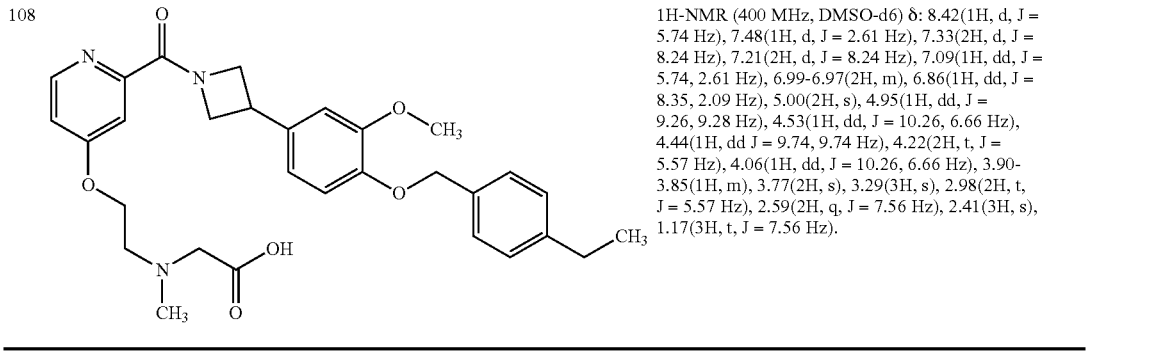 | 1H-NMR (400 MHz, DMSO-d6) δ: 8.42(1H, d, J = 5.74 Hz), 7.48(1H, d, J = 2.61 Hz), 7.33(2H, d, J = 8.24 Hz), 7.21(2H, d, J = 8.24 Hz), 7.09(1H, dd, J = 5.74, 2.61 Hz), 6.99-6.97(2H, m), 6.86(1H, dd, J = 8.35, 2.09 Hz), 5.00(2H, s), 4.95(1H, dd, J = 9.26, 9.28 Hz), 4.53(1H, dd, J = 10.26, 6.66 Hz), 4.44(1H, dd J = 9.74, 9.74 Hz), 4.22(2H, t, J = 5.57 Hz), 4.06(1H, dd, J = 10.26, 6.66 Hz), 3.90-3.85(1H, m), 3.77(2H, s), 3.29(3H, s), 2.98(2H, t, J = 5.57 Hz), 2.59(2H, q, J = 7.56 Hz), 2.41(3H, s), 1.17(3H, t, J = 7.56 Hz). |

TABLE 1-24

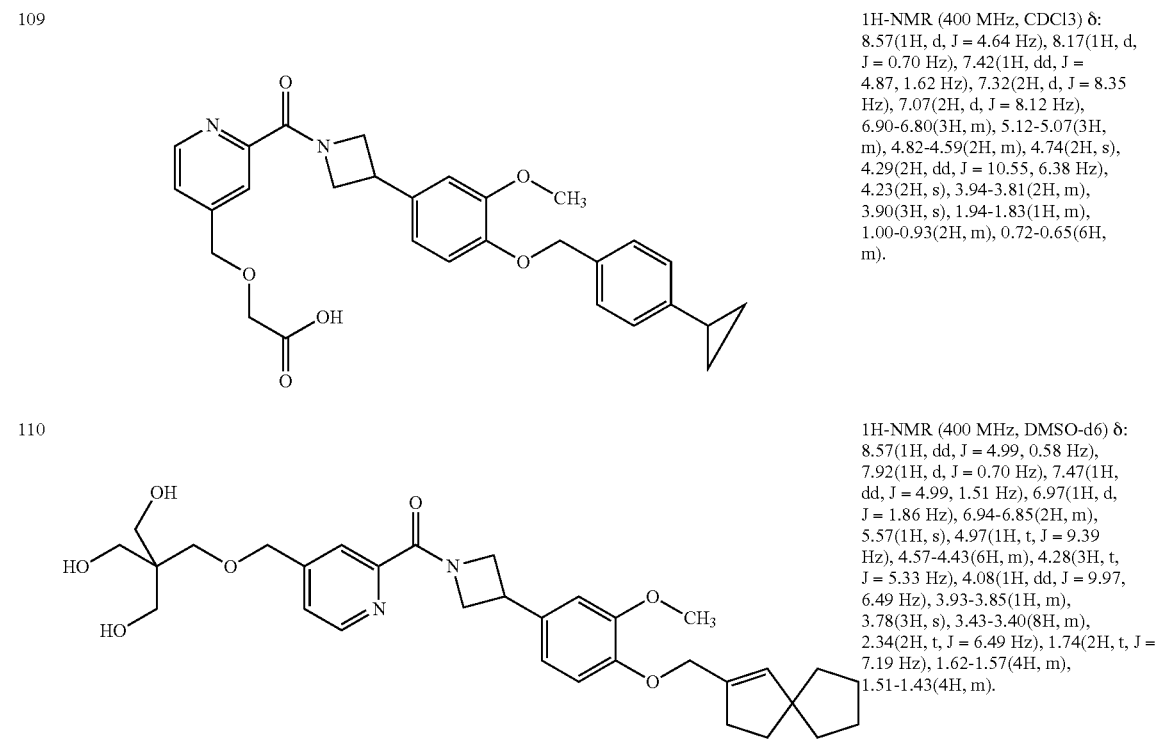

| 109 | | 1H-NMR (400 MHz, CDCl3) δ: 8.57(1H, d, J = 4.64 Hz), 8.17(1H, d, J = 0.70 Hz), 7.42(1H, dd, J = 4.87, 1.62 Hz), 7.32(2H, d, J = 8.35 Hz), 7.07(2H, d, J = 8.12 Hz), 6.90-6.80(3H, m), 5.12-5.07(3H, m), 4.82-4.59(2H, m), 4.74(2H, s), 4.29(2H, dd, J = 10.55, 6.38 Hz), 4.23(2H, s), 3.94-3.81(2H, m), 3.90(3H, s), 1.94-1.83(1H, m), 1.00-0.93(2H, m), 0.72-0.65(6H, m). |

| 110 | | 1H-NMR (400 MHz, DMSO-d6) δ: 8.57(1H, dd, J = 4.99, 0.58 Hz), 7.92(1H, d, J = 0.70 Hz), 7.47(1H, dd, J = 4.99, 1.51 Hz), 6.97(1H, d, J = 1.86 Hz), 6.94-6.85(2H, m), 5.57(1H, s), 4.97(1H, t, J = 9.39 Hz), 4.57-4.43(6H, m), 4.28(3H, t, J = 5.33 Hz), 4.08(1H, dd, J = 9.97, 6.49 Hz), 3.93-3.85(1H, m), 3.78(3H, s), 3.43-3.40(8H, m), 2.34(2H, t, J = 6.49 Hz), 1.74(2H, t, J = 7.19 Hz), 1.62-1.57(4H, m), 1.51-1.43(4H, m). |

| 111 | 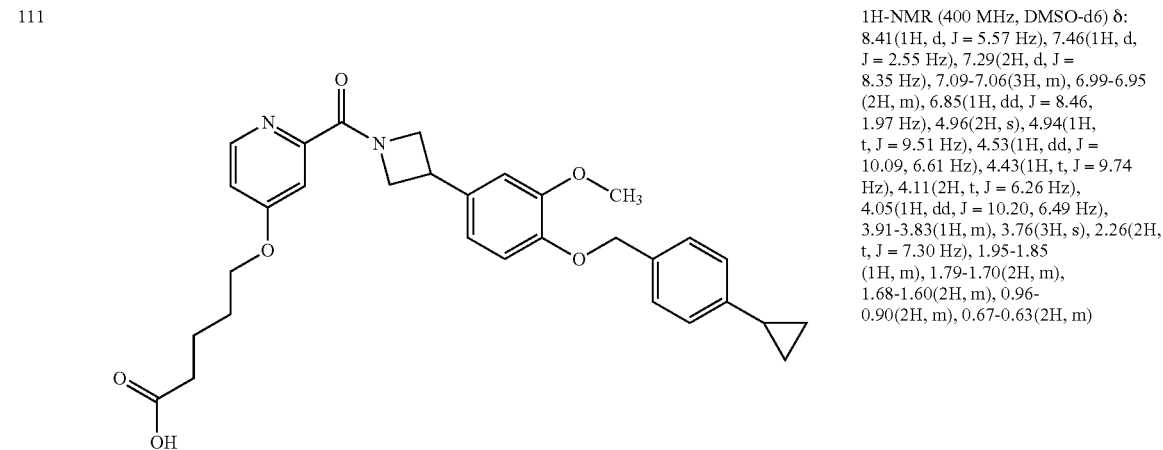 | 1H-NMR (400 MHz, DMSO-d6) δ: 8.41(1H, d, J = 5.57 Hz), 7.46(1H, d, J = 2.55 Hz), 7.29(2H, d, J = 8.35 Hz), 7.09-7.06(3H, m), 6.99-6.95 (2H, m), 6.85(1H, dd, J = 8.46, 1.97 Hz), 4.96(2H, s), 4.94(1H, t, J = 9.51 Hz), 4.53(1H, dd, J = 10.09, 6.61 Hz), 4.43(1H, t, J = 9.74 Hz), 4.11(2H, t, J = 6.26 Hz), 4.05(1H, dd, J = 10.20, 6.49 Hz), 3.91-3.83(1H, m), 3.76(3H, s), 2.26(2H, t, J = 7.30 Hz), 1.95-1.85 (1H, m), 1.79-1.70(2H, m), 1.68-1.60(2H, m), 0.96-0.90(2H, m), 0.67-0.63(2H, m) |

| | | |
|---|---|---|
| 112 | 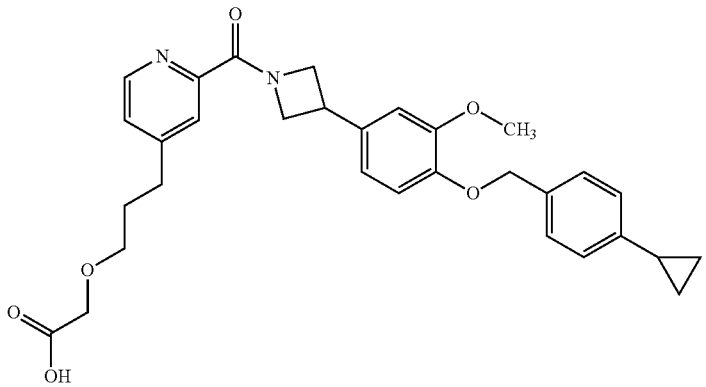 [SMILES: COc1cc(C2CN(C(=O)c3cc(CCCOCC(=O)O)ccn3)C2)ccc1OCc1ccc(C2CC2)cc1] | 1H-NMR (400 MHz, CDCl3) δ: 8.48(1H, d, J = 4.87 Hz), 8.01(1H, d, J = 0.93 Hz), 7.32(2H, d, J = 8.35 Hz), 7.23(1H, dd, J = 4.99, 1.74 Hz), 7.10-7.00(2H, m), 6.90-6.80(3H, m), 5.10(2H, s), 5.08(1H, t, J = 9.86 Hz), 4.71(1H, dd, J = 10.78, 6.61 Hz), 4.64(1H, t, J = 9.97 Hz), 4.29(1H, dd, J = 10.90, 6.49 Hz), 4.12(2H, s), 3.90-3.80(1H, m), 3.90(3H, s), 3.57(2H, t, J = 6.03 Hz), 2.82(2H, t, J = 7.54 Hz), 2.05-1.95(2H, m), 1.95-1.85(1H, m), 1.00-0.90(2H, m), 0.75-0.65(2H, m). |

TABLE 1-25

| | | |
|---|---|---|
| 113 | 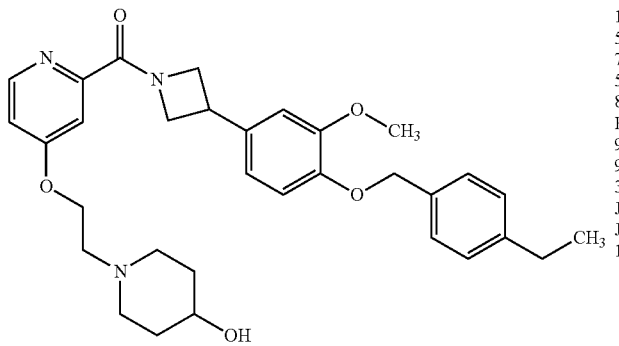 | 1H-NMR (400 MHz, DMSO-d6) δ: 8.40(1H, d, J = 5.57 Hz), 7.47(1H, d, J = 2.78 Hz), 7.33(2H, d, J = 7.88 Hz), 7.21(2H, d, J = 7.88 Hz), 7.09(1H, dd, J = 5.80, 2.55 Hz), 6.99-6.97(2H, m), 6.86(1H, dd, J = 8.23, 1.97 Hz), 5.00(2H, s), 4.94(1H, t, J = 9.51 Hz), 4.53(2H, dd, J = 10.32, 6.15 Hz), 4.43(1H, t, J = 9.62 Hz), 4.19(2H, t, J = 5.80 Hz), 4.06(1H, dd, J = 9.97, 6.49 Hz), 3.91-3.83(1H, m), 3.77(3H, s), 3.43-3.39(1H, m), 2.77-2.76(2H, br m), 2.67(2H, t, J = 5.80 Hz), 2.59(2H, q, J = 7.58 H), 2.12(2H, t, J = 9.86 Hz), 1.70-1.66(2H, m), 1.39-1.33(2H, m), 1.17(3H, t, J = 7.65 Hz). |
| 114 | 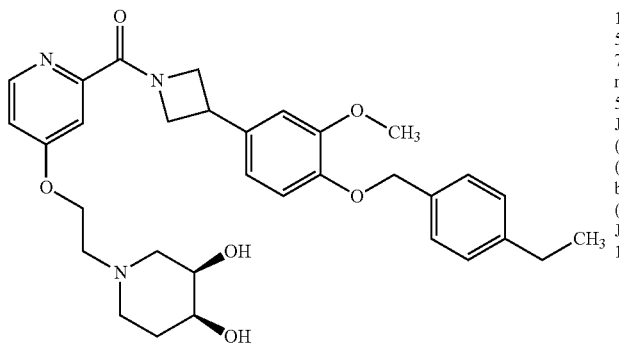 | 1H-NMR (400 MHz, DMSO-d6) δ: 8.41(1H, d, J = 5.80 Hz), 7.48(1H, d, J = 2.09 Hz), 7.33(2H, d, J = 7.65 Hz), 7.21(2H, d, J = 7.88 Hz), 7.10-7.09(1H, m), 6.99-6.97(2H, m), 6.86(1H, d, J = 8.35 Hz), 5.00(2H, s), 4.94(1H, t, J = 9.39 Hz), 4.53(1H, dd, J = 9.74, 6.72 Hz), 4.43(1H, t, J = 9.62 Hz), 4.32 (1H, d, J = 5.57 Hz), 4.24-4.18(2H, m), 4.07-4.05 (1H, m), 3.91-3.84(1H, m), 3.77(3H, s), 3.62(1H, br s), 3.47(1H, s), 2.71(2H, t, J = 5.45 Hz), 2.59 (2H, q, J = 7.58 Hz), 2.48-2.46(2H, m), 2.40(3H, d, J = 8.81 Hz), 1.66-1.61(1H, m), 1.54-1.52(1H, m), 1.17(3H, t, J = 7.54 Hz). |
| 115 | 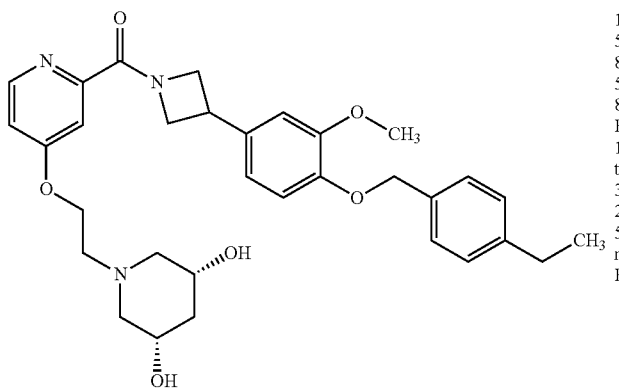 | 1H-NMR (400 MHz, DMSO-d6) δ: 8.41(1H, d, J = 5.57 Hz), 7.47(1H, d, J = 2.55 Hz), 7.33(2H, d, J = 8.12 Hz), 7.21(2H, d, J = 8.12 Hz), 7.10(1H, dd, J = 5.68, 2.67 Hz), 6.99-6.97(2H, m), 6.86(1H, dd, J = 8.35, 2.09 Hz), 5.00(2H, s), 4.94(1H, t, J = 9.39 Hz), 4.68(2H, d, J = 5.10 Hz), 4.53(1H, dd, J = 10.09, 6.61 Hz), 4.44(1H, t, J = 9.51 Hz), 4.20(2H, t, J = 5.57 Hz), 4.06(1H, dd, J = 10.20, 6.49 Hz), 3.91-3.84(1H, m), 3.77(3H, s), 3.46-3.42(2H, m), 2.89(2H, dd, J = 10.20, 4.17 Hz), 2.75(2H, t, J = 5.57 Hz), 2.59(2H, q, J = 7.58 Hz), 2.05-2.03(1H, m), 1.73(2H, t, J = 10.20 Hz), 1.17(3H, t, J = 7.65 Hz), 0.97(1H, q, J = 11.21 Hz). |

TABLE 1-25-continued

| 116 | 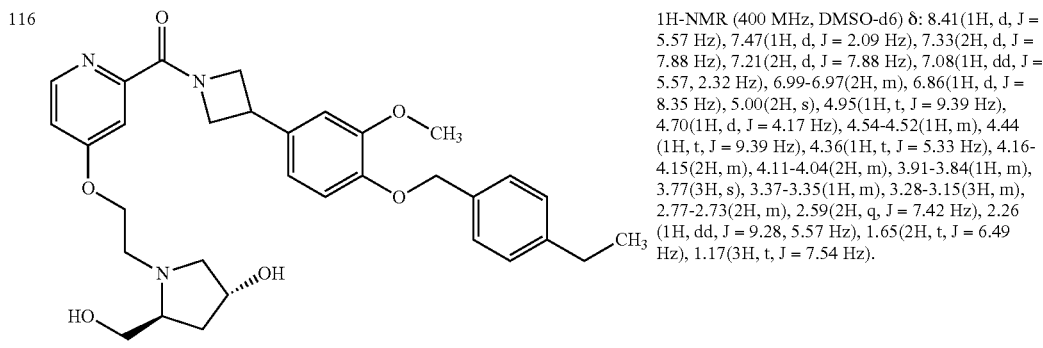 | 1H-NMR (400 MHz, DMSO-d6) δ: 8.41(1H, d, J = 5.57 Hz), 7.47(1H, d, J = 2.09 Hz), 7.33(2H, d, J = 7.88 Hz), 7.21(2H, d, J = 7.88 Hz), 7.08(1H, dd, J = 5.57, 2.32 Hz), 6.99-6.97(2H, m), 6.86(1H, d, J = 8.35 Hz), 5.00(2H, s), 4.95(1H, t, J = 9.39 Hz), 4.70(1H, d, J = 4.17 Hz), 4.54-4.52(1H, m), 4.44 (1H, t, J = 9.39 Hz), 4.36(1H, t, J = 5.33 Hz), 4.16-4.15(2H, m), 4.11-4.04(2H, m), 3.91-3.84(1H, m), 3.77(3H, s), 3.37-3.35(1H, m), 3.28-3.15(3H, m), 2.77-2.73(2H, m), 2.59(2H, q, J = 7.42 Hz), 2.26 (1H, dd, J = 9.28, 5.57 Hz), 1.65(2H, t, J = 6.49 Hz), 1.17(3H, t, J = 7.54 Hz). |

TABLE 1-26

| 117 | 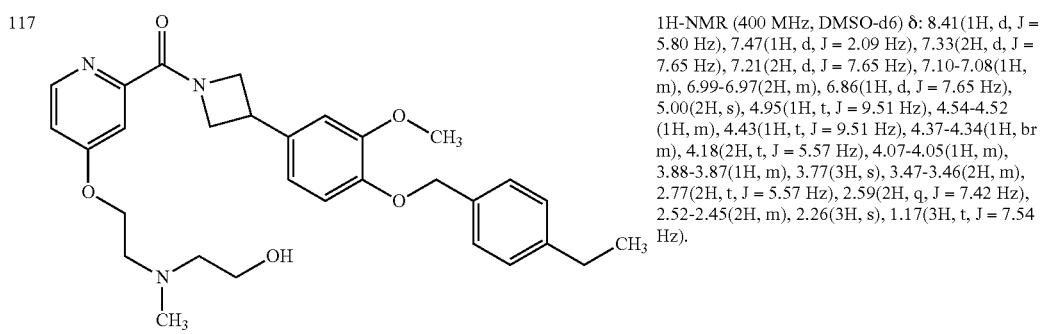 | 1H-NMR (400 MHz, DMSO-d6) δ: 8.41(1H, d, J = 5.80 Hz), 7.47(1H, d, J = 2.09 Hz), 7.33(2H, d, J = 7.65 Hz), 7.21(2H, d, J = 7.65 Hz), 7.10-7.08(1H, m), 6.99-6.97(2H, m), 6.86(1H, d, J = 7.65 Hz), 5.00(2H, s), 4.95(1H, t, J = 9.51 Hz), 4.54-4.52 (1H, m), 4.43(1H, t, J = 9.51 Hz), 4.37-4.34(1H, br m), 4.18(2H, t, J = 5.57 Hz), 4.07-4.05(1H, m), 3.88-3.87(1H, m), 3.77(3H, s), 3.47-3.46(2H, m), 2.77(2H, t, J = 5.57 Hz), 2.59(2H, q, J = 7.42 Hz), 2.52-2.45(2H, m), 2.26(3H, s), 1.17(3H, t, J = 7.54 Hz). |
| 118 | 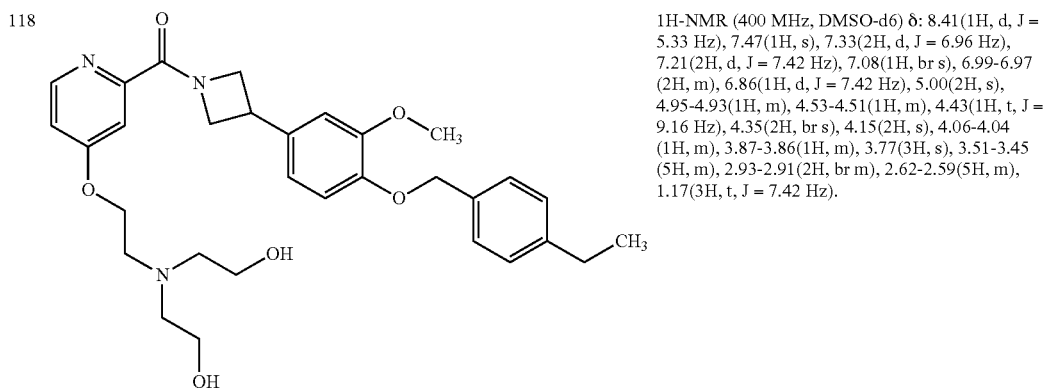 | 1H-NMR (400 MHz, DMSO-d6) δ: 8.41(1H, d, J = 5.33 Hz), 7.47(1H, s), 7.33(2H, d, J = 6.96 Hz), 7.21(2H, d, J = 7.42 Hz), 7.08(1H, br s), 6.99-6.97 (2H, m), 6.86(1H, d, J = 7.42 Hz), 5.00(2H, s), 4.95-4.93(1H, m), 4.53-4.51(1H, m), 4.43(1H, t, J = 9.16 Hz), 4.35(2H, br s), 4.15(2H, s), 4.06-4.04 (1H, m), 3.87-3.86(1H, m), 3.77(3H, s), 3.51-3.45 (5H, m), 2.93-2.91(2H, br m), 2.62-2.59(5H, m), 1.17(3H, t, J = 7.42 Hz). |
| 119 | 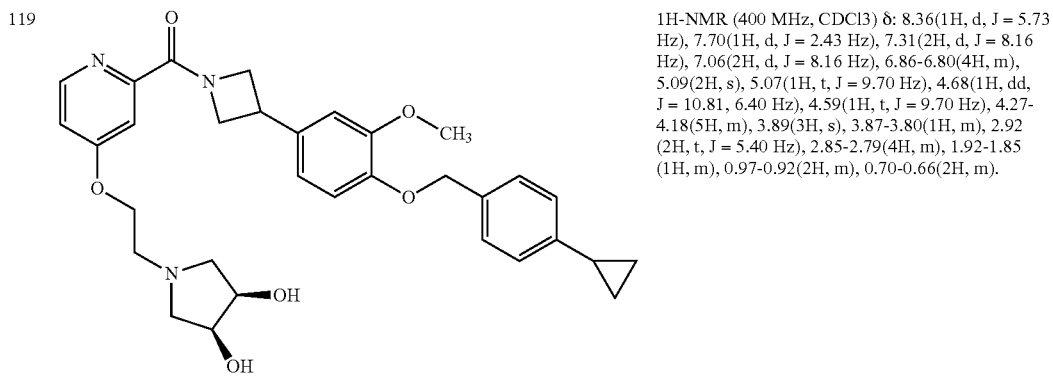 | 1H-NMR (400 MHz, CDCl3) δ: 8.36(1H, d, J = 5.73 Hz), 7.70(1H, d, J = 2.43 Hz), 7.31(2H, d, J = 8.16 Hz), 7.06(2H, d, J = 8.16 Hz), 6.86-6.80(4H, m), 5.09(2H, s), 5.07(1H, t, J = 9.70 Hz), 4.68(1H, dd, J = 10.81, 6.40 Hz), 4.59(1H, t, J = 9.70 Hz), 4.27-4.18(5H, m), 3.89(3H, s), 3.87-3.80(1H, m), 2.92 (2H, t, J = 5.40 Hz), 2.85-2.79(4H, m), 1.92-1.85 (1H, m), 0.97-0.92(2H, m), 0.70-0.66(2H, m). |

TABLE 1-26-continued

| 120 | 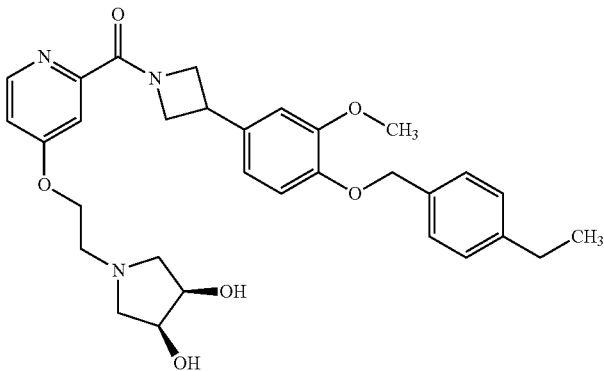 [SMILES: CCc1ccc(COc2ccc(C3CN(C(=O)c4cc(OCCN5C[C@@H](O)[C@@H](O)C5)ccn4)C3)cc2OC)cc1] | 1H-NMR (400 MHz, CDCl3) δ: 8.36(1H, d, J = 5.51 Hz), 7.70(1H, d, J = 2.65 Hz), 7.34(2H, d, J = 8.16 Hz), 7.19(2H, d, J = 8.38 Hz), 6.88-6.80(4H, m), 5.11(2H, s), 5.07(1H, t, J = 9.70 Hz), 4.69(1H, dd, J = 10.92, 8.51 Hz), 4.59(1H, t, J = 9.70 Hz), 4.25 (1H, dd, J = 11.03, 6.40 Hz), 4.23-4.18(4H, m), 3.89(3H, s), 3.88-3.80(1H, m), 2.92(2H, t, J = 5.40 Hz), 2.84-2.79(4H, m), 2.64(2H, q, J = 7.57 Hz), 1.23(3H, t, J = 7.61 Hz). |

TABLE 1-27

| 121 | 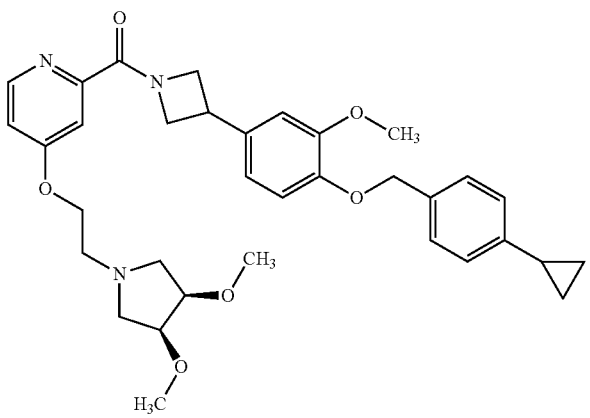 [SMILES: COc1cc(C2CN(C(=O)c3cc(OCCN4C[C@H](OC)[C@H](OC)C4)ccn3)C2)ccc1OCc1ccc(C2CC2)cc1] | 1H-NMR (400 MHz, CDCl3) δ: 8.35(1H, d, J = 5.64 Hz), 7.67(1H, d, J = 2.62 Hz), 7.31(2H, d, J = 8.06 Hz), 7.06(2H, d, J = 8.26 Hz), 6.88-6.80(4H, m), 5.10(2H, s), 5.07(1H, t, J = 9.67 Hz), 4.68(1H, dd, J = 10.58, 6.55 Hz), 4.59(1H, t, J = 9.77 Hz), 4.25 (1H, dd, J = 10.58, 6.35 Hz), 4.17(2H, t, J = 5.84 Hz), 3.89-3.79(6H, m), 3.42(6H, s), 3.16(2H, dd, J = 9.87, 5.84 Hz), 2.97(2H, t, J = 5.54 Hz), 2.68(2H, dd, J = 9.67, 5.04 Hz), 1.92-1.85(1H, m), 0.97-0.92 (2H, m), 0.70-0.66(2H, m). |
| 122 | 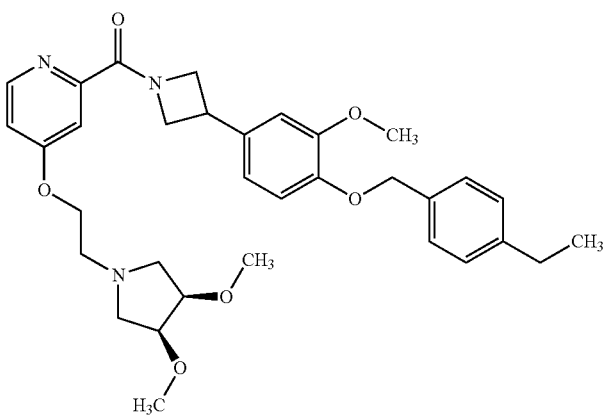 [SMILES: CCc1ccc(COc2ccc(C3CN(C(=O)c4cc(OCCN5C[C@H](OC)[C@H](OC)C5)ccn4)C3)cc2OC)cc1] | 1H-NMR (400 MHz, CDCl3) δ: 8.35(1H, d, J = 5.64 Hz), 7.67(1H, d, J = 2.62 Hz), 7.35(2H, d, J = 8.06 Hz), 7.19(2H, d, J = 8.26 Hz), 6.88-6.80(4H, m), 5.11(2H, s), 5.07(1H, t, J = 9.67 Hz), 4.68(1H, dd, J = 10.58, 6.55 Hz), 4.59(1H, t, J = 9.67 Hz), 4.25 (1H, dd, J = 10.58, 6.35 Hz), 4.17(2H, t, J = 5.54 Hz), 3.89(3H, s), 3.87-3.81(3H, m), 3.42(6H, s), 3.16(2H, dd, J = 9.67, 5.84 Hz), 2.97(2H, t, J = 5.54 Hz), 2.68(2H, dd, J = 9.87, 5.24 Hz), 2.64(2H, q, J = 7.66 Hz), 1.23(3H, t, J = 7.56 Hz). |

TABLE 1-27-continued

| 123 | 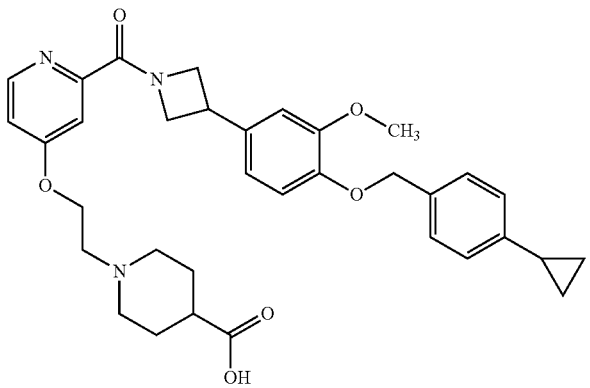 [SMILES: COc1cc(C2CN(C(=O)c3cc(OCCN4CCC(C(=O)O)CC4)ccn3)C2)ccc1OCc1ccc(C2CC2)cc1] | 1H-NMR (400 MHz, DMSO-d6) δ: 8.40(1H, d, J = 5.80 Hz), 7.47(1H, d, J = 2.55 Hz), 7.29(2H, d, J = 8.12 Hz), 7.09(1H, dd, J = 5.86, 2.67 Hz), 7.07(2H, d, J = 8.12 Hz), 6.97(1H, d, J = 6.26 Hz), 6.96(1H, s), 6.85(1H, dd, J = 8.35, 1.86 Hz), 4.98(2H, s), 4.94(1H, t, J = 9.51 Hz), 4.52(1H, dd, J = 10.20, 6.49 Hz), 4.43(1H, t, J = 9.51 Hz), 4.20(2H, t, J = 5.80 Hz), 4.05(1H, dd, J = 10.09, 6.38 Hz), 3.91-3.83(1H, m), 3.76(3H, s), 2.87-2.84(2H, m), 2.69 (2H, t, J = 5.88 Hz), 2.17(1H, tt, J = 11.13, 3.94 Hz), 2.09-2.06(2H, m), 1.93-1.87(1H, m), 1.78-1.76(2H, m), 1.55-1.49(2H, m), 0.94-0.92(2H, m), 0.67-0.63(2H, m). |
|---|---|---|
| 124 | 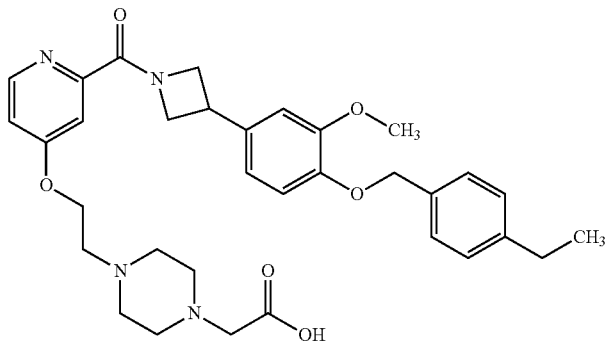 [SMILES: CCc1ccc(COc2ccc(C3CN(C(=O)c4cc(OCCN5CCN(CC(=O)O)CC5)ccn4)C3)cc2OC)cc1] | 1H-NMR (400 MHz, DMSO-d6) δ: 8.41(1H, d, J = 5.68 Hz), 7.48(1H, d, J = 2.71 Hz), 7.34(2H, d, J = 8.04 Hz), 7.22(2H, d, J = 8.04 Hz), 7.10(1H, dd, J = 5.68, 2.71 Hz), 7.00-6.97(2H, m), 6.86(1H, dd, J = 8.38, 1.98 Hz), 5.01(2H, s), 4.95(1H, dd, J = 9.59, 9.59 Hz), 4.53(1H, dd, J = 10.26, 7.17 Hz), 4.44(1H, dd, J = 9.59, 9.59 Hz), 4.22(2H, t, J = 5.45 Hz), 4.06(1H, dd, J = 10.26, 6.06 Hz), 3.90-3.86(1H, m), 3.78(3H, s), 3.12(2H, s), 2.72(2H, t, J = 5.45 Hz), 2.65-2.50(10H, m), 1.17(3H, t, J = 7.50 Hz). |

TABLE 1-28

| 125 | 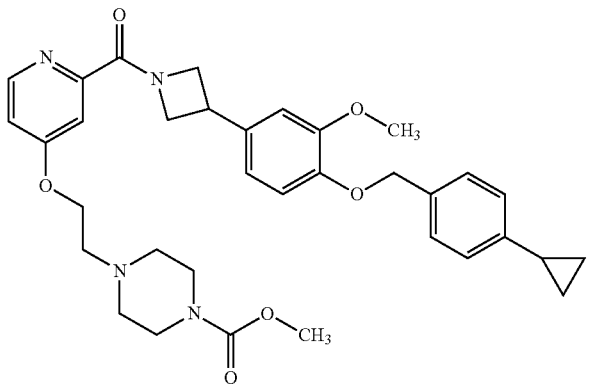 [SMILES: COC(=O)N1CCN(CCOc2ccnc(C(=O)N3CC(c4ccc(OCc5ccc(C6CC6)cc5)c(OC)c4)C3)c2)CC1] | 1H-NMR (400 MHz, DMSO-d6) δ: 8.42(1H, d, J = 5.73 Hz), 7.50(1H, d, J = 2.43 Hz), 7.29(2H, d, J = 8.16 Hz), 7.12-7.06(3H, m), 6.99-6.96(2H, m), 6.86 (1H, dd, J = 8.38, 1.98 Hz), 4.99-4.93(3H, m), 4.53 (1H, dd, J = 9.97, 6.73 Hz), 4.44(1H, dd, J = 9.59, 9.59 Hz), 4.24(2H, br s), 4.06(1H, dd, J = 9.97, 6.84 Hz), 3.90-3.85(1H, m), 3.77(3H, s), 3.59(3H, s), 3.37-3.31(4H, br m), 2.75(2H, s), 2.49-2.42 (4H, br m), 1.93-1.88(1H, m), 0.96-0.92(2H, m), 0.67-0.64(2H, m). |
|---|---|---|
| 127 | 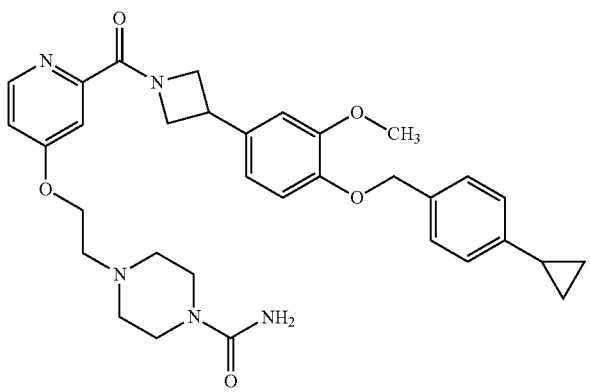 [SMILES: COc1cc(C2CN(C(=O)c3cc(OCCN4CCN(C(N)=O)CC4)ccn3)C2)ccc1OCc1ccc(C2CC2)cc1] | 1H-NMR (400 MHz, DMSO-d6) δ: 8.41(1H, d, J = 5.57 Hz), 7.49(1H, d, J = 2.55 Hz), 7.29(2H, d, J = 8.12 Hz), 7.11-7.05(3H, m), 6.98-6.96(2H, m), 6.85 (1H, dd, J = 8.23, 1.97 Hz), 5.94(2H, s), 4.99-4.91 (3H, m), 4.53(1H, dd, J = 10.15, 6.49 Hz), 4.43 (1H, dd, J = 9.62, 9.62 Hz), 4.23(2H, t, J = 5.33 Hz), 4.05(1H, dd, J = 10.15, 6.61 Hz), 3.90-3.84 (1H, m), 3.76(3H, s), 3.27-3.23(4H, br m), 2.73-2.71(2H, br m), 2.42-2.40(4H, br m), 1.92-1.88 (1H, m), 0.96-0.91(2H, m), 0.67-0.63(2H, m). |

TABLE 1-28-continued

| | | |
|---|---|---|
| 127 | 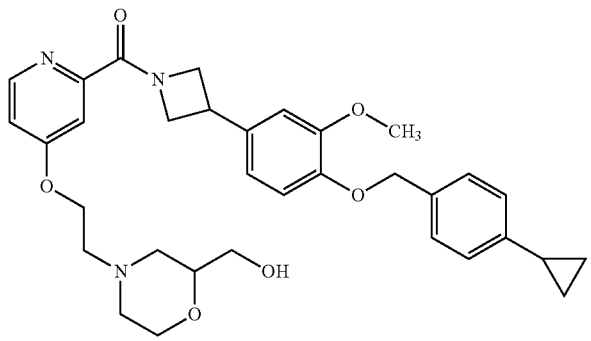 [SMILES: COc1cc(C2CN(C(=O)c3cc(OCCN4CCOC(CO)C4)ccn3)C2)ccc1OCc1ccc(C2CC2)cc1] | 1H-NMR (400 MHz, DMSO-d6) δ: 8.42(1H, d, J = 5.73 Hz), 7.49(1H, d, J = 2.65 Hz), 7.29(2H, d, J = 8.16 Hz), 7.12-7.06(3H, m), 6.99-6.96(2H, m), 6.86 (1H, dd, J = 8.27, 1.87 Hz), 4.99-4.92(3H, m), 4.64 (1H, t, J = 5.18 Hz), 4.53(1H, dd, J = 9.97, 6.67 Hz), 4.44(1H, dd, J = 9.59, 9.59 Hz), 4.24(2H, t, J = 5.29 Hz), 4.06(1H, dd, J = 9.97, 6.87 Hz), 3.91-3.85(1H, m), 3.77-3.75(4H, m), 3.51-3.27(4H, m), 2.89(1H, d, J = 9.70 Hz), 2.78-2.71(3H, m), 2.16-2.09(1H, br m), 1.93-1.85(2H, m), 0.96-0.92(2H, m), 0.68-0.64(2H, m). |
| 128 | 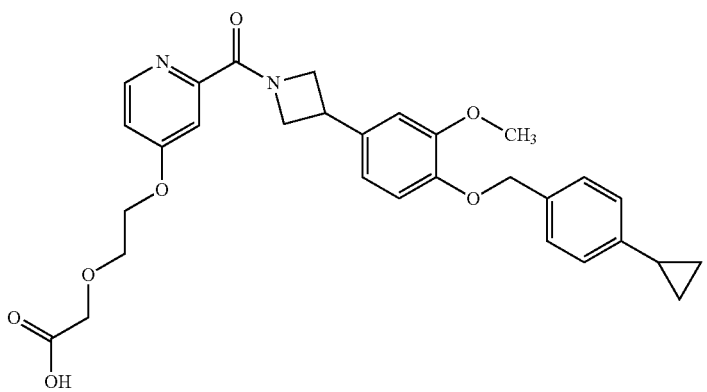 [SMILES: COc1cc(C2CN(C(=O)c3cc(OCCOCC(=O)O)ccn3)C2)ccc1OCc1ccc(C2CC2)cc1] | 1H-NMR (400 MHz, DMSO-d6) δ: 8.42(1H, d, J = 5.95 Hz), 7.49(1H, d, J = 2.85 Hz), 7.29(2H, d, J = 8.16 Hz), 7.11(1H, dd, J = 5.73, 2.65 Hz), 7.08(2H, d, J = 8.16 Hz), 7.00-6.95(2H, m), 6.86(1H, d, J = 8.38 Hz), 4.99(2H, s), 4.95(1H, t, J = 9.81 Hz), 4.54(1H, dd, J = 8.38, 4.19 Hz), 4.44(1H, t, J = 9.70 Hz), 4.27(2H, br s), 4.10-4.00(3H, m), 3.89 (1H, t, J = 8.16 Hz), 3.84(2H, br s), 3.77(3H, s), 1.95-1.85(1H, m), 0.96-0.91(2H, m), 0.70-0.60 (2H, m). |

TABLE 1-29

| | | |
|---|---|---|
| 129 | 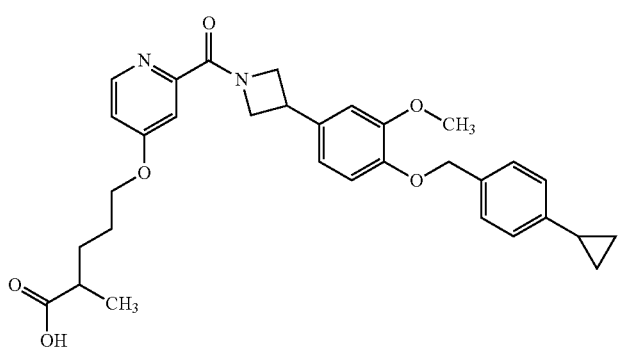 [SMILES: COc1cc(C2CN(C(=O)c3cc(OCCCC(C)C(=O)O)ccn3)C2)ccc1OCc1ccc(C2CC2)cc1] | 1H-NMR (400 MHz, DMSO-d6) δ: 8.41(1H, d, J = 5.73 Hz), 7.47(1H, d, J = 2.65 Hz), 7.29(2H, d, J = 8.16 Hz), 7.10-7.05(3H, m), 7.00-6.95(2H, m), 6.86 (1H, dd, J = 8.38, 1.54 Hz), 4.99(2H, s), 4.95(1H, t, J = 9.48 Hz), 4.53(1H, dd, J = 10.14, 6.62 Hz), 4.44(1H, t, J = 9.70 Hz), 4.11(2H, t, J = 6.06 Hz), 4.06(1H, dd, J = 10.26, 6.29 Hz), 3.95-3.80(1H, m), 3.77(3H, s), 2.45-2.30(1H, m), 1.93-1.89(1H, m), 1.80-1.65(3H, m), 1.55-1.45(1H, m), 1.08(3H, d, J = 7.06 Hz), 1.00-0.90(2H, m), 0.70-0.60(2H, m). |
| 130 | 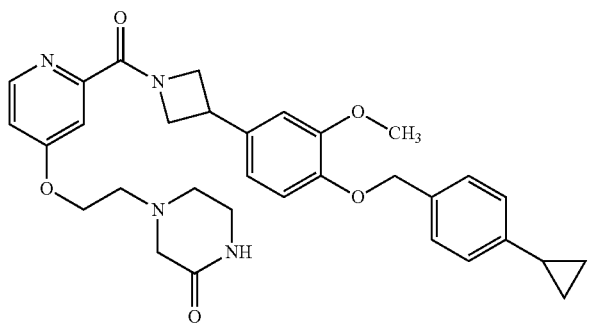 [SMILES: COc1cc(C2CN(C(=O)c3cc(OCCN4CCNC(=O)C4)ccn3)C2)ccc1OCc1ccc(C2CC2)cc1] | 1H-NMR (400 MHz, DMSO-d6) δ: 8.42(1H, d, J = 5.80 Hz), 7.75(1H, s), 7.50(1H, d, J = 2.55 Hz), 7.30(2H, d, J = 8.12 Hz), 7.11(1H, dd, J = 5.68, 2.67 Hz), 7.08(2H, d, J = 8.12 Hz), 6.99-6.97(2H, m), 6.86(1H, dd, J = 8.35, 1.86 Hz), 4.99(2H, s), 4.95(1H, t, J = 9.62 Hz), 4.53(1H, dd, J = 10.44, 6.49 Hz), 4.44(1H, t, J = 9.51 Hz), 4.26(2H, t, J = 5.45 Hz), 4.06(1H, dd, J = 10.20, 8.49 Hz), 3.92-3.84(1H, m), 3.77(3H, s), 3.17-3.13(2H, m), 3.05 (2H, s), 2.80(2H, t, J = 5.45 Hz), 2.88(2H, t, J = 5.33 Hz), 1.94-1.88(1H, m), 0.96-0.92(2H, m), 0.68-0.64(2H, m). |

TABLE 1-29-continued

| 131 | 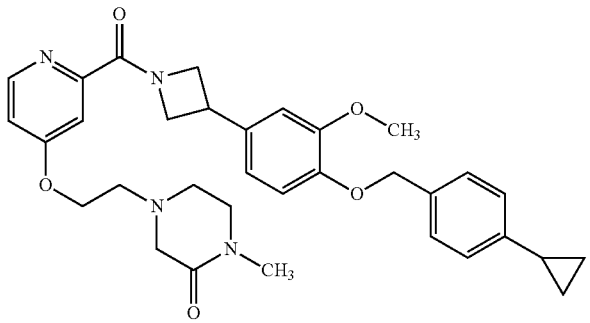 [SMILES: COc1cc(C2CN(C(=O)c3cc(OCCN4CCN(C)C(=O)C4)ccn3)C2)ccc1OCc1ccc(C2CC2)cc1] | 1H-NMR (400 MHz, DMSO-d6) δ: 8.42(1H, d, J = 5.57 Hz), 7.50(1H, d, J = 2.55 Hz), 7.29(2H, d, J = 8.12 Hz), 7.11(1H, dd, J = 5.68, 2.67 Hz), 7.08(2H, d, J = 8.12 Hz), 6.99-6.97(2H, m), 6.86(1H, dd, J = 8.35, 1.86 Hz), 4.99(2H, s), 4.95(1H, t, J = 9.51 Hz), 4.53(1H, dd, J = 10.20, 6.49 Hz), 4.44(1H, t, J = 9.51 Hz), 4.25(2H, t, J = 5.57 Hz), 4.06(1H, dd, J = 9.97, 6.49 Hz), 3.92-3.84(1H, m), 3.77(3H, s), 3.26(2H, t, J = 5.45 Hz), 3.10(2H, s), 2.81(3H, s), 2.80-2.73(4H, m), 1.94-1.88(1H, m), 0.96-0.92(2H, m), 0.68-0.64(2H, m). |
|---|---|---|
| 132 | 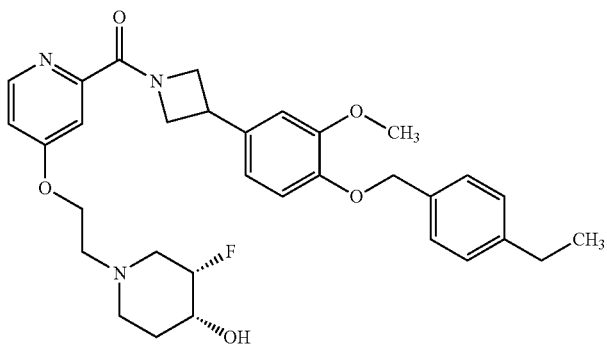 [SMILES: CCc1ccc(COc2ccc(C3CN(C(=O)c4cc(OCCN5CC[C@@H](O)[C@@H](F)C5)ccn4)C3)cc2OC)cc1] | 1H-NMR (400 MHz, DMSO-d6) δ: 8.42(1H, d, J = 5.57 Hz), 7.48(1H, d, J = 2.55 Hz), 7.34(2H, d, J = 8.12 Hz), 7.22(2H, d, J = 7.88 Hz), 7.11(1H, dd, J = 5.68, 2.67 Hz), 7.00-6.97(2H, m), 6.87(1H, dd, J = 8.35, 1.86 Hz), 5.01(2H, s), 4.97-4.90(2H, m), 4.59-4.42(3H, m), 4.21(2H, t, J = 5.57 Hz), 4.06(1H, dd, J = 9.97, 6.49 Hz), 3.92-3.84(1H, m), 3.78(3H, s), 3.69-3.61(1H, br m), 2.89(1H, br s), 2.76(2H, t, J = 5.45 Hz), 2.67(1H, br s), 2.60(2H, q, J = 7.58 Hz), 2.47-2.43(1H, br m), 2.34-2.26(1H, br m), 1.72-1.65(1H, br m), 1.59-1.55(1H, br m), 1.17(3H, t, J = 7.54 Hz). |

TABLE 1-30

| 133 | 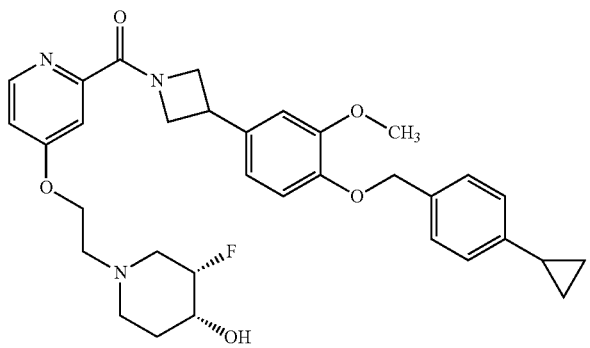 [SMILES: COc1cc(C2CN(C(=O)c3cc(OCCN4CC[C@@H](O)[C@@H](F)C4)ccn3)C2)ccc1OCc1ccc(C2CC2)cc1] | 1H-NMR (400 MHz, DMSO-d6): δ: 8.42(1H, d, J = 5.57 Hz), 7.48(1H, d, J = 2.55 Hz), 7.30(2H, d, J = 8.12 Hz), 7.11(1H, dd, J = 5.68, 2.67 Hz), 7.08(2H, d, J = 8.12 Hz), 6.99-6.97(2H, m), 6.86(1H, dd, J = 8.35, 1.86 Hz), 4.99(2H, s), 4.97-4.90(2H, m), 4.58-4.42(3H, m), 4.21(2H, t, J = 5.57 Hz), 4.06(1H, dd, J = 10.09, 6.61 Hz), 3.92-3.84(2H, m), 3.77(3H, s), 3.65(1H, d, J = 17.16 Hz), 2.89(1H, s), 2.76(2H, t, J = 5.57 Hz), 2.67(1H, s), 2.46(1H, br s), 2.32-2.28(1H, br m), 1.94-1.88(1H, m), 1.70-1.65(1H, m), 1.60-1.55(1H, m), 0.96-0.92(2H, m), 0.66-0.64(2H, m). |
|---|---|---|
| 134 | 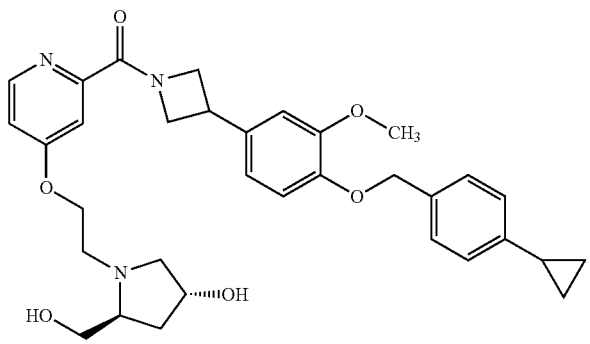 [SMILES: COc1cc(C2CN(C(=O)c3cc(OCCN4C[C@H](O)C[C@H]4CO)ccn3)C2)ccc1OCc1ccc(C2CC2)cc1] | 1H-NMR (400 MHz, DMSO-d6): δ: 8.41(1H, d, J = 5.80 Hz), 7.47(1H, d, J = 2.78 Hz), 7.29(2H, d, J = 8.12 Hz), 7.09-7.06(3H, m), 6.97(2H, t, J = 4.06 Hz), 6.85(1H, dd, J = 8.35, 1.86 Hz), 4.98(2H, s), 4.95(1H, t, J = 9.51 Hz), 4.70(1H, d, J = 3.94 Hz), 4.53(1H, dd, J = 10.20, 6.49 Hz), 4.43(1H, t, J = 9.51 Hz), 4.35(1H, br s), 4.19-4.17(2H, m), 4.06-4.05(2H, m), 3.91-3.85(1H, m), 3.77(3H, s), 3.40-3.34(1H, m), 3.30-3.17(3H, m), 2.77-2.73(2H, m), 2.27-2.25(1H, m), 1.92-1.88(1H, m), 1.65(1H, t, J = 6.72 Hz), 0.94-0.92(2H, m), 0.67-0.63(2H, m). |

TABLE 1-30-continued

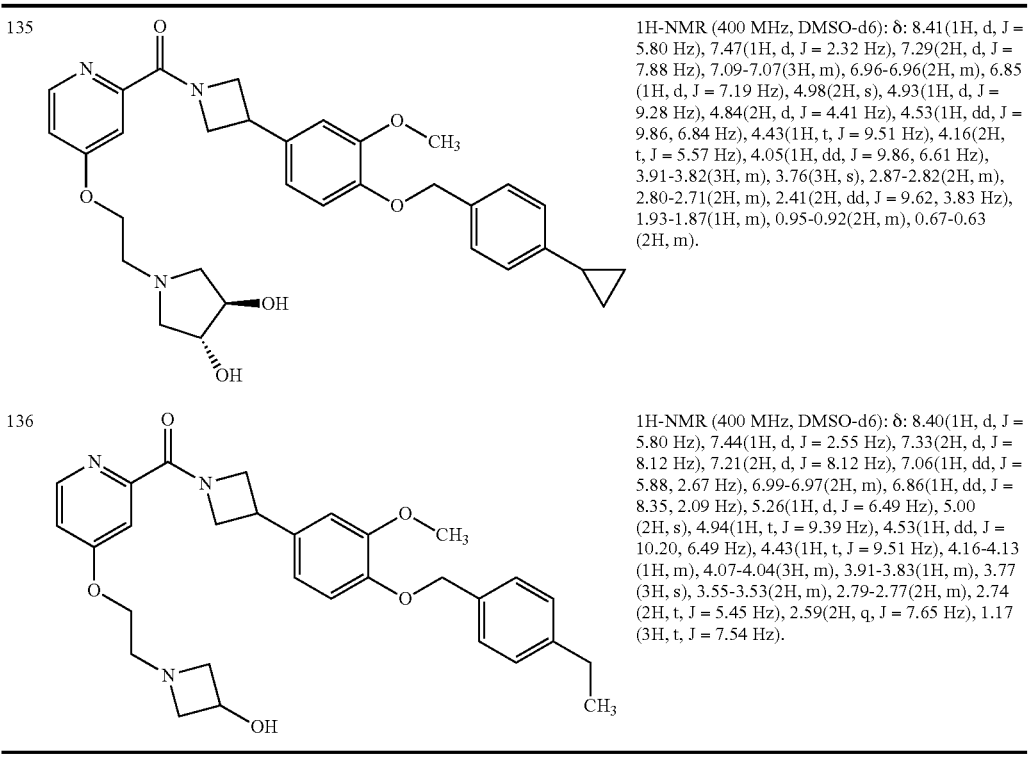

| 135 | 1H-NMR (400 MHz, DMSO-d6): δ: 8.41(1H, d, J = 5.80 Hz), 7.47(1H, d, J = 2.32 Hz), 7.29(2H, d, J = 7.88 Hz), 7.09-7.07(3H, m), 6.96-6.96(2H, m), 6.85 (1H, d, J = 7.19 Hz), 4.98(2H, s), 4.93(1H, d, J = 9.28 Hz), 4.84(2H, d, J = 4.41 Hz), 4.53(1H, dd, J = 9.86, 6.84 Hz), 4.43(1H, t, J = 9.51 Hz), 4.16(2H, t, J = 5.57 Hz), 4.05(1H, dd, J = 9.86, 6.61 Hz), 3.91-3.82(3H, m), 3.76(3H, s), 2.87-2.82(2H, m), 2.80-2.71(2H, m), 2.41(2H, dd, J = 9.62, 3.83 Hz), 1.93-1.87(1H, m), 0.95-0.92(2H, m), 0.67-0.63 (2H, m). |
|---|---|
| 136 | 1H-NMR (400 MHz, DMSO-d6): δ: 8.40(1H, d, J = 5.80 Hz), 7.44(1H, d, J = 2.55 Hz), 7.33(2H, d, J = 8.12 Hz), 7.21(2H, d, J = 8.12 Hz), 7.06(1H, dd, J = 5.88, 2.67 Hz), 6.99-6.97(2H, m), 6.86(1H, dd, J = 8.35, 2.09 Hz), 5.26(1H, d, J = 6.49 Hz), 5.00 (2H, s), 4.94(1H, t, J = 9.39 Hz), 4.53(1H, dd, J = 10.20, 6.49 Hz), 4.43(1H, t, J = 9.51 Hz), 4.16-4.13 (1H, m), 4.07-4.04(3H, m), 3.91-3.83(1H, m), 3.77 (3H, s), 3.55-3.53(2H, m), 2.79-2.77(2H, m), 2.74 (2H, t, J = 5.45 Hz), 2.59(2H, q, J = 7.65 Hz), 1.17 (3H, t, J = 7.54 Hz). |

TABLE 1-31

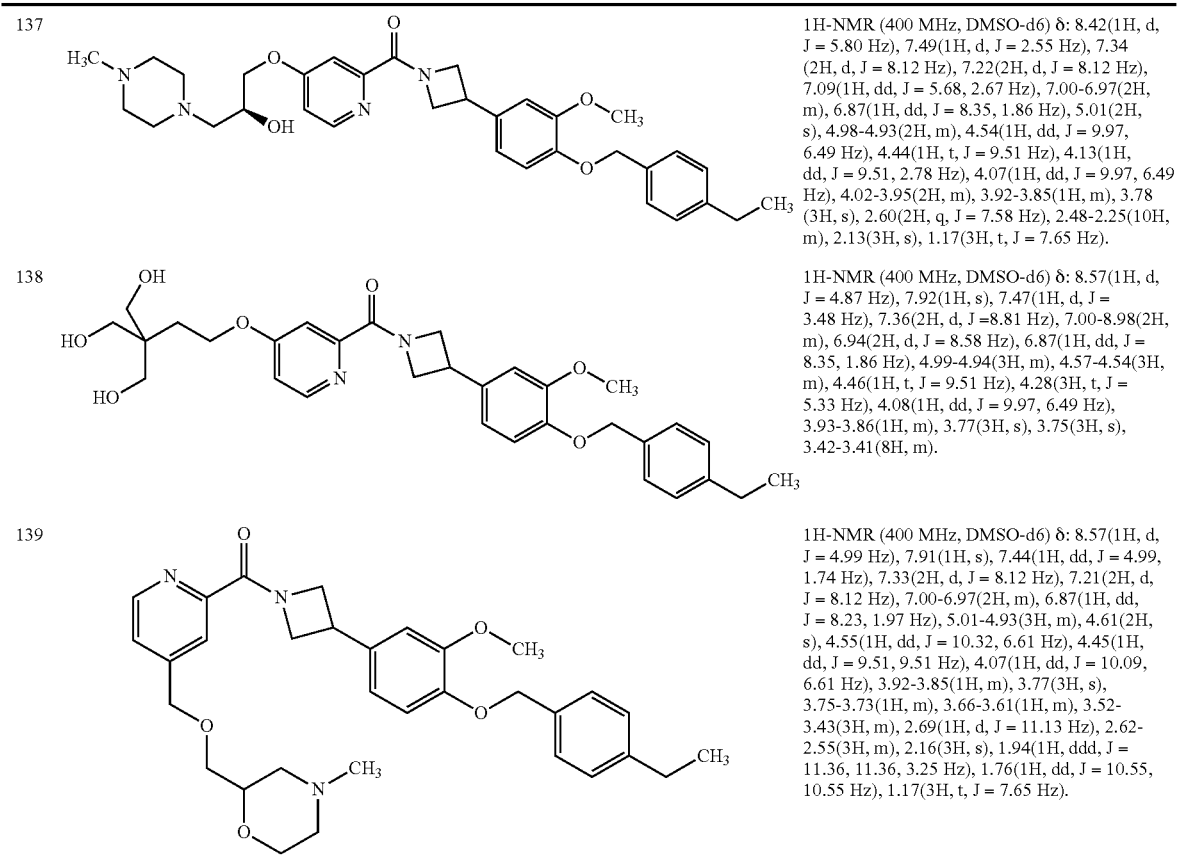

| 137 | 1H-NMR (400 MHz, DMSO-d6) δ: 8.42(1H, d, J = 5.80 Hz), 7.49(1H, d, J = 2.55 Hz), 7.34 (2H, d, J = 8.12 Hz), 7.22(2H, d, J = 8.12 Hz), 7.09(1H, dd, J = 5.68, 2.67 Hz), 7.00-6.97(2H, m), 6.87(1H, dd, J = 8.35, 1.86 Hz), 5.01(2H, s), 4.98-4.93(2H, m), 4.54(1H, dd, J = 9.97, 6.49 Hz), 4.44(1H, t, J = 9.51 Hz), 4.13(1H, dd, J = 9.51, 2.78 Hz), 4.07(1H, dd, J = 9.97, 6.49 Hz), 4.02-3.95(2H, m), 3.92-3.85(1H, m), 3.78 (3H, s), 2.60(2H, q, J = 7.58 Hz), 2.48-2.25(10H, m), 2.13(3H, s), 1.17(3H, t, J = 7.65 Hz). |
|---|---|
| 138 | 1H-NMR (400 MHz, DMSO-d6) δ: 8.57(1H, d, J = 4.87 Hz), 7.92(1H, s), 7.47(1H, d, J = 3.48 Hz), 7.36(2H, d, J = 8.81 Hz), 7.00-8.98(2H, m), 6.94(2H, d, J = 8.58 Hz), 6.87(1H, dd, J = 8.35, 1.86 Hz), 4.99-4.94(3H, m), 4.57-4.54(3H, m), 4.46(1H, t, J = 9.51 Hz), 4.28(3H, t, J = 5.33 Hz), 4.08(1H, dd, J = 9.97, 6.49 Hz), 3.93-3.86(1H, m), 3.77(3H, s), 3.75(3H, s), 3.42-3.41(8H, m). |
| 139 | 1H-NMR (400 MHz, DMSO-d6) δ: 8.57(1H, d, J = 4.99 Hz), 7.91(1H, s), 7.44(1H, dd, J = 4.99, 1.74 Hz), 7.33(2H, d, J = 8.12 Hz), 7.21(2H, d, J = 8.12 Hz), 7.00-6.97(2H, m), 6.87(1H, dd, J = 8.23, 1.97 Hz), 5.01-4.93(3H, m), 4.61(2H, s), 4.55(1H, dd, J = 10.32, 6.61 Hz), 4.45(1H, dd, J = 9.51, 9.51 Hz), 4.07(1H, dd, J = 10.09, 6.61 Hz), 3.92-3.85(1H, m), 3.77(3H, s), 3.75-3.73(1H, m), 3.66-3.61(1H, m), 3.52-3.43(3H, m), 2.69(1H, d, J = 11.13 Hz), 2.62-2.55(3H, m), 2.16(3H, s), 1.94(1H, ddd, J = 11.36, 11.36, 3.25 Hz), 1.76(1H, dd, J = 10.55, 10.55 Hz), 1.17(3H, t, J = 7.65 Hz). |

TABLE 1-31-continued

140 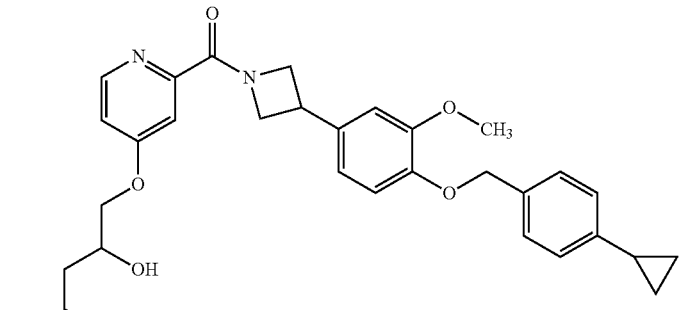

1H-NMR (400 MHz, DMSO-d6) δ: 8.42(1H, d, J = 5.73 Hz), 7.49(1H, d, J = 2.43 Hz), 7.29 (2H, d, J = 8.16 Hz), 7.11-7.07(3H, m), 7.00-6.95(2H, m), 6.86(1H, dd, J = 8.16, 2.10 Hz), 4.99(2H, s), 4.95(1H, t, J = 9.70 Hz), 4.54 (1H, dd, J = 9.70, 5.00 Hz), 4.44(1H, t, J = 9.26 Hz), 4.25-4.15(1H, m), 4.08-4.02 (3H, m), 3.95-3.85(1H, m), 3.77(3H, s), 2.48 (1H, dd, J = 13.00, 7.00 Hz), 2.34(1H, dd, J = 13.00, 7.00 Hz), 1.95-1.85(1H, m), 0.96-0.92(2H, m), 0.70-0.60(2H, m).

TABLE 1-32

141 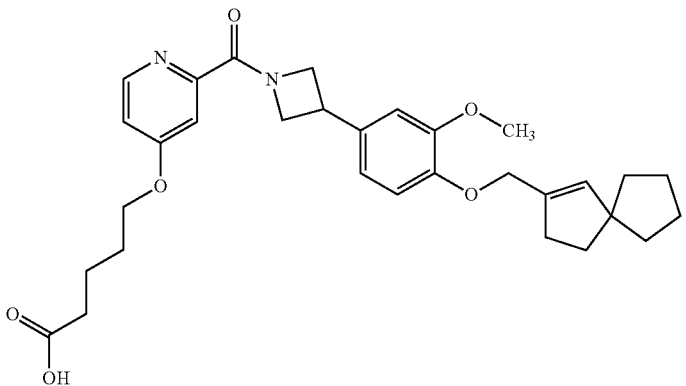 [SMILES: COc1cc(C2CN(C(=O)c3cc(OCCCCC(=O)O)ccn3)C2)ccc1OCC1=CC2(CCCC2)CC1]

1H-NMR (400 MHz, DMSO-d6) δ: 12.05(1H, br s), 8.41(1H, d, J = 5.80 Hz), 7.46(1H, d, J = 2.56 Hz), 7.08(1H, dd, J = 5.80, 2.55 Hz), 6.95(1H, d, J = 1.86 Hz), 6.92(1H, d, J = 8.12 Hz), 6.85(1H, dd, J = 8.23, 1.97 Hz), 5.56(1H, br s), 4.94(1H, t, J = 9.62 Hz), 4.53(1H, dd, J = 9.62, 4.30 Hz), 4.50(2H, s), 4.44(1H, t, J = 9.51 Hz), 4.11(2H, t, J = 6.26 Hz), 4.06(1H, dd, J = 10.20, 6.49 Hz), 3.91-3.83 (1H, m), 3.76(3H, s), 2.33(2H, t, J = 6.49 Hz), 2.28 (2H, t, J = 7.19 Hz), 1.80-1.70(4H, m), 1.67-1.54 (6H, m), 1.51-1.42(4H, m).

142 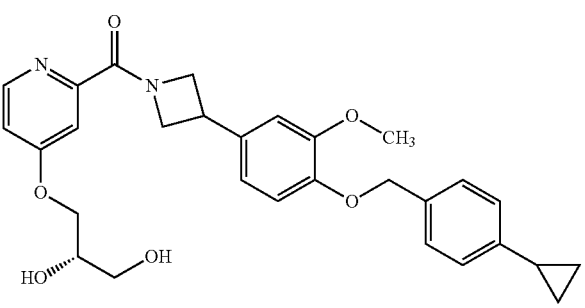

1H-NMR (400 MHz, DMSO-d6) δ: 8.42(1H, d, J = 5.64 Hz), 7.49(1H, d, J = 2.42 Hz), 7.30(2H, d, J = 8.26 Hz), 7.10-7.07(3H, m), 6.99-6.97(2H, m), 6.86 (1H, dd, J = 8.36, 1.91 Hz), 5.04(1H, d, J = 5.04 Hz), 4.99(2H, s), 4.96(1H, t, J = 9.57 Hz), 4.73 (1H, t, J = 5.74 Hz), 4.54(1H, dd, J = 10.07, 6.45 Hz), 4.44(1H, t, J = 9.57 Hz), 4.16(1H, dd, J = 10.17, 3.73 Hz), 4.09-3.98(2H, m), 3.92-3.79(2H, m), 3.77(3H, s), 3.48-3.42(2H, m), 1.94-1.88(1H, m), 0.96-0.91(2H, m), 0.68-0.64(2H, m).

143 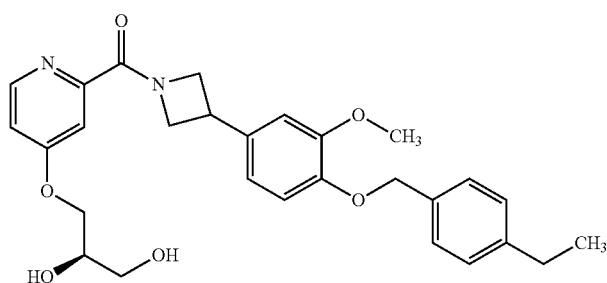 [SMILES: CCc1ccc(COc2ccc(C3CN(C(=O)c4cc(OC[C@H](O)CO)ccn4)C3)cc2OC)cc1]

1H-NMR (400 MHz, DMSO-d6) δ: 8.42(1H, d, J = 5.73 Hz), 7.49(1H, d, J = 2.43 Hz), 7.34(2H, d, J = 7.94 Hz), 7.22(2H, d, J = 7.94 Hz), 7.09(1H, dd, J = 5.73, 2.65 Hz), 7.00-6.98(2H, m), 6.87(1H, dd, J = 8.27, 1.87 Hz), 5.04(1H, d, J = 5.07 Hz), 5.01 (2H, s), 4.96(1H, t, J = 9.37 Hz), 4.72(1H, t, J = 5.73 Hz), 4.54(1H, dd, J = 10.26, 6.73 Hz), 4.44 (1H, t, J = 9.59 Hz), 4.16(1H, dd, J = 10.26, 3.64 Hz), 4.09-3.98(2H, m), 3.92-3.79(2H, m), 3.78(3H, s), 3.46-3.43(2H, m), 2.60(2H, q, J = 7.50 Hz), 1.17(3H, t, J = 7.61 Hz).

TABLE 1-32-continued

| 144 | 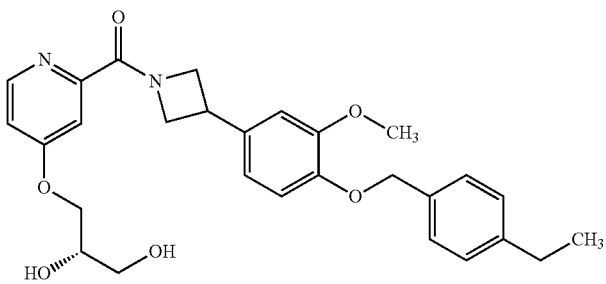 [SMILES: CCc1ccc(COc2ccc(C3CN(C(=O)c4cc(OC[C@@H](O)CO)ccn4)C3)cc2OC)cc1] | 1H-NMR (400 MHz, DMSO-d6) δ: 8.42(1H, d, J = 5.95 Hz), 7.49(1H, d, J = 2.43 Hz), 7.34(2H, d, J = 8.16 Hz), 7.22(2H, d, J = 8.16 Hz), 7.09(1H, dd, J = 5.73, 2.65 Hz), 7.00-6.98(2H, m), 6.87(1H, dd, J = 8.16, 1.98 Hz), 5.04(1H, d, J = 5.07 Hz), 5.01 (2H, s), 4.96(1H, t, J = 9.70 Hz), 4.72(1H, t, J = 5.73 Hz), 4.54(1H, dd, J = 10.14, 6.40 Hz), 4.45 (1H, t, J = 9.70 Hz), 4.16(1H, dd, J = 10.14, 3.97 Hz), 4.09-3.98(2H, m), 3.92-3.80(2H, m), 3.78(3H, s), 3.46-3.43(2H, m), 2.60(2H, q, J = 7.61 Hz), 1.17(3H, t, J = 7.61 Hz). |
|---|---|---|

TABLE 1-33

| 145 | 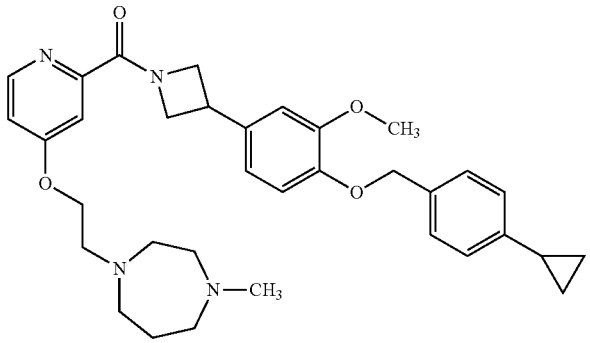 [SMILES: COc1cc(C2CN(C(=O)c3cc(OCCN4CCCN(C)CC4)ccn3)C2)ccc1OCc1ccc(C2CC2)cc1] | 1H-NMR (400 MHz, CDCl3) δ: 8.36(1H, d, J = 5.44 Hz), 7.68(1H, d, J = 2.62 Hz), 7.31(2H, d, J = 8.06 Hz), 7.06(2H, d, J = 8.06 Hz), 6.87-6.80(4H, m), 5.10(2H, s), 5.08(1H, t, J = 9.67 Hz), 4.68(1H, dd, J = 10.78, 6.55 Hz), 4.59(1H, t, J = 9.67 Hz), 4.25 (1H, dd, J = 10.07, 6.85 Hz), 4.17(2H, t, J = 5.64 Hz), 3.89(3H, s), 3.86-3.80(1H, m), 3.01-2.88 (10H, br m), 2.54(3H, br s), 2.07-1.85(3H, br m), 0.97-0.92(2H, m), 0.70-0.66(2H, m). |
|---|---|---|
| 146 | 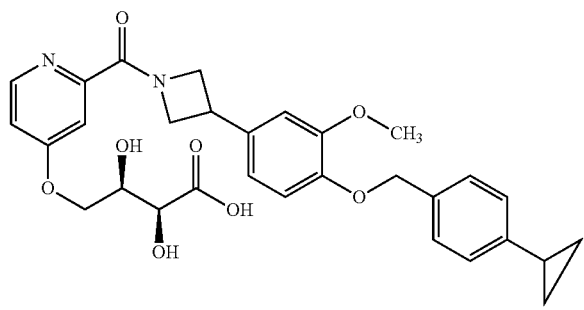 [SMILES: COc1cc(C2CN(C(=O)c3cc(OC[C@@H](O)[C@H](O)C(=O)O)ccn3)C2)ccc1OCc1ccc(C2CC2)cc1] | 1H-NMR (400 MHz, DMSO-d6) δ: 8.39(1H, d, J = 5.64 Hz), 7.44(1H, d, J = 2.62 Hz), 7.30(2H, d, J = 8.06 Hz), 7.08(2H, d, J = 8.06 Hz), 7.06-7.03(1H, m), 7.00-6.96(2H, m), 6.89-6.84(1H, m), 5.65(1H, br s), 4.99(2H, s), 4.97-4.92(1H, m), 4.57-4.51 (1H, m), 4.48-4.36(2H, m), 4.20-4.15(1H, m), 4.09-4.03(1H, m), 3.96-3.80(3H, m), 3.77(3H, s), 3.71 (0H, s), 3.55(1H, d, J = 4.43 Hz), 1.95-1.87(1H, m), 0.96-0.90(2H, m), 0.69-0.62(2H, m). |
| 147 | 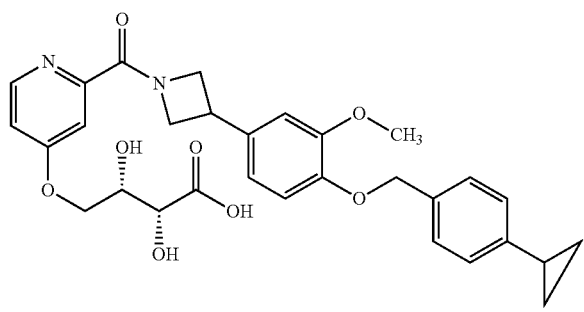 [SMILES: COc1cc(C2CN(C(=O)c3cc(OC[C@H](O)[C@@H](O)C(=O)O)ccn3)C2)ccc1OCc1ccc(C2CC2)cc1] | 1H-NMR (400 MHz, CDCl3) δ: 8.39(1H, d, J = 5.64 Hz), 7.43(1H, s), 7.29(2H, d, J = 7.86 Hz), 7.09-7.02(3H, m), 6.99-6.94(2H, m), 6.86(1H, d, J = 8.06 Hz), 5.69-5.62(1H, m), 4.98(2H, s), 4.95 (1H, t, J = 9.67 Hz), 4.57-4.49(1H, m), 4.47-4.35 (2H, m), 4.19-4.13(1H, m), 4.06-4.02(1H, m), 3.95-3.80(3H, m), 3.78(3H, s), 3.54(1H, d, J = 4.23 Hz), 1.95-1.85(1H, m), 0.97-0.89(2H, m), 0.68-0.61(2H, m). |
| 148 | 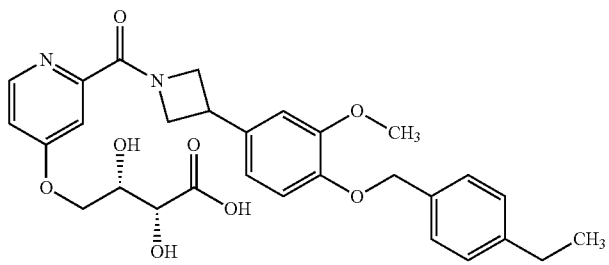 [SMILES: CCc1ccc(COc2ccc(C3CN(C(=O)c4cc(OC[C@H](O)[C@@H](O)C(=O)O)ccn4)C3)cc2OC)cc1] | 1H-NMR (400 MHz, CDCl3) δ: 8.45-8.37(1H, m), 7.47-7.41(1H, m), 7.34(2H, d, J = 5.64 Hz), 7.26-7.19(2H, m), 7.09-7.03(1H, m), 6.96-6.96 (2H, m), 6.88(1H, s), 5.65(1H, br s), 5.01(2H, s), 4.96(1H, t, J = 8.26 Hz), 4.59-4.50(1H, m), 4.50-4.34(2H, m), 4.22-4.14(1H, m), 4.11-4.03(1H, m), 3.97-3.82(3H, m), 3.81-3.76(3H, m), 3.59-3.53 (1H, m), 2.66-2.56(2H, m), 1.22-1.14(3H, m). |

TABLE 1-34

| | | |
|---|---|---|
| 149 | 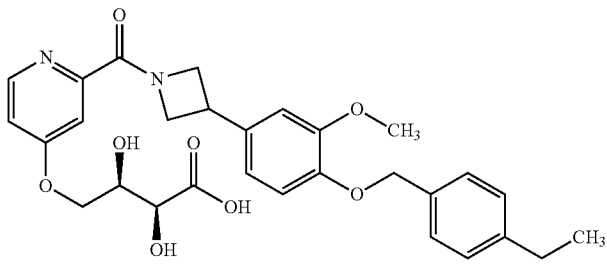 [SMILES: CCc1ccc(COc2ccc(C3CN(C(=O)c4cc(OC[C@@H](O)[C@H](O)C(=O)O)ccn4)C3)cc2OC)cc1] | 1H-NMR (400 MHz, DMSO-d6) δ: 8.39(1H, d, J = 5.84 Hz), 7.44-7.39(1H, m), 7.33(2H, d, J = 7.86Hz), 7.21(2H, d, J = 8.06 Hz), 7.06-7.01(1H, m), 7.00-6.93 (2H, m), 6.88-6.82 (1H, m), 5.00(2H, s), 4.95(1H, t, J = 10.28 Hz), 4.57-4.49(1H, m), 4.48-4.27(2H, m), 4.20-4.11 (1H, m), 3.94-3.79(2H, m), 3.76(3H, s), 3.27(1H, d, J = 4.43 Hz), 2.59(2H, q, J = 7.59 Hz), 1.17(3H, t, J = 7.56 Hz). |
| 150 | 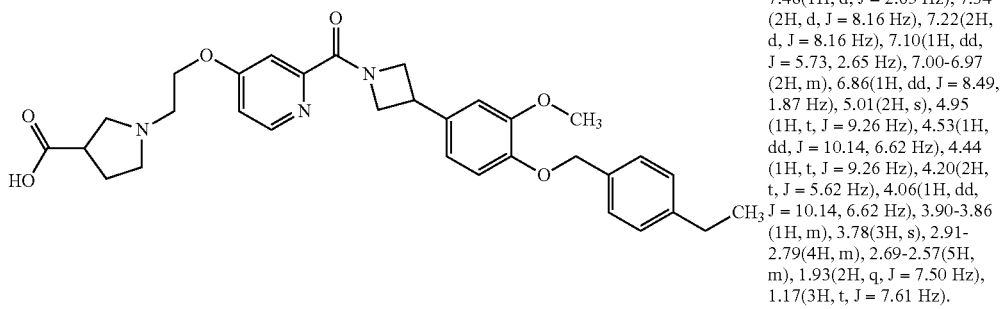 | 1H-NMR (400 MHz, DMSO-d6) δ: 8.42(1H, d, J = 5.73 Hz), 7.48(1H, d, J = 2.65 Hz), 7.34 (2H, d, J = 8.16 Hz), 7.22(2H, d, J = 8.16 Hz), 7.10(1H, dd, J = 5.73, 2.65 Hz), 7.00-6.97 (2H, m), 6.86(1H, dd, J = 8.49, 1.87 Hz), 5.01(2H, s), 4.95 (1H, t, J = 9.26 Hz), 4.53(1H, dd, J = 10.14, 6.62 Hz), 4.44 (1H, t, J = 9.26 Hz), 4.20(2H, t, J = 5.62 Hz), 4.06(1H, dd, J = 10.14, 6.62 Hz), 3.90-3.86 (1H, m), 3.78(3H, s), 2.91-2.79(4H, m), 2.69-2.57(5H, m), 1.93(2H, q, J = 7.50 Hz), 1.17(3H, t, J = 7.61 Hz). |
| 151 | 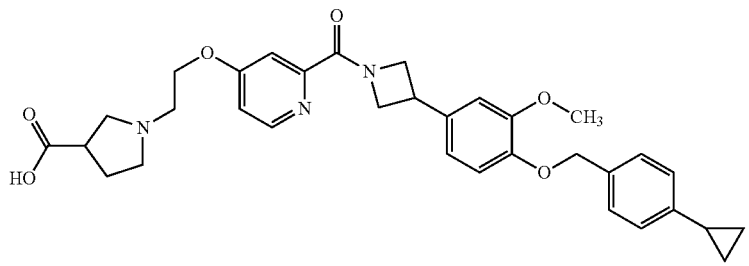 [SMILES: COc1cc(C2CN(C(=O)c3cc(OCCN4CCC(C(=O)O)C4)ccn3)C2)ccc1OCc1ccc(C2CC2)cc1] | 1H-NMR (400 MHz, DMSO-d6) δ: 8.42(1H, d, J =5.73 Hz), 7.48(1H, d, J = 2.65 Hz), 7.29 (2H, d, J = 8.16 Hz), 7.11(1H, dd, J = 5.73, 2.65 Hz), 7.08 (2H, d, J = 8.16 Hz), 6.99-6.97(2H, m), 6.86(1H, dd, J = 8.27, 1.87 Hz), 4.99(2H, s), 4.95(1H, t, J = 9.48 Hz), 4.53 (1H, dd, J = 10.03, 6.51 Hz), 4.44(1H, t, J = 9.70 Hz), 4.22 (2H, t, J = 5.62 Hz), 4.06(1H, dd, J = 10.26, 6.29 Hz), 3.91-3.85(1H, m), 3.77(3H, s), 2.96-2.82(4H, m), 2.76-2.61 (3H, m), 1.98-1.88(3H, m), 0.96-0.92(2H, m), 0.68-0.64 (2H, m). |
| 152 | 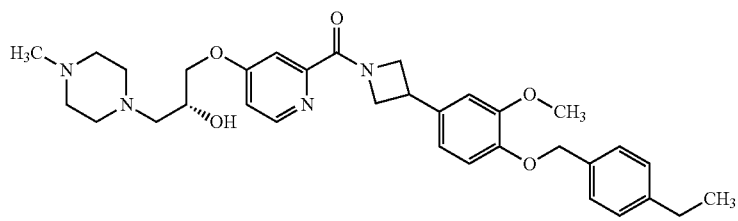 [SMILES: CCc1ccc(COc2ccc(C3CN(C(=O)c4cc(OC[C@H](O)CN5CCN(C)CC5)ccn4)C3)cc2OC)cc1] | 1H-NMR (400 MHz, DMSO-d6) δ: 8.42(1H, d, J = 5.80 Hz), 7.49(1H, d, J = 2.55 Hz), 7.34 (2H, d, J = 8.12 Hz), 7.22(2H, d, J = 8.12 Hz), 7.09(1H, dd, J =5.68, 2.67 Hz), 7.00-6.98 (2H, m), 6.87(1H, d, J = 8.35 Hz), 5.01(2H, s), 4.96(2H, t, J = 9.39 Hz), 4.54(1H, dd, J = 10.09, 6.61 Hz), 4.44(1H, t, J = 9.51 Hz), 4.13(1H, d, J = 6.72 Hz), 4.07(1H, dd, J = 10.09, 6.61 Hz), 4.02-3.95 (2H, m), 3.92-3.85(1H, m), 3.78(3H, s), 2.60(2H, q, J = 7.58 Hz), 2.46-2.30(10H, m), 2.13(3H, s), 1.17(3H, t, J = 7.65 Hz). |

TABLE 1-35

| | | |
|---|---|---|
| 153 | 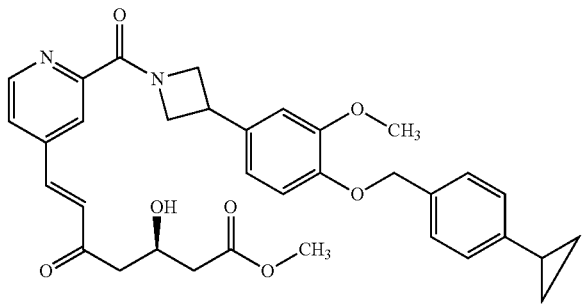 [SMILES: COC(=O)C[C@H](O)CC(=O)/C=C/c1ccnc(C(=O)N2CC(c3ccc(OCc4ccc(C5CC5)cc4)c(OC)c3)C2)c1] | 1H-NMR (400 MHz, CDCl3) δ: 8.60(1H, dd, J =9.17, 6.35 Hz), 8.30(1H, t, J = 5.34 Hz), 7.61-7.54(1H, m), 7.45-7.39(1H, m), 7.32(3H, t, J = 9.77 Hz), 7.09-7.02(4H, m), 6.83(4H, dt, J = 15.85, 7.45 Hz), 6.55(1H, dt, J = 35.93, 10.43 Hz), 5.10-5.07(1H, m), 5.09(3H, s), 4.71(1H, dd, J = 8.46, 4.23 Hz), 4.62(1H, t, J = 9.57 Hz), 4.29(1H, dd, J = 6.25, 84.22 Hz), 3.88-3.85(3H, m), 3.86(3H, s), 3.79-3.76(3H, m), 3.36-3.31(1H, m), 1.89-1.87(1H, m), 0.96-0.95(2H, m), 0.71-0.66(2H, m). |
| 154 | 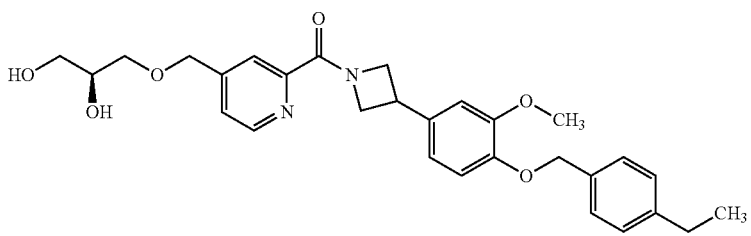 [SMILES: CCc1ccc(COc2ccc(C3CN(C(=O)c4cc(COC[C@@H](O)CO)ccn4)C3)cc2OC)cc1] | 1H-NMR (400 MHz, DMSO-d6) δ: 8.57(1H, d, J = 5.10 Hz), 7.94(1H, s), 7.48(1H, d, J = 5.10 Hz), 7.34(2H, d, J = 7.88 Hz), 7.22(2H, d, J = 7.88 Hz), 7.00-6.98(2H, m), 6.87(1H, dd, J = 8.23, 1.74 Hz), 5.01(2H, s), 4.97(1H, t, J = 9.39 Hz), 4.78(1H, d, J = 5.10 Hz), 4.62(2H, s), 4.57-4.54(2H, m), 4.46 (1H, t, J = 9.39 Hz), 4.08(1H, dd, J = 9.97, 6.72 Hz), 3.93-3.85(1H, m), 3.78(3H, s), 3.68-3.62(1H, m), 3.52(1H, dd, J = 9.97, 4.41 Hz), 3.42-3.35(3H, m), 2.60(2H, q, J = 7.58 Hz), 1.17(3H, t, J = 7.54 Hz). |
| 155 | 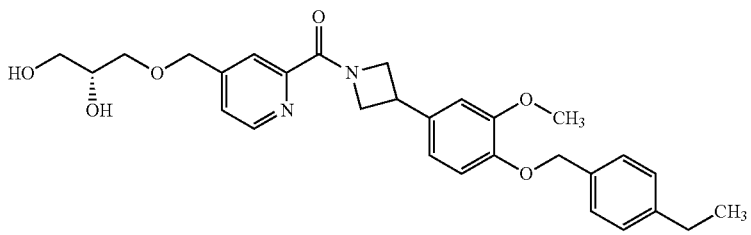 [SMILES: CCc1ccc(COc2ccc(C3CN(C(=O)c4cc(COC[C@H](O)CO)ccn4)C3)cc2OC)cc1] | 1H-NMR (400 MHz, DMSO-d6) δ: 8.58(1H, d, J = 5.10 Hz), 7.94(1H, s), 7.49(1H, d, J = 4.87 Hz), 7.34(2H, d, J = 7.88 Hz), 7.22(2H, d, J = 8.12 Hz), 7.00-6.98(2H, m), 6.87(1H, dd, J = 8.35, 1.86 Hz), 5.01(2H, s), 4.97(1H, t, J = 9.51 Hz), 4.78(1H, d, J = 5.10 Hz), 4.62(2H, s), 4.57-4.54(2H, m), 4.46(1H, t, J = 9.62 Hz), 4.08(1H, dd, J = 10.09, 6.61Hz), 3.93-3.85(1H, m), 3.78(3H, s), 3.66-3.63(1H, m), 3.52(1H, dd, J = 9.97, 4.41 Hz), 3.42-3.35(3H, m), 2.60(2H, q, J = 7.50 Hz), 1.17(3H, t, J = 7.54 Hz). |
| 156 | 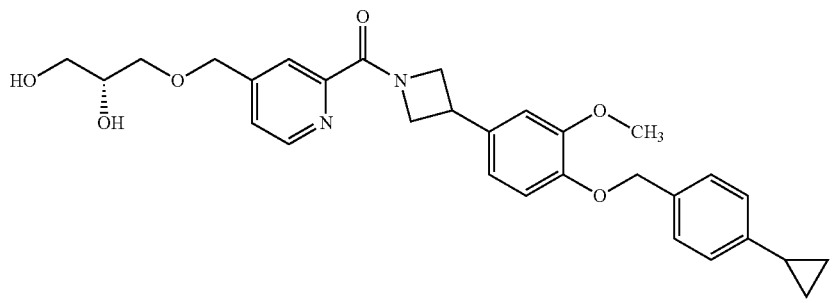 [SMILES: COc1cc(C2CN(C(=O)c3cc(COC[C@H](O)CO)ccn3)C2)ccc1OCc1ccc(C2CC2)cc1] | 1H-NMR (400 MHz, DMSO-d6) δ: 8.58(1H, d, J = 4.87 Hz), 7.94(1H, s), 7.48(1H, dd, J = 4.99, 1.51 Hz), 7.30(2H, d, J = 8.12 Hz), 7.08(2H, d, J = 8.12 Hz), 6.98(2H, dd, J = 4.99, 3.13 Hz), 6.87(1H, dd, J = 8.35, 1.86 Hz), 4.99-4.94(3H, m), 4.77(1H, d, J = 4.87 Hz), 4.62(2H, s), 4.58-4.53 (2H, m), 4.46(1H, t, J = 9.51 Hz), 4.08(1H, dd, J = 10.20, 6.49 Hz), 3.93-3.85(1H, m), 3.77(3H, s), 3.69-3.62(1H, m), 3.52(1H, dd, J = 9.97, 4.41 Hz), 3.42-3.35(3H, m), 1.94-1.88(1H, m), 0.96-0.92 (2H, m), 0.68-0.64(2H, m). |

TABLE 1-36

| 157 | 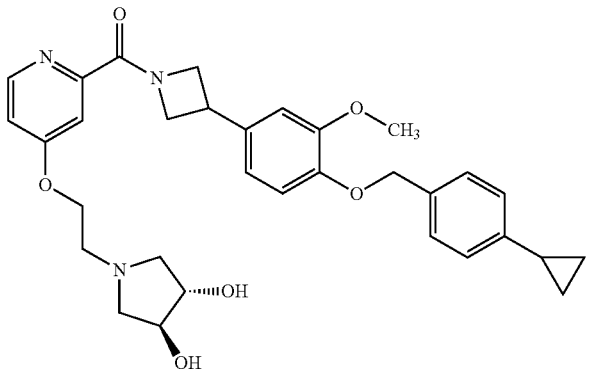 [SMILES: COc1cc(C2CN(C(=O)c3cc(OCCN4C[C@H](O)[C@@H](O)C4)ccn3)C2)ccc1OCc1ccc(C2CC2)cc1] | 1H-NMR (400 MHz, DMSO-d6) δ: 8.41(1H, d, J = 5.80 Hz), 7.47(1H, d, J = 2.32 Hz), 7.29(2H, d, J = 7.88 Hz), 7.09-7.07(3H, m), 6.96-6.96(2H, m), 6.85 (1H, d, J = 7.19 Hz), 4.98(2H, s), 4.93(1H, d, J = 9.28 Hz), 4.84(2H, d, J = 4.41 Hz), 4.53(1H, dd, J = 9.86, 8.84 Hz), 4.43(1H, t, J = 9.51 Hz), 4.16(2H, t, J = 5.57 Hz), 4.05(1H, dd, J = 9.86, 6.61 Hz), 3.91-3.82(3H, m), 3.76(3H, s), 2.87-2.82(2H, m), 2.80-2.71(2H, m), 2.41(2H, dd, J = 9.62, 3.83 Hz), 1.93-1.87(1H, m), 0.95-0.92(2H, m), 0.67-0.63 (2H, m). |
| --- | --- | --- |
| 158 | 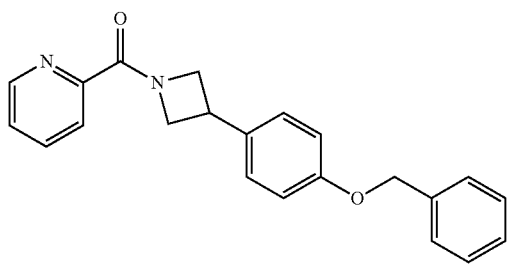 [SMILES: O=C(c1ccccn1)N1CC(c2ccc(OCc3ccccc3)cc2)C1] | 1H-NMR (400 MHz, DMSO-d6) δ: 8.61(1H, dd, J = 4.75, 1.04 Hz), 7.98-7.94(2H, m), 7.56-7.49(1H, m), 7.43(2H, d, J = 7.42 Hz), 7.38(2H, t, J = 7.54 Hz), 7.34-7.28(3H, m), 6.99(2H, d, J = 8.35 Hz), 5.09(2H, s), 4.97(1H, t, J = 9.39 Hz), 4.54-4.44 (2H, m), 4.05-3.97(1H, m), 3.91-3.84(1H, m). |
| 159 | 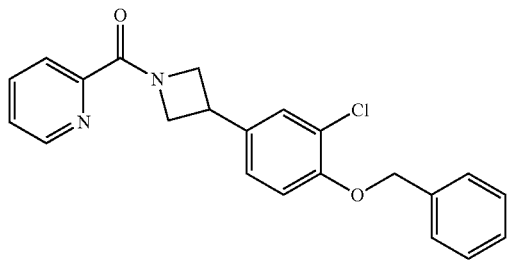 [SMILES: O=C(c1ccccn1)N1CC(c2ccc(OCc3ccccc3)c(Cl)c2)C1] | 1H-NMR (400 MHz, DMSO-d6) δ: 8.62(1H, d, J = 4.63 Hz), 7.99-7.94(2H, m), 7.55-7.52(1H, m), 7.50-7.46(3H, m), 7.42-7.39(2H, m), 7.35-7.32 (2H, m), 7.22(1H, d, J = 8.46 Hz), 5.21(2H, s), 4.97(1H, t, J = 9.57 Hz), 4.54(1H, dd, J = 10.07, 6.25 Hz), 4.46(1H, t, J = 9.57 Hz), 4.04(1H, dd, J = 10.48, 6.65 Hz), 3.94-3.87(1H, m). |
| 160 | 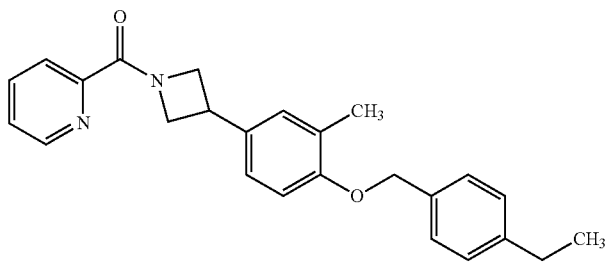 [SMILES: CCc1ccc(COc2ccc(C3CN(C(=O)c4ccccn4)C3)cc2C)cc1] | 1H-NMR (400 MHz, DMSO-d6) δ: 8.57(1H, s), 8.14 (1H, d, J = 7.25 Hz), 7.81(1H, t, J = 7.45 Hz), 7.39-7.32(3H, m), 7.29-7.23(1H, m), 7.19(2H, d, J = 14.51 Hz), 7.11(1H, d, J = 8.06 Hz), 6.86(1H, d, J = 8.46 Hz), 5.07(1H, t, J = 13.10 Hz), 5.04(2H, s), 4.70(1H, br s), 4.61(1H, t, J = 9.87 Hz), 4.26(1H, br s), 3.83(1H, br s), 2.66(2H, q, J = 7.45 Hz), 2.28 (3H, s), 1.25(3H, t, J = 8.46 Hz). |

TABLE 1-37

| 161 | 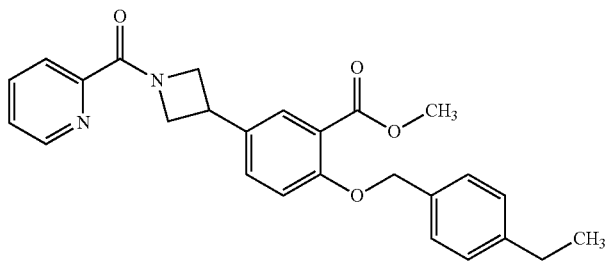 [SMILES: CCc1ccc(COc2ccc(C3CN(C(=O)c4ccccn4)C3)cc2C(=O)OC)cc1] | 1H-NMR (400 MHz, CDCl3) δ: 8.56(1H, d, J = 4.84 Hz), 8.14(1H, d, J = 7.66 Hz), 7.85-7.77(2H, m), 7.46-7.33(4H, m), 7.21(2H, d, J = 8.06 Hz), 7.01 (1H, d, J = 8.87 Hz), 5.15(2H, s), 5.11(1H, t, J = 9.67 Hz), 4.71(1H, dd, J = 1068, 6.25 Hz), 4.62 (1H, t, J = 9.87 Hz), 4.25(1H, dd, J = 10.28, 6.25 Hz), 3.90(3H, s), 3.90-3.82(1H, m), 2.65(2H, q, J = 7.52 Hz), 1.23(3H, t, J = 7.66 Hz). |
| --- | --- | --- |

TABLE 1-37-continued

| | | |
|---|---|---|
| 162 | | 1H-NMR (400 MHz, CDCl3) δ: 8.57(1H, ddd, J = 4.63, 1.81, 1.01 Hz), 8.14(1H, d, J = 7.86 Hz), 7.84-7.80(1H, m), 7.38-7.35(1H, m), 7.33(2H, d, J = 8.26 Hz), 7.24-7.20(4H, m), 7.01(1H, d, J = 9.07 Hz), .14-5.09(3H, m), 4.69(1H, dd, J = 10.68, 6.25 Hz), 4.62(1H, t, J = 9.67 Hz), 4.23(1H, dd, J = 10.48, 6.45 Hz), 3.89-3.81(1H, m), 2.66(2H, q, J = 7.66 Hz), 1.24(3H, t, J = 7.66 Hz). |
| 163 | | 1H-NMR (400 MHz, DMSO-d6) δ: 8.63-8.61(0.8H, m), 7.99-7.96(1.9H, m), 7.69(1.0H, dd, J = 8.70, 1.97 Hz), 7.61(1.0H, d, J = 2.08 Hz), 7.56-7.52 (0.9H, m), 7.36-7.32(3.0H, m), 7.24(2.0H, d, J = 8.12 Hz), 5.22(2.1H, s), 4.99(1.0H, t, J = 9.39 Hz), 4.56(1.0H, dd, J = 10.09, 6.38 Hz), 4.48(1.0H, t, J = 9.51 Hz), 4.07(1.1H, dd, J = 9.97, 6.49 Hz), 4.03-3.95(1.1H, m), 2.60(2.2H, q, J = 7.58 Hz), 1.17 (2.9H, t, J = 7.54 Hz). |
| 164 | | 1H-NMR (400 MHz, DMSO-d6) δ: 8.92(1H, d, J = 5.10 Hz), 8.19(1H, s), 7.95(1H, d, J = 4.17 Hz), 7.33(2H, d, J = 8.12 Hz), 7.21(2H, d, J = 7.88 Hz), 7.03-6.96(2H, m), 6.88(1H, d, J = 8.12 Hz), 5.01 (2H, s), 4.98(1H, t, J = 8.58 Hz), 4.58(1H, dd, J = 10.20, 6.72 Hz), 4.49(1H, t, J = 9.74 Hz), 4.11(1H, dd, J = 10.20, 6.49 Hz), 3.95-3.88(1H, m), 3.77 (3H, s), 2.59(2H, q, J = 7.58 Hz), 1.16(3H, t, J = 7.77 Hz). |

TABLE 1-38

| | | |
|---|---|---|
| 165 | | 1H-NMR (400 MHz, DMSO-d6) δ: 8.60(1H, d, J = 4.64 Hz), 7.99(1H, br s), 7.70(1H, dt, J = 5.33, 1.04 Hz), 7.33(2H, d, J = 7.65 Hz), 7.21(2H, d, J = 7.65 Hz), 7.01-6.96(2H, m), 6.87(1H, d, J = 8.12 Hz), 5.00(2H, s), 4.96(1H, t, J = 9.39 Hz), 4.55 (1H, dd, J = 9.97, 6.49 Hz), 4.46(1H, t, J = 9.62 Hz), 4.08(1H, dd, J = 10.20, 6.49 Hz), 3.94-3.85 (1H, m), 3.77(3H, s), 2.59(2H, q, J = 7.58 Hz), 1.17(3H, t, J = 7.54 Hz). |
| 166 | | 1H-NMR (400 MHz, DMSO-d6) δ: 8.56(1H, d, J = 2.09 Hz), 8.15-8.07(1H, m), 7.34(2H, d, J = 8.12 Hz), 7.22(2H, d, J = 8.12 Hz), 7.00(1H, d, J = 8.12 Hz), 6.96(1H, d, J = 1.62 Hz), 6.86(1H, dd, J = 8.12, 1.62 Hz), 5.02(2H, s), 4.58(1H, t, J = 9.04 Hz), 4.46(1H, t, J = 9.51 Hz), 4.22(1H, dd, J = 9.16, 6.38 Hz), 4.08(1H, dd, J = 10.09, 6.38 Hz), 3.93-3.85(1H, m), 3.78(3H, s), 2.60(2H, q, J = 7.58 Hz), 1.17(3H, t, J = 7.54 Hz). |

TABLE 1-38-continued

| | | |
|---|---|---|
| 167 | 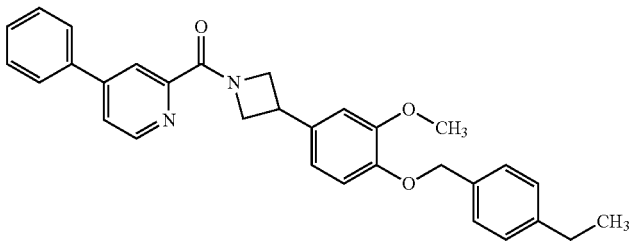 [SMILES: CCc1ccc(COc2ccc(C3CN(C(=O)c4cc(-c5ccccc5)ccn4)C3)cc2OC)cc1] | 1H-NMR (400 MHz, DMSO-d6) δ: 8.69(1H, d, J = 5.29 Hz), 8.23(1H, d, J = 1.76 Hz), 7.90-7.80(3H, m), 7.60-7.49(3H, m), 7.34(2H, d, J = 7.94 Hz), 7.22(2H, d, J = 7.94 Hz), 7.03-6.97(2H, m), 6.89 (1H, dd, J = 8.38, 1.98 Hz), 5.02(2H, s), 5.01(1H, t, J = 9.15 Hz), 4.60(1H, dd, J = 9.92, 6.62 Hz), 4.49(1H, t, J = 9.70 Hz), 4.11(1H, dd, J = 10.03, 6.73 Hz), 3.97-3.87(1H, m), 3.79(3H, s), 2.60(2H, q, J = 7.65 Hz), 1.17(3H, t, J = 7.61 Hz). |
| 168 | 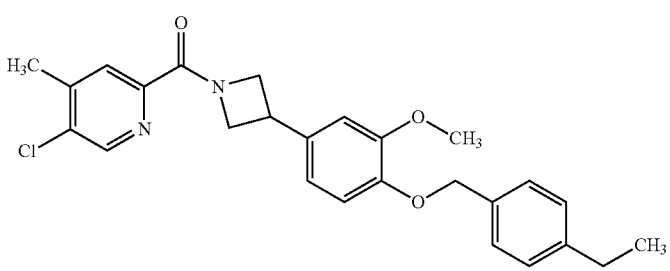 [SMILES: CCc1ccc(COc2ccc(C3CN(C(=O)c4cc(C)c(Cl)cn4)C3)cc2OC)cc1] | 1H-NMR (400 MHz, DMSO-d6) δ: 8.59(1H, s), 7.99 (1H, s), 7.34(2H, d, J = 8.16 Hz), 7.22(2H, d, J = 8.16 Hz), 7.00-6.98(2H, m), 6.87(1H, dd, J = 8.27, 1.87 Hz), 5.01(2H, s), 4.94(1H, t, J = 9.15 Hz), 4.53(1H, dd, J = 10.03, 6.73 Hz0, 4.45(1H, t, J = 9.48 Hz), 4.07(1H, dd, J = 10.14, 6.62 Hz), 3.93-3.87(1H, m), 3.78(3H, s), 2.60(2H, q, J = 7.57 Hz), 2.43(3H, s), 1.17(3H, t, J = 7.61 Hz). |

TABLE 1-39

| | | |
|---|---|---|
| 169 | 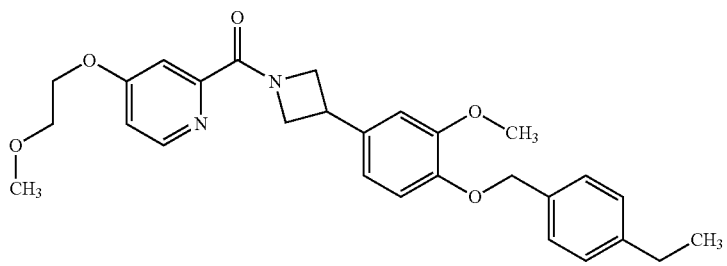 [SMILES: CCc1ccc(COc2ccc(C3CN(C(=O)c4cc(OCCOC)ccn4)C3)cc2OC)cc1] | 1H-NMR (400 MHz, DMSO-d6) δ: 8.42(1H, d, J = 5.51 Hz), 7.49(1H, d, J = 2.65 Hz), 7.34(2H, d, J = 7.94 Hz), 7.22(2H, d, J = 7.94 Hz), 7.11(1H, dd, J = 5.62, 2.76 Hz), 7.02-6.95(2H, m), 6.87(1H, dd, J = 8.38, 1.98 Hz), 5.01(2H, s), 4.95 (1H, t, J = 9.59 Hz), 4.54(1H, dd, J = 10.14, 6.62 Hz), 4.44(1H, t, J = 9.48 Hz), 4.26-4.24(2H, m), 4.07(1H, dd, J = 10.03, 6.73 Hz), 3.93-3.83(1H, m), 3.78(3H, s), 3.69-3.67(2H, m), 3.31(3H, s), 2.60(2H, q, J = 7.65 Hz), 1.17(3H, t, J = 7.61 Hz). |
| 170 | 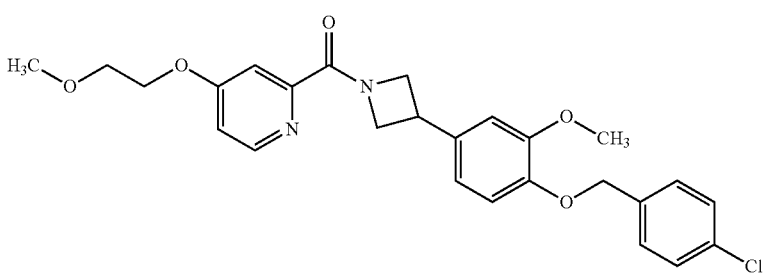 [SMILES: COCCOc1ccnc(C(=O)N2CC(c3ccc(OCc4ccc(Cl)cc4)c(OC)c3)C2)c1] | 1H-NMR (400 MHz, DMSO-d6) δ: 8.42(1H, d, J = 5.73 Hz), 7.49(1H, d, J = 2.65 Hz), 7.44(4H, br s), 7.11(1H, dd, J = 5.73, 2.65 Hz), 6.99(1H, br s), 6.98(1H, d, J = 7.06 Hz), 6.87(1H, dd, J = 8.38, 1.98 Hz), 5.06(2H, s), 4.95(1H, t, J = 9.48 Hz), 4.54(1H, dd, J = 10.26, 6.51 Hz), 4.45(1H, t, J = 9.70 Hz), 4.26-4.24(2H, m), 4.07(1H, dd, J = 10.14, 6.62 Hz), 3.91-3.87(1H, m), 3.79(3H, s), 3.69-3.67(2H, m), 3.31(3H, s). |
| 171 | 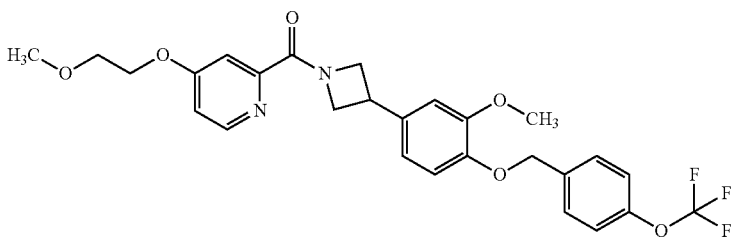 [SMILES: COCCOc1ccnc(C(=O)N2CC(c3ccc(OCc4ccc(OC(F)(F)F)cc4)c(OC)c3)C2)c1] | 1H-NMR (400 MHz, DMSO-d6) δ: 8.42(1H, d, J = 5.73 Hz), 7.56(2H, d, J = 8.82 Hz), 7.49(1H, d, J = 2.43 Hz), 7.39(2H, d, J = 8.38 Hz), 7.11(1H, dd, J = 5.73, 2.65 Hz), 7.01(1H, d, J = 4.41 Hz), 6.99(1H, d, J = 1.76 Hz), 6.88(1H, dd, J = 8.27, 1.87 Hz), 5.10(2H, s), 4.96(1H, t, J = 9.26 Hz), 4.54(1H, dd, J = 10.26, 6.51 Hz), 4.45(1H, t, J = 9.59 Hz), 4.26-4.24(2H, m), 4.07(1H, dd, J = 9.92, 6.62 Hz), 3.93-3.85(1H, m), 3.79(3H, s), 3.69-3.67(2H, m), 3.31(3H, s). |

TABLE 1-39-continued

| 172 | 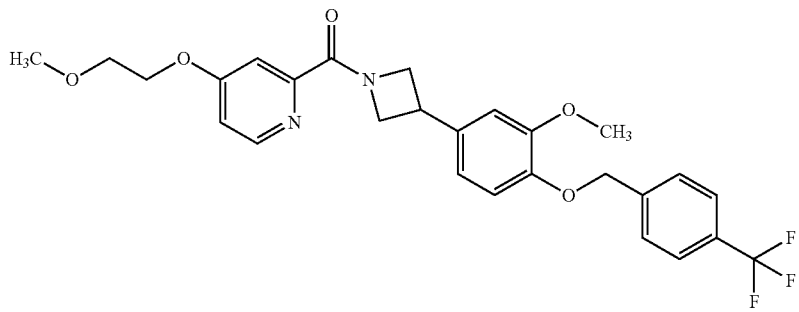 [SMILES: COCCOc1ccnc(C(=O)N2CC(c3ccc(OCc4ccc(C(F)(F)F)cc4)c(OC)c3)C2)c1] | 1H-NMR (400 MHz, DMSO-d6) δ: 8.42(1H, d, J = 5.51 Hz), 7.76(2H, d, J = 8.16 Hz), 7.66(2H, d, J = 7.94 Hz), 7.49(1H, d, J = 2.65 Hz), 7.11(1H, dd, J = 5.73, 2.65 Hz), 7.01 (1H, d, J = 1.98 Hz), 6.99 (1H, d, J = 8.38 Hz), 6.88(1H, dd, J = 8.16, 1.96 Hz), 5.19(2H, s), 4.95(1H, t, J = 9.37 Hz), 4.54 (1H, dd, J = 10.14, 6.62 Hz), 4.45(1H, t, J = 9.26 Hz), 4.26-4.24 (2H, m), 4.07(1H, dd, J = 9.81, 6.51 Hz), 3.93-3.86(1H, m), 3.81(3H, s), 3.69-3.67(2H, m), 3.31(3H, s). |

TABLE 1-40

| 173 | 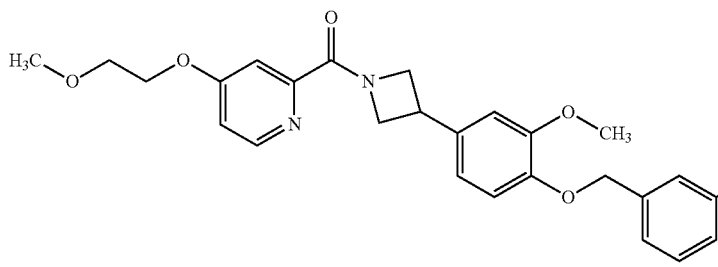 | 1H-NMR (400 MHz, DMSO-d6) δ: 8.42(1H, d, J = 5.73 Hz), 8.05(1H, br s), 7.91(1H, dt, J = 7.50, 1.76 Hz), 7.71(1H, d, J = 7.94 Hz), 7.55 (1H, t, J = 7.61 Hz), 7.49(1H, d, J = 2.65 Hz), 7.11(1H, dd, J =5.62, 2.76 Hz), 7.01(1H, d, J = 4.19 Hz), 7.00(1H, d, J = 1.98 Hz), 6.86(1H, dd, J = 8.49, 1.87 Hz), 5.16(2H, s), 4.95(1H, t, J = 9.26 Hz), 4.54 (1H, dd, J = 10.14, 6.62 Hz), 4.45 (1H, t, J = 9.70 Hz), 4.26-4.24(2H, m), 4.07(1H, dd, J = 10.26, 6.51 Hz), 3.92-3.82(1H, m), 3.86(3H, s), 3.80(3H, s), 3.69-3.67(2H, m), 3.31(3H, s). |
| 174 | 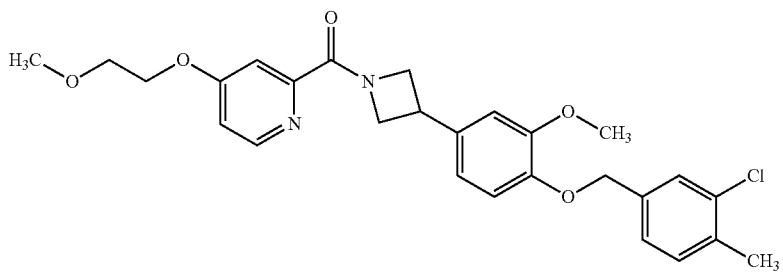 [SMILES: COCCOc1ccnc(C(=O)N2CC(c3ccc(OCc4ccc(C)c(Cl)c4)c(OC)c3)C2)c1] | 1H-NMR (400 MHz, DMSO-d6) δ: 8.42(1H, d, J = 5.73 Hz), 7.49(1H, d, J = 2.43 Hz), 7.47(1H, d, J = 1.54 Hz), 7.36(1H, d, J = 7.94 Hz), 7.29(1H, dd, J = 7.72, 1.54 Hz), 7.11(1H, dd, J = 5.62, 2.76 Hz), 6.99(1H, br s), 6.96(1H, d, J = 8.16 Hz), 6.87(1H, dd, J = 8.38, 1.96 Hz), 5.04(2H, s), 4.95(1H, t, J = 9.15 Hz), 4.54(1H, dd, J = 10.14, 6.62 Hz), 4.44(1H, t, J = 9.59 Hz), 4.26-4.24(2H, m), 4.07(1H, dd, J = 10.26, 6.51 Hz), 3.92-3.85 (1H, m), 3.79(3H, s), 3.69-3.67 (2H, m), 3.31(3H, s), 2.32(3H, s). |
| 175 | 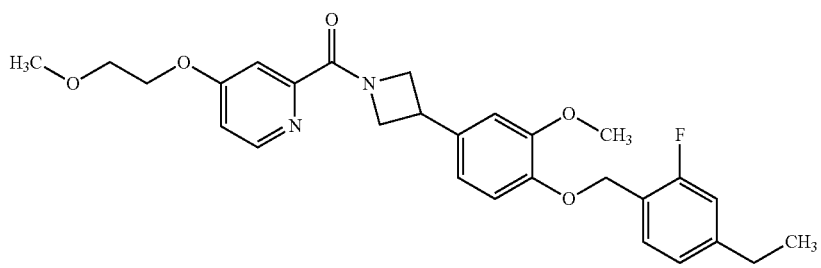 [SMILES: CCc1ccc(COc2ccc(C3CN(C(=O)c4cc(OCCOC)ccn4)C3)cc2OC)c(F)c1] | 1H-NMR (400 MHz, DMSO-d6) δ: 8.42(1H, d, J = 5.73 Hz), 7.49(1H, d, J = 2.43 Hz), 7.42(1H, t, J = 7.83 Hz), 7.12-7.06(3H, m), 7.03(1H, d, J = 8.16 Hz), 6.98(1H, d, J = 1.96 Hz), 6.89(1H, dd, J = 8.38, 1.98 Hz), 5.04(2H, s), 4.96(1H, t, J = 9.26 Hz), 4.54(1H, dd, J = 10.03, 6.51 Hz), 4.45 (1H, t, J = 9.48 Hz), 4.27-4.23 (2H, m), 4.07(1H, dd, J = 10.14, 6.62 Hz), 3.95-3.85(1H, m), 3.77 (3H, s), 3.69-3.67(2H, m), 3.31 (3H, s), 2.63(2H, q, J = 7.65 Hz), 1.18(3H, t, J = 7.50 Hz). |

TABLE 1-40-continued

| 176 | 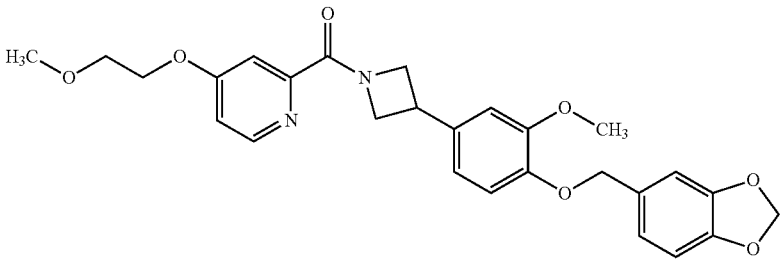 [SMILES: COCCOc1ccnc(C(=O)N2CC(c3ccc(OCc4ccc5c(c4)OCO5)c(OC)c3)C2)c1] | 1H-NMR (400 MHz, DMSO-d6) δ: 8.42(1H, d, J = 5.73 Hz), 7.49(1H, d, J = 2.65 Hz), 7.11(1H, dd, J = 5.73, 2.65 Hz), 7.01-6.97(3H, m), 6.92-6.89(2H, m), 6.87(1H, dd, J = 8.16, 1.98 Hz), 6.01(2H, s), 4.95(1H, t, J = 9.48 Hz), 4.95(2H, s), 4.54(1H, dd, J = 10.26, 6.51 Hz), 4.45(1H, t, J = 9.59 Hz), 4.26-4.24(2H, m), 4.07(1H, dd, J = 9.92, 6.62 Hz), 3.92-3.84(1H, m), 3.78(3H, s), 3.69-3.67(2H, m), 3.31(3H, s). |

TABLE 1-41

| 177 | 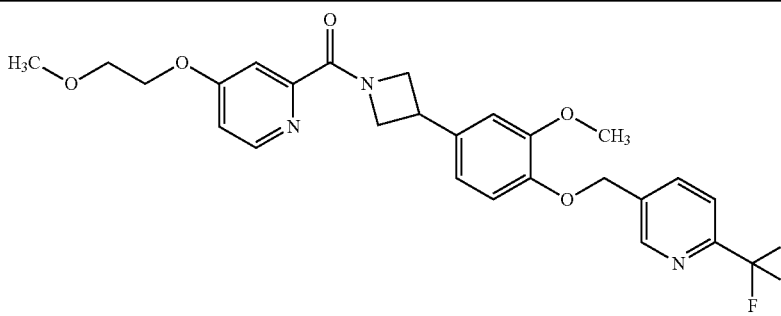 | 1H-NMR (400 MHz, DMSO-d6) δ: 8.83(1H, s), 8.41(1H, d, J = 5.57 Hz), 8.12(1H, d, J = 8.12 Hz), 7.94 (1H, d, J = 8.12 Hz), 7.48(1H, d, J = 2.55 Hz), 7.10(1H, dd, J = 5.68, 2.67 Hz), 7.03(1H, d, J = 8.35 Hz), 7.01(1H, d, J = 1.86 Hz), 6.89(1H, dd, J = 8.35, 1.86 Hz), 5.24(2H, s), 4.95(1H, t, J = 9.51 Hz), 4.54(1H, dd, J = 10.09, 6.61 Hz), 4.44(1H, t, J = 9.62 Hz), 4.27-4.22(2H, m), 4.07(1H, dd, J = 9.97, 6.49 Hz), 3.93-3.85(1H, m), 3.80(3H, s), 3.69-3.66(2H, m), 3.30(3H, s). |
| 178 | 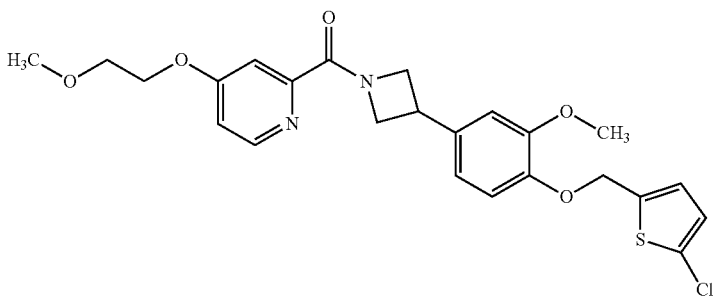 [SMILES: COCCOc1ccnc(C(=O)N2CC(c3ccc(OCc4ccc(Cl)s4)c(OC)c3)C2)c1] | 1H-NMR (400 MHz, DMSO-d6) δ: 8.41(1H, d, J = 5.57 Hz), 7.48(1H, d, J = 2.55 Hz), 7.10(1H, dd, J = 5.80, 2.78 Hz), 7.05(1H, d, J = 3.71 Hz), 7.02(1H, d, J = 3.71 Hz), 7.02(1H, d, J = 8.35 Hz), 6.99(1H, d, J = 2.09 Hz), 6.87(1H, dd, J = 8.23, 1.97 Hz), 5.17(2H, s), 4.95(1H, t, J = 9.51 Hz), 4.53(1H, dd, J = 10.20, 6.49 Hz), 4.44(1H, t, J = 9.51 Hz), 4.25-4.23(2H, m), 4.06(1H, dd, J = 10.20, 6.49 Hz), 3.92-3.85(1H, m), 3.77 (3H, s), 3.68-3.66(2H, m), 3.30(3H, s). |
| 179 | 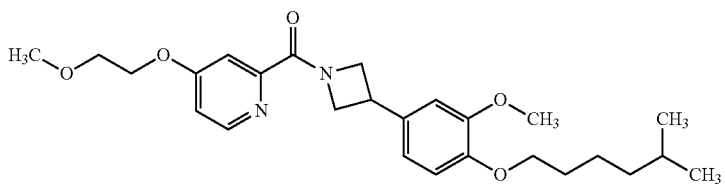 [SMILES: COCCOc1ccnc(C(=O)N2CC(c3ccc(OCCCCC(C)C)c(OC)c3)C2)c1] | 1H-NMR (400 MHz, DMSO-d6) δ: 8.42 (1H, d, J = 5.73 Hz), 7.49(1H, d, J = 2.43 Hz), 7.11(1H, dd, J = 5.73, 2.65 Hz), 6.95(1H, d, J = 1.98 Hz), 6.91(1H, d, J = 8.38 Hz), 6.87(1H, dd, J = 8.27, 1.87 Hz), 4.95(1H, t, J = 9.26 Hz), 4.54(1H, dd, J =10.14, 6.40 Hz), 4.45(1H, t, J = 9.59 Hz), 4.26-4.24(2H, m), 4.06(1H, dd, J = 10.03, 6.51 Hz), 3.94-3.85(3H, m), 3.92(1H, t, J = 6.51 Hz), 3.76(3H, s), 3.69-3.67(2H, m), 3.31(3H, s), 1.71-1.63(2H, m), 1.52(1H, td, J = 13.29, 6.69 Hz), 1.43-1.36(2H, m), 1.20(2H, dd, J = 15.66, 6.84 Hz), 0.86(6H, d, J = 6.62 Hz). |
| 180 | 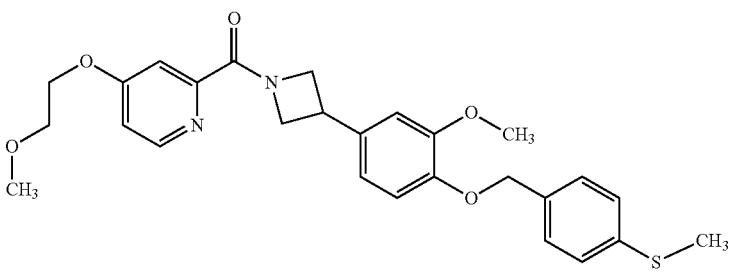 [SMILES: COCCOc1ccnc(C(=O)N2CC(c3ccc(OCc4ccc(SC)cc4)c(OC)c3)C2)c1] | 1H-NMR (400 MHz, DMSO-d6) δ: 8.42(1H, d, J = 5.73 Hz), 7.49(1H, d, J = 2.65 Hz), 7.37(2H, d, J = 8.38 Hz), 7.27(2H, d, J = 8.82 Hz), 7.11(1H, dd, J = 5.73, 2.65 Hz), 6.99(1H, d, J = 4.19 Hz), 6.98(1H, d, J = 1.98 Hz), 6.87(1H, dd, J = 8.38, 1.98 Hz), 5.02 (2H, s), 4.95(1H, t, J = 9.48 Hz), 4.54 (1H, dd, J = 10.26, 6.51 Hz), 4.44(1H, t, J = 9.59 Hz), 4.26-4.24(2H, m), 4.07 (1H, dd, J = 10.03, 6.51 Hz), 3.92-3.84 (1H, m), 3.77(3H, d, J = 6.84 Hz), 3.69-3.67(2H, m), 3.31(3H, s), 2.47(3H, s). |

TABLE 1-42

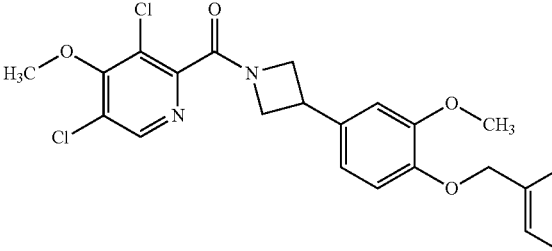

| 181 | | 1H-NMR (400 MHz, DMSO-d6) (mixture of rotamers) δ: 8.42(0.5H, s), 8.39(0.5H, s), 7.34 (1.0H, d, J = 7.94 Hz), 7.33(1.0H, d, J = 8.16 Hz), 7.22(2.0H, d, J = 6.84 Hz), 7.02(0.5H, d, J = 8.38 Hz), 6.99(0.5H, d, J = 8.38 Hz), 6.97(0.5H, d, J = 1.98 Hz), 6.95(0.5H, d, J = 1.96 Hz), 6.87(0.5H, dd, J = 6.18, 1.76 Hz), 6.85(0.5H, dd, J = 5.95, 1.76 Hz), 5.02(2.0H, s), 4.55-4.46(1.5H, m), 4.31 (0.5H, t, J = 9.15 Hz), 4.20-4.05(1.5H, m), 4.00-3.85(1.5H, m), 3.78(3.0H, s), 3.70(1.5H, s), 3.68 (1.5H, s), 2.60(2.0H, q, J = 7.50 Hz), 1.17(1.5H, t, J = 7.61 Hz), 1.17(1.5H, t, J = 7.61 Hz). |
|---|---|---|

$^1$H-NMR spectra were determined in CDCl$_3$, CD$_3$OD or DMSO-D$_6$ using tetramethylsilane as an internal standard. All δ values were showed in ppm.

Symbols showed in the Tables mean as follows.

s: singlet
d: doublet
t: triplet
q: quartet
dd: double doublet
dt: double triplet
dq: double quartet
ddd: double double doublet
m: multiplet
brs: broad singlet
brm: broad multiplet
J: coupling constant Formulation examples of the present invention include for example the following, but which should not be construed as limitative.

Formulation Example 1

Preparation of Capsule

| (1) Compound of Example 1 | 30 mg |
|---|---|
| (2) Microcrystalline cellulose | 10 mg |
| (3) Lactose | 19 mg |
| (4) Magnesium stearate | 1 mg |

(1), (2), (3) and (4) are mixed and filled in a gelatin capsule.

Formulation Example 2

Preparation of Tablet

| (1) Compound of Example 1 | 10 g |
|---|---|
| (2) Lactose | 50 g |
| (3) Corn starch | 15 g |
| (4) Carmellose calcium | 44 g |
| (5) Magnesium stearate | 1 g |

The entire amounts of (1), (2) and (3) and 30 g of (4) are mixed with water and dried in vacuo and then granulated. The granulated powder is mixed with 14 g of (4) and 1 g of (5) and tableted by a tableting machine. In this way, 1000 tablets can be obtained, each of which contains 10 mg of Compound of Example 1.

Biological Assay 1
Inhibitory Action Against CSF-1R Activity In Vitro

The following kinase reactions were conducted to evaluate the inhibitory action against CSF-1R activity of the test compounds. With respect to the preparation of wild-type human CSF-1R cytoplasmic domain (hCSF-1R, Genbank Accession Number NM_005211), an altered hCSF-1R cDNA was prepared by the addition of His-Tag sequence to N-terminal of hCSF-1R cDNA clone (human cDNA clone (hCSF-1R/pCMV6-XL4)-ORIGENE) via polymerase chain reaction, and the resulting altered hCSF-1RcDNA was inserted into a transfer vector (pVL1393-BD). The resulting recombinants were transfected into *Escherichia coli* (DH5α-TOYOBO). The recombinant clones were identified and the plasmid DNA was isolated and then the DNA base sequences were analyzed. The clones comprising the desired base sequences were selected for expression procedures.

The pVL1393 transfer vectors comprising the altered hCSF-1R cDNA and the linear BD BaculoGold DNA (BD) were introduced into Sf9 insect cell to express hCSF-1R cytoplasmic domain. Culture supernatants of the insect cells were centrifuged to collect the recombinant baculovirus. *Spodoptera Frugiperda* egg-derived cells (expres SF+ cell) were infected with the resulting recombinant baculovirus to amplify the virus titer. The virus titer of the final recombinant virus fluid for infection was determined using BacPAK Baculovirus Rapid Titer Kit (Clontech). Expres SF+ cells (1.5×10$^6$ cells/mL) were seeded and the final recombinant baculovirus fluid for infection was added thereto so as to result in the multiplicity of infection (MOI)=0.1, which was cultivated at 27° C. for 72 hr. After the incubation, the centrifugation was performed to collect the infected cells. A suspension of the infected cells was crushed by sonication. His-Tag fused proteins were separated using Cobalt Affinity Resin (TALON Superflow, Clontech). The gels were washed with 50 mmol/L 2-amino-2-(hydroxymethyl)propane-1,3-diol (Tris HCl) (pH7.5), 150 mmol/L sodium chloride, 5% glycerol, 5 mmol/L 2-mercaptoethanol, 0.03% Brij-35 (Sigma), 5 mmol/L 1,3-diaza-2,4-cyclopentadiene (Imidazole). The binding proteins were eluted using 50 mmol/L Tris HCl (pH7.5), 150 mmol/L sodium chloride, 5% glycerol, 5 mmol/L 2-mercaptoethanol, 0.03% Brij-35, and 100 mmol/L Imidazole. The fractions containing the His-Tag fused proteins were pooled and dialyzed against 50 mmol/L Tris HCl (pH7.5), 150 mmol/L sodium chloride, 5% glycerol and 0.03% Brij-35 and then stored at −80° C.

For the kinase reaction, 96 well half-area white plates (plate, Corning 3642) were used. The plates were charged with each 10 μL/well of 20 μg/mL poly(GT)-biotin diluented with a kinase buffer solution (20 mmol/L 3-morpholinopropanesulfonic acid (pH7.0), 10 mmol/L magnesium chloride, 1 mmol/L dithiothreitol, 0.01% bovine serum albumin), 500 μmol/L ATP solution and a solution of the test article prepared with 5% dimethylsulfoxide-containing kinase buffer solution. Then, the reactions were started by the addition of a solution of hCSF-1R enzyme diluted with the kinase buffer solution at 30 μL/well. The concentration of the hCSF-1R enzyme added to a well was 8.33 ng/mL. The wells without only the addition of ATP were prepared as blank wells. After the reaction initiation, the plates were still stood at room temperature for 30 min. A buffer solution for detection (50 μL/well) which contains Europium Cryptate-labeled anti-phosphotyrosine antibody (0.92 μg/mL) and XL665 with streptavidin (2.5 μg/mL) reagent was added to the plates, wherein said buffer solution for detection comprised 50 mmol/L HEPES (pH 7.4), 100 mM EDTA, 200 mmol/L potassium fluoride, 0.05% bovine serum albumin, 0.1% Triton X-100. 2 hr after the addition of the buffer solution for detection, the fluorescent counts of each well were determined using a Fluorescence microplate reader. As for the fluorescent count, the fluorescent count at 620 nm which was excited at 337 nm and the fluorescent count at 665 nm which was excited at 620 nm of fluorescence were determined.

The ratio (fluorescent count at 665 nm/fluorescent count at 620 nm×10000) was calculated from the determined fluorescent counts of each well. The data were obtained by subtracting the mean ratio of the blank well from the ratio of each well. The $IC_{50}$ value of each test article was calculated from percentages of the control values of two points across the 50% inhibition wherein the solvent control was the control value (100%).

The results are showed in Tables 2-1 to 2-7. The inhibitory activity of compounds was represented as $IC_{50}$ (μmol/L). In the tables, the symbol "+++" means less than 0.1 μmol/L of $IC_{50}$, the symbol "++" means more than 0.1 μmol/L but less than 1 μmol/L of $IC_{50}$, and the symbol "+" means more than 1 μmol/L of $IC_{50}$. In addition, the $IC_{50}$ values are showed in the rightmost column of the tables. The values with % optionally-showed in the rightmost column mean the inhibition rate (%) of the test articles when the inhibition rate of the solvent control is 100%.

TABLE 2-1

| Example No. | Inhibitory activity | CSF-1R IC50 (μM) |
|---|---|---|
| 1 | +++ | 0.014 |
| 2 | +++ | 0.015 |
| 3 | +++ | 0.02 |
| 4 | ++ | 0.39 |
| 5 | +++ | 0.0091 |
| 6 | +++ | 0.0089 |
| 7 | +++ | 0.015 |
| 8 | +++ | 0.01 |
| 9 | +++ | 0.011 |
| 10 | ++ | 0.39 |
| 11 | +++ | 0.023 |
| 12 | +++ | 0.012 |
| 13 | +++ | 0.024 |
| 14 | +++ | 0.021 |
| 15 | +++ | 0.017 |
| 16 | +++ | 0.043 |
| 17 | +++ | 0.062 |
| 18 | + | 2.2 |
| 19 | +++ | 0.042 |
| 20 | +++ | 0.086 |
| 21 | ++ | 0.14 |
| 22 | +++ | 0.069 |
| 23 | + | 1.1 |
| 24 | +++ | 0.06 |
| 25 | +++ | 0.044 |
| 26 | +++ | 0.013 |
| 27 | +++ | 0.0074 |

TABLE 2-2

| Example No. | Inhibitory activity | CSF-1R IC50 (μM) |
|---|---|---|
| 28 | +++ | 0.025 |
| 29 | +++ | 0.017 |
| 30 | +++ | 0.018 |
| 31 | +++ | 0.044 |
| 32 | +++ | 0.011 |
| 33 | +++ | 0.034 |
| 34 | +++ | 0.013 |
| 35 | +++ | 0.0061 |
| 36 | +++ | 0.062 |
| 37 | +++ | 0.052 |
| 38 | +++ | 0.016 |
| 39 | +++ | 0.028 |
| 40 | +++ | 0.034 |
| 41 | ++ | 0.39 |
| 42 | +++ | 0.012 |
| 43 | +++ | 0.012 |
| 44 | +++ | 0.033 |
| 45 | +++ | 0.027 |
| 46 | +++ | 0.0044 |
| 47 | ++ | 0.14 |
| 48 | +++ | 0.01 |
| 49 | ++ | 0.11 |
| 50 | ++ | 0.2 |
| 51 | +++ | 0.03 |
| 52 | +++ | 0.036 |
| 53 | +++ | 0.021 |
| 54 | +++ | 0.014 |

TABLE 2-3

| Example No. | Inhibitory activity | CSF-1R IC50 (μM) |
|---|---|---|
| 55 | ++ | 0.12 |
| 56 | +++ | 0.01 |
| 57 | +++ | 0.015 |
| 58 | ++ | 0.39 |
| 59 | +++ | 0.03 |
| 60 | +++ | 0.018 |
| 61 | +++ | 0.019 |
| 62 | +++ | 0.0092 |
| 63 | +++ | 0.064 |
| 64 | +++ | 0.011 |
| 65 | +++ | 0.02 |
| 66 | +++ | 0.067 |
| 67 | +++ | 0.012 |
| 68 | +++ | 0.057 |
| 69 | +++ | 0.017 |
| 70 | +++ | 0.012 |
| 71 | +++ | 0.011 |
| 72 | +++ | 0.0078 |
| 73 | +++ | 0.014 |
| 74 | +++ | 0.012 |
| 75 | +++ | 0.011 |
| 76 | +++ | 0.013 |
| 77 | +++ | 0.027 |
| 78 | +++ | 0.027 |
| 79 | +++ | 0.014 |
| 80 | +++ | 0.029 |
| 81 | +++ | 0.012 |

TABLE 2-4

| Example No. | Inhibitory activity | CSF-1R IC50 (μM) |
|---|---|---|
| 82 | +++ | 0.025 |
| 83 | +++ | 0.01 |
| 84 | +++ | 0.011 |
| 85 | +++ | 0.014 |
| 86 | +++ | 0.017 |
| 87 | +++ | 0.018 |

TABLE 2-4-continued

| Example No. | Inhibitory activity | CSF-1R IC50 (μM) |
|---|---|---|
| 88 | +++ | 0.026 |
| 89 | +++ | 0.017 |
| 90 | +++ | 0.01 |
| 91 | +++ | 0.019 |
| 92 | +++ | 0.018 |
| 93 | +++ | 0.021 |
| 94 | +++ | 0.018 |
| 95 | +++ | 0.022 |
| 96 | +++ | 0.018 |
| 97 | +++ | 0.028 |
| 98 | +++ | 0.02 |
| 99 | +++ | 0.019 |
| 100 | +++ | 0.022 |
| 101 | +++ | 0.021 |
| 102 | +++ | 0.052 |
| 103 | +++ | 0.011 |
| 104 | +++ | 0.023 |
| 105 | +++ | 0.014 |
| 106 | +++ | 0.013 |
| 107 | +++ | 0.08 |
| 108 | +++ | 0.018 |

TABLE 2-5

| Example No. | Inhibitory activity | CSF-1R IC50 (μM) |
|---|---|---|
| 109 | +++ | 0.033 |
| 110 | +++ | 0.037 |
| 111 | +++ | 0.03 |
| 112 | +++ | 0.026 |
| 113 | +++ | 0.0098 |
| 114 | +++ | 0.012 |
| 115 | +++ | 0.015 |
| 116 | +++ | 0.011 |
| 117 | +++ | 0.013 |
| 118 | +++ | 0.016 |
| 119 | +++ | 0.0088 |
| 120 | +++ | 0.01 |
| 121 | +++ | 0.014 |
| 122 | +++ | 0.015 |
| 123 | +++ | 0.016 |
| 124 | +++ | 0.015 |
| 125 | +++ | 0.032 |
| 126 | +++ | 0.012 |
| 127 | +++ | 0.013 |
| 128 | +++ | 0.017 |
| 129 | +++ | 0.041 |
| 130 | +++ | 0.015 |
| 131 | +++ | 0.015 |
| 132 | +++ | 0.013 |
| 133 | +++ | 0.012 |
| 134 | +++ | 0.01 |
| 135 | +++ | 0.0078 |

TABLE 2-6

| Example No. | Inhibitory activity | CSF-1R IC50 (μM) |
|---|---|---|
| 136 | +++ | 0.0085 |
| 137 | +++ | 0.0088 |
| 138 | +++ | 0.025 |
| 139 | +++ | 0.01 |
| 140 | +++ | 0.022 |
| 141 | +++ | 0.066 |
| 142 | +++ | 0.015 |
| 143 | +++ | 0.015 |
| 144 | +++ | 0.016 |
| 145 | +++ | 0.01 |
| 146 | +++ | 0.038 |
| 147 | +++ | 0.037 |

TABLE 2-6-continued

| Example No. | Inhibitory activity | CSF-1R IC50 (μM) |
|---|---|---|
| 148 | +++ | 0.034 |
| 149 | +++ | 0.027 |
| 150 | +++ | 0.015 |
| 151 | +++ | 0.015 |
| 152 | +++ | 0.0068 |
| 153 | ++ | 0.28 |
| 154 | +++ | 0.018 |
| 155 | +++ | 0.016 |
| 156 | +++ | 0.013 |
| 157 | +++ | 0.0088 |
| 158 | ++ | 0.68 |
| 159 | + | >30 55.9% |
| 160 | + | 8.2 |
| 161 | + | 20 |
| 162 | + | 3.8 |

TABLE 2-7

| Example No. | Inhibitory activity | CSF-1R IC50 (μM) |
|---|---|---|
| 163 | + | >30 66.8% |
| 164 | ++ | 0.16 |
| 165 | +++ | 0.079 |
| 166 | ++ | 0.81 |
| 167 | ++ | 0.11 |
| 168 | ++ | 0.18 |
| 169 | +++ | <0.03 41.8% |
| 170 | +++ | <0.03 45.1% |
| 171 | +++ | 0.052 |
| 172 | +++ | <0.03 42.3% |
| 173 | +++ | <0.03 42.6% |
| 174 | +++ | 0.033 |
| 175 | +++ | 0.031 |
| 176 | +++ | <0.03 39.5% |
| 177 | +++ | 0.066 |
| 178 | +++ | <0.03 42.1% |
| 179 | +++ | 0.08 |
| 180 | +++ | <0.03 33.6% |
| 181 | + | >30 66.5% |

As is clear from the biological assay 1, the present invention compounds have an inhibitory action against CSF-1R activity.

Thus, the present invention compounds inhibit CSF-1R activity.

Thereby, the present invention compound may be a medicine for treating or preventing rheumatoid arthritis, multiple sclerosis, osteoporosis including bone loss after ovariectomy, osteolysis and cancer such as lung cancer and breast cancer.

In addition, the present invention compound may be a medicine for treating or preventing diabetic nephropathy.

The invention claimed is:
1. A compound of formula [I]:

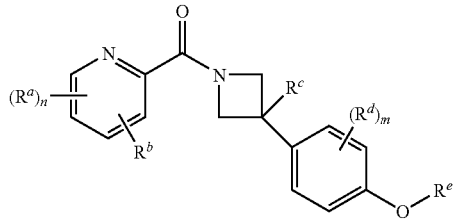

wherein
$R^a$ is
(1) $C_{1-6}$ alkyl group, or
(2) halogen atom;
n is an integer selected from 0, and 1 to 3;
$R^b$ is a group selected from the following (1) to (8)
(1) hydrogen atom,
(2) halogen atom,
(3) $C_{1-6}$ alkyl group which is optionally substituted with the same or different 1 to 5 substituents selected from Group A,
(4) —O—$(CH_2)_{n1}$—$(O)_{n2}$—$R^{b1}$ wherein
$R^{b1}$ is hydrogen atom, or $C_{1-6}$ alkyl group which is optionally substituted with the same or different 1 to 5 substituents selected from Group A,
n1 is an integer selected from 0 or 1 to 4, and
n2 is 0 or 1,
provided that n1 is an integer selected from 1 to 4 when n2 is 1,
(5)

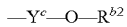

wherein
$Y^c$ is $C_{1-6}$ alkylene which is optionally substituted with the same or different 1 to 5 substituents selected from $C_{1-4}$ alkyl group and hydroxyl group, and
$R^{b2}$ is $C_{1-6}$ alkyl group which is substituted with the same or different 1 to 5 substituents selected from Group A,
(6) —CH=CH—C(=O)—$R^{b3}$ wherein $R^{b3}$ is $C_{1-6}$ alkyl group which is optionally substituted with the same or different 1 to 5 substituents selected from Group A,
(7) —$NR^{b4}R^{b5}$ wherein $R^{b4}$ and $R^{b5}$ are independently selected from hydrogen atom and $C_{1-6}$ alkyl group, and
(8)

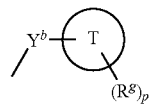

wherein
$Y^b$ is a group selected from the following (i) to (v):
(i) single bond,
(ii) $C_{1-6}$ alkylene which is optionally substituted with $C_{1-4}$ alkyl group,
(iii)

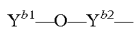

wherein $Y^{b1}$ and $Y^{b2}$ are independently selected from single bond, and $C_{1-6}$ alkylene which is optionally sub-
stituted with the same or different 1 to 5 substituents selected from $C_{1-4}$ alkyl group, halogen atom and hydroxyl group,
(iv) —O—$(CH_2)_{n4}$—C(=O)—, and
(v) —O—$(CH_2)_{n5}$—O—C(=O)—,
wherein n4 and n5 are each an integer selected from 1 to 4;
cyclic moiety T is
(i) nonaromatic monocyclic heterocyclic group wherein the nonaromatic monocyclic heterocyclic ring consists of carbon atoms and 1 to 4 hetero atoms independently selected from nitrogen atom, oxygen atom and sulfur atom, and is 5- or 6-membered,
(ii) monocyclic heteroaromatic group wherein the monocyclic heteroaromatic ring consists of carbon atoms and 1 to 4 hetero atoms independently selected from nitrogen atom, oxygen atom and sulfur atom, and is 5- or 6-membered, or
(iii) $C_{6-10}$ aryl group;
$R^g$ is a group independently selected from the following (i) to (vii):
(i) halogen atom,
(ii) $C_{1-6}$ alkyl group wherein $C_{1-6}$ alkyl is optionally substituted with the same or different 1 to 5 —$OR^{g1}$ or —C(=O)—$OR^{g1}$,
(iii) —C(=O)—$OR^{g2}$,
(iv) —C(=O)—$R^{g3}$,
(v) —C(=O)—$NR^{g4}R^{g5}$,
(vi) —$OR^{g6}$, and
(vii) —$SO_2$—$R^{g7}$,
wherein
$R^{g1}$, $R^{g2}$, $R^{g4}$, $R^{g5}$, $R^{g6}$ and $R^{g7}$ are independently selected from hydrogen atom and $C_{1-6}$ alkyl group, and
$R^{g3}$ is $C_{1-6}$ alkyl group which is optionally substituted with hydroxyl group;
p is an integer selected from 0, and 1 to 4;
$R^c$ is hydrogen atom or hydroxyl group;
$R^d$ is a group selected from the following (1) to (4):
(1) —$OR^{d1}$ wherein $R^{d1}$ is hydrogen atom or $C_{1-6}$ alkyl group which is optionally substituted with the same or different 1 to 5 halogen atoms,
(2) halogen atom,
(3) —C(=O)—$OR^{d2}$ wherein $R^{d2}$ is hydrogen atom or $C_{1-6}$ alkyl group, and
(4) $C_{1-6}$ alkyl group which is optionally substituted with the same or different 1 to 5 halogen atoms;
m is an integer selected from 0, and 1 to 4;
$R^e$ is a group selected from the following (1) and (2):
(1) $C_{1-12}$ alkyl group, and
(2)

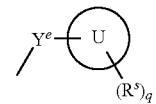

wherein
V is $C_{1-6}$ alkylene which is optionally substituted with $C_{1-4}$ alkyl group;
cyclic moiety U is a group selected from the following (i) to (v):
(i) $C_{6-10}$ aryl group,
(ii) $C_{3-10}$ cycloalkyl group,
(iii) $C_{8-11}$ spirocyclic cycloalkyl or spirocyclic cycloalkenyl group, (iv) monocyclic heteroaromatic group wherein the monocyclic heteroaromatic ring consists of carbon atoms and 1 to 4 hetero atoms independently selected from nitrogen atom, oxygen atom and sulfur atom, and is 5- or 6-membered, and
(v) fused heterocyclic group wherein the fused heterocyclic ring consists of carbon atoms and 1 to 4 hetero atoms independently selected from nitrogen atom, oxygen atom and sulfur atom, and is 9-membered;

$R^5$ is a group independently selected from the following (i) to (vi):
(i) $C_{1-6}$ alkyl group which is optionally substituted with the same or different 1 to 5 halogen atoms,
(ii) $C_{3-6}$ cycloalkyl group,
(iii) —$OR^{S1}$ wherein $R^{S1}$ is hydrogen atom or $C_{1-12}$ alkyl group which is optionally substituted with the same or different 1 to 5 halogen atoms,
(iv) halogen atom,
(v) —C(=O)—$OR^{S2}$ wherein $R^{S2}$ is hydrogen atom or $C_{1-6}$ alkyl group, and
(vi) —$SR^{S3}$ wherein $R^{S3}$ is hydrogen atom or $C_{1-6}$ alkyl group; and q is an integer selected from 0, and 1 to 4;
Group A is selected from the group consisting of the following (a) to (e):
(a) halogen atom,
(b) —$OR^{41}$ wherein $R^{41}$ is hydrogen atom or $C_{1-6}$ alkyl group,
(c) —$NR^{42}R^{43}$ wherein $R^{42}$ and $R^{43}$ are independently selected from hydrogen atom and $C_{1-6}$ alkyl group which is optionally substituted with
  (c1) hydroxyl group, and/or
  (c2) —C(=O)—$OR^{44}$ wherein $R^{44}$ is hydrogen atom or $C_{1-6}$ alkyl group,
(d) —C(=O)—$OR^{45}$ wherein $R^{45}$ is hydrogen atom or $C_{1-6}$ alkyl group, and
(e) —C(=O)—$NR^{46}R^{47}$ wherein $R^{46}$ and $R^{47}$ are independently selected from hydrogen atom and $C_{1-6}$ alkyl group which is optionally substituted with
  (e1) hydroxyl group, and/or
  (e2) —$NR^{48}R^{49}$ wherein $R^{48}$ and $R^{49}$ are independently selected from hydrogen atom and $C_{1-6}$ alkyl group,
or a pharmaceutically acceptable salt thereof, or a solvate of the compound or salt thereof.

2. The compound according to claim 1:
wherein
$R^b$ is
(1) $C_{1-6}$ alkyl group which is optionally substituted with the same or different 1 to 5 substituents selected from Group A,
(2) —O—$(CH_2)_{N1}$—$(O)_{N2}$—$R^{b1}$,
(3) —$Y^c$—O—$R^{b2}$
(4) —CH=CH—C(=O)—$R^{b3}$,
(5) —$NR^{b4}R^{b5}$, or
(6)

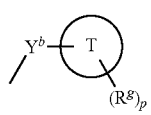

wherein each symbol and Group A are as defined in claim 1,
or a pharmaceutically acceptable salt thereof, or a solvate of the compound or salt thereof.

3. The compound of formula [II] according to claim 1:

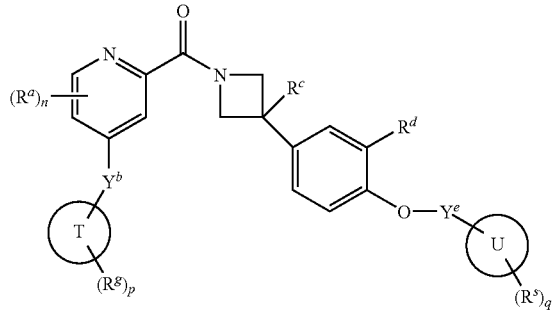

[II]

wherein each symbol is as defined in claim 1,
or a pharmaceutically acceptable salt thereof, or a solvate of the compound or salt thereof.

4. The compound of formula [III] according to claim 1:

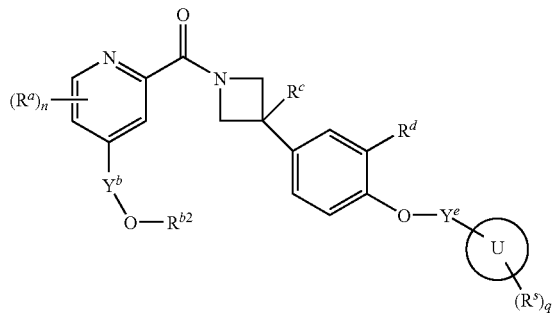

[III]

wherein each symbol is as defined in claim 1,
or a pharmaceutically acceptable salt thereof, or a solvate of the compound or salt thereof.

5. The compound of formula [II-C] according to claim 1:

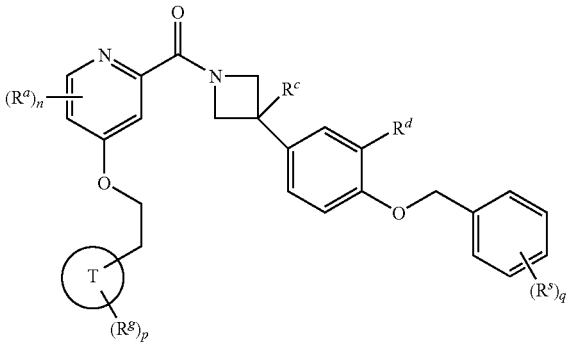

[II-C]

wherein each symbol is as defined in claim 1,
or a pharmaceutically acceptable salt thereof, or a solvate of the compound or salt thereof.

6. The compound of formula [III-B] according to claim 1:

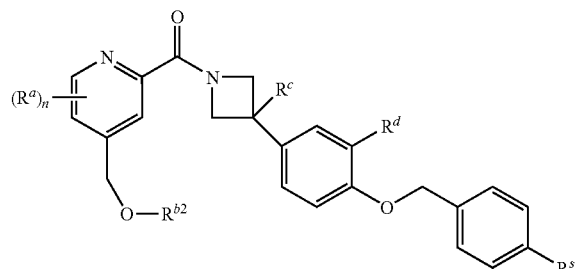

[III-B]

wherein each symbol is as defined in claim 1,
or a pharmaceutically acceptable salt thereof, or a solvate of the compound or salt thereof.

7. The compound of formula [IV-A] according to claim 1:

[IV-A]

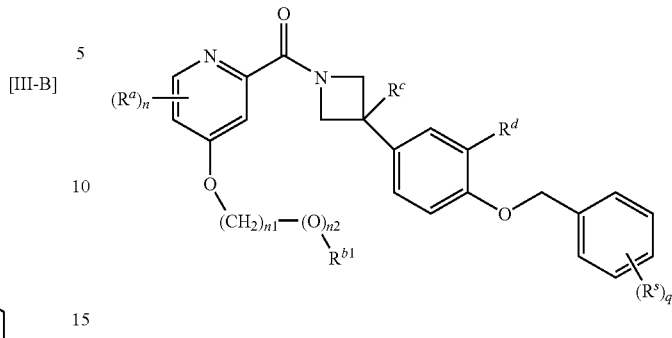

wherein each symbol is as defined in claim 1,
or a pharmaceutically acceptable salt thereof, or a solvate of the compound or salt thereof.

8. A compound having one of the formulas listed below, or a pharmaceutically acceptable salt thereof, or a solvate of the compound or salt thereof:

| Structure |
| --- |
| 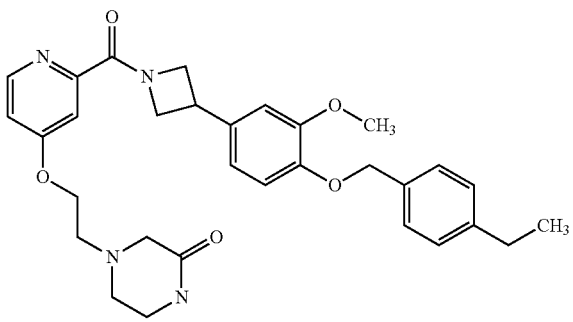 [SMILES: CCc1ccc(COc2ccc(C3CN(C(=O)c4cc(OCCN5CCNC(=O)C5)ccn4)C3)cc2OC)cc1] |
| 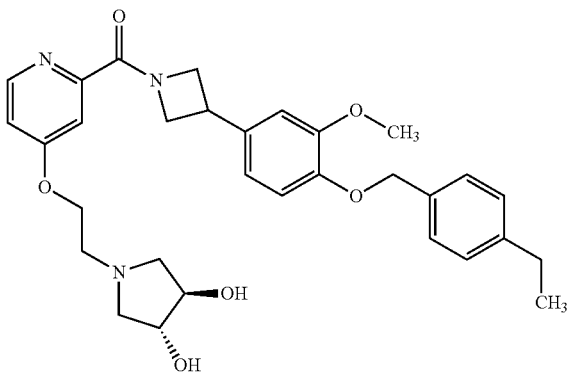 [SMILES: CCc1ccc(COc2ccc(C3CN(C(=O)c4cc(OCCN5C[C@@H](O)[C@H](O)C5)ccn4)C3)cc2OC)cc1] |
| 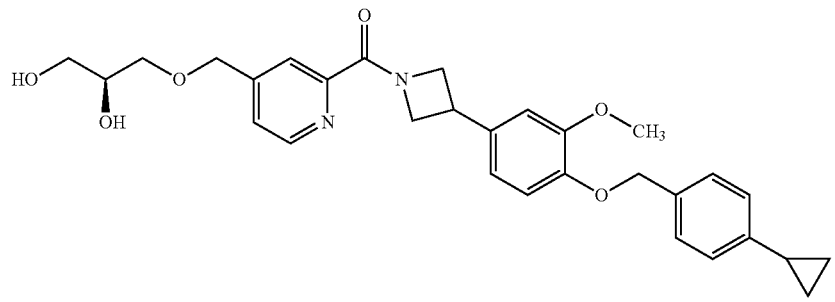 [SMILES: COc1cc(C2CN(C(=O)c3cc(COC[C@@H](O)CO)ccn3)C2)ccc1OCc1ccc(C2CC2)cc1] |

-continued
| Structure |
|---|
| 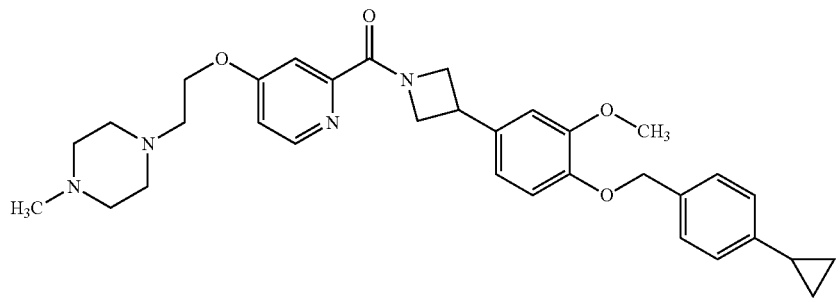 [SMILES: COc1cc(C2CN(C(=O)c3cc(OCCN4CCN(C)CC4)ccn3)C2)ccc1OCc1ccc(C2CC2)cc1] |
| 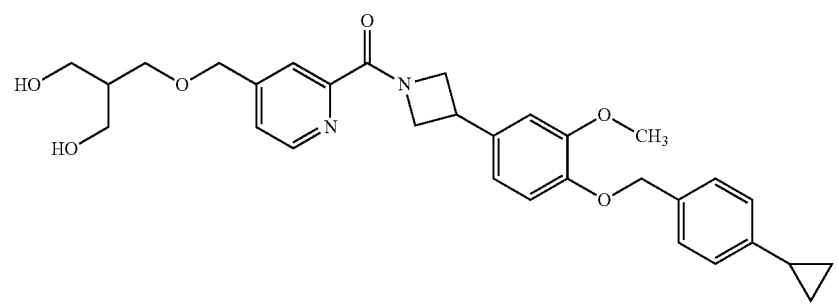 [SMILES: COc1cc(C2CN(C(=O)c3cc(COCC(CO)CO)ccn3)C2)ccc1OCc1ccc(C2CC2)cc1] |
| 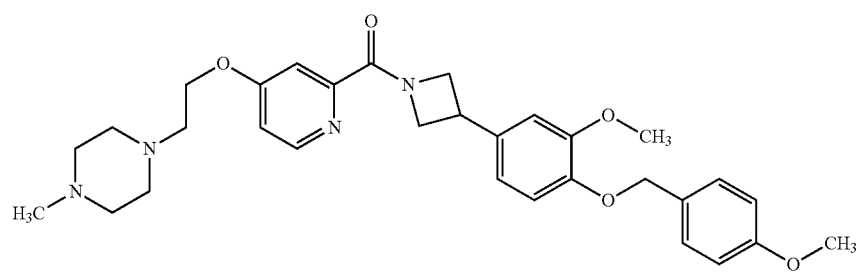 |
| 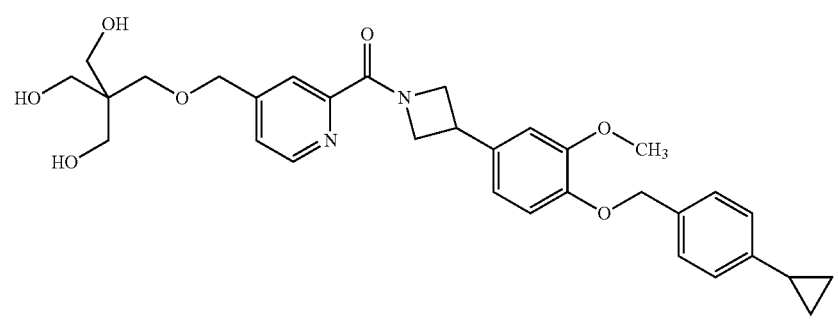 [SMILES: COc1cc(C2CN(C(=O)c3cc(COCC(CO)(CO)CO)ccn3)C2)ccc1OCc1ccc(C2CC2)cc1] |
| 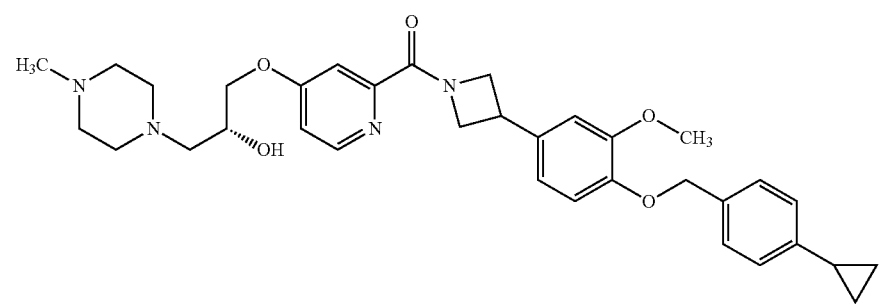 [SMILES: COc1cc(C2CN(C(=O)c3cc(OC[C@H](O)CN4CCN(C)CC4)ccn3)C2)ccc1OCc1ccc(C2CC2)cc1] |

-continued
| Structure |
|---|
| 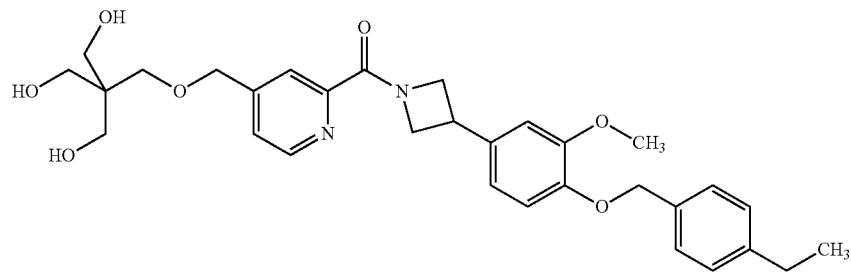 [SMILES: CCc1ccc(COc2ccc(C3CN(C(=O)c4cc(COCC(CO)(CO)CO)ccn4)C3)cc2OC)cc1] |
| 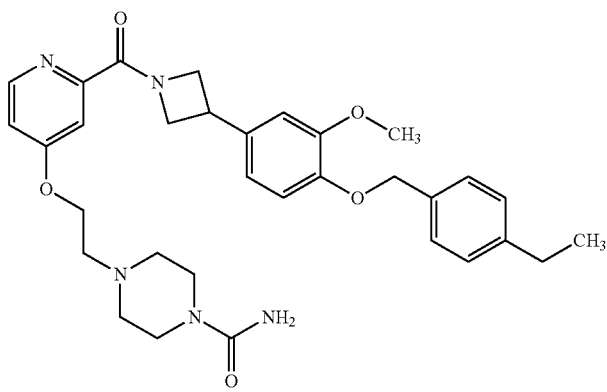 [SMILES: CCc1ccc(COc2ccc(C3CN(C(=O)c4cc(OCCN5CCN(C(N)=O)CC5)ccn4)C3)cc2OC)cc1] |
| 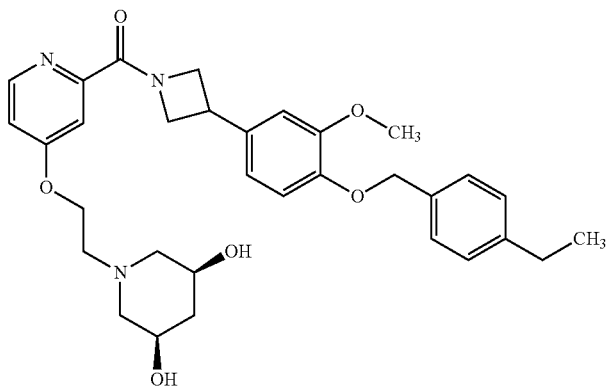 [SMILES: CCc1ccc(COc2ccc(C3CN(C(=O)c4cc(OCCN5C[C@H](O)C[C@H](O)C5)ccn4)C3)cc2OC)cc1] |
| 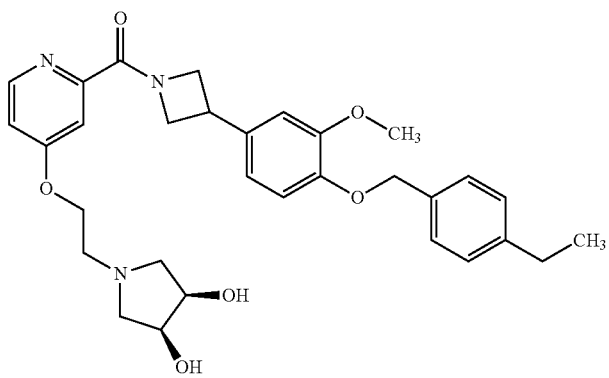 [SMILES: CCc1ccc(COc2ccc(C3CN(C(=O)c4cc(OCCN5C[C@@H](O)[C@@H](O)C5)ccn4)C3)cc2OC)cc1] |

| Structure |
|---|
| 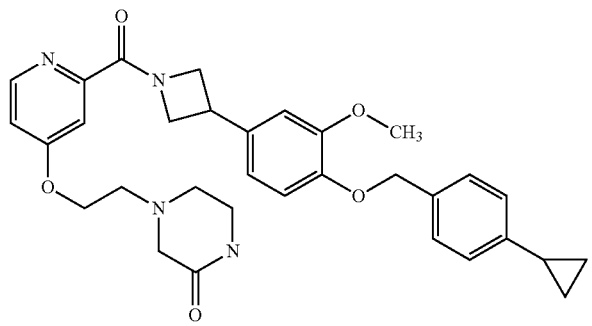 [SMILES: COc1cc(C2CN(C(=O)c3cc(OCCN4CCNC(=O)C4)ccn3)C2)ccc1OCc1ccc(C2CC2)cc1] |
| 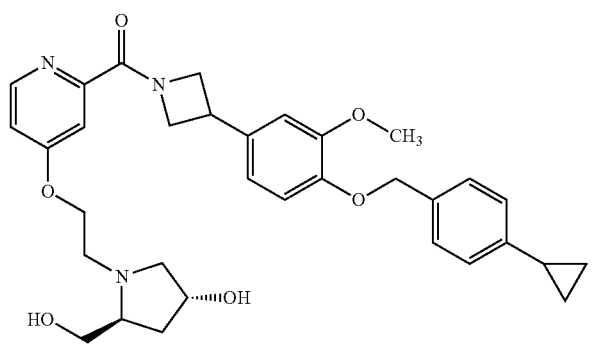 [SMILES: COc1cc(C2CN(C(=O)c3cc(OCCN4C[C@H](O)C[C@H]4CO)ccn3)C2)ccc1OCc1ccc(C2CC2)cc1] |
| 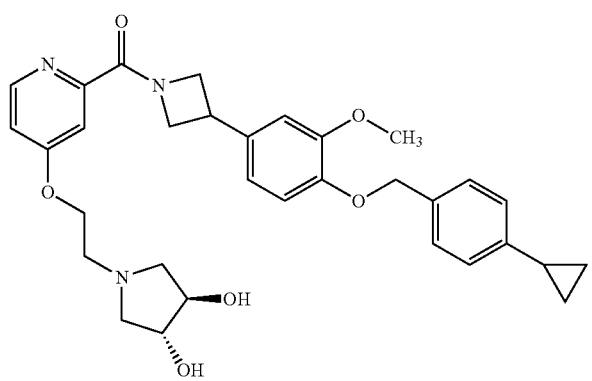 [SMILES: COc1cc(C2CN(C(=O)c3cc(OCCN4C[C@@H](O)[C@H](O)C4)ccn3)C2)ccc1OCc1ccc(C2CC2)cc1] |
| 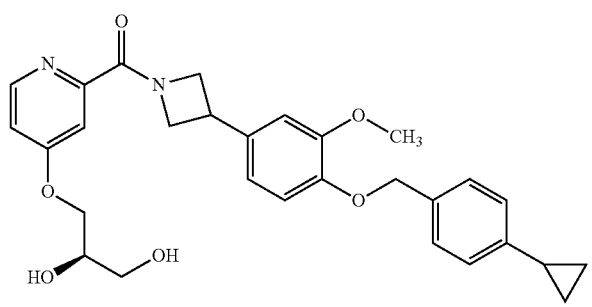 [SMILES: COc1cc(C2CN(C(=O)c3cc(OC[C@H](O)CO)ccn3)C2)ccc1OCc1ccc(C2CC2)cc1] |

| Structure |
|---|
| 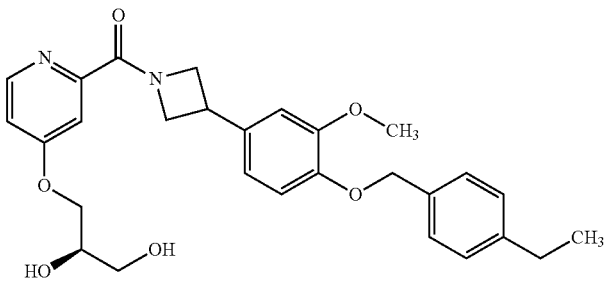 [SMILES: CCc1ccc(COc2ccc(C3CN(C(=O)c4cc(OC[C@H](O)CO)ccn4)C3)cc2OC)cc1] |
| 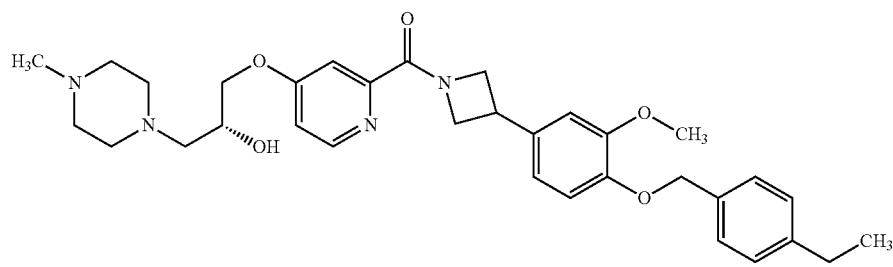 [SMILES: CCc1ccc(COc2ccc(C3CN(C(=O)c4cc(OC[C@H](O)CN5CCN(C)CC5)ccn4)C3)cc2OC)cc1] |
| 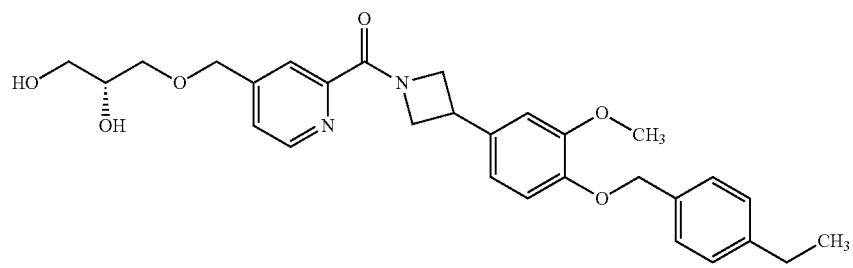 |
| 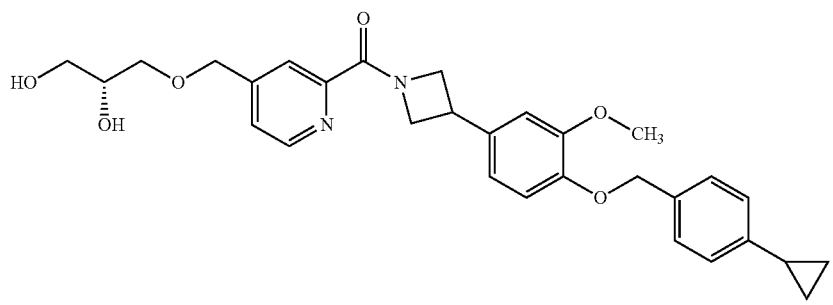 |

9. A pharmaceutical composition comprising the compound according to claim 1, or a pharmaceutically acceptable salt thereof, or a solvate of the compound or salt thereof, and a pharmaceutically acceptable carrier.

10. A method of treating rheumatoid arthritis in a mammal in need thereof, comprising administering to the mammal a therapeutically effective amount of the compound according to claim 1, or a pharmaceutically acceptable salt thereof, or a solvate of the compound or salt thereof.

* * * * *

UNITED STATES PATENT AND TRADEMARK OFFICE
CERTIFICATE OF CORRECTION

| | | |
|---|---|---|
| PATENT NO. | : 8,765,739 B2 | Page 1 of 1 |
| APPLICATION NO. | : 12/780146 | |
| DATED | : July 1, 2014 | |
| INVENTOR(S) | : Kazutaka Ikegashira et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 145 days.

Signed and Sealed this
Fifteenth Day of September, 2015

Michelle K. Lee
*Director of the United States Patent and Trademark Office*